United States Patent
Martin et al.

(10) Patent No.: US 10,408,843 B2
(45) Date of Patent: Sep. 10, 2019

(54) COMPOSITIONS AND METHODS FOR DETECTING S-NITROSYLATION AND S-SULFINYLATION

(71) Applicant: The Regents of the University of Michigan, Ann Arbor, MI (US)

(72) Inventors: Brent R. Martin, Ann Arbor, MI (US); Jaimeen D. Majmudar, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 62 days.

(21) Appl. No.: 15/436,247

(22) Filed: Feb. 17, 2017

(65) Prior Publication Data

US 2017/0192012 A1 Jul. 6, 2017

Related U.S. Application Data

(63) Continuation of application No. 14/888,904, filed as application No. PCT/US2014/037111 on May 7, 2014.

(60) Provisional application No. 61/820,401, filed on May 7, 2013.

(51) Int. Cl.
*C07C 313/00* (2006.01)
*G01N 33/68* (2006.01)
*G01N 33/58* (2006.01)

(52) U.S. Cl.
CPC ....... *G01N 33/6848* (2013.01); *G01N 33/582* (2013.01); *G01N 2440/26* (2013.01); *G01N 2440/30* (2013.01); *G01N 2458/15* (2013.01); *G01N 2500/02* (2013.01); *G01N 2560/00* (2013.01); *G01N 2570/00* (2013.01)

(58) Field of Classification Search
None
See application file for complete search history.

(56) References Cited

U.S. PATENT DOCUMENTS

| 8,226,992 | B1 | 7/2012 | Okerlin | |
|---|---|---|---|---|
| 8,906,605 | B2 * | 12/2014 | Chen | G01N 33/6848 435/4 |
| 2008/0305495 | A1 | 12/2008 | Lipscombe et al. | |

OTHER PUBLICATIONS

Hart, 1985, Tetrahedron Letters, 26, 2013-2016 (Year: 1985).*
https://www.collinsdictionary.com/us/dictionary/english/polypeptide, retrieved on Nov. 7, 2018 (Year: 2018).*
Schwarz, Analytical chemistry, vol. 48, No. 3, Mar. 1976 (Year: 1976).*
Tsikas, Analytical Biochemistry 273, 32-40 (1999) (Year: 1999).*
Murray, Circ Cardiovasc Genet. 2012;5:591 (Year: 2012).*
Hoffman, Molecular & Cellular Proteomics 8:887-903, 2009 (Year: 2009).*
Ahrne et al. "Critical assessment of proteome-wide label-free absolute abundance estimation strategies." Proteomics 13, 2567-78 (2013).
Anand and Stamler "Enzymatic mechanisms regulating protein S-nitrosylation: implications in health and disease." J. Mol. Med. 90(3): 233-244 (2012)
Aranda et al. "Nitric oxide and cancer: the emerging role of S-nitrosylation." Curr. Mol. Med. 12(1):50-67 (2012).
Benhar et al. "Nitrosative stress in the ER: a new role for S-nitrosylation in neurodegenerative diseases." ACS Chem. Biol. 1(6):355-8 (2006).
Benitez et al. "The inactivation of the acyl phosphatase activity catalyzed by the sulfenic acid form of glyceraldehyde 3-phosphate dehydrogenase by dimedone and olefins." J Biol Chem 249, 6234-43 (1974).
Canet-Aviles et al. "The Parkinson's disease protein DJ-1 is neuroprotective due to cysteine-sulfinic acid-driven mitochondrial localization." Proc Natl Acad Sci U S A 101, 9103-8 (2004).
Cho et al. "S-nitrosylation of Drp1 mediates beta-amyloid-related mitochondrial fission and neuronal injury." Science 324(5923):102-5 (2009).
Doulias et al. "Nitric oxide regulates mitochondrial fatty acid metabolism through reversible protein S-nitrosylation." Sci Signal 6, rs1 (2013).
Fang et al. "Dexras1: a G protein specifically coupled to neuronal nitric oxide synthase via CAPON." Neuron 28:183-193 (2000).
Forrester et al. "Assessment and application of the biotin switch technique for examining protein S-nitrosylation under conditions of pharmacologically induced oxidative stress." J Biol Chem 282, 13977-83 (2007).
Giustarini et al. "Is ascorbate able to reduce disulfide bridges? A cautionary note." Nitric Oxide-Biology and Chemistry 19, 252-258 (2008).
Gu et al. "S-nitrosylation of matrix metalloproteinases: signaling pathway to neuronal cell death." Science 297 (5584)1186-90 (2002).
Hart, T.W. "Some Observations Concerning the S-nitroso and S-phenylsulphonyl derivatives of L-Cysteine and glutathione" Tetrahedron Letters 26, 2013-2016 (1985).
Hess et al. "Protein S-nitrosylation: purview and parameters." Nat. Rev. Mol. Cell. Biol. 6:150-166 (2005).
Hoffmann et al. "Shear stress increases the amount of S-nitrosylated molecules in endothelial cells: important role for signal transduction." FEBS Lett. 551:153-158 (2003).
Huang et al. "Systematic and integrative analysis of large gene lists using DAVID bioinformatics resources." Nat Protoc 4, 44-57 (2009).
International Search Report and Written Opinion, International Patent Application No. PCT/US2014/037111, dated May 7, 2014.
Iwakiri et al. "Nitric oxide synthase generates nitric oxide locally to regulate compartmentalized protein S-nitrosylation and protein trafficking." Proc. Natl. Acad. Sci. U S A 103:19777-19782 (2006).

(Continued)

Primary Examiner — Satyanarayana R Gudibande
(74) Attorney, Agent, or Firm — Casimir Jones, SC; Robert A. Goetz

(57) ABSTRACT

The present invention relates to methods for detecting protein S-sulfinylation and S-sulfinylation within thiol groups in proteins, metabolites, or materials.

23 Claims, 142 Drawing Sheets

(56) References Cited

OTHER PUBLICATIONS

Jackson et al. "Human Sulfide: Quinone Oxidoreductase Catalyzes the First Step in Hydrogen Sulfide Metabolism and Produces a Sulfane Sulfer Metabolite." Biochemistry 51, 6804-6815 (2012).
Jaffrey et al. "The biotin switch method for the detection of S-nitrosylated proteins." Sci STKE 2001, pl1 (2001).
Jaffrey et al. "Protein S-nitrosylation: a physiological signal for neuronal nitric oxide." Nat Cell Biol 3, 193-7 (2001).
Kornberg et al. "GAPDH mediates nitrosylation of nuclear proteins." Nat Cell Biol 12, 1094-100 (2010).
Lo Conte et al. "Chemoselective ligation of sulfinic acids with aryl-nitroso compounds." Angew Chem Int Ed Engl 51, 6502-5 (2012).
Majmudar and Martin "Strategies for profiling native S-nitrosylation" Biopolymers, vol. 101, Issue 2, pp. 173-179 (2013).
Murray et al., "Chasing cysteine oxidative modifications: proteomic tools for characterizing cysteine redox status" Cardiovascular Genetics, 2012, vol. 5, No. 5, pp. 1-10.
Nakamura et al. "Aberrant protein s-nitrosylation in neurodegenerative diseases." Neuron 78, 596-614 (2013).
Padgett and Whorton et al. "S-nitrosoglutathione reversibly inhibits GAPDH by S-nitrosylation." Am. J. Physiol. 269:739-749 (1995).
Pan and Carroll "Persulfide reactivity in the detection of protein s-sulfhydration." ACS Chem Biol 8, 1110-6 (2013).
Paulsen et al., "Cysteine-mediated redox signaling: chemistry, biology, and tools for discovery." Chemical Reviews, vol. 113, No. 7, pp. 4633-4679.
Reeves et al., "Selective trapping of SNO-BSA and GSNO by benzenesulfinic acid sodium salt: mechanistic study of thiosulfonate formation and feasibility as a protein S-nitrosothiol detection strategy." Tetrahedron Lett 54 (2013).
Reisz et al. "Thiol-blocking electrophiles interfere with labeling and detection of protein sulfenic acids." FEBS J 280, 6150-61 (2013).
Schonhoff et al. "S-nitrosothiol depletion in amyotrophic lateral sclerosis." Proc. Natl. Acad. Sci. U S A 103 (7):2404-9 (2006).
Silva et al. "Absolute Quantification of Proteins by LCMSE A Virtue of Parallel ms Acquisition" Molecular & Cellular Proteomics 5, 144-156 (2006).
Sun et al. "Cysteine-3635 is responsible for skeletal muscle ryanodine receptor modulation by NO." Proc. Natl. Acad. Sci. U S A 98:11158-11162 (2003).
Uehara et al. "S-nitrosylated protein-disulphide isomerase links protein misfolding to neurodegeneration." Nature 2441(7092):513-7 (2006).
Yang et al. "Comparative Analysis of Cleavable Azobenzene-Based Affinity Tags for Bioorthogonal Chemical Proteomics." Chem Biol 17, 1212-22 (2010).
Yao et al. "Nitrosative stress linked to sporadic Parkinson's disease: S-nitrosylation of parkin regulates its E3 ubiquitin igase activity." Proc. Natl. Acad. Sci. U S A 101(29):10810-4 (2004).

\* cited by examiner

FIG. 15
Protein: Human GAPDH, recombinant
Peptide: IISNASC†TTNC*LAPLAK
Modification: C† = carbamidomethyl, C* = S-S(O$_2$)-biotin (thiosulfonate-biotin)
Retention Time: 44.70 minutes
Drift Time: 49.36
Peptide Charge: +3
Peptide [M+H]$^+$: 2109.9885
Product Ions Observed:
b2b3b5b6b10b13b13°b16b17b17*y1y2y3y4y5y7y8y9y10y11y12y14 y15y15*y16 y17y17*
Mass Error: 3.9832 ppm
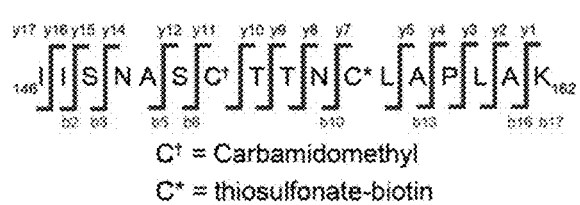
C† = Carbamidomethyl
C* = thiosulfonate-biotin
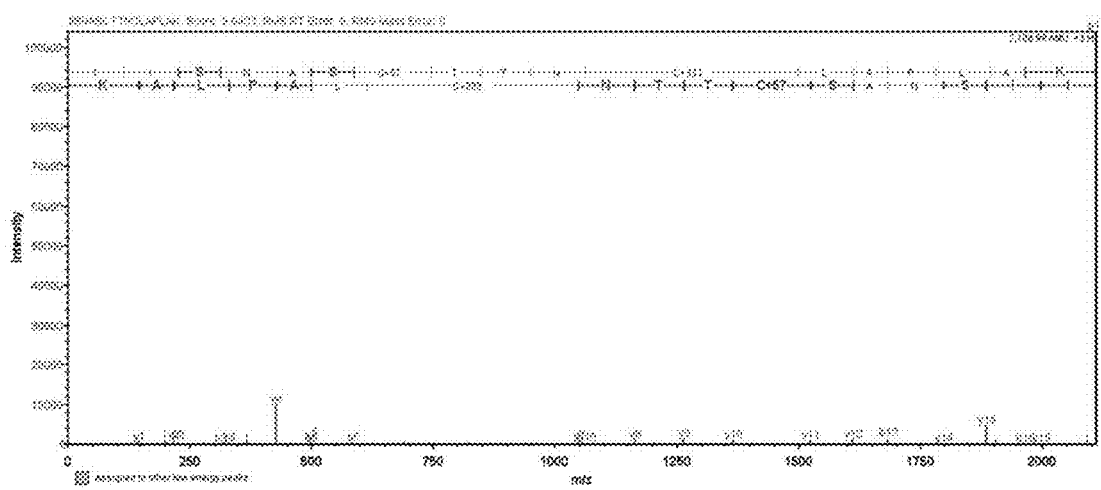

FIG. 16

| Protein Accession | SILAC Directions Quantified ~ | Protein Description | SILAC RATIO (SO : H$_2$OS) (H$_3$O) | # Peptides | Standard Error | Times Detected | Top3 Value |
|---|---|---|---|---|---|---|---|
| P23919 | F & R | Thymidylate kinase | 1000.00 | 23 | 0.00 | 5 | 9679.6 |
| P25685 | F & R | DnaJ homolog subfamily B member 1 | 1000.00 | 22 | 0.00 | 5 | 69749.7 |
| Q99426 | F & R | Tubulin-folding cofactor B | 1000.00 | 20 | 0.00 | 5 | 22474.5 |
| Q9Y2Q3 | F & R | Glutathione S-transferase kappa 1 | 1000.00 | 20 | 0.00 | 5 | 5545.2 |
| P22090 | F & R | 40S ribosomal protein S4 | 1000.00 | 16 | 0.00 | 6 | 0.0 |
| P39019 | F & R | 40S ribosomal protein S19 | 1000.00 | 15 | 0.00 | 4 | 205939.5 |
| Q08257 | F & R | Quinone oxidoreductase | 1000.00 | 15 | 0.00 | 4 | 0.0 |
| Q9Y3B4 | F & R | Pre-mRNA branch site protein p14 | 1000.00 | 14 | 0.00 | 6 | 90383.0 |
| P62244 | F & R | 40S ribosomal protein S15a | 1000.00 | 13 | 0.00 | 5 | 247182.8 |
| Q96C01 | F & R | Protein FAM136A | 1000.00 | 12 | 0.00 | 6 | 66067.5 |
| P63279 | F & R | SUMO-conjugating enzyme UBC9 | 1000.00 | 12 | 0.00 | 3 | 0.0 |
| Q9UHQ9 | F & R | NADH-cytochrome b5 reductase 1 | 1000.00 | 12 | 0.00 | 3 | 0.0 |
| P04080 | F & R | Cystatin-B | 1000.00 | 11 | 0.00 | 4 | 63616.5 |
| P30405 | F & R | Peptidyl-prolyl cis-trans isomerase F, mitochondrial | 1000.00 | 9 | 0.00 | 5 | 93663.8 |
| P61956 | F & R | Small ubiquitin-related modifier 2 | 1000.00 | 9 | 0.00 | 4 | 107013.2 |
| P35914 | F & R | Hydroxymethylglutaryl-CoA lyase, mitochondrial | 1000.00 | 8 | 0.00 | 4 | 0.0 |
| P60981 | F & R | Destrin | 1000.00 | 8 | 0.00 | 4 | 46415.8 |
| P19388 | F & R | DNA-directed RNA polymerases I, II, and III subunit RPABC1 | 1000.00 | 7 | 0.00 | 5 | 0.0 |
| Q9UL46 | F & R | Proteasome activator complex subunit 2 | 1000.00 | 7 | 0.00 | 4 | 46029.6 |
| Q15843 | F & R | NEDD8 | 1000.00 | 7 | 0.00 | 3 | 73965.8 |
| Q96FJ2 | F & R | Dynein light chain 2, cytoplasmic | 1000.00 | 7 | 0.00 | 3 | 0.0 |
| P18077 | F & R | 60S ribosomal protein L35a | 1000.00 | 5 | 0.00 | 5 | 91320.0 |
| Q00526 | F & R | Cyclin-dependent kinase 3 | 1000.00 | 5 | 0.00 | 3 | 0.0 |
| P55854 | F & R | Small ubiquitin-related modifier 3 | 1000.00 | 4 | 0.00 | 4 | 0.0 |
| Q6EEV6 | F & R | Small ubiquitin-related modifier 4 | 1000.00 | 4 | 0.00 | 4 | 0.0 |
| P30050 | F & R | 60S ribosomal protein L12 | 107.53 | 8 | 0.00 | 7 | 453842.8 |
| Q92526 | F & R | T-complex protein 1 subunit zeta-2 | 55.35 | 10 | 0.00 | 8 | 6363.2 |
| Q9Y2J2 | F & R | Band 4.1-like protein 3 | 54.35 | 14 | 0.00 | 8 | 32431.3 |
| P12532 | F & R | Creatine kinase U-type, mitochondrial | 52.91 | 8 | 0.00 | 8 | 50902.0 |
| P48643 | F & R | T-complex protein 1 subunit epsilon | 49.95 | 12 | 0.00 | 8 | 336274.1 |

FIG. 16 (cont'd)

| | | | | | | | |
|---|---|---|---|---|---|---|---|
| P52948 | F & R | Nuclear pore complex protein Nup98-Nup96 | 49.75 | 14 | 0.00 | 8 | 11565.4 |
| P53597 | F & R | Succinyl-CoA ligase [ADP/GDP-forming] subunit alpha, mitochondrial | 47.96 | 6 | 0.00 | 7 | 332458.3 |
| Q99623 | F & R | Prohibitin-2 | 46.95 | 10 | 0.00 | 6 | 144161.2 |
| P25398 | F & R | 40S ribosomal protein S12 | 46.12 | 14 | 0.00 | 8 | 487315.4 |
| P32969 | F & R | 60S ribosomal protein L9 | 45.77 | 6 | 0.00 | 7 | 142051.5 |
| Q9Y277 | F & R | Voltage-dependent anion-selective channel protein 3 | 44.44 | 12 | 0.00 | 7 | 69904.9 |
| O00232 | F & R | 26S proteasome non-ATPase regulatory subunit 12 | 44.25 | 8 | 0.00 | 8 | 41211.6 |
| P24534 | F & R | Elongation factor 1-beta | 43.38 | 6 | 0.00 | 8 | 734476.4 |
| P31040 | F & R | Succinate dehydrogenase [ubiquinone] flavoprotein subunit, mitochondrial | 43.05 | 9 | 0.00 | 8 | 277253.0 |
| P37837 | F & R | Transaldolase | 42.55 | 4 | 0.00 | 8 | 151326.4 |
| P11177 | F & R | Pyruvate dehydrogenase E1 component subunit beta, mitochondrial | 41.58 | 24 | 1.73 | 8 | 128475.0 |
| P43686 | F & R | 26S protease regulatory subunit 6B | 40.16 | 8 | 0.00 | 8 | 220943.6 |
| P17987 | F & R | T-complex protein 1 subunit alpha | 39.62 | 31 | 0.00 | 8 | 407017.8 |
| P13010 | F & R | X-ray repair cross-complementing protein 5 | 39.49 | 69 | 1.87 | 8 | 681350.6 |
| P15531 | F & R | Nucleoside diphosphate kinase A | 39.42 | 20 | 0.47 | 8 | 74780.6 |
| P22392 | F & R | Nucleoside diphosphate kinase B | 39.42 | 8 | 0.00 | 8 | 8640.9 |
| P18754 | F & R | Regulator of chromosome condensation | 38.74 | 32 | 3.15 | 8 | 158947.4 |
| P40227 | F & R | T-complex protein 1 subunit zeta | 38.35 | 100 | 1.62 | 8 | 510533.5 |
| P46782 | F & R | 40S ribosomal protein S5 | 38.31 | 4 | 0.00 | 8 | 285861.0 |
| O76021 | F & R | Ribosomal L1 domain-containing protein 1 | 37.95 | 6 | 0.00 | 8 | 158260.5 |
| O43776 | F & R | Asparagine--tRNA ligase, cytoplasmic | 37.74 | 6 | 0.00 | 8 | 109517.8 |
| O60361 | F & R | Putative nucleoside diphosphate kinase | 37.31 | 4 | 0.00 | 6 | 11756.9 |
| Q96AE4 | F & R | Far upstream element-binding protein 1 | 37.07 | 20 | 0.00 | 8 | 159148.0 |
| P07355 | F & R | Annexin A2 | 36.90 | 8 | 0.00 | 8 | 21679.0 |
| P38159 | F & R | RNA-binding motif protein, X chromosome | 36.63 | 24 | 0.00 | 8 | 79620.9 |
| P46777 | F & R | 60S ribosomal protein L5 | 36.36 | 24 | 1.32 | 8 | 332370.3 |
| P61604 | F & R | 10 kDa heat shock protein, mitochondrial | 35.95 | 11 | 3.10 | 8 | 246231.0 |
| P42704 | F & R | Leucine-rich PPR motif-containing protein, mitochondrial | 35.89 | 29 | 2.06 | 8 | 304909.3 |
| P62241 | F & R | 40S ribosomal protein S8 | 35.36 | 16 | 5.87 | 8 | 327514.5 |

FIG. 16 (cont'd)

| | | | | | | | |
|---|---|---|---|---|---|---|---|
| P39687 | F & R | Acidic leucine-rich nuclear phosphoprotein 32 family member A | 34.58 | 14 | 6.34 | 8 | 319565.6 |
| O43143 | F & R | Putative pre-mRNA-splicing factor ATP-dependent RNA helicase DHX15 | 34.48 | 6 | 0.00 | 8 | 61516.8 |
| Q07065 | F & R | Cytoskeleton-associated protein 4 | 34.01 | 8 | 0.00 | 8 | 117546.3 |
| P62847 | F & R | 40S ribosomal protein S24 | 33.90 | 24 | 0.00 | 7 | 111382.3 |
| P07954 | F & R | Fumarate hydratase, mitochondrial | 33.90 | 12 | 0.00 | 7 | 95793.5 |
| P22234 | F & R | Multifunctional protein ADE2 | 33.85 | 54 | 0.00 | 8 | 182582.0 |
| Q13838 | F & R | Spliceosome RNA helicase DDX39B | 33.64 | 90 | 1.25 | 8 | 284444.4 |
| P30084 | F & R | Enoyl-CoA hydratase, mitochondrial | 33.32 | 24 | 0.00 | 8 | 317658.5 |
| Q9UMS4 | F & R | Pre-mRNA-processing factor 19 | 33.20 | 10 | 0.00 | 8 | 387332.8 |
| Q1KMD3 | F & R | Heterogeneous nuclear ribonucleoprotein U-like protein 2 | 33.17 | 6 | 0.00 | 8 | 185112.6 |
| P30048 | F & R | Thioredoxin-dependent peroxide reductase, mitochondrial | 32.72 | 16 | 2.78 | 8 | 333580.9 |
| O00148 | F & R | ATP-dependent RNA helicase DDX39A | 32.62 | 23 | 2.02 | 8 | 256300.2 |
| Q15046 | F & R | Lysine--tRNA ligase | 32.57 | 6 | 0.00 | 8 | 65377.7 |
| P06744 | F & R | Glucose-6-phosphate isomerase | 32.36 | 76 | 1.68 | 8 | 237296.2 |
| P83916 | F & R | Chromobox protein homolog 1 | 32.21 | 10 | 0.00 | 8 | 259186.6 |
| P50395 | F & R | Rab GDP dissociation inhibitor beta | 32.13 | 28 | 0.00 | 8 | 117304.6 |
| P40939 | F & R | Trifunctional enzyme subunit alpha, mitochondrial | 32.11 | 36 | 1.76 | 8 | 429478.2 |
| P61247 | F & R | 40S ribosomal protein S3a | 31.95 | 6 | 0.00 | 8 | 185211.0 |
| Q5JTV8 | F & R | Torsin-1A-interacting protein 1 | 31.75 | 4 | 0.00 | 4 | 37626.0 |
| P43243 | F & R | Matrin-3 | 31.40 | 53 | 1.78 | 8 | 161497.6 |
| P09429 | F & R | High mobility group protein B1 | 30.94 | 18 | 8.14 | 7 | 105228.4 |
| P55769 | F & R | NHP2-like protein 1 | 30.77 | 6 | 0.00 | 4 | 287614.3 |
| P26599 | F & R | Polypyrimidine tract-binding protein 1 | 30.60 | 228 | 1.22 | 8 | 157688.6 |
| P63244 | F & R | Guanine nucleotide-binding protein subunit beta-2-like 1 | 30.52 | 20 | 4.56 | 8 | 328092.8 |
| Q16836 | F & R | Hydroxyacyl-coenzyme A dehydrogenase, mitochondrial | 30.49 | 8 | 0.00 | 6 | 9978.1 |
| Q9Y3I0 | F & R | tRNA-splicing ligase RtcB homolog | 30.37 | 18 | 0.00 | 8 | 411497.8 |
| Q9UQE7 | F & R | Structural maintenance of chromosomes protein 3 | 30.33 | 8 | 0.00 | 8 | 188331.4 |
| P50990 | F & R | T-complex protein 1 subunit theta | 30.32 | 23 | 1.38 | 8 | 403626.9 |
| P46778 | F & R | 60S ribosomal protein L21 | 29.76 | 6 | 0.00 | 7 | 286488.8 |
| Q8WXX5 | F & R | DnaJ homolog subfamily C member 9 | 29.76 | 4 | 0.00 | 7 | 111483.6 |
| P78371 | F & R | T-complex protein 1 subunit beta | 29.74 | 90 | 1.59 | 8 | 252159.6 |

FIG. 16 (cont'd)

| | | | | | | | |
|---|---|---|---|---|---|---|---|
| O14818 | F & R | Proteasome subunit alpha type-7 | 29.72 | 28 | 1.76 | 8 | 142743.9 |
| P26641 | F & R | Elongation factor 1-gamma | 29.71 | 38 | 1.50 | 8 | 510450.9 |
| P63241 | F & R | Eukaryotic translation initiation factor 5A-1 | 29.71 | 36 | 1.85 | 8 | 278270.8 |
| P36776 | F & R | Lon protease homolog, mitochondrial | 29.70 | 10 | 3.44 | 8 | 119383.3 |
| Q9P258 | F & R | Protein RCC2 | 29.46 | 19 | | 8 | 280571.9 |
| P10599 | F & R | Thioredoxin | 29.46 | 16 | 0.61 | 8 | 194772.6 |
| P50991 | F & R | T-complex protein 1 subunit delta | 29.44 | 80 | 0.95 | 8 | 184038.9 |
| P06576 | F & R | ATP synthase subunit beta, mitochondrial | 29.30 | 57 | 1.98 | 8 | 710018.1 |
| O95758 | F & R | Polypyrimidine tract-binding protein 3 | 29.20 | 36 | 0.00 | 4 | 0.0 |
| Q14974 | F & R | Importin subunit beta-1 | 29.16 | 4 | 0.00 | 8 | 262272.6 |
| P20700 | F & R | Lamin-B1 | 28.99 | 38 | 1.51 | 8 | 495772.6 |
| Q13283 | F & R | Ras GTPase-activating protein-binding protein 1 | 28.93 | 5 | 0.00 | 6 | 281735.4 |
| P41252 | F & R | Isoleucine--tRNA ligase, cytoplasmic | 28.72 | 54 | 0.00 | 8 | 364962.0 |
| Q9Y265 | F & R | RuvB-like 1 | 28.57 | 84 | 1.39 | 8 | 194716.6 |
| P99999 | F & R | Cytochrome c | 28.57 | 10 | 0.00 | 8 | 332430.2 |
| P05455 | F & R | Lupus La protein | 28.57 | 32 | 1.88 | 8 | 382152.2 |
| P53618 | F & R | Coatomer subunit beta | 28.41 | 4 | 0.00 | 8 | 33389.1 |
| Q9HC35 | F & R | Echinoderm microtubule-associated protein-like 4 | 28.17 | 4 | 0.00 | 8 | 140932.6 |
| Q04760 | F & R | Lactoylglutathione lyase | 27.89 | 24 | 2.33 | 5 | 167047.1 |
| P05023 | F & R | Sodium/potassium-transporting ATPase subunit alpha-1 | 27.75 | 66 | 0.00 | 8 | 159045.1 |
| P39023 | F & R | 60S ribosomal protein L3 | 27.74 | 12 | 2.23 | 8 | 487443.3 |
| Q9NZI8 | F & R | Insulin-like growth factor 2 mRNA-binding protein 1 | 27.64 | 100 | 0.76 | 8 | 250130.0 |
| Q7L014 | F & R | Probable ATP-dependent RNA helicase DDX46 | 27.44 | 6 | 0.00 | 8 | 139537.1 |
| P30041 | F & R | Peroxiredoxin-6 | 27.39 | 18 | 0.00 | 8 | 343097.9 |
| Q07021 | F & R | Complement component 1 Q subcomponent-binding protein, mitochondrial | 27.29 | 40 | 1.78 | 8 | 826465.3 |
| P08670 | F & R | Vimentin | 27.27 | 35 | 2.16 | 8 | 543882.9 |
| Q6IS14 | F & R | Eukaryotic translation initiation factor 5A-1-like | 27.23 | 16 | 2.15 | 8 | 0.0 |
| P61978 | F & R | Heterogeneous nuclear ribonucleoprotein K | 27.19 | 93 | 1.11 | 8 | 188149.5 |
| Q13423 | F & R | NAD(P) transhydrogenase, mitochondrial | 27.10 | 5 | 0.00 | 8 | 85989.5 |
| P13804 | F & R | Electron transfer flavoprotein subunit alpha, mitochondrial | 27.00 | 18 | 2.41 | 8 | 184845.0 |
| P15121 | F & R | Aldose reductase | 26.99 | 24 | 1.02 | 8 | 228176.5 |

FIG. 16 (cont'd)

| | | | | | | | |
|---|---|---|---|---|---|---|---|
| O75390 | F & R | Citrate synthase, mitochondrial | 26.98 | 16 | 0.00 | 8 | 318886.5 |
| Q15185 | F & R | Prostaglandin E synthase 3 | 26.95 | 6 | 0.00 | 5 | 191129.3 |
| Q13185 | F & R | Chromobox protein homolog 3 | 26.81 | 14 | 0.00 | 8 | 368542.5 |
| P78527 | F & R | DNA-dependent protein kinase catalytic subunit | 26.80 | 134 | 2.08 | 8 | 111532.7 |
| P53396 | F & R | ATP-citrate synthase | 26.74 | 10 | 0.00 | 8 | 28204.5 |
| P15880 | F & R | 40S ribosomal protein S2 | 26.74 | 6 | 0.00 | 8 | 323319.0 |
| Q9UQ80 | F & R | Proliferation-associated protein 2G4 | 26.59 | 48 | 1.63 | 8 | 355385.1 |
| P55795 | F & R | Heterogeneous nuclear ribonucleoprotein H2 | 26.52 | 18 | 1.69 | 8 | 88030.4 |
| P51991 | F & R | Heterogeneous nuclear ribonucleoprotein A3 | 26.51 | 46 | 0.63 | 8 | 248894.8 |
| P27797 | F & R | Calreticulin | 26.39 | 28 | 5.22 | 8 | 598576.6 |
| P62701 | F & R | 40S ribosomal protein S4, X isoform | 26.29 | 20 | 0.00 | 8 | 256997.4 |
| P62424 | F & R | 60S ribosomal protein L7a | 26.28 | 14 | 7.38 | 7 | 179095.8 |
| O75369 | F & R | Filamin-B | 26.18 | 204 | 0.00 | 8 | 19264.8 |
| P41219 | F & R | Peripherin | 26.02 | 16 | 0.00 | 8 | 0.0 |
| Q9UHD1 | F & R | Cysteine and histidine-rich domain-containing protein 1 | 26.01 | 26 | 0.00 | 8 | 124698.9 |
| Q08945 | F & R | FACT complex subunit SSRP1 | 25.58 | 19 | 1.64 | 8 | 237266.9 |
| P14866 | F & R | Heterogeneous nuclear ribonucleoprotein L | 25.34 | 150 | 1.09 | 8 | 427055.6 |
| P49411 | F & R | Elongation factor Tu, mitochondrial | 25.32 | 56 | 1.54 | 8 | 496801.6 |
| Q9P2J5 | F & R | Leucine--tRNA ligase, cytoplasmic | 25.22 | 34 | 0.00 | 8 | 352493.5 |
| P38919 | F & R | Eukaryotic initiation factor 4A-III | 25.19 | 11 | 0.63 | 8 | 88626.5 |
| Q99798 | F & R | Aconitate hydratase, mitochondrial | 25.13 | 49 | 1.07 | 8 | 367201.7 |
| P00558 | F & R | Phosphoglycerate kinase 1 | 25.11 | 73 | 2.34 | 8 | 639951.0 |
| P17844 | F & R | Probable ATP-dependent RNA helicase DDX5 | 25.00 | 6 | 0.00 | 8 | 97277.5 |
| P55060 | F & R | Exportin-2 | 24.60 | 20 | 0.00 | 8 | 131511.8 |
| A6NHL2 | F & R | Tubulin alpha chain-like 3 | 24.47 | 20 | 0.72 | 7 | 0.0 |
| P41250 | F & R | Glycine--tRNA ligase | 24.46 | 11 | 0.00 | 8 | 163329.2 |
| O76094 | F & R | Signal recognition particle subunit SRP72 | 24.45 | 24 | 2.81 | 8 | 70842.8 |
| P26639 | F & R | Threonine--tRNA ligase, cytoplasmic | 24.29 | 52 | 1.06 | 8 | 123583.5 |
| P31948 | F & R | Stress-induced-phosphoprotein 1 | 24.22 | 52 | 1.29 | 8 | 654334.8 |
| P07237 | F & R | Protein disulfide-isomerase | 24.11 | 25 | 1.57 | 8 | 215581.8 |
| P56192 | F & R | Methionine--tRNA ligase, cytoplasmic | 24.10 | 5 | 1.24 | 8 | 150118.7 |
| P03243 | F & R | E1B protein, large T-antigen | 24.04 | 54 | 1.45 | 8 | 442696.2 |
| P23246 | F & R | Splicing factor, proline- and glutamine-rich | 23.74 | 124 | 0.85 | 8 | 315609.7 |
| P53675 | F & R | Clathrin heavy chain 2 | 23.64 | 8 | 0.00 | 8 | 0.0 |
| P26583 | F & R | High mobility group protein B2 | 23.52 | 14 | 3.15 | 8 | 310988.7 |

FIG. 16 (cont'd)

| | | | | | | | |
|---|---|---|---|---|---|---|---|
| Q12906 | F & R | Interleukin enhancer-binding factor 3 | 23.50 | 316 | 0.39 | 8 | 75520.7 |
| O60506 | F & R | Heterogeneous nuclear ribonucleoprotein Q | 23.41 | 266 | 0.38 | 8 | 90132.0 |
| P61204 | F & R | ADP-ribosylation factor 3 | 23.24 | 14 | 0.00 | 8 | 0.0 |
| P84077 | F & R | ADP-ribosylation factor 1 | 23.24 | 14 | 0.00 | 8 | 169385.9 |
| P03244 | F & R | E1B 55 kDa protein | 23.16 | 44 | 1.34 | 8 | 205845.8 |
| P09622 | F & R | Dihydrolipoyl dehydrogenase, mitochondrial | 23.04 | 6 | 0.00 | 6 | 195970.6 |
| P07814 | F & R | Bifunctional glutamate/proline--tRNA ligase | 23.03 | 64 | 4.72 | 8 | 341214.5 |
| O14979 | F & R | Heterogeneous nuclear ribonucleoprotein D-like | 23.03 | 60 | 0.00 | 8 | 117321.3 |
| P52597 | F & R | Heterogeneous nuclear ribonucleoprotein F | 22.77 | 24 | 1.19 | 8 | 278383.5 |
| Q14257 | F & R | Reticulocalbin-2 | 22.76 | 16 | 2.28 | 8 | 368211.9 |
| Q6P2Q9 | F & R | Pre-mRNA-processing-splicing factor 8 | 22.76 | 22 | 1.81 | 8 | 112000.3 |
| Q00688 | F & R | Peptidyl-prolyl cis-trans isomerase FKBP3 | 22.70 | 13 | 1.29 | 8 | 448645.6 |
| Q15393 | F & R | Splicing factor 3B subunit 3 | 22.61 | 12 | 0.00 | 8 | 89743.1 |
| P05141 | F & R | ADP/ATP translocase 2 | 22.44 | 31 | 2.97 | 8 | 277247.1 |
| Q99832 | F & R | T-complex protein 1 subunit eta | 22.41 | 68 | 0.00 | 8 | 203029.9 |
| P62081 | F & R | 40S ribosomal protein S7 | 22.32 | 3 | 1.34 | 7 | 347765.7 |
| Q00839 | F & R | Heterogeneous nuclear ribonucleoprotein U | 22.31 | 144 | 1.05 | 8 | 381081.2 |
| P11940 | F & R | Polyadenylate-binding protein 1 | 22.19 | 14 | 4.53 | 8 | 34427.7 |
| Q07666 | F & R | KH domain-containing, RNA-binding, signal transduction-associated protein 1 | 22.19 | 26 | 0.00 | 8 | 209558.2 |
| O43707 | F & R | Alpha-actinin-4 | 22.15 | 62 | 1.33 | 8 | 387256.7 |
| P10809 | F & R | 60 kDa heat shock protein, mitochondrial | 22.10 | 170 | 1.08 | 8 | 1233092.6 |
| P13929 | F & R | Beta-enolase | 22.08 | 96 | 1.32 | 8 | 60880.5 |
| Q13162 | F & R | Peroxiredoxin-4 | 21.94 | 17 | 1.06 | 8 | 302684.5 |
| P18124 | F & R | 60S ribosomal protein L7 | 21.93 | 10 | 2.36 | 7 | 109397.7 |
| P27695 | F & R | DNA-(apurinic or apyrimidinic site) lyase | 21.87 | 10 | 0.00 | 8 | 223970.9 |
| P60842 | F & R | Eukaryotic initiation factor 4A-I | 21.82 | 34 | 1.62 | 8 | 97367.7 |
| P11171 | F & R | Protein 4.1 | 21.79 | 22 | 0.00 | 8 | 46830.2 |
| Q99460 | F & R | 26S proteasome non-ATPase regulatory subunit 1 | 21.73 | 28 | 0.00 | 8 | 93678.9 |
| P42167 | F & R | Lamina-associated polypeptide 2, isoforms beta/gamma | 21.72 | 62 | 1.23 | 8 | 177444.1 |
| P42166 | F & R | Lamina-associated polypeptide 2, isoform alpha | 21.71 | 32 | 2.21 | 8 | 187696.5 |

FIG. 16 (cont'd)

| | | | | | | | |
|---|---|---|---|---|---|---|---|
| P40925 | F & R | Malate dehydrogenase, cytoplasmic | 21.64 | 69 | 1.22 | 8 | 152817.2 |
| P27824 | F & R | Calnexin | 21.53 | 28 | 1.57 | 8 | 339747.7 |
| P13637 | F & R | Sodium/potassium-transporting ATPase subunit alpha-3 | 21.44 | 6 | 0.00 | 8 | 0.0 |
| P50993 | F & R | Sodium/potassium-transporting ATPase subunit alpha-2 | 21.44 | 6 | 0.00 | 8 | 201986.5 |
| Q02878 | F & R | 60S ribosomal protein L6 | 21.38 | 22 | 2.56 | 8 | 179290.1 |
| P00492 | F & R | Hypoxanthine-guanine phosphoribosyltransferase | 21.38 | 10 | 0.00 | 8 | 162222.2 |
| Q00610 | F & R | Clathrin heavy chain 1 | 21.28 | 72 | 4.39 | 8 | 170410.7 |
| Q9NYF8 | F & R | Bcl-2-associated transcription factor 1 | 21.27 | 92 | 1.58 | 8 | 74115.8 |
| P12956 | F & R | X-ray repair cross-complementing protein 6 | 21.18 | 73 | 1.35 | 8 | 519049.6 |
| P09104 | F & R | Gamma-enolase | 20.94 | 26 | 2.15 | 8 | 238063.6 |
| O43660 | F & R | Pleiotropic regulator 1 | 20.62 | 8 | 0.00 | 6 | 38530.5 |
| P62826 | F & R | GTP-binding nuclear protein Ran | 20.55 | 18 | 0.00 | 8 | 499080.1 |
| O00567 | F & R | Nucleolar protein 56 | 20.40 | 9 | 0.00 | 8 | 190807.5 |
| Q14697 | F & R | Neutral alpha-glucosidase AB | 20.39 | 48 | 0.00 | 8 | 134751.6 |
| Q9Y2L1 | F & R | Exosome complex exonuclease RRP44 | 20.16 | 14 | 0.00 | 8 | 91708.4 |
| Q06830 | F & R | Peroxiredoxin-1 | 20.04 | 39 | 1.65 | 8 | 632437.6 |
| P43487 | F & R | Ran-specific GTPase-activating protein | 20.04 | 10 | 0.56 | 8 | 485792.8 |
| P62995 | F & R | Transformer-2 protein homolog beta | 19.85 | 28 | 0.32 | 8 | 162427.4 |
| Q6PEY2 | F & R | Tubulin alpha-3E chain | 19.84 | 108 | 0.95 | 8 | 55364.4 |
| P22314 | F & R | Ubiquitin-like modifier-activating enzyme 1 | 19.78 | 69 | 0.86 | 8 | 669519.9 |
| Q58FF7 | F & R | Putative heat shock protein HSP 90-beta-3 | 19.74 | 16 | 2.53 | 8 | 0.0 |
| P12277 | F & R | Creatine kinase B-type | 19.70 | 90 | 1.09 | 8 | 804091.8 |
| P07737 | F & R | Profilin-1 | 19.69 | 38 | 1.36 | 8 | 393427.1 |
| Q08043 | F & R | Alpha-actinin-3 | 19.63 | 16 | 1.89 | 8 | 0.0 |
| P13667 | F & R | Protein disulfide-isomerase A4 | 19.53 | 35 | 0.00 | 8 | 331324.7 |
| Q8NC51 | F & R | Plasminogen activator inhibitor 1 RNA-binding protein | 19.41 | 88 | 0.00 | 8 | 161767.5 |
| P60709 | F & R | Actin, cytoplasmic 1 | 19.34 | 126 | 0.94 | 8 | 863263.8 |
| P63261 | F & R | Actin, cytoplasmic 2 | 19.34 | 126 | 0.94 | 8 | 56143.4 |
| P14618 | F & R | Pyruvate kinase PKM | 19.23 | 320 | 0.44 | 8 | 378555.9 |
| P31943 | F & R | Heterogeneous nuclear ribonucleoprotein H | 18.96 | 54 | 0.68 | 8 | 591420.7 |
| Q13748 | F & R | Tubulin alpha-3C/D chain | 18.96 | 220 | 0.68 | 8 | 104392.2 |
| Q14498 | F & R | RNA-binding protein 39 | 18.90 | 36 | 0.00 | 8 | 77385.0 |
| P36578 | F & R | 60S ribosomal protein L4 | 18.79 | 40 | 1.66 | 8 | 356685.0 |

FIG. 16 (cont'd)

| | | | | | | | |
|---|---|---|---|---|---|---|---|
| Q9NTJ3 | F & R | Structural maintenance of chromosomes protein 4 | 18.73 | 12 | 0.00 | 8 | 69339.5 |
| P04350 | F & R | Tubulin beta-4A chain | 18.70 | 30 | 1.68 | 8 | 42534.4 |
| O43390 | F & R | Heterogeneous nuclear ribonucleoprotein R | 18.42 | 112 | 0.95 | 8 | 271775.9 |
| Q13151 | F & R | Heterogeneous nuclear ribonucleoprotein A0 | 18.41 | 18 | 1.15 | 8 | 479245.3 |
| Q5VTE0 | F & R | Putative elongation factor 1-alpha-like 3 | 18.36 | 103 | 1.28 | 8 | 0.0 |
| P68104 | F & R | Elongation factor 1-alpha 1 | 18.36 | 103 | 1.28 | 8 | 862411.6 |
| O00571 | F & R | ATP-dependent RNA helicase DDX3X | 18.30 | 34 | 0.50 | 8 | 32553.3 |
| O15523 | F & R | ATP-dependent RNA helicase DDX3Y | 18.30 | 15 | 0.00 | 8 | 9968.1 |
| P62753 | F & R | 40S ribosomal protein S6 | 18.28 | 12 | 0.74 | 7 | 399934.0 |
| Q14103 | F & R | Heterogeneous nuclear ribonucleoprotein D0 | 18.09 | 144 | 0.72 | 8 | 174855.1 |
| P68371 | F & R | Tubulin beta-4B chain | 17.99 | 52 | 1.84 | 8 | 312685.3 |
| Q9GZL7 | F & R | Ribosome biogenesis protein WDR12 | 17.95 | 4 | 0.00 | 8 | 58971.9 |
| P54819 | F & R | Adenylate kinase 2, mitochondrial | 17.61 | 134 | 0.00 | 8 | 54378.3 |
| P35609 | F & R | Alpha-actinin-2 | 17.53 | 20 | 1.38 | 8 | 3867.8 |
| Q14247 | F & R | Src substrate cortactin | 17.40 | 48 | 0.00 | 8 | 174213.7 |
| P68366 | F & R | Tubulin alpha-4A chain | 17.26 | 82 | 0.95 | 8 | 4746.0 |
| P07195 | F & R | L-lactate dehydrogenase B chain | 17.24 | 73 | 1.25 | 8 | 682167.0 |
| P13639 | F & R | Elongation factor 2 | 17.23 | 93 | 1.58 | 8 | 599956.8 |
| Q9BVA1 | F & R | Tubulin beta-2B chain | 17.16 | 46 | 1.30 | 8 | 47133.2 |
| Q01105 | F & R | Protein SET | 17.11 | 126 | 0.59 | 8 | 284922.9 |
| Q99729 | F & R | Heterogeneous nuclear ribonucleoprotein A/B | 17.07 | 120 | 0.76 | 8 | 144794.7 |
| P13797 | F & R | Plastin-3 | 17.04 | 14 | 9.03 | 8 | 213812.5 |
| Q5JRX3 | F & R | Presequence protease, mitochondrial | 17.04 | 12 | 0.00 | 8 | 14830.0 |
| Q15366 | F & R | Poly(rC)-binding protein 2 | 16.99 | 100 | 0.72 | 8 | 47689.8 |
| P04406 | F & R | Glyceraldehyde-3-phosphate dehydrogenase | 16.96 | 96 | 0.92 | 8 | 1381156.7 |
| Q562R1 | F & R | Beta-actin-like protein 2 | 16.82 | 34 | 1.95 | 8 | 0.0 |
| P68032 | F & R | Actin, alpha cardiac muscle 1 | 16.62 | 56 | 1.27 | 8 | 0.0 |
| P62736 | F & R | Actin, aortic smooth muscle | 16.62 | 54 | 1.27 | 8 | 366.3 |
| Q9NY65 | F & R | Tubulin alpha-8 chain | 16.59 | 132 | 0.74 | 8 | 0.0 |
| Q58FG1 | F & R | Putative heat shock protein HSP 90-alpha A4 | 16.52 | 18 | 0.96 | 8 | 0.0 |
| Q05639 | F & R | Elongation factor 1-alpha 2 | 16.48 | 69 | 1.20 | 8 | 97902.8 |
| P63267 | F & R | Actin, gamma-enteric smooth muscle | 16.48 | 92 | 0.95 | 8 | 430886.9 |
| Q13509 | F & R | Tubulin beta-3 chain | 16.46 | 38 | 1.30 | 8 | 119819.0 |
| P61353 | F & R | 60S ribosomal protein L27 | 16.41 | 6 | 0.00 | 6 | 177736.0 |

FIG. 16 (cont'd)

| | | | | | | | |
|---|---|---|---|---|---|---|---|
| Q92841 | F & R | Probable ATP-dependent RNA helicase DDX17 | 16.37 | 150 | 0.35 | 8 | 87835.8 |
| P25705 | F & R | ATP synthase subunit alpha, mitochondrial | 16.37 | 64 | 2.41 | 8 | 263868.1 |
| P09874 | F & R | Poly [ADP-ribose] polymerase 1 | 16.36 | 154 | 0.64 | 8 | 948426.9 |
| Q15365 | F & R | Poly(rC)-binding protein 1 | 16.33 | 32 | 1.25 | 8 | 347636.3 |
| P08107 | F & R | Heat shock 70 kDa protein 1A/1B | 16.31 | 150 | 0.83 | 8 | 275431.6 |
| Q13885 | F & R | Tubulin beta-2A chain | 16.31 | 42 | 1.28 | 8 | 196596.1 |
| B2RPK0 | F & R | Putative high mobility group protein B1-like 1 | 16.31 | 8 | 2.34 | 7 | 179602.3 |
| Q6S8J3 | F & R | POTE ankyrin domain family member E | 16.15 | 44 | 1.72 | 8 | 47525.4 |
| P57721 | F & R | Poly(rC)-binding protein 3 | 16.14 | 60 | 0.91 | 6 | 0.0 |
| P52272 | F & R | Heterogeneous nuclear ribonucleoprotein M | 16.10 | 134 | 1.81 | 8 | 203756.0 |
| P22626 | F & R | Heterogeneous nuclear ribonucleoproteins A2/B1 | 16.04 | 178 | 0.64 | 8 | 342445.4 |
| P00338 | F & R | L-lactate dehydrogenase A chain | 15.99 | 193 | 0.49 | 8 | 118900.2 |
| P60174 | F & R | Triosephosphate isomerase | 15.96 | 134 | 0.79 | 8 | 286432.4 |
| P08238 | F & R | Heat shock protein HSP 90-beta | 15.70 | 122 | 0.91 | 8 | 844884.1 |
| P54577 | F & R | Tyrosine--tRNA ligase, cytoplasmic | 15.63 | 48 | 1.15 | 8 | 422569.4 |
| P04075 | F & R | Fructose-bisphosphate aldolase A | 15.61 | 38 | 1.00 | 8 | 638304.5 |
| P63104 | F & R | 14-3-3 protein zeta/delta | 15.57 | 52 | 0.99 | 8 | 552340.2 |
| P19338 | F & R | Nucleolin | 15.40 | 103 | 1.00 | 8 | 887612.5 |
| P53999 | F & R | Activated RNA polymerase II transcriptional coactivator p15 | 15.34 | 4 | 0.00 | 6 | 94199.0 |
| Q58FF6 | F & R | Putative heat shock protein HSP 90-beta 4 | 15.23 | 10 | 0.00 | 8 | 0.0 |
| P68363 | F & R | Tubulin alpha-1B chain | 15.18 | 152 | 0.85 | 8 | 11503.3 |
| Q02790 | F & R | Peptidyl-prolyl cis-trans isomerase FKBP4 | 15.14 | 26 | 4.54 | 8 | 373971.0 |
| Q71U36 | F & R | Tubulin alpha-1A chain | 15.09 | 150 | 0.89 | 8 | 1146962.8 |
| Q08211 | F & R | ATP-dependent RNA helicase A | 14.87 | 102 | 4.88 | 8 | 377078.6 |
| Q9Y536 | F & R | Peptidyl-prolyl cis-trans isomerase A-like 4A/B/C | 14.82 | 12 | 0.00 | 8 | 0.0 |
| P40429 | F & R | 60S ribosomal protein L13a | 14.70 | 12 | 0.26 | 7 | 20717.1 |
| Q6NVV1 | F & R | Putative 60S ribosomal protein L13a-like MGC87657 | 14.70 | 12 | 0.26 | 7 | 412753.5 |
| Q08170 | F & R | Serine/arginine-rich splicing factor 4 | 14.64 | 14 | 1.22 | 8 | 55803.6 |
| Q15233 | F & R | Non-POU domain-containing octamer-binding protein | 14.59 | 22 | 0.09 | 8 | 167741.9 |
| P06748 | F & R | Nucleophosmin | 14.46 | 148 | 1.17 | 8 | 272666.0 |
| Q9BQE3 | F & R | Tubulin alpha-1C chain | 14.38 | 130 | 0.87 | 8 | 660524.1 |

FIG. 16 (cont'd)

| | | | | | | | |
|---|---|---|---|---|---|---|---|
| P07900 | F & R | Heat shock protein HSP 90-alpha | 13.68 | 272 | 0.39 | 8 | 358835.9 |
| P34931 | F & R | Heat shock 70 kDa protein 1-like | 13.61 | 47 | 1.24 | 8 | 86163.3 |
| Q01130 | F & R | Serine/arginine-rich splicing factor 2 | 13.52 | 9 | 0.00 | 8 | 108786.2 |
| P62937 | F & R | Peptidyl-prolyl cis-trans isomerase A | 13.43 | 64 | 0.94 | 8 | 653908.1 |
| Q15287 | F & R | RNA-binding protein with serine-rich domain 1 | 13.37 | 36 | 1.18 | 8 | 104692.3 |
| P06733 | F & R | Alpha-enolase | 13.16 | 292 | 1.07 | 8 | 650301.7 |
| P23528 | F & R | Cofilin-1 | 13.12 | 37 | 4.05 | 8 | 688314.5 |
| P46776 | F & R | 60S ribosomal protein L27a | 13.03 | 15 | 0.17 | 8 | 397424.9 |
| P38646 | F & R | Stress-70 protein, mitochondrial | 12.90 | 61 | 2.83 | 8 | 645420.3 |
| P49591 | F & R | Serine--tRNA ligase, cytoplasmic | 12.51 | 13 | 0.00 | 8 | 271361.5 |
| P0CG38 | F & R | POTE ankyrin domain family member I | 11.67 | 8 | 0.76 | 8 | 173131.0 |
| P0CG39 | F & R | POTE ankyrin domain family member J | 11.67 | 8 | 0.76 | 8 | 0.0 |
| Q32P51 | F & R | Heterogeneous nuclear ribonucleoprotein A1-like 2 | 11.64 | 60 | 1.82 | 8 | 64713.1 |
| P09651 | F & R | Heterogeneous nuclear ribonucleoprotein A1 | 11.59 | 234 | 0.86 | 8 | 267197.6 |
| Q58FF8 | F & R | Putative heat shock protein HSP 90-beta 2 | 11.31 | 28 | 0.46 | 8 | 0.0 |
| P17066 | F & R | Heat shock 70 kDa protein 6 | 11.04 | 32 | 0.82 | 8 | 0.0 |
| P07437 | F & R | Tubulin beta chain | 11.03 | 70 | 2.74 | 8 | 720238.8 |
| P11021 | F & R | 78 kDa glucose-regulated protein | 11.00 | 89 | 1.73 | 8 | 493882.5 |
| Q9Y281 | F & R | Cofilin-2 | 10.96 | 18 | 1.15 | 8 | 486860.6 |
| Q9Y617 | F & R | Phosphoserine aminotransferase | 10.85 | 70 | 2.17 | 8 | 196697.6 |
| Q8WUM4 | F & R | Programmed cell death 6-interacting protein | 10.85 | 8 | 0.00 | 8 | 77595.7 |
| O43175 | F & R | D-3-phosphoglycerate dehydrogenase | 10.76 | 70 | 1.53 | 8 | 494025.1 |
| P48741 | F & R | Putative heat shock 70 kDa protein 7 | 10.57 | 18 | 0.00 | 8 | 79603.7 |
| A5A3E0 | F & R | POTE ankyrin domain family member F | 10.48 | 22 | 0.31 | 8 | 0.0 |
| P61313 | F & R | 60S ribosomal protein L15 | 10.33 | 28 | 0.60 | 8 | 259891.7 |
| Q07020 | F & R | 60S ribosomal protein L18 | 10.33 | 11 | 0.00 | 7 | 210955.3 |
| P07864 | F & R | L-lactate dehydrogenase C chain | 10.23 | 9 | 0.03 | 7 | 0.0 |
| P54652 | F & R | Heat shock-related 70 kDa protein 2 | 10.21 | 61 | 0.46 | 8 | 0.0 |
| P30101 | F & R | Protein disulfide-isomerase A3 | 10.19 | 46 | 2.88 | 8 | 510283.3 |
| Q14568 | F & R | Putative heat shock protein HSP 90-alpha A2 | 10.02 | 20 | 0.19 | 8 | 0.0 |
| Q9BYX7 | F & R | Putative beta-actin-like protein 3 | 9.97 | 18 | 0.11 | 8 | 58244.6 |
| Q16576 | F & R | Histone-binding protein RBBP7 | 9.73 | 28 | 0.00 | 8 | 18807.3 |
| P14625 | F & R | Endoplasmin | 9.57 | 41 | 2.23 | 8 | 272594.5 |

FIG. 16 (cont'd)

| | | | | | | | |
|---|---|---|---|---|---|---|---|
| Q09028 | F & R | Histone-binding protein RBBP4 | 9.50 | 75 | 0.49 | 8 | 79313.5 |
| P16152 | F & R | Carbonyl reductase [NADPH] 1 | 9.23 | 14 | 4.36 | 8 | 165216.5 |
| Q58FG0 | F & R | Putative heat shock protein HSP 90-alpha A5 | 9.22 | 10 | 0.00 | 8 | 0.0 |
| P62979 | F & R | Ubiquitin-40S ribosomal protein S27a | 8.96 | 30 | 0.78 | 8 | 712462.4 |
| P22102 | F & R | Trifunctional purine biosynthetic protein adenosine-3 | 8.48 | 46 | 0.00 | 8 | 155187.6 |
| P21333 | F & R | Filamin-A | 8.43 | 64 | 2.61 | 8 | 75969.4 |
| P47756 | F & R | F-actin-capping protein subunit beta | 8.41 | 6 | 0.00 | 6 | 33959.8 |
| P11586 | F & R | C-1-tetrahydrofolate synthase, cytoplasmic | 8.36 | 26 | 3.30 | 8 | 321699.1 |
| Q13642 | F & R | Four and a half LIM domains protein 1 | 8.01 | 352 | 1.08 | 8 | 171369.8 |
| P42766 | F & R | 60S ribosomal protein L35 | 7.52 | 12 | 0.19 | 6 | 124166.3 |
| P62987 | F & R | Ubiquitin-60S ribosomal protein L40 | 7.28 | 20 | 0.23 | 8 | 165775.2 |
| P40926 | F & R | Malate dehydrogenase, mitochondrial | 7.07 | 71 | 2.85 | 8 | 860861.9 |
| P12814 | F & R | Alpha-actinin-1 | 6.61 | 96 | 1.62 | 8 | 28402.5 |
| P13796 | F & R | Plastin-2 | 6.37 | 4 | 0.00 | 5 | 0.0 |
| Q5T4S7 | F & R | E3 ubiquitin-protein ligase UBR4 | 5.73 | 13 | 0.00 | 8 | 0.0 |
| Q29RF7 | F & R | Sister chromatid cohesion protein PDS5 homolog A | 5.03 | 6 | 0.00 | 6 | 4978.1 |
| Q7Z406 | R | Myosin-14 | 52.91 | 10 | 0.00 | 4 | 1959.8 |
| Q8WVV9 | R | Heterogeneous nuclear ribonucleoprotein L-like | 51.55 | 8 | 0.00 | 3 | 40622.6 |
| Q12905 | R | Interleukin enhancer-binding factor 2 | 51.28 | 4 | 0.26 | 4 | 356718.9 |
| O60832 | R | H/ACA ribonucleoprotein complex subunit 4 | 50.25 | 8 | 8.84 | 4 | 106975.6 |
| P33316 | R | Deoxyuridine 5'-triphosphate nucleotidohydrolase, mitochondrial | 49.75 | 4 | 0.00 | 3 | 46128.0 |
| P04844 | R | Dolichyl-diphosphooligosaccharide--protein glycosyltransferase subunit 2 | 49.51 | 8 | 2.94 | 4 | 40817.1 |
| P45974 | R | Ubiquitin carboxyl-terminal hydrolase 5 | 49.51 | 4 | 0.00 | 4 | 50453.9 |
| P08708 | R | 40S ribosomal protein S17 | 49.14 | 4 | 3.85 | 4 | 0.0 |
| P0CW22 | R | 40S ribosomal protein S17-like | 49.14 | 4 | 3.85 | 4 | 159867.5 |
| P31939 | R | Bifunctional purine biosynthesis protein PURH | 48.21 | 24 | 3.49 | 4 | 228110.1 |
| P11532 | R | Dystrophin | 47.85 | 4 | 0.00 | 3 | 0.0 |
| P09960 | R | Leukotriene A-4 hydrolase | 47.72 | 52 | 1.82 | 4 | 59181.2 |
| P08133 | R | Annexin A6 | 47.62 | 4 | 0.00 | 4 | 55652.1 |
| Q9UJZ1 | R | Stomatin-like protein 2, mitochondrial | 47.28 | 4 | 3.12 | 3 | 153625.1 |
| P27361 | R | Mitogen-activated protein kinase 3 | 45.66 | 12 | 1.67 | 4 | 4305.9 |
| Q03252 | R | Lamin-B2 | 44.64 | 4 | 10.56 | 4 | 227741.7 |
| P08621 | R | U1 small nuclear ribonucleoprotein 70 kDa | 44.52 | 30 | 0.99 | 4 | 37190.5 |

FIG. 16 (cont'd)

| | | | | | | |
|---|---|---|---|---|---|---|
| P48047 | R | ATP synthase subunit O, mitochondrial | 44.12 | 6 | 2.92 | 4 | 194773.0 |
| Q96EP5 | R | DAZ-associated protein 1 | 43.81 | 16 | 3.07 | 4 | 76092.8 |
| Q16543 | R | Hsp90 co-chaperone Cdc37 | 42.92 | 4 | 4.42 | 4 | 195857.5 |
| Q93084 | R | Sarcoplasmic/endoplasmic reticulum calcium ATPase 3 | 42.49 | 42 | 1.81 | 4 | 0.0 |
| P08559 | R | Pyruvate dehydrogenase E1 component subunit alpha, somatic form, mitochondrial | 42.37 | 40 | 2.16 | 4 | 44270.4 |
| Q5BKZ1 | R | DBIRD complex subunit ZNF326 | 41.99 | 12 | 0.71 | 3 | 20100.0 |
| Q9Y262 | R | Eukaryotic translation initiation factor 3 subunit L | 41.24 | 8 | 0.68 | 4 | 68600.3 |
| Q9Y2X3 | R | Nucleolar protein 58 | 41.24 | 4 | 5.60 | 4 | 158569.9 |
| P62195 | R | 26S protease regulatory subunit 8 | 40.98 | 16 | 3.53 | 4 | 71898.9 |
| P52209 | R | 6-phosphogluconate dehydrogenase, decarboxylating | 40.46 | 12 | 1.97 | 4 | 284433.1 |
| P25789 | R | Proteasome subunit alpha type-4 | 40.08 | 4 | 2.08 | 3 | 132262.9 |
| P48739 | R | Phosphatidylinositol transfer protein beta isoform | 40.00 | 8 | 2.72 | 4 | 28051.6 |
| O94826 | R | Mitochondrial import receptor subunit TOM70 | 39.76 | 4 | 9.94 | 4 | 190460.0 |
| P05388 | R | 60S acidic ribosomal protein P0 | 39.37 | 4 | 1.40 | 4 | 91241.6 |
| Q9Y3F4 | R | Serine-threonine kinase receptor-associated protein | 38.65 | 8 | 7.46 | 4 | 199504.3 |
| Q15181 | R | Inorganic pyrophosphatase | 37.61 | 16 | 3.54 | 4 | 371334.5 |
| P30837 | R | Aldehyde dehydrogenase X, mitochondrial | 36.90 | 8 | 2.32 | 4 | 61289.4 |
| Q14683 | R | Structural maintenance of chromosomes protein 1A | 36.81 | 6 | 12.18 | 4 | 199280.3 |
| Q92499 | R | ATP-dependent RNA helicase DDX1 | 36.62 | 42 | 1.61 | 4 | 309376.6 |
| O43583 | R | Density-regulated protein | 36.50 | 4 | 4.26 | 3 | 108589.4 |
| P35749 | R | Myosin-11 | 36.45 | 24 | 1.73 | 4 | 146.4 |
| Q9UKV3 | R | Apoptotic chromatin condensation inducer in the nucleus | 36.19 | 24 | 0.39 | 4 | 75767.3 |
| Q14739 | R | Lamin-B receptor | 36.17 | 4 | 2.09 | 3 | 376780.8 |
| O15020 | R | Spectrin beta chain, non-erythrocytic 2 | 36.10 | 4 | 0.00 | 4 | 255.0 |
| P11277 | R | Spectrin beta chain, erythrocytic | 36.10 | 6 | 0.00 | 3 | 0.0 |
| Q08J23 | R | tRNA (cytosine(34)-C(5))-methyltransferase | 36.06 | 6 | 4.04 | 4 | 46568.8 |
| P60891 | R | Ribose-phosphate pyrophosphokinase 1 | 35.34 | 4 | 1.25 | 4 | 132673.2 |
| Q00325 | R | Phosphate carrier protein, mitochondrial | 34.66 | 8 | 1.92 | 3 | 90756.3 |

FIG. 16 (cont'd)

| | | | | | | | |
|---|---|---|---|---|---|---|---|
| O43423 | R | Acidic leucine-rich nuclear phosphoprotein 32 family member C | 34.52 | 6 | 2.62 | 4 | 0.0 |
| Q13561 | R | Dynactin subunit 2 | 34.48 | 6 | 0.00 | 4 | 50734.2 |
| P18621 | R | 60S ribosomal protein L17 | 34.44 | 12 | 2.61 | 4 | 118369.0 |
| Q13126 | R | S-methyl-5'-thioadenosine phosphorylase | 34.44 | 42 | 0.59 | 3 | 14563.6 |
| P35998 | R | 26S protease regulatory subunit 7 | 34.36 | 4 | 0.12 | 4 | 40834.7 |
| P24752 | R | Acetyl-CoA acetyltransferase, mitochondrial | 34.03 | 20 | 1.85 | 4 | 305446.6 |
| Q53H12 | R | Acylglycerol kinase, mitochondrial | 33.98 | 6 | 2.31 | 4 | 95111.1 |
| Q15029 | R | 116 kDa U5 small nuclear ribonucleoprotein component | 33.93 | 16 | 2.19 | 4 | 123489.0 |
| Q14315 | R | Filamin-C | 33.22 | 8 | 0.55 | 4 | 7388.3 |
| P11908 | R | Ribose-phosphate pyrophosphokinase 2 | 33.22 | 4 | 0.00 | 3 | 0.0 |
| P05091 | R | Aldehyde dehydrogenase, mitochondrial | 32.87 | 10 | 2.49 | 4 | 152860.1 |
| Q16181 | R | Septin-7 | 32.77 | 12 | 1.29 | 3 | 58984.7 |
| P11766 | R | Alcohol dehydrogenase class-3 | 32.73 | 4 | 0.54 | 4 | 314167.4 |
| P09936 | R | Ubiquitin carboxyl-terminal hydrolase isozyme L1 | 32.73 | 4 | 10.48 | 4 | 183465.3 |
| Q9ULX6 | R | A-kinase anchor protein 8-like | 32.57 | 4 | 0.00 | 4 | 37328.9 |
| Q9Y5B9 | R | FACT complex subunit SPT16 | 32.43 | 19 | 2.11 | 4 | 316558.0 |
| Q13618 | R | Cullin-3 | 32.36 | 6 | 0.00 | 3 | 11861.5 |
| P16615 | R | Sarcoplasmic/endoplasmic reticulum calcium ATPase 2 | 32.28 | 46 | 1.98 | 4 | 18281.6 |
| O94906 | R | Pre-mRNA-processing factor 6 | 32.26 | 4 | 0.00 | 4 | 15018.8 |
| Q3SY69 | R | Mitochondrial 10-formyltetrahydrofolate dehydrogenase | 32.21 | 4 | 10.36 | 4 | 130633.6 |
| O00151 | R | PDZ and LIM domain protein 1 | 32.15 | 4 | 2.07 | 4 | 190997.7 |
| Q13427 | R | Peptidyl-prolyl cis-trans isomerase G | 32.10 | 8 | 0.21 | 4 | 2402.5 |
| P61964 | R | WD repeat-containing protein 5 | 32.09 | 6 | 6.17 | 4 | 37660.7 |
| Q12904 | R | Aminoacyl tRNA synthase complex-interacting multifunctional protein 1 | 31.97 | 16 | 1.12 | 4 | 108586.0 |
| P61081 | R | NEDD8-conjugating enzyme Ubc12 | 31.90 | 4 | 0.41 | 4 | 205056.4 |
| Q12931 | R | Heat shock protein 75 kDa, mitochondrial | 31.79 | 13 | 1.11 | 4 | 188705.9 |
| Q9NQ29 | R | Putative RNA-binding protein Luc7-like 1 | 31.75 | 12 | 0.91 | 3 | 37347.3 |
| P11310 | R | Medium-chain specific acyl-CoA dehydrogenase, mitochondrial | 31.75 | 4 | 0.00 | 3 | 65743.6 |

FIG. 16 (cont'd)

| | | | | | | | |
|---|---|---|---|---|---|---|---|
| P62304 | R | Small nuclear ribonucleoprotein E | 31.70 | 4 | 0.00 | 3 | 128497.9 |
| O95831 | R | Apoptosis-inducing factor 1, mitochondrial | 31.66 | 20 | 1.70 | 4 | 60742.3 |
| Q14157 | R | Ubiquitin-associated protein 2-like | 31.55 | 10 | 0.00 | 4 | 26540.5 |
| O15355 | R | Protein phosphatase 1G | 31.25 | 4 | 1.37 | 3 | 82017.4 |
| P34897 | R | Serine hydroxymethyltransferase, mitochondrial | 31.18 | 48 | 0.58 | 4 | 66454.8 |
| P20810 | R | Calpastatin | 31.06 | 32 | 0.19 | 4 | 3661.4 |
| O95757 | R | Heat shock 70 kDa protein 4L | 30.89 | 20 | 2.19 | 4 | 171424.8 |
| Q9NR45 | R | Sialic acid synthase | 30.86 | 16 | 2.57 | 4 | 285372.7 |
| O15145 | R | Actin-related protein 2/3 complex subunit 3 | 30.82 | 4 | 0.28 | 3 | 13233.7 |
| Q53EL6 | R | Programmed cell death protein 4 | 30.77 | 8 | 0.19 | 3 | 14858.5 |
| Q9GZS3 | R | WD repeat-containing protein 61 | 30.72 | 4 | 1.41 | 3 | 46676.3 |
| P17980 | R | 26S protease regulatory subunit 6A | 30.64 | 3 | 0.85 | 4 | 80816.1 |
| P35580 | R | Myosin-10 | 30.37 | 144 | 0.83 | 4 | 65354.5 |
| Q9UGI8 | R | Testin | 30.29 | 14 | 1.56 | 4 | 110308.6 |
| Q92878 | R | DNA repair protein RAD50 | 30.21 | 6 | 0.00 | 4 | 51881.9 |
| P49368 | R | T-complex protein 1 subunit gamma | 30.16 | 26 | 0.73 | 4 | 178761.5 |
| Q14203 | R | Dynactin subunit 1 | 29.94 | 20 | 0.09 | 4 | 20929.7 |
| P30044 | R | Peroxiredoxin-5, mitochondrial | 29.84 | 36 | 0.36 | 4 | 36361.4 |
| P16989 | R | Y-box-binding protein 3 | 29.79 | 18 | 0.09 | 4 | 58330.7 |
| P67809 | R | Nuclease-sensitive element-binding protein 1 | 29.79 | 6 | 0.18 | 4 | 79065.1 |
| Q9Y2T7 | R | Y-box-binding protein 2 | 29.79 | 6 | 0.18 | 4 | 109255.5 |
| Q9Y490 | R | Talin-1 | 29.67 | 6 | 4.93 | 4 | 115177.0 |
| Q99497 | R | Protein DJ-1 | 29.64 | 10 | 2.64 | 4 | 465314.4 |
| Q99459 | R | Cell division cycle 5-like protein | 29.60 | 5 | 4.47 | 4 | 114811.9 |
| P04637 | R | Cellular tumor antigen p53 | 29.50 | 12 | 0.00 | 3 | 25118.4 |
| Q9BTT0 | R | Acidic leucine-rich nuclear phosphoprotein 32 family member E | 29.44 | 6 | 0.09 | 3 | 59419.1 |
| Q13620 | R | Cullin-4B | 29.41 | 6 | 0.00 | 4 | 19926.3 |
| Q9Y2B0 | R | Protein canopy homolog 2 | 29.41 | 8 | 0.43 | 3 | 52874.7 |
| Q13619 | R | Cullin-4A | 29.41 | 4 | 0.00 | 3 | 0.0 |
| Q9UBE0 | R | SUMO-activating enzyme subunit 1 | 29.40 | 18 | 1.04 | 4 | 91909.5 |
| O00410 | R | Importin-5 | 29.33 | 6 | 0.00 | 3 | 4740.4 |
| P23634 | R | Plasma membrane calcium-transporting ATPase 4 | 29.16 | 16 | 0.00 | 4 | 2584.8 |
| P20020 | R | Plasma membrane calcium-transporting ATPase 1 | 29.16 | 12 | 0.00 | 4 | 6157.4 |
| Q01814 | R | Plasma membrane calcium-transporting ATPase 2 | 29.16 | 16 | 0.00 | 3 | 0.0 |

FIG. 16 (cont'd)

| | | | | | | | |
|---|---|---|---|---|---|---|---|
| Q16720 | R | Plasma membrane calcium-transporting ATPase 3 | 29.16 | 16 | 0.00 | 3 | 0.0 |
| P26196 | R | Probable ATP-dependent RNA helicase DDX6 | 29.16 | 6 | 3.49 | 3 | 94514.9 |
| Q9BXP5 | R | Serrate RNA effector molecule homolog | 29.02 | 50 | 0.76 | 4 | 50450.4 |
| Q8TAQ2 | R | SWI/SNF complex subunit SMARCC2 | 28.94 | 12 | 0.17 | 3 | 32606.5 |
| Q92922 | R | SWI/SNF complex subunit SMARCC1 | 28.94 | 4 | 0.34 | 3 | 41626.5 |
| Q92945 | R | Far upstream element-binding protein 2 | 28.20 | 6 | 2.30 | 4 | 370344.8 |
| P39748 | R | Flap endonuclease 1 | 28.13 | 8 | 2.69 | 4 | 224725.4 |
| P30086 | R | Phosphatidylethanolamine-binding protein 1 | 27.98 | 18 | 1.49 | 4 | 515791.9 |
| P35268 | R | 60S ribosomal protein L22 | 27.70 | 4 | 2.07 | 3 | 152828.0 |
| Q12874 | R | Splicing factor 3A subunit 3 | 27.57 | 6 | 3.57 | 4 | 128208.6 |
| P35613 | R | Basigin | 27.32 | 16 | 3.14 | 3 | 51731.4 |
| P61221 | R | ATP-binding cassette sub-family E member 1 | 27.32 | 4 | 5.90 | 3 | 102085.4 |
| Q15717 | R | ELAV-like protein 1 | 27.15 | 6 | 5.68 | 3 | 62305.6 |
| O75643 | R | U5 small nuclear ribonucleoprotein 200 kDa helicase | 27.12 | 50 | 1.10 | 4 | 118338.0 |
| P02545 | R | Prelamin-A/C | 27.03 | 16 | 3.43 | 4 | 76158.6 |
| Q9HC38 | R | Glyoxalase domain-containing protein 4 | 26.88 | 8 | 0.00 | 3 | 47269.7 |
| P41091 | R | Eukaryotic translation initiation factor 2 subunit 3 | 26.74 | 4 | 2.93 | 3 | 33087.7 |
| P07197 | R | Neurofilament medium polypeptide | 26.70 | 16 | 1.85 | 4 | 10804.7 |
| Q9BZZ5 | R | Apoptosis inhibitor 5 | 26.40 | 30 | 0.63 | 4 | 63418.7 |
| Q96SI9 | R | Spermatid perinuclear RNA-binding protein | 26.28 | 32 | 1.45 | 4 | 8914.6 |
| P46060 | R | Ran GTPase-activating protein 1 | 26.28 | 4 | 7.24 | 3 | 109896.1 |
| P28482 | R | Mitogen-activated protein kinase 1 | 26.13 | 6 | 7.10 | 4 | 44539.6 |
| P55072 | R | Transitional endoplasmic reticulum ATPase | 26.02 | 40 | 3.86 | 4 | 387710.4 |
| P15311 | R | Ezrin | 25.57 | 12 | 0.92 | 4 | 277198.0 |
| Q9Y6M1 | R | Insulin-like growth factor 2 mRNA-binding protein 2 | 25.46 | 72 | 0.52 | 4 | 5473.6 |
| P31946 | R | 14-3-3 protein beta/alpha | 25.44 | 48 | 2.40 | 4 | 157073.9 |
| P49321 | R | Nuclear autoantigenic sperm protein | 25.36 | 26 | 1.09 | 4 | 109085.5 |
| P23381 | R | Tryptophan--tRNA ligase, cytoplasmic | 25.19 | 12 | 1.33 | 4 | 63667.1 |
| Q8NBS9 | R | Thioredoxin domain-containing protein 5 | 25.19 | 4 | 0.00 | 3 | 13708.3 |
| P46940 | R | Ras GTPase-activating-like protein IQGAP1 | 25.16 | 8 | 0.70 | 4 | 139403.3 |

FIG. 16 (cont'd)

| | | | | | | | |
|---|---|---|---|---|---|---|---|
| P00918 | R | Carbonic anhydrase 2 | 25.10 | 28 | 1.20 | 4 | 514685.8 |
| Q9Y5A9 | R | YTH domain family protein 2 | 25.06 | 4 | 0.00 | 3 | 2466.0 |
| Q92598 | R | Heat shock protein 105 kDa | 25.05 | 42 | 1.44 | 4 | 42060.4 |
| P62906 | R | 60S ribosomal protein L10a | 25.04 | 6 | 1.19 | 3 | 157435.1 |
| P21796 | R | Voltage-dependent anion-selective channel protein 1 | 24.97 | 8 | 3.99 | 4 | 204664.8 |
| P12036 | R | Neurofilament heavy polypeptide | 24.96 | 12 | 1.99 | 3 | 0.0 |
| P07196 | R | Neurofilament light polypeptide | 24.96 | 6 | 2.99 | 3 | 0.0 |
| P17661 | R | Desmin | 24.96 | 6 | 2.99 | 3 | 0.0 |
| P23193 | R | Transcription elongation factor A protein 1 | 24.95 | 16 | 1.68 | 3 | 70507.4 |
| P37802 | R | Transgelin-2 | 24.83 | 5 | 2.16 | 3 | 422672.5 |
| Q9Y4L1 | R | Hypoxia up-regulated protein 1 | 24.81 | 6 | 0.99 | 4 | 221059.2 |
| Q9UBS4 | R | DnaJ homolog subfamily B member 11 | 24.75 | 4 | 1.65 | 3 | 119143.6 |
| O14980 | R | Exportin-1 | 24.59 | 17 | 1.39 | 4 | 123463.3 |
| O75083 | R | WD repeat-containing protein 1 | 24.40 | 18 | 4.94 | 4 | 83521.1 |
| P38117 | R | Electron transfer flavoprotein subunit beta | 24.27 | 4 | 0.00 | 3 | 42227.8 |
| P49755 | R | Transmembrane emp24 domain-containing protein 10 | 24.23 | 6 | 3.29 | 4 | 92925.0 |
| P00505 | R | Aspartate aminotransferase, mitochondrial | 24.18 | 26 | 1.05 | 4 | 320494.0 |
| Q02880 | R | DNA topoisomerase 2-beta | 24.04 | 16 | 0.75 | 4 | 28249.4 |
| O75694 | R | Nuclear pore complex protein Nup155 | 23.92 | 4 | 0.00 | 3 | 29100.9 |
| Q9BVK6 | R | Transmembrane emp24 domain-containing protein 9 | 23.90 | 3 | 0.06 | 3 | 186395.8 |
| O00425 | R | Insulin-like growth factor 2 mRNA-binding protein 3 | 23.89 | 14 | 0.86 | 4 | 106150.3 |
| O75367 | R | Core histone macro-H2A.1 | 23.88 | 36 | 1.20 | 4 | 59991.2 |
| Q9BQ52 | R | Zinc phosphodiesterase ELAC protein 2 | 23.87 | 6 | 0.00 | 3 | 9396.7 |
| Q6DN03 | R | Putative histone H2B type 2-C | 23.82 | 10 | 2.89 | 4 | 248973.3 |
| Q9HAV7 | R | GrpE protein homolog 1, mitochondrial | 23.63 | 10 | 1.51 | 4 | 128600.7 |
| P14314 | R | Glucosidase 2 subunit beta | 23.59 | 8 | 0.33 | 4 | 123780.1 |
| Q13263 | R | Transcription intermediary factor 1-beta | 23.54 | 36 | 0.50 | 4 | 136598.6 |
| Q14684 | R | Ribosomal RNA processing protein 1 homolog B | 23.47 | 4 | 0.00 | 4 | 36506.7 |
| Q01518 | R | Adenylyl cyclase-associated protein 1 | 23.46 | 48 | 0.66 | 4 | 170023.7 |
| Q15019 | R | Septin-2 | 23.42 | 4 | 0.00 | 3 | 59623.6 |
| Q10567 | R | AP-1 complex subunit beta-1 | 23.31 | 12 | 0.33 | 4 | 2497.5 |
| P63010 | R | AP-2 complex subunit beta | 23.31 | 6 | 0.49 | 4 | 0.0 |
| P27816 | R | Microtubule-associated protein 4 | 23.30 | 79 | 1.09 | 4 | 69092.5 |
| P32119 | R | Peroxiredoxin-2 | 23.26 | 4 | 0.00 | 4 | 167617.9 |

FIG. 16 (cont'd)

| | | | | | | | |
|---|---|---|---|---|---|---|---|
| O15371 | R | Eukaryotic translation initiation factor 3 subunit D | 22.88 | 3 | 0.73 | 4 | 50994.7 |
| A0AVT1 | R | Ubiquitin-like modifier-activating enzyme 6 | 22.81 | 10 | 2.03 | 4 | 13955.7 |
| P43246 | R | DNA mismatch repair protein Msh2 | 22.73 | 4 | 0.00 | 4 | 25536.5 |
| O43852 | R | Calumenin | 22.65 | 185 | 0.21 | 4 | 48246.5 |
| Q8TAA3 | R | Proteasome subunit alpha type-7-like | 22.47 | 6 | 0.00 | 3 | 42411.4 |
| Q9NX63 | R | Coiled-coil-helix-coiled-coil-helix domain-containing protein 3, mitochondrial | 22.29 | 6 | 0.30 | 4 | 159719.9 |
| O14983 | R | Sarcoplasmic/endoplasmic reticulum calcium ATPase 1 | 22.25 | 8 | 1.73 | 4 | 2064.2 |
| Q9UKX7 | R | Nuclear pore complex protein Nup50 | 22.22 | 4 | 0.00 | 4 | 38290.0 |
| O75223 | R | Gamma-glutamylcyclotransferase | 22.17 | 4 | 0.30 | 3 | 37086.9 |
| Q14980 | R | Nuclear mitotic apparatus protein 1 | 21.95 | 16 | 0.77 | 4 | 46554.1 |
| P11388 | R | DNA topoisomerase 2-alpha | 21.85 | 32 | 0.29 | 4 | 24609.8 |
| P45880 | R | Voltage-dependent anion-selective channel protein 2 | 21.71 | 18 | 0.24 | 4 | 105977.8 |
| Q9NVA2 | R | Septin-11 | 21.60 | 4 | 0.00 | 4 | 62488.3 |
| P84085 | R | ADP-ribosylation factor 5 | 21.39 | 4 | 1.14 | 3 | 0.0 |
| P18085 | R | ADP-ribosylation factor 4 | 21.39 | 4 | 1.14 | 3 | 0.0 |
| Q04917 | R | 14-3-3 protein eta | 21.29 | 12 | 4.03 | 4 | 131680.7 |
| Q92769 | R | Histone deacetylase 2 | 21.25 | 8 | 1.90 | 3 | 17270.1 |
| O60812 | R | Heterogeneous nuclear ribonucleoprotein C-like 1 | 21.08 | 18 | 1.16 | 4 | 78833.7 |
| P50454 | R | Serpin H1 | 21.06 | 10 | 0.53 | 4 | 115531.6 |
| Q16352 | R | Alpha-internexin | 21.05 | 4 | 0.49 | 3 | 0.0 |
| P12268 | R | Inosine-5'-monophosphate dehydrogenase 2 | 21.04 | 6 | 2.61 | 4 | 196266.8 |
| O95292 | R | Vesicle-associated membrane protein-associated protein B/C | 21.03 | 4 | 2.08 | 4 | 100265.3 |
| Q02543 | R | 60S ribosomal protein L18a | 21.03 | 14 | 1.68 | 4 | 302081.9 |
| P06737 | R | Glycogen phosphorylase, liver form | 20.79 | 12 | 2.46 | 4 | 68804.4 |
| P35221 | R | Catenin alpha-1 | 20.79 | 8 | 0.26 | 4 | 21871.2 |
| A2BFH1 | R | Peptidyl-prolyl cis-trans isomerase A-like 4G | 20.76 | 6 | 1.08 | 4 | 0.0 |
| F5H284 | R | Peptidyl-prolyl cis-trans isomerase A-like 4D | 20.76 | 6 | 1.08 | 4 | 0.0 |
| Q9BUF5 | R | Tubulin beta-6 chain | 20.76 | 11 | 1.77 | 4 | 73014.0 |
| P35241 | R | Radixin | 20.41 | 4 | 0.00 | 4 | 77567.4 |
| P13995 | R | Bifunctional methylenetetrahydrofolate dehydrogenase/cyclohydrolase, mitochondrial | 20.38 | 6 | 0.91 | 4 | 300983.8 |
| Q8NFI4 | R | Putative protein FAM10A5 | 20.21 | 8 | 0.86 | 4 | 0.0 |

FIG. 16 (cont'd)

| | | | | | | | |
|---|---|---|---|---|---|---|---|
| P43034 | R | Platelet-activating factor acetylhydrolase IB subunit alpha | 20.19 | 3 | 1.18 | 4 | 95641.3 |
| Q06203 | R | Amidophosphoribosyltransferase | 20.19 | 6 | 0.41 | 3 | 53604.7 |
| P35637 | R | RNA-binding protein FUS | 20.08 | 46 | 1.05 | 4 | 219143.6 |
| P22061 | R | Protein-L-isoaspartate(D-aspartate) O-methyltransferase | 20.00 | 4 | 0.00 | 3 | 92927.9 |
| P36873 | R | Serine/threonine-protein phosphatase PP1-gamma catalytic subunit | 19.80 | 4 | 0.00 | 3 | 0.0 |
| P62136 | R | Serine/threonine-protein phosphatase PP1-alpha catalytic subunit | 19.80 | 4 | 0.00 | 3 | 36688.7 |
| P62917 | R | 60S ribosomal protein L8 | 19.78 | 10 | 0.74 | 4 | 322112.3 |
| P50502 | R | Hsc70-interacting protein | 19.68 | 18 | 1.12 | 4 | 207506.0 |
| Q02952 | R | A-kinase anchor protein 12 | 19.57 | 6 | 0.00 | 4 | 26543.0 |
| Q3ZCM7 | R | Tubulin beta-8 chain | 19.42 | 3 | 6.00 | 3 | 416526.4 |
| P12270 | R | Nucleoprotein TPR | 19.42 | 13 | 5.84 | 4 | 154336.5 |
| Q8IZP2 | R | Putative protein FAM10A4 | 19.27 | 10 | 1.89 | 4 | 336189.0 |
| Q15459 | R | Splicing factor 3A subunit 1 | 19.21 | 4 | 1.62 | 4 | 190721.0 |
| P25205 | R | DNA replication licensing factor MCM3 | 19.14 | 10 | 2.24 | 4 | 154778.4 |
| P08758 | R | Annexin A5 | 18.99 | 12 | 3.42 | 4 | 216430.4 |
| P55786 | R | Puromycin-sensitive aminopeptidase | 18.93 | 3 | 1.86 | 4 | 75752.2 |
| P25786 | R | Proteasome subunit alpha type-1 | 18.80 | 4 | 0.00 | 3 | 41697.7 |
| Q01780 | R | Exosome component 10 | 18.78 | 8 | 0.53 | 4 | 32618.1 |
| Q13547 | R | Histone deacetylase 1 | 18.75 | 6 | 0.42 | 3 | 215272.7 |
| Q9NR30 | R | Nucleolar RNA helicase 2 | 18.73 | 16 | 1.09 | 4 | 53386.1 |
| P49589 | R | Cysteine--tRNA ligase, cytoplasmic | 18.70 | 22 | 1.68 | 4 | 18351.0 |
| Q00341 | R | Vigilin | 18.25 | 4 | 0.00 | 4 | 51680.9 |
| P49792 | R | E3 SUMO-protein ligase RanBP2 | 18.23 | 6 | 1.66 | 4 | 109361.6 |
| Q13765 | R | Nascent polypeptide-associated complex subunit alpha | 18.20 | 8 | 0.43 | 3 | 123827.6 |
| P28370 | R | Probable global transcription activator SNF2L1 | 18.08 | 4 | 0.00 | 3 | 8814.7 |
| P27348 | R | 14-3-3 protein theta | 17.86 | 14 | 2.78 | 4 | 366307.9 |
| P45973 | R | Chromobox protein homolog 5 | 17.83 | 14 | 1.59 | 4 | 409952.9 |
| Q8WU90 | R | Zinc finger CCCH domain-containing protein 15 | 17.72 | 8 | 0.88 | 4 | 87507.3 |
| Q15149 | R | Plectin | 17.70 | 18 | 0.00 | 4 | 128.5 |
| Q04637 | R | Eukaryotic translation initiation factor 4 gamma 1 | 17.48 | 10 | 0.00 | 3 | 4812.8 |
| O75533 | R | Splicing factor 3B subunit 1 | 17.40 | 9 | 5.57 | 4 | 169073.1 |
| P30613 | R | Pyruvate kinase PKLR | 17.05 | 16 | 0.58 | 4 | 0.0 |
| Q13155 | R | Aminoacyl tRNA synthase complex-interacting multifunctional protein 2 | 16.95 | 8 | 1.93 | 4 | 105726.6 |

FIG. 16 (cont'd)

| | | | | | | | |
|---|---|---|---|---|---|---|---|
| Q9BVP2 | R | Guanine nucleotide-binding protein-like 3 | 16.71 | 12 | 1.20 | 4 | 119698.7 |
| P28838 | R | Cytosol aminopeptidase | 16.58 | 4 | 0.00 | 4 | 25589.6 |
| Q6NZY4 | R | Zinc finger CCHC domain-containing protein 8 | 16.58 | 4 | 0.00 | 3 | 22398.9 |
| Q92804 | R | TATA-binding protein-associated factor 2N | 16.40 | 28 | 0.59 | 4 | 99345.0 |
| P23284 | R | Peptidyl-prolyl cis-trans isomerase B | 16.40 | 14 | 1.02 | 4 | 437710.7 |
| P55209 | R | Nucleosome assembly protein 1-like 1 | 16.16 | 8 | 3.50 | 4 | 45759.8 |
| Q9H0A0 | R | N-acetyltransferase 10 | 16.14 | 6 | 6.77 | 4 | 66469.0 |
| P55036 | R | 26S proteasome non-ATPase regulatory subunit 4 | 15.90 | 4 | 0.00 | 3 | 98204.1 |
| P31947 | R | 14-3-3 protein sigma | 15.86 | 12 | 2.61 | 3 | 0.0 |
| Q14566 | R | DNA replication licensing factor MCM6 | 15.80 | 5 | 3.44 | 4 | 77087.0 |
| Q15293 | R | Reticulocalbin-1 | 15.72 | 22 | 0.99 | 4 | 332119.6 |
| P07205 | R | Phosphoglycerate kinase 2 | 15.57 | 14 | 3.01 | 4 | 0.0 |
| P12236 | R | ADP/ATP translocase 3 | 15.46 | 10 | 4.59 | 4 | 175781.1 |
| P78347 | R | General transcription factor II-I | 15.28 | 60 | 0.86 | 4 | 31632.8 |
| Q96Q15 | R | Serine/threonine-protein kinase SMG1 | 15.15 | 8 | 0.00 | 3 | 0.0 |
| Q8TCU4 | R | Alstrom syndrome protein 1 | 15.11 | 6 | 0.00 | 4 | 0.0 |
| Q14008 | R | Cytoskeleton-associated protein 5 | 14.75 | 6 | 0.00 | 4 | 20184.1 |
| P23526 | R | Adenosylhomocysteinase | 14.43 | 40 | 1.98 | 4 | 173308.1 |
| P16949 | R | Stathmin | 13.74 | 12 | 0.34 | 3 | 131920.0 |
| Q93045 | R | Stathmin-2 | 13.74 | 12 | 0.34 | 3 | 78355.1 |
| P35579 | R | Myosin-9 | 13.58 | 60 | 2.75 | 4 | 191817.4 |
| P09211 | R | Glutathione S-transferase P | 13.53 | 4 | 5.57 | 4 | 172131.4 |
| Q86UP2 | R | Kinectin | 13.43 | 48 | 1.88 | 4 | 62312.8 |
| Q06124 | R | Tyrosine-protein phosphatase non-receptor type 11 | 13.17 | 12 | 2.04 | 3 | 56630.4 |
| P12235 | R | ADP/ATP translocase 1 | 13.02 | 6 | 5.44 | 4 | 13989.5 |
| P10515 | R | Dihydrolipoyllysine-residue acetyltransferase component of pyruvate dehydrogenase complex, mitochondrial | 12.78 | 3 | 4.63 | 4 | 133684.5 |
| Q8IVF4 | R | Dynein heavy chain 10, axonemal | 12.45 | 4 | 1.12 | 4 | 0.0 |
| O00159 | R | Unconventional myosin-Ic | 12.44 | 6 | 0.00 | 3 | 4112.5 |
| O95347 | R | Structural maintenance of chromosomes protein 2 | 12.30 | 16 | 1.17 | 4 | 74568.5 |
| Q15637 | R | Splicing factor 1 | 10.82 | 14 | 0.00 | 3 | 11189.5 |
| P49588 | R | Alanine--tRNA ligase, cytoplasmic | 10.43 | 22 | 4.10 | 4 | 179144.7 |
| Q16891 | R | Mitochondrial inner membrane protein | 10.00 | 40 | 2.56 | 4 | 116733.9 |
| P62633 | R | Cellular nucleic acid-binding protein | 9.95 | 102 | 0.75 | 4 | 53399.5 |

FIG. 16 (cont'd)

| | | | | | | | |
|---|---|---|---|---|---|---|---|
| P28331 | R | NADH-ubiquinone oxidoreductase 75 kDa subunit, mitochondrial | 9.83 | 10 | 0.00 | 3 | 12370.3 |
| Q13428 | R | Treacle protein | 9.43 | 58 | 0.51 | 4 | 23529.4 |
| Q9NYU2 | R | UDP-glucose:glycoprotein glucosyltransferase 1 | 9.38 | 4 | 0.00 | 3 | 13893.9 |
| Q8WWM7 | R | Ataxin-2-like protein | 9.24 | 28 | 1.09 | 4 | 13648.2 |
| P46779 | R | 60S ribosomal protein L28 | 8.43 | 12 | 0.49 | 3 | 48441.1 |
| Q86VP6 | R | Cullin-associated NEDD8-dissociated protein 1 | 8.34 | 16 | 2.95 | 4 | 39048.3 |
| Q5VZ89 | R | DENN domain-containing protein 4C | 8.16 | 4 | 0.00 | 3 | 0.0 |
| P35659 | R | Protein DEK | 8.13 | 3 | 1.75 | 3 | 35515.0 |
| Q9H2U2 | R | Inorganic pyrophosphatase 2, mitochondrial | 7.39 | 28 | 0.60 | 4 | 74278.6 |
| Q09666 | R | Neuroblast differentiation-associated protein AHNAK | 7.17 | 6 | 1.06 | 4 | 80354.0 |
| P55884 | R | Eukaryotic translation initiation factor 3 subunit B | 5.73 | 4 | 0.00 | 4 | 18986.9 |
| Q9Y4G6 | R | Talin-2 | 5.70 | 6 | 2.74 | 4 | 0.0 |
| Q9NSE4 | R | Isoleucine--tRNA ligase, mitochondrial | 5.61 | 16 | 3.32 | 4 | 210777.8 |
| P04843 | R | Dolichyl-diphosphooligosaccharide--protein glycosyltransferase subunit 1 | 5.49 | 3 | 4.18 | 4 | 97490.7 |
| O14686 | R | Histone-lysine N-methyltransferase 2D | 5.48 | 8 | 1.50 | 3 | 0.0 |
| P61981 | R | 14-3-3 protein gamma | 5.42 | 16 | 2.86 | 4 | 153996.6 |
| Q6ZUT1 | R | Uncharacterized protein C11orf57 | 5.28 | 6 | 0.00 | 3 | 0.0 |
| P56537 | R | Eukaryotic translation initiation factor 6 | 1000.00 | 10 | 0.00 | 4 | 50492.0 |
| P39656 | R | Dolichyl-diphosphooligosaccharide--protein glycosyltransferase 48 kDa subunit | 1000.00 | 4 | 0.00 | 4 | 140037.9 |
| P06730 | R | Eukaryotic translation initiation factor 4E | 1000.00 | 18 | 0.00 | 3 | 10771.3 |
| Q7Z3B4 | R | Nucleoporin p54 | 1000.00 | 18 | 0.00 | 3 | 15875.5 |
| P00387 | R | NADH-cytochrome b5 reductase 3 | 1000.00 | 16 | 0.00 | 3 | 40586.3 |
| Q9NZW5 | R | MAGUK p55 subfamily member 6 | 1000.00 | 9 | 0.00 | 3 | 106569.0 |
| P63167 | R | Dynein light chain 1, cytoplasmic | 1000.00 | 8 | 0.00 | 3 | 211276.8 |
| Q13363 | R | C-terminal-binding protein 1 | 1000.00 | 8 | 0.00 | 3 | 51127.9 |
| O75821 | R | Eukaryotic translation initiation factor 3 subunit G | 1000.00 | 6 | 0.00 | 3 | 88071.0 |
| O14602 | R | Eukaryotic translation initiation factor 1A, Y-chromosomal | 1000.00 | 3 | 0.00 | 3 | 42347.4 |
| Q9Y6G9 | R | Cytoplasmic dynein 1 light intermediate chain 1 | 1000.00 | 7 | 0.00 | 3 | 23983.6 |
| Q9Y263 | R | Phospholipase A-2-activating protein | 1000.00 | 6 | 0.00 | 3 | 5759.7 |

FIG. 16 (cont'd)

| | | | | | | | |
|---|---|---|---|---|---|---|---|
| Q2VIR3 | R | Putative eukaryotic translation initiation factor 2 subunit 3-like protein | 1000.00 | 4 | 0.00 | 3 | 10781.3 |
| P62269 | R | 40S ribosomal protein S18 | 1000.00 | 3 | 0.00 | 3 | 52418.0 |
| Q9H2W6 | R | 39S ribosomal protein L46, mitochondrial | 1000.00 | 3 | 0.00 | 3 | 20769.8 |
| O60610 | R | Protein diaphanous homolog 1 | 1000.00 | 12 | 0.00 | 3 | 2447.7 |
| Q9BY44 | R | Eukaryotic translation initiation factor 2A | 1000.00 | 10 | 0.00 | 3 | 11240.0 |
| Q8TAF3 | R | WD repeat-containing protein 48 | 1000.00 | 9 | 0.00 | 3 | 0.0 |
| Q13098 | R | COP9 signalosome complex subunit 1 | 1000.00 | 6 | 0.00 | 3 | 330.9 |
| Q9NR22 | R | Protein arginine N-methyltransferase 8 | 1000.00 | 6 | 0.00 | 3 | 0.0 |
| O75663 | R | TIP41-like protein | 1000.00 | 5 | 0.00 | 3 | 29168.6 |
| Q13243 | R | Serine/arginine-rich splicing factor 5 | 1000.00 | 5 | 0.00 | 3 | 5758.6 |
| Q16134 | R | Electron transfer flavoprotein-ubiquinone oxidoreductase, mitochondrial | 1000.00 | 5 | 0.00 | 3 | 0.0 |
| O00154 | R | Cytosolic acyl coenzyme A thioester hydrolase | 1000.00 | 4 | 0.00 | 3 | 5025.2 |
| O00487 | R | 26S proteasome non-ATPase regulatory subunit 14 | 1000.00 | 4 | 0.00 | 3 | 0.0 |
| O43172 | R | U4/U6 small nuclear ribonucleoprotein Prp4 | 1000.00 | 4 | 0.00 | 3 | 26460.4 |
| O95104 | R | Splicing factor, arginine/serine-rich 15 | 1000.00 | 4 | 0.00 | 3 | 22632.0 |
| P50213 | R | Isocitrate dehydrogenase [NAD] subunit alpha, mitochondrial | 1000.00 | 4 | 0.00 | 3 | 41848.9 |
| Q8TBC4 | R | NEDD8-activating enzyme E1 catalytic subunit | 1000.00 | 4 | 0.00 | 3 | 26321.3 |
| Q99961 | R | Endophilin-A2 | 1000.00 | 4 | 0.00 | 3 | 53160.3 |
| Q9Y5K3 | R | Choline-phosphate cytidylyltransferase B | 1000.00 | 4 | 0.00 | 3 | 14198.4 |
| O14744 | R | Protein arginine N-methyltransferase 5 | 1000.00 | 3 | 0.00 | 3 | 2317.2 |
| P55010 | R | Eukaryotic translation initiation factor 5 | 1000.00 | 3 | 0.00 | 3 | 40970.1 |
| Q96EY1 | R | DnaJ homolog subfamily A member 3, mitochondrial | 1000.00 | 3 | 0.00 | 3 | 49200.2 |
| Q9BVJ6 | R | U3 small nucleolar RNA-associated protein 14 homolog A | 1000.00 | 3 | 0.00 | 3 | 10709.2 |
| Q9Y3A5 | R | Ribosome maturation protein SBDS | 1000.00 | 3 | 0.00 | 3 | 72192.9 |
| Q9H6R3 | R | Acyl-CoA synthetase short-chain family member 3, mitochondrial | 1000.00 | 10 | 0.00 | 3 | 0.0 |
| P40938 | R | Replication factor C subunit 3 | 1000.00 | 7 | 0.00 | 3 | 6931.9 |
| P11413 | R | Glucose-6-phosphate 1-dehydrogenase | 1000.00 | 6 | 0.00 | 3 | 3482.7 |
| P29558 | R | RNA-binding motif, single-stranded-interacting protein 1 | 1000.00 | 4 | 0.00 | 3 | 5074.0 |

FIG. 16 (cont'd)

| | | | | | | | |
|---|---|---|---|---|---|---|---|
| O75822 | R | Eukaryotic translation initiation factor 3 subunit J | 1000.00 | 3 | 0.00 | 3 | 6250.1 |
| Q6IN85 | R | Serine/threonine-protein phosphatase 4 regulatory subunit 3A | 1000.00 | 8 | 0.00 | 3 | 0.0 |
| Q9UBT2 | F | SUMO-activating enzyme subunit 2 | 1000.00 | 103 | 0.00 | 4 | 85473.8 |
| P17858 | F | 6-phosphofructokinase, liver type | 1000.00 | 98 | 0.00 | 4 | 72902.3 |
| P27694 | F | Replication protein A 70 kDa DNA-binding subunit | 1000.00 | 73 | 0.00 | 4 | 70226.6 |
| Q8IWS0 | F | PHD finger protein 6 | 1000.00 | 66 | 0.00 | 4 | 29680.2 |
| O75131 | F | Copine-3 | 1000.00 | 62 | 0.00 | 4 | 97047.3 |
| P15927 | F | Replication protein A 32 kDa subunit | 1000.00 | 57 | 0.00 | 4 | 49198.4 |
| Q92541 | F | RNA polymerase-associated protein RTF1 homolog | 1000.00 | 50 | 0.00 | 4 | 16702.6 |
| P61158 | F | Actin-related protein 3 | 1000.00 | 43 | 0.00 | 4 | 72921.4 |
| Q15050 | F | Ribosome biogenesis regulatory protein homolog | 1000.00 | 42 | 0.00 | 4 | 110229.2 |
| Q9H9B4 | F | Sideroflexin-1 | 1000.00 | 40 | 0.00 | 4 | 110590.9 |
| O00566 | F | U3 small nucleolar ribonucleoprotein protein MPP10 | 1000.00 | 36 | 0.00 | 4 | 24573.4 |
| Q8NHW5 | F | 60S acidic ribosomal protein P0-like | 1000.00 | 26 | 0.00 | 4 | 135224.9 |
| Q9NQ48 | F | Leucine zipper transcription factor-like protein 1 | 1000.00 | 26 | 0.00 | 4 | 38157.3 |
| Q9Y224 | F | UPF0568 protein C14orf166 | 1000.00 | 25 | 0.00 | 4 | 124408.9 |
| P48735 | F | Isocitrate dehydrogenase [NADP], mitochondrial | 1000.00 | 23 | 0.00 | 4 | 114485.1 |
| Q16186 | F | Proteasomal ubiquitin receptor ADRM1 | 1000.00 | 14 | 0.00 | 4 | 36102.9 |
| P13693 | F | Translationally-controlled tumor protein | 1000.00 | 13 | 0.00 | 4 | 123231.8 |
| Q9Y6E2 | F | Basic leucine zipper and W2 domain-containing protein 2 | 1000.00 | 10 | 0.00 | 4 | 54405.2 |
| Q5T8P6 | F | RNA-binding protein 26 | 1000.00 | 192 | 0.00 | 4 | 5138.0 |
| Q13557 | F | Calcium/calmodulin-dependent protein kinase type II subunit delta | 1000.00 | 160 | 0.00 | 4 | 6577.6 |
| O00231 | F | 26S proteasome non-ATPase regulatory subunit 11 | 1000.00 | 121 | 0.00 | 4 | 4403.9 |
| Q9BWF3 | F | RNA-binding protein 4 | 1000.00 | 100 | 0.00 | 4 | 14393.7 |
| P48444 | F | Coatomer subunit delta | 1000.00 | 95 | 0.00 | 4 | 17257.5 |
| A6NEC2 | F | Puromycin-sensitive aminopeptidase-like protein | 1000.00 | 84 | 0.00 | 4 | 0.0 |
| P57740 | F | Nuclear pore complex protein Nup107 | 1000.00 | 82 | 0.00 | 4 | 13318.0 |
| P51858 | F | Hepatoma-derived growth factor | 1000.00 | 81 | 0.00 | 4 | 113154.1 |
| Q14141 | F | Septin-6 | 1000.00 | 68 | 0.00 | 4 | 930.6 |
| P62191 | F | 26S protease regulatory subunit 4 | 1000.00 | 57 | 0.00 | 4 | 243459.4 |
| P28074 | F | Proteasome subunit beta type-5 | 1000.00 | 56 | 0.00 | 4 | 19397.7 |

FIG. 16 (cont'd)

| P28066 | F | Proteasome subunit alpha type-5 | 1000.00 | 44 | 0.00 | 4 | 28135.6 |
|---|---|---|---|---|---|---|---|
| P22087 | F | rRNA 2'-O-methyltransferase fibrillarin | 1000.00 | 43 | 0.00 | 4 | 215023.1 |
| Q9BQ04 | F | RNA-binding protein 4B | 1000.00 | 38 | 0.00 | 4 | 10646.5 |
| Q9Y696 | F | Chloride intracellular channel protein 4 | 1000.00 | 38 | 0.00 | 4 | 205678.9 |
| Q9HB71 | F | Calcyclin-binding protein | 1000.00 | 37 | 0.00 | 4 | 85949.3 |
| Q13596 | F | Sorting nexin-1 | 1000.00 | 36 | 0.00 | 4 | 2560.7 |
| Q9H0U4 | F | Ras-related protein Rab-1B | 1000.00 | 22 | 0.00 | 4 | 11014.6 |
| Q14696 | F | LDLR chaperone MESD | 1000.00 | 21 | 0.00 | 4 | 33760.4 |
| P09234 | F | U1 small nuclear ribonucleoprotein C | 1000.00 | 9 | 0.00 | 4 | 89629.5 |
| Q13526 | F | Peptidyl-prolyl cis-trans isomerase NIMA-interacting 1 | 1000.00 | 5 | 0.00 | 4 | 178903.8 |
| Q12959 | F | Disks large homolog 1 | 1000.00 | 395 | 0.00 | 4 | 3670.1 |
| P00390 | F | Glutathione reductase, mitochondrial | 1000.00 | 221 | 0.00 | 4 | 1759.2 |
| Q9UJS0 | F | Calcium-binding mitochondrial carrier protein Aralar2 | 1000.00 | 162 | 0.00 | 4 | 19068.0 |
| Q14444 | F | Caprin-1 | 1000.00 | 95 | 0.00 | 4 | 19433.8 |
| Q8NCN5 | F | Pyruvate dehydrogenase phosphatase regulatory subunit, mitochondrial | 1000.00 | 82 | 0.00 | 4 | 25371.9 |
| Q52LJ0 | F | Protein FAM98B | 1000.00 | 79 | 0.00 | 4 | 20601.9 |
| P23396 | F | 40S ribosomal protein S3 | 1000.00 | 69 | 0.00 | 4 | 128590.6 |
| O43684 | F | Mitotic checkpoint protein BUB3 | 1000.00 | 51 | 0.00 | 4 | 29015.3 |
| P61160 | F | Actin-related protein 2 | 1000.00 | 48 | 0.00 | 4 | 19530.8 |
| Q9Y5S9 | F | RNA-binding protein 8A | 1000.00 | 43 | 0.00 | 4 | 40888.4 |
| O75947 | F | ATP synthase subunit d, mitochondrial | 1000.00 | 38 | 0.00 | 4 | 16782.1 |
| Q08752 | F | Peptidyl-prolyl cis-trans isomerase D | 1000.00 | 26 | 0.00 | 4 | 28159.5 |
| Q9NQG5 | F | Regulation of nuclear pre-mRNA domain-containing protein 1B | 1000.00 | 18 | 0.00 | 4 | 35486.7 |
| P00568 | F | Adenylate kinase isoenzyme 1 | 1000.00 | 16 | 0.00 | 4 | 37598.4 |
| P26440 | F | Isovaleryl-CoA dehydrogenase, mitochondrial | 1000.00 | 15 | 0.00 | 3 | 22893.6 |
| Q3MHD2 | F | Protein LSM12 homolog | 1000.00 | 14 | 0.00 | 4 | 69184.7 |
| P21108 | F | Ribose-phosphate pyrophosphokinase 3 | 1000.00 | 5 | 0.00 | 4 | 0.0 |
| Q9Y450 | F | HBS1-like protein | 1000.00 | 120 | 0.00 | 4 | 8226.2 |
| Q8IX12 | F | Cell division cycle and apoptosis regulator protein 1 | 1000.00 | 108 | 0.00 | 4 | 5699.3 |
| P33991 | F | DNA replication licensing factor MCM4 | 1000.00 | 96 | 0.00 | 4 | 57897.2 |
| Q96QK1 | F | Vacuolar protein sorting-associated protein 35 | 1000.00 | 78 | 0.00 | 4 | 30155.4 |
| P04181 | F | Ornithine aminotransferase, mitochondrial | 1000.00 | 68 | 0.00 | 4 | 17391.4 |
| P06493 | F | Cyclin-dependent kinase 1 | 1000.00 | 57 | 0.00 | 4 | 60375.1 |

FIG. 16 (cont'd)

| | | | | | | | |
|---|---|---|---|---|---|---|---|
| P49821 | F | NADH dehydrogenase [ubiquinone] flavoprotein 1, mitochondrial | 1000.00 | 44 | 0.00 | 4 | 8924.9 |
| P22059 | F | Oxysterol-binding protein 1 | 1000.00 | 41 | 0.00 | 4 | 0.0 |
| Q9Y285 | F | Phenylalanine--tRNA ligase alpha subunit | 1000.00 | 37 | 0.00 | 4 | 8320.0 |
| O00186 | F | Syntaxin-binding protein 3 | 1000.00 | 34 | 0.00 | 4 | 32924.2 |
| Q9BWS9 | F | Chitinase domain-containing protein 1 | 1000.00 | 28 | 0.00 | 3 | 0.0 |
| Q99986 | F | Serine/threonine-protein kinase VRK1 | 1000.00 | 25 | 0.00 | 4 | 18841.4 |
| Q8IYB8 | F | ATP-dependent RNA helicase SUPV3L1, mitochondrial | 1000.00 | 24 | 0.00 | 4 | 0.0 |
| P62263 | F | 40S ribosomal protein S14 | 1000.00 | 19 | 0.00 | 4 | 91546.8 |
| O43765 | F | Small glutamine-rich tetratricopeptide repeat-containing protein alpha | 1000.00 | 18 | 0.00 | 4 | 25256.3 |
| P58546 | F | Myotrophin | 1000.00 | 4 | 0.00 | 4 | 69182.3 |
| P29692 | F | Elongation factor 1-delta | 1000.00 | 183 | 0.00 | 4 | 76522.3 |
| Q13409 | F | Cytoplasmic dynein 1 intermediate chain 2 | 1000.00 | 168 | 0.00 | 4 | 14857.6 |
| P08243 | F | Asparagine synthetase [glutamine-hydrolyzing] | 1000.00 | 140 | 0.00 | 4 | 3930.8 |
| Q12765 | F | Secernin-1 | 1000.00 | 137 | 0.00 | 4 | 12312.8 |
| P26232 | F | Catenin alpha-2 | 1000.00 | 130 | 0.00 | 4 | 0.0 |
| Q96I24 | F | Far upstream element-binding protein 3 | 1000.00 | 112 | 0.00 | 4 | 51414.4 |
| O60828 | F | Polyglutamine-binding protein 1 | 1000.00 | 104 | 0.00 | 4 | 32184.2 |
| O00273 | F | DNA fragmentation factor subunit alpha | 1000.00 | 96 | 0.00 | 4 | 20267.0 |
| Q86WJ1 | F | Chromodomain-helicase-DNA-binding protein 1-like | 1000.00 | 96 | 0.00 | 4 | 1303.0 |
| Q9Y2Z0 | F | Suppressor of G2 allele of SKP1 homolog | 1000.00 | 76 | 0.00 | 4 | 2405.9 |
| Q9UJU6 | F | Drebrin-like protein | 1000.00 | 75 | 0.00 | 4 | 0.0 |
| Q7Z4V5 | F | Hepatoma-derived growth factor-related protein 2 | 1000.00 | 73 | 0.00 | 4 | 30370.0 |
| Q9Y5A7 | F | NEDD8 ultimate buster 1 | 1000.00 | 73 | 0.00 | 4 | 8371.6 |
| Q9UPN9 | F | E3 ubiquitin-protein ligase TRIM33 | 1000.00 | 71 | 0.00 | 4 | 0.0 |
| O14964 | F | Hepatocyte growth factor-regulated tyrosine kinase substrate | 1000.00 | 70 | 0.00 | 4 | 22365.0 |
| Q8NEY8 | F | Periphilin-1 | 1000.00 | 68 | 0.00 | 4 | 0.0 |
| Q14738 | F | Serine/threonine-protein phosphatase 2A 56 kDa regulatory subunit delta isoform | 1000.00 | 66 | 0.00 | 4 | 0.0 |
| Q96ST3 | F | Paired amphipathic helix protein Sin3a | 1000.00 | 66 | 0.00 | 4 | 9528.4 |
| O60664 | F | Perilipin-3 | 1000.00 | 62 | 0.00 | 4 | 14738.0 |
| O96017 | F | Serine/threonine-protein kinase Chk2 | 1000.00 | 59 | 0.00 | 4 | 5272.9 |

FIG. 16 (cont'd)

| P25440 | F | Bromodomain-containing protein 2 | 1000.00 | 58 | 0.00 | 4 | 0.0 |
|---|---|---|---|---|---|---|---|
| Q9NQX3 | F | Gephyrin | 1000.00 | 56 | 0.00 | 4 | 0.0 |
| Q14677 | F | Clathrin interactor 1 | 1000.00 | 54 | 0.00 | 4 | 0.0 |
| Q9UQ16 | F | Dynamin-3 | 1000.00 | 52 | 0.00 | 4 | 0.0 |
| Q86UE4 | F | Protein LYRIC | 1000.00 | 47 | 0.00 | 4 | 14110.2 |
| Q13404 | F | Ubiquitin-conjugating enzyme E2 variant 1 | 1000.00 | 45 | 0.00 | 3 | 1316.3 |
| Q9NQI0 | F | Probable ATP-dependent RNA helicase DDX4 | 1000.00 | 45 | 0.00 | 4 | 0.0 |
| Q9Y4W6 | F | AFG3-like protein 2 | 1000.00 | 45 | 0.00 | 3 | 1935.6 |
| Q9BY77 | F | Polymerase delta-interacting protein 3 | 1000.00 | 43 | 0.00 | 4 | 15675.4 |
| Q9UBB9 | F | Tuftelin-interacting protein 11 | 1000.00 | 43 | 0.00 | 4 | 0.0 |
| P25788 | F | Proteasome subunit alpha type-3 | 1000.00 | 42 | 0.00 | 3 | 0.0 |
| P63208 | F | S-phase kinase-associated protein 1 | 1000.00 | 41 | 0.00 | 4 | 16034.3 |
| Q8TED0 | F | U3 small nucleolar RNA-associated protein 15 homolog | 1000.00 | 38 | 0.00 | 4 | 0.0 |
| Q99541 | F | Perilipin-2 | 1000.00 | 35 | 0.00 | 4 | 62028.0 |
| Q9NYL9 | F | Tropomodulin-3 | 1000.00 | 32 | 0.00 | 4 | 125381.6 |
| P41240 | F | Tyrosine-protein kinase CSK | 1000.00 | 31 | 0.00 | 4 | 8674.5 |
| P29966 | F | Myristoylated alanine-rich C-kinase substrate | 1000.00 | 28 | 0.00 | 4 | 140919.6 |
| Q96ME7 | F | Zinc finger protein 512 | 1000.00 | 28 | 0.00 | 4 | 7243.7 |
| Q9H269 | F | Vacuolar protein sorting-associated protein 16 homolog | 1000.00 | 28 | 0.00 | 4 | 0.0 |
| Q9NPJ3 | F | Acyl-coenzyme A thioesterase 13 | 1000.00 | 28 | 0.00 | 4 | 0.0 |
| O00264 | F | Membrane-associated progesterone receptor component 1 | 1000.00 | 27 | 0.00 | 4 | 84932.9 |
| P61326 | F | Protein mago nashi homolog | 1000.00 | 26 | 0.00 | 4 | 74180.4 |
| O60508 | F | Pre-mRNA-processing factor 17 | 1000.00 | 25 | 0.00 | 4 | 0.0 |
| O95817 | F | BAG family molecular chaperone regulator 3 | 1000.00 | 25 | 0.00 | 4 | 77484.2 |
| Q13011 | F | Delta(3,5)-Delta(2,4)-dienoyl-CoA isomerase, mitochondrial | 1000.00 | 25 | 0.00 | 4 | 133775.8 |
| Q8WWK9 | F | Cytoskeleton-associated protein 2 | 1000.00 | 25 | 0.00 | 4 | 0.0 |
| P31153 | F | S-adenosylmethionine synthase isoform type-2 | 1000.00 | 24 | 0.00 | 4 | 46962.8 |
| P47755 | F | F-actin-capping protein subunit alpha-2 | 1000.00 | 24 | 0.00 | 4 | 8042.6 |
| Q2NL82 | F | Pre-rRNA-processing protein TSR1 homolog | 1000.00 | 24 | 0.00 | 4 | 43029.7 |
| Q9UBV2 | F | Protein sel-1 homolog 1 | 1000.00 | 24 | 0.00 | 4 | 0.0 |
| Q00796 | F | Sorbitol dehydrogenase | 1000.00 | 23 | 0.00 | 4 | 17053.8 |
| Q9NRX4 | F | 14 kDa phosphohistidine phosphatase | 1000.00 | 23 | 0.00 | 4 | 88524.0 |

FIG. 16 (cont'd)

| | | | | | | | |
|---|---|---|---|---|---|---|---|
| P82979 | F | SAP domain-containing ribonucleoprotein | 1000.00 | 22 | 0.00 | 4 | 0.0 |
| Q7L2H7 | F | Eukaryotic translation initiation factor 3 subunit M | 1000.00 | 22 | 0.00 | 4 | 85795.4 |
| Q7Z7H5 | F | Transmembrane emp24 domain-containing protein 4 | 1000.00 | 22 | 0.00 | 4 | 0.0 |
| P62888 | F | 60S ribosomal protein L30 | 1000.00 | 21 | 0.00 | 4 | 407262.0 |
| Q9P035 | F | Very-long-chain (3R)-3-hydroxyacyl-[acyl-carrier protein] dehydratase 3 | 1000.00 | 21 | 0.00 | 4 | 164256.3 |
| Q969V3 | F | Nicalin | 1000.00 | 20 | 0.00 | 3 | 0.0 |
| Q9H9P8 | F | L-2-hydroxyglutarate dehydrogenase, mitochondrial | 1000.00 | 20 | 0.00 | 4 | 0.0 |
| Q15631 | F | Translin | 1000.00 | 18 | 0.00 | 4 | 92866.3 |
| Q13868 | F | Exosome complex component RRP4 | 1000.00 | 17 | 0.00 | 4 | 0.0 |
| Q92820 | F | Gamma-glutamyl hydrolase | 1000.00 | 17 | 0.00 | 4 | 46199.3 |
| P47985 | F | Cytochrome b-c1 complex subunit Rieske, mitochondrial | 1000.00 | 15 | 0.00 | 4 | 117839.4 |
| Q13685 | F | Angio-associated migratory cell protein | 1000.00 | 15 | 0.00 | 4 | 15690.4 |
| Q9NZZ3 | F | Charged multivesicular body protein 5 | 1000.00 | 15 | 0.00 | 4 | 30551.6 |
| O60493 | F | Sorting nexin-3 | 1000.00 | 14 | 0.00 | 4 | 5173.3 |
| P62942 | F | Peptidyl-prolyl cis-trans isomerase FKBP1A | 1000.00 | 14 | 0.00 | 4 | 196532.1 |
| Q96GX9 | F | Methylthioribulose-1-phosphate dehydratase | 1000.00 | 14 | 0.00 | 3 | 9436.0 |
| Q9BSD7 | F | Cancer-related nucleoside-triphosphatase | 1000.00 | 14 | 0.00 | 4 | 0.0 |
| Q9BX68 | F | Histidine triad nucleotide-binding protein 2, mitochondrial | 1000.00 | 14 | 0.00 | 4 | 48506.1 |
| P62318 | F | Small nuclear ribonucleoprotein Sm D3 | 1000.00 | 12 | 0.00 | 4 | 111404.8 |
| Q15417 | F | Calponin-3 | 1000.00 | 12 | 0.00 | 4 | 70468.0 |
| Q9UBQ5 | F | Eukaryotic translation initiation factor 3 subunit K | 1000.00 | 12 | 0.00 | 4 | 8896.8 |
| P49643 | F | DNA primase large subunit | 1000.00 | 11 | 0.00 | 4 | 3097.6 |
| Q99598 | F | Translin-associated protein X | 1000.00 | 11 | 0.00 | 4 | 70813.1 |
| Q9H7B2 | F | Ribosome production factor 2 homolog | 1000.00 | 11 | 0.00 | 4 | 63162.0 |
| O43347 | F | RNA-binding protein Musashi homolog 1 | 1000.00 | 10 | 0.00 | 3 | 0.0 |
| P62277 | F | 40S ribosomal protein S13 | 1000.00 | 10 | 0.00 | 4 | 51840.6 |
| Q9UMY4 | F | Sorting nexin-12 | 1000.00 | 10 | 0.00 | 4 | 15163.5 |
| P05387 | F | 60S acidic ribosomal protein P2 | 1000.00 | 9 | 0.00 | 4 | 0.0 |
| P52815 | F | 39S ribosomal protein L12, mitochondrial | 1000.00 | 9 | 0.00 | 4 | 33450.7 |
| P62857 | F | 40S ribosomal protein S28 | 1000.00 | 9 | 0.00 | 4 | 190972.7 |
| Q8N183 | F | Mimitin, mitochondrial | 1000.00 | 9 | 0.00 | 3 | 61424.0 |

FIG. 16 (cont'd)

| | | | | | | | |
|---|---|---|---|---|---|---|---|
| Q8N5M1 | F | ATP synthase mitochondrial F1 complex assembly factor 2 | 1000.00 | 9 | 0.00 | 4 | 0.0 |
| Q96DB5 | F | Regulator of microtubule dynamics protein 1 | 1000.00 | 9 | 0.00 | 4 | 10557.3 |
| Q9HAV0 | F | Guanine nucleotide-binding protein subunit beta-4 | 1000.00 | 9 | 0.00 | 4 | 0.0 |
| O60869 | F | Endothelial differentiation-related factor 1 | 1000.00 | 8 | 0.00 | 4 | 125550.8 |
| O60551 | F | Glycylpeptide N-tetradecanoyltransferase 2 | 1000.00 | 7 | 0.00 | 4 | 58066.3 |
| O75526 | F | RNA-binding motif protein, X-linked-like-2 | 1000.00 | 7 | 0.00 | 3 | 0.0 |
| Q969R2 | F | Oxysterol-binding protein 2 | 1000.00 | 7 | 0.00 | 4 | 0.0 |
| P62745 | F | Rho-related GTP-binding protein RhoB | 1000.00 | 4 | 0.00 | 4 | 0.0 |
| Q5VWX1 | F | KH domain-containing, RNA-binding, signal transduction-associated protein 2 | 1000.00 | 4 | 0.00 | 4 | 0.0 |
| Q9NR56 | F | Muscleblind-like protein 1 | 1000.00 | 108 | 0.00 | 3 | 13760.6 |
| O60701 | F | UDP-glucose 6-dehydrogenase | 1000.00 | 98 | 0.00 | 3 | 3004.2 |
| Q5SSJ5 | F | Heterochromatin protein 1-binding protein 3 | 1000.00 | 85 | 0.00 | 3 | 11585.4 |
| P51398 | F | 28S ribosomal protein S29, mitochondrial | 1000.00 | 81 | 0.00 | 3 | 0.0 |
| P13591 | F | Neural cell adhesion molecule 1 | 1000.00 | 80 | 0.00 | 3 | 0.0 |
| Q86X55 | F | Histone-arginine methyltransferase CARM1 | 1000.00 | 70 | 0.00 | 3 | 6097.4 |
| Q5VT25 | F | Serine/threonine-protein kinase MRCK alpha | 1000.00 | 66 | 0.00 | 3 | 0.0 |
| Q14126 | F | Desmoglein-2 | 1000.00 | 65 | 0.00 | 3 | 25585.1 |
| Q9H410 | F | Kinetochore-associated protein DSN1 homolog | 1000.00 | 64 | 0.00 | 3 | 0.0 |
| O95782 | F | AP-2 complex subunit alpha-1 | 1000.00 | 58 | 0.00 | 3 | 0.0 |
| P42566 | F | Epidermal growth factor receptor substrate 15 | 1000.00 | 56 | 0.00 | 3 | 4375.2 |
| Q6WCQ1 | F | Myosin phosphatase Rho-interacting protein | 1000.00 | 51 | 0.00 | 3 | 0.0 |
| Q96G74 | F | OTU domain-containing protein 5 | 1000.00 | 46 | 0.00 | 3 | 0.0 |
| Q8IZ21 | F | Phosphatase and actin regulator 4 | 1000.00 | 42 | 0.00 | 3 | 0.0 |
| Q9ULV4 | F | Coronin-1C | 1000.00 | 39 | 0.00 | 3 | 4034.0 |
| P20839 | F | Inosine-5'-monophosphate dehydrogenase 1 | 1000.00 | 32 | 0.00 | 3 | 0.0 |
| Q7Z3T8 | F | Zinc finger FYVE domain-containing protein 16 | 1000.00 | 32 | 0.00 | 3 | 0.0 |
| Q9H910 | F | Hematological and neurological expressed 1-like protein | 1000.00 | 30 | 0.00 | 3 | 43644.7 |

FIG. 16 (cont'd)

| | | | | | | | |
|---|---|---|---|---|---|---|---|
| Q9UN86 | F | Ras GTPase-activating protein-binding protein 2 | 1000.00 | 30 | 0.00 | 3 | 50936.7 |
| Q9Y5S2 | F | Serine/threonine-protein kinase MRCK beta | 1000.00 | 30 | 0.00 | 3 | 0.0 |
| Q9Y6X4 | F | Soluble lamin-associated protein of 75 kDa | 1000.00 | 29 | 0.00 | 3 | 0.0 |
| P42126 | F | Enoyl-CoA delta isomerase 1, mitochondrial | 1000.00 | 28 | 0.00 | 3 | 16751.3 |
| P52594 | F | Arf-GAP domain and FG repeat-containing protein 1 | 1000.00 | 28 | 0.00 | 3 | 0.0 |
| Q9BXW7 | F | Cat eye syndrome critical region protein 5 | 1000.00 | 28 | 0.00 | 3 | 8455.8 |
| Q9UEE9 | F | Craniofacial development protein 1 | 1000.00 | 27 | 0.00 | 3 | 17859.3 |
| O75528 | F | Transcriptional adapter 3 | 1000.00 | 26 | 0.00 | 3 | 0.0 |
| Q9P2B2 | F | Prostaglandin F2 receptor negative regulator | 1000.00 | 26 | 0.00 | 3 | 0.0 |
| Q9UIJ7 | F | GTP:AMP phosphotransferase AK3, mitochondrial | 1000.00 | 26 | 0.00 | 3 | 0.0 |
| P51572 | F | B-cell receptor-associated protein 31 | 1000.00 | 25 | 0.00 | 3 | 11594.4 |
| Q9H9A6 | F | Leucine-rich repeat-containing protein 40 | 1000.00 | 25 | 0.00 | 3 | 0.0 |
| Q9P2K5 | F | Myelin expression factor 2 | 1000.00 | 25 | 0.00 | 3 | 0.0 |
| Q96HS1 | F | Serine/threonine-protein phosphatase PGAM5, mitochondrial | 1000.00 | 23 | 0.00 | 3 | 2866.2 |
| Q8TDD1 | F | ATP-dependent RNA helicase DDX54 | 1000.00 | 22 | 0.00 | 3 | 0.0 |
| Q9NQT5 | F | Exosome complex component RRP40 | 1000.00 | 22 | 0.00 | 3 | 0.0 |
| Q9UNN5 | F | FAS-associated factor 1 | 1000.00 | 22 | 0.00 | 3 | 3932.6 |
| P19784 | F | Casein kinase II subunit alpha' | 1000.00 | 21 | 0.00 | 3 | 0.0 |
| Q15022 | F | Polycomb protein SUZ12 | 1000.00 | 19 | 0.00 | 3 | 0.0 |
| Q7Z739 | F | YTH domain family protein 3 | 1000.00 | 19 | 0.00 | 3 | 0.0 |
| Q96CX2 | F | BTB/POZ domain-containing protein KCTD12 | 1000.00 | 19 | 0.00 | 3 | 0.0 |
| P60866 | F | 40S ribosomal protein S20 | 1000.00 | 18 | 0.00 | 3 | 64829.3 |
| O96008 | F | Mitochondrial import receptor subunit TOM40 homolog | 1000.00 | 17 | 0.00 | 3 | 0.0 |
| Q92947 | F | Glutaryl-CoA dehydrogenase, mitochondrial | 1000.00 | 17 | 0.00 | 3 | 11355.4 |
| Q9NVM9 | F | Protein asunder homolog | 1000.00 | 17 | 0.00 | 3 | 0.0 |
| P46781 | F | 40S ribosomal protein S9 | 1000.00 | 16 | 0.00 | 3 | 24507.4 |
| Q96H79 | F | Zinc finger CCCH-type antiviral protein 1-like | 1000.00 | 16 | 0.00 | 3 | 10269.8 |
| Q9NYK5 | F | 39S ribosomal protein L39, mitochondrial | 1000.00 | 16 | 0.00 | 3 | 0.0 |
| P61106 | F | Ras-related protein Rab-14 | 1000.00 | 15 | 0.00 | 3 | 0.0 |
| Q01081 | F | Splicing factor U2AF 35 kDa subunit | 1000.00 | 15 | 0.00 | 3 | 21021.6 |

FIG. 16 (cont'd)

| | | | | | | | |
|---|---|---|---|---|---|---|---|
| Q8N0Y7 | F | Probable phosphoglycerate mutase 4 | 1000.00 | 15 | 0.00 | 3 | 0.0 |
| Q9NXV6 | F | CDKN2A-interacting protein | 1000.00 | 15 | 0.00 | 3 | 0.0 |
| Q8IXQ4 | F | GPALPP motifs-containing protein 1 | 1000.00 | 14 | 0.00 | 3 | 23527.3 |
| Q9NRL3 | F | Striatin-4 | 1000.00 | 14 | 0.00 | 3 | 0.0 |
| Q9UGP8 | F | Translocation protein SEC63 homolog | 1000.00 | 14 | 0.00 | 3 | 0.0 |
| Q9Y3C6 | F | Peptidyl-prolyl cis-trans isomerase-like 1 | 1000.00 | 14 | 0.00 | 3 | 34760.6 |
| Q9Y3Y2 | F | Chromatin target of PRMT1 protein | 1000.00 | 14 | 0.00 | 3 | 9951.0 |
| O00629 | F | Importin subunit alpha-3 | 1000.00 | 13 | 0.00 | 3 | 0.0 |
| P48637 | F | Glutathione synthetase | 1000.00 | 13 | 0.00 | 3 | 0.0 |
| Q9H000 | F | Probable E3 ubiquitin-protein ligase makorin-2 | 1000.00 | 13 | 0.00 | 3 | 38568.5 |
| P15374 | F | Ubiquitin carboxyl-terminal hydrolase isozyme L3 | 1000.00 | 12 | 0.00 | 3 | 0.0 |
| Q13951 | F | Core-binding factor subunit beta | 1000.00 | 12 | 0.00 | 3 | 0.0 |
| P55145 | F | Mesencephalic astrocyte-derived neurotrophic factor | 1000.00 | 11 | 0.00 | 3 | 0.0 |
| Q96J01 | F | THO complex subunit 3 | 1000.00 | 11 | 0.00 | 3 | 0.0 |
| O43447 | F | Peptidyl-prolyl cis-trans isomerase H | 1000.00 | 10 | 0.00 | 3 | 73443.9 |
| O75351 | F | Vacuolar protein sorting-associated protein 4B | 1000.00 | 10 | 0.00 | 3 | 0.0 |
| P31749 | F | RAC-alpha serine/threonine-protein kinase | 1000.00 | 10 | 0.00 | 3 | 0.0 |
| P61289 | F | Proteasome activator complex subunit 3 | 1000.00 | 10 | 0.00 | 3 | 7012.8 |
| Q96K17 | F | Transcription factor BTF3 homolog 4 | 1000.00 | 10 | 0.00 | 3 | 55791.6 |
| Q9BRX8 | F | Redox-regulatory protein FAM213A | 1000.00 | 10 | 0.00 | 3 | 0.0 |
| Q9BYG3 | F | MKI67 FHA domain-interacting nucleolar phosphoprotein | 1000.00 | 10 | 0.00 | 3 | 0.0 |
| Q9NVA1 | F | Ubiquinol-cytochrome-c reductase complex assembly factor 1 | 1000.00 | 10 | 0.00 | 3 | 0.0 |
| O14562 | F | Ubiquitin domain-containing protein UBFD1 | 1000.00 | 9 | 0.00 | 3 | 0.0 |
| P09525 | F | Annexin A4 | 1000.00 | 9 | 0.00 | 3 | 0.0 |
| P13984 | F | General transcription factor IIF subunit 2 | 1000.00 | 9 | 0.00 | 3 | 0.0 |
| P41567 | F | Eukaryotic translation initiation factor 1 | 1000.00 | 9 | 0.00 | 3 | 0.0 |
| Q96C36 | F | Pyrroline-5-carboxylate reductase 2 | 1000.00 | 9 | 0.00 | 3 | 0.0 |
| Q9BVG4 | F | Protein PBDC1 | 1000.00 | 9 | 0.00 | 3 | 19019.0 |
| A8MWD9 | F | Small nuclear ribonucleoprotein G-like protein | 1000.00 | 8 | 0.00 | 3 | 0.0 |
| O15260 | F | Surfeit locus protein 4 | 1000.00 | 8 | 0.00 | 3 | 0.0 |
| P30260 | F | Cell division cycle protein 27 homolog | 1000.00 | 8 | 0.00 | 3 | 0.0 |

FIG. 16 (cont'd)

| | | | | | | | |
|---|---|---|---|---|---|---|---|
| P55283 | F | Cadherin-4 | 1000.00 | 8 | 0.00 | 3 | 0.0 |
| P61018 | F | Ras-related protein Rab-4B | 1000.00 | 8 | 0.00 | 3 | 0.0 |
| P62314 | F | Small nuclear ribonucleoprotein Sm D1 | 1000.00 | 8 | 0.00 | 3 | 76033.1 |
| P78318 | F | Immunoglobulin-binding protein 1 | 1000.00 | 8 | 0.00 | 3 | 9921.9 |
| Q7L9L4 | F | MOB kinase activator 1B | 1000.00 | 8 | 0.00 | 3 | 0.0 |
| Q95604 | F | HLA class I histocompatibility antigen, Cw-17 alpha chain | 1000.00 | 8 | 0.00 | 3 | 0.0 |
| Q9NZJ6 | F | Hexaprenyldihydroxybenzoate methyltransferase, mitochondrial | 1000.00 | 8 | 0.00 | 3 | 0.0 |
| Q9UFN0 | F | Protein NipSnap homolog 3A | 1000.00 | 8 | 0.00 | 3 | 0.0 |
| O15173 | F | Membrane-associated progesterone receptor component 2 | 1000.00 | 7 | 0.00 | 3 | 0.0 |
| O95336 | F | 6-phosphogluconolactonase | 1000.00 | 7 | 0.00 | 3 | 31731.4 |
| P28070 | F | Proteasome subunit beta type-4 | 1000.00 | 7 | 0.00 | 3 | 0.0 |
| Q9BYD6 | F | 39S ribosomal protein L1, mitochondrial | 1000.00 | 7 | 0.00 | 3 | 0.0 |
| Q9H8H3 | F | Methyltransferase-like protein 7A | 1000.00 | 7 | 0.00 | 3 | 0.0 |
| Q9NWS8 | F | Required for meiotic nuclear division protein 1 homolog | 1000.00 | 7 | 0.00 | 3 | 0.0 |
| Q9NX40 | F | OCIA domain-containing protein 1 | 1000.00 | 7 | 0.00 | 3 | 0.0 |
| Q9Y5M8 | F | Signal recognition particle receptor subunit beta | 1000.00 | 7 | 0.00 | 3 | 0.0 |
| P10314 | F | HLA class I histocompatibility antigen, A-32 alpha chain | 1000.00 | 6 | 0.00 | 3 | 0.0 |
| P16189 | F | HLA class I histocompatibility antigen, A-31 alpha chain | 1000.00 | 6 | 0.00 | 3 | 0.0 |
| P16190 | F | HLA class I histocompatibility antigen, A-33 alpha chain | 1000.00 | 6 | 0.00 | 3 | 0.0 |
| P18462 | F | HLA class I histocompatibility antigen, A-25 alpha chain | 1000.00 | 6 | 0.00 | 3 | 0.0 |
| P30450 | F | HLA class I histocompatibility antigen, A-26 alpha chain | 1000.00 | 6 | 0.00 | 3 | 0.0 |
| P30453 | F | HLA class I histocompatibility antigen, A-34 alpha chain | 1000.00 | 6 | 0.00 | 3 | 0.0 |
| P30456 | F | HLA class I histocompatibility antigen, A-43 alpha chain | 1000.00 | 6 | 0.00 | 3 | 0.0 |
| P30457 | F | HLA class I histocompatibility antigen, A-66 alpha chain | 1000.00 | 6 | 0.00 | 3 | 0.0 |
| P30459 | F | HLA class I histocompatibility antigen, A-74 alpha chain | 1000.00 | 6 | 0.00 | 3 | 0.0 |
| P30504 | F | HLA class I histocompatibility antigen, Cw-4 alpha chain | 1000.00 | 6 | 0.00 | 3 | 0.0 |
| P30512 | F | HLA class I histocompatibility antigen, A-29 alpha chain | 1000.00 | 6 | 0.00 | 3 | 0.0 |

FIG. 16 (cont'd)

| | | | | | | | |
|---|---|---|---|---|---|---|---|
| P62308 | F | Small nuclear ribonucleoprotein G | 1000.00 | 6 | 0.00 | 3 | 0.0 |
| Q09160 | F | HLA class I histocompatibility antigen, A-80 alpha chain | 1000.00 | 6 | 0.00 | 3 | 0.0 |
| Q8WU68 | F | Splicing factor U2AF 26 kDa subunit | 1000.00 | 6 | 0.00 | 3 | 0.0 |
| Q8WVY7 | F | Ubiquitin-like domain-containing CTD phosphatase 1 | 1000.00 | 6 | 0.00 | 3 | 52348.5 |
| Q9BRA2 | F | Thioredoxin domain-containing protein 17 | 1000.00 | 6 | 0.00 | 3 | 79891.0 |
| Q9BRL6 | F | Serine/arginine-rich splicing factor 8 | 1000.00 | 6 | 0.00 | 3 | 0.0 |
| Q9GZN8 | F | UPF0687 protein C20orf27 | 1000.00 | 6 | 0.00 | 3 | 0.0 |
| Q9Y5V3 | F | Melanoma-associated antigen D1 | 1000.00 | 6 | 0.00 | 3 | 0.0 |
| O75431 | F | Metaxin-2 | 1000.00 | 5 | 0.00 | 3 | 0.0 |
| O95478 | F | Ribosome biogenesis protein NSA2 homolog | 1000.00 | 5 | 0.00 | 3 | 71473.2 |
| P04222 | F | HLA class I histocompatibility antigen, Cw-3 alpha chain | 1000.00 | 5 | 0.00 | 3 | 0.0 |
| P20338 | F | Ras-related protein Rab-4A | 1000.00 | 5 | 0.00 | 3 | 0.0 |
| P30510 | F | HLA class I histocompatibility antigen, Cw-14 alpha chain | 1000.00 | 5 | 0.00 | 3 | 0.0 |
| Q15006 | F | ER membrane protein complex subunit 2 | 1000.00 | 5 | 0.00 | 3 | 0.0 |
| Q15102 | F | Platelet-activating factor acetylhydrolase IB subunit gamma | 1000.00 | 5 | 0.00 | 3 | 0.0 |
| Q9NQZ2 | F | Something about silencing protein 10 | 1000.00 | 5 | 0.00 | 3 | 10757.7 |
| O43402 | F | ER membrane protein complex subunit 8 | 1000.00 | 4 | 0.00 | 3 | 0.0 |
| P83881 | F | 60S ribosomal protein L36a | 1000.00 | 4 | 0.00 | 3 | 129155.3 |
| Q6UXV4 | F | Apolipoprotein O-like | 1000.00 | 4 | 0.00 | 3 | 0.0 |
| Q96A35 | F | 39S ribosomal protein L24, mitochondrial | 1000.00 | 4 | 0.00 | 3 | 36093.8 |
| Q969Q0 | F | 60S ribosomal protein L36a-like | 1000.00 | 3 | 0.00 | 3 | 0.0 |
| Q9UNL2 | F | Translocon-associated protein subunit gamma | 1000.00 | 3 | 0.00 | 3 | 89988.0 |
| Q92688 | F | Acidic leucine-rich nuclear phosphoprotein 32 family member B | 195.81 | 8 | 0.00 | 4 | 0.0 |
| Q13310 | F | Polyadenylate-binding protein 4 | 178.19 | 6 | 0.00 | 4 | 79345.3 |
| P68036 | F | Ubiquitin-conjugating enzyme E2 L3 | 122.22 | 4 | 0.00 | 3 | 82867.5 |
| P84098 | F | 60S ribosomal protein L19 | 79.61 | 6 | 0.00 | 4 | 395680.0 |
| Q9BXJ9 | F | N-alpha-acetyltransferase 15, NatA auxiliary subunit | 69.46 | 4 | 0.00 | 4 | 22090.8 |
| Q8IYB3 | F | Serine/arginine repetitive matrix protein 1 | 58.84 | 8 | 0.00 | 3 | 64337.3 |
| P15170 | F | Eukaryotic peptide chain release factor GTP-binding subunit ERF3A | 53.75 | 8 | 0.00 | 4 | 50601.5 |
| Q14847 | F | LIM and SH3 domain protein 1 | 53.36 | 4 | 0.00 | 3 | 0.0 |

FIG. 16 (cont'd)

| | | | | | | | |
|---|---|---|---|---|---|---|---|
| Q9UNZ2 | F | NSFL1 cofactor p47 | 50.52 | 6 | 0.00 | 4 | 17563.8 |
| Q96PK6 | F | RNA-binding protein 14 | 49.28 | 18 | 0.00 | 4 | 95395.1 |
| Q99873 | F | Protein arginine N-methyltransferase 1 | 46.71 | 8 | 0.00 | 4 | 62356.0 |
| P26368 | F | Splicing factor U2AF 65 kDa subunit | 38.41 | 8 | 0.00 | 4 | 201293.2 |
| Q9Y237 | F | Peptidyl-prolyl cis-trans isomerase NIMA-interacting 4 | 29.57 | 12 | 0.00 | 4 | 42535.3 |
| O43242 | F | 26S proteasome non-ATPase regulatory subunit 3 | 29.18 | 4 | 0.00 | 4 | 115303.9 |
| Q96FW1 | F | Ubiquitin thioesterase OTUB1 | 27.77 | 4 | 0.00 | 4 | 117194.9 |
| Q13148 | F | TAR DNA-binding protein 43 | 27.06 | 4 | 0.00 | 4 | 34689.0 |
| Q16555 | F | Dihydropyrimidinase-related protein 2 | 26.34 | 4 | 0.00 | 4 | 20114.0 |
| Q9NTK5 | F | Obg-like ATPase 1 | 22.86 | 4 | 0.00 | 4 | 13985.6 |
| Q9HCC0 | F | Methylcrotonoyl-CoA carboxylase beta chain, mitochondrial | 22.80 | 6 | 0.00 | 4 | 6575.0 |
| Q9HCE1 | F | Putative helicase MOV-10 | 22.12 | 4 | 0.00 | 4 | 7452.5 |
| Q96E39 | F | RNA binding motif protein, X-linked-like-1 | 19.95 | 4 | 0.00 | 4 | 0.0 |
| Q8NF91 | F | Nesprin-1 | 19.27 | 12 | 0.00 | 4 | 0.0 |
| P26373 | F | 60S ribosomal protein L13 | 18.41 | 4 | 0.00 | 4 | 100043.3 |
| Q7Z6E9 | F | E3 ubiquitin-protein ligase RBBP6 | 18.14 | 3 | 0.00 | 4 | 6174.5 |
| Q13247 | F | Serine/arginine-rich splicing factor 6 | 17.05 | 6 | 0.00 | 4 | 27065.8 |
| Q13813 | F | Spectrin alpha chain, non-erythrocytic 1 | 14.03 | 18 | 0.00 | 4 | 86893.2 |
| P49915 | F | GMP synthase [glutamine-hydrolyzing] | 13.84 | 6 | 0.00 | 4 | 99978.0 |
| Q14789 | F | Golgin subfamily B member 1 | 11.94 | 12 | 0.00 | 4 | 803.7 |
| Q8WUM0 | F | Nuclear pore complex protein Nup133 | 11.43 | 3 | 0.00 | 4 | 1376.8 |
| Q9UBC2 | F | Epidermal growth factor receptor substrate 15-like 1 | 11.26 | 6 | 0.00 | 4 | 29176.0 |
| Q9NQH7 | F | Probable Xaa-Pro aminopeptidase 3 | 11.07 | 6 | 0.00 | 4 | 9105.9 |
| Q8NE71 | F | ATP-binding cassette sub-family F member 1 | 10.32 | 8 | 0.00 | 4 | 24539.9 |
| Q5JSZ5 | F | Protein PRRC2B | 9.33 | 4 | 0.00 | 4 | 0.0 |
| O95202 | F | LETM1 and EF-hand domain-containing protein 1, mitochondrial | 8.59 | 6 | 0.00 | 4 | 62491.5 |
| P52907 | F | F-actin-capping protein subunit alpha-1 | 7.92 | 4 | 0.00 | 4 | 33269.3 |
| Q7Z7K6 | F | Centromere protein V | 7.01 | 12 | 0.00 | 4 | 49439.0 |
| Q9P2R7 | F | Succinyl-CoA ligase [ADP-forming] subunit beta, mitochondrial | 6.80 | 8 | 0.00 | 4 | 5772.3 |
| Q96I99 | F | Succinyl-CoA ligase [GDP-forming] subunit beta, mitochondrial | 5.50 | 6 | 0.00 | 4 | 73283.5 |
| Q15654 | F | Thyroid receptor-interacting protein 6 | 5.39 | 4 | 0.00 | 4 | 0.0 |
| O96019 | F | Actin-like protein 6A | 5.36 | 8 | 0.00 | 3 | 3875.4 |

\* Silac Directions Quantified: Forward (F) and/or Reverse (R)

FIG. 17

| Uniprot ID | Protein Name | Protein MW | Peptides Identified | % Sequence Coverage | Times Detected | Top3 Score |
|---|---|---|---|---|---|---|
| P05387 | 60S acidic ribosomal protein P2 | 11665.0 | 8 | 92.2 | 10 | 483836 |
| P22626 | Heterogeneous nuclear ribonucleoproteins A2/B1 | 36774.9 | 28 | 85.0 | 10 | 2134718 |
| P60174 | Triosephosphate isomerase | 25386.8 | 16 | 83.1 | 10 | 191864 |
| Q5BKZ1 | DBIRD complex subunit ZNF326 | 53305.7 | 14 | 81.4 | 10 | 53034 |
| P08670 | Vimentin | 53708.8 | 40 | 80.9 | 10 | 1113048 |
| P09651 | Heterogeneous nuclear ribonucleoprotein A1 | 34223.8 | 24 | 79.4 | 10 | 1832798 |
| P06576 | ATP synthase subunit beta, mitochondrial | 56560.0 | 28 | 77.1 | 10 | 587965 |
| P10809 | 60 kDa heat shock protein, mitochondrial | 61225.9 | 49 | 77.0 | 10 | 1562579 |
| P63244 | Guanine nucleotide-binding protein subunit beta-2-like 1 | 35533.0 | 19 | 76.3 | 10 | 226018 |
| P51149 | Ras-related protein Rab-7a | 23774.9 | 14 | 76.3 | 10 | 152622 |
| Q99714 | 3-hydroxyacyl-CoA dehydrogenase type-2 | 26681.6 | 12 | 76.3 | 10 | 145304 |
| P35232 | Prohibitin | 29861.1 | 14 | 75.7 | 10 | 311019 |
| P04181 | Ornithine aminotransferase, mitochondrial | 41007.6 | 18 | 74.8 | 10 | 233137 |
| P60709 | Actin, cytoplasmic 1 | 42079.0 | 31 | 74.4 | 10 | 3998794 |
| P23396 | 40S ribosomal protein S3 | 26859.4 | 18 | 74.1 | 10 | 280460 |
| P15531 | Nucleoside diphosphate kinase A | 18600.8 | 9 | 73.7 | 10 | 23040 |
| P30044 | Peroxiredoxin-5, mitochondrial | 19047.2 | 10 | 73.5 | 10 | 71923 |
| P22392 | Nucleoside diphosphate kinase B | 23888.7 | 12 | 72.4 | 10 | 180200 |
| P62258 | 14-3-3 protein epsilon | 28010.1 | 19 | 71.0 | 10 | 254613 |
| P62937 | Peptidyl-prolyl cis-trans isomerase A | 18240.6 | 13 | 70.9 | 10 | 350689 |
| P25398 | 40S ribosomal protein S12 | 14914.2 | 8 | 70.5 | 10 | 166803 |
| P49006 | MARCKS-related protein | 19585.8 | 6 | 70.3 | 10 | 94871 |
| P63261 | Actin, cytoplasmic 2 | 42135.1 | 30 | 69.9 | 10 | 0 |
| P61604 | 10 kDa heat shock protein, mitochondrial | 10931.7 | 10 | 69.6 | 10 | 659124 |
| P50402 | Emerin | 29050.9 | 11 | 69.3 | 10 | 51543 |
| P07437 | Tubulin beta chain | 50127.2 | 24 | 68.2 | 10 | 486040 |
| O75947 | ATP synthase subunit d, mitochondrial | 17189.3 | 9 | 67.9 | 10 | 164157 |
| P04075 | Fructose-bisphosphate aldolase A | 39876.3 | 17 | 67.9 | 10 | 193818 |
| P68363 | Tubulin alpha-1B chain | 50836.0 | 22 | 67.6 | 10 | 678591 |
| P68371 | Tubulin beta-4B chain | 50287.4 | 23 | 67.4 | 10 | 168285 |
| P45880 | Voltage-dependent anion-selective channel protein 2 | 32277.7 | 15 | 67.0 | 10 | 329669 |
| P60660 | Myosin light polypeptide 6 | 17116.7 | 9 | 66.9 | 10 | 73250 |
| P05386 | 60S acidic ribosomal protein P1 | 11628.0 | 3 | 66.7 | 10 | 543385.5 |
| Q9NS69 | Mitochondrial import receptor subunit TOM22 homolog | 15521.7 | 5 | 66.2 | 10 | 104559 |
| P14866 | Heterogeneous nuclear | 57974.2 | 26 | 65.8 | 10 | 448298 |

FIG. 17 (cont'd)

| | | ribonucleoprotein L | | | | |
|---|---|---|---|---|---|---|
| P63104 | 14-3-3 protein zeta/delta | 27916.2 | 15 | 65.7 | 10 | 217195 |
| P31942 | Heterogeneous nuclear ribonucleoprotein H3 | 26299.1 | 15 | 64.7 | 10 | 203493 |
| Q71U36 | Tubulin alpha-1A chain | 50820.0 | 21 | 64.5 | 10 | 439304 |
| Q13885 | Tubulin beta-2A chain | 50306.3 | 20 | 64.5 | 10 | 157642 |
| Q9BVA1 | Tubulin beta-2B chain | 50409.4 | 20 | 64.5 | 10 | 0 |
| P84077 | ADP-ribosylation factor 1 | 20753.8 | 10 | 64.1 | 10 | 213194 |
| P08107 | Heat shock 70 kDa protein 1A/1B | 67279.9 | 34 | 64.0 | 10 | 654895 |
| P21796 | Voltage-dependent anion-selective channel protein 1 | 30886.7 | 15 | 64.0 | 10 | 290499 |
| P06733 | Alpha-enolase | 42390.8 | 28 | 63.8 | 10 | 429620 |
| Q9H0U4 | Ras-related protein Rab-1B | 22342.3 | 13 | 63.2 | 10 | 166371 |
| P20700 | Lamin-B1 | 66693.6 | 39 | 62.8 | 10 | 289187 |
| Q07021 | Complement component 1 Q subcomponent-binding protein, mitochondrial | 31761.5 | 11 | 62.8 | 10 | 1178724 |
| P07737 | Profilin-1 | 15225.3 | 8 | 62.1 | 10 | 265716 |
| Q12905 | Interleukin enhancer-binding factor 2 | 43290.3 | 16 | 62.1 | 10 | 304900 |
| P24752 | Acetyl-CoA acetyltransferase, mitochondrial | 45484.8 | 16 | 61.8 | 10 | 146574 |
| P11142 | Heat shock cognate 71 kDa protein | 62379.0 | 34 | 61.7 | 10 | 622915.7 |
| P14618 | Pyruvate kinase PKM | 57994.4 | 25 | 61.6 | 10 | 255214 |
| P23528 | Cofilin-1 | 18730.6 | 11 | 61.5 | 10 | 193892 |
| Q99623 | Prohibitin-2 | 31170.0 | 17 | 61.2 | 10 | 270041 |
| P62805 | Histone H4 | 11367.4 | 14 | 61.2 | 10 | 24654960 |
| Q9Y5L4 | Mitochondrial import inner membrane translocase subunit Tim13 | 10728.2 | 7 | 61.1 | 10 | 130090 |
| P26599 | Polypyrimidine tract-binding protein 1 | 58801.8 | 16 | 61.0 | 10 | 366647 |
| P61978 | Heterogeneous nuclear ribonucleoprotein K | 50455.2 | 22 | 60.9 | 10 | 1323490 |
| Q9UJZ1 | Stomatin-like protein 2, mitochondrial | 38648.2 | 14 | 60.4 | 10 | 155633 |
| Q15365 | Poly(rC)-binding protein 1 | 38011.1 | 13 | 60.1 | 10 | 157355 |
| P55072 | Transitional endoplasmic reticulum ATPase | 90006.3 | 37 | 60.1 | 10 | 210496 |
| P62820 | Ras-related protein Rab-1A | 17581.7 | 9 | 60.0 | 10 | 191431 |
| Q04837 | Single-stranded DNA-binding protein, mitochondrial | 17259.7 | 10 | 59.5 | 10 | 265344 |
| Q13162 | Peroxiredoxin-4 | 30768.0 | 11 | 59.4 | 10 | 113355 |
| Q06830 | Peroxiredoxin-1 | 22338.5 | 12 | 59.3 | 10 | 261217 |
| Q12906 | Interleukin enhancer-binding factor 3 | 80654.7 | 32 | 59.2 | 10 | 287900 |
| P07900 | Heat shock protein HSP 90-alpha | 91895.3 | 37 | 59.2 | 10 | 323914 |
| P63241 | Eukaryotic translation initiation factor 5A-1 | 18757.9 | 10 | 59.1 | 10 | 115530 |
| P25705 | ATP synthase subunit alpha, mitochondrial | 57236.2 | 28 | 59.1 | 10 | 576520 |
| P82979 | SAP domain-containing ribonucleoprotein | 23727.9 | 9 | 59.1 | 10 | 101782 |
| P31943 | Heterogeneous nuclear ribonucleoprotein H | 49514.7 | 21 | 59.0 | 10 | 633389.5 |
| P49411 | Elongation factor Tu, mitochondrial | 49883.8 | 21 | 58.9 | 10 | 315477 |
| Q71UI9 | Histone H2A.V | 11521.4 | 5 | 58.8 | 10 | 326748 |

FIG. 17 (cont'd)

| | | | | | | |
|---|---|---|---|---|---|---|
| Q9BQE3 | Tubulin alpha-1C chain | 50579.7 | 21 | 58.8 | 10 | 552580 |
| P08238 | Heat shock protein HSP 90-beta | 83606.5 | 41 | 58.7 | 10 | 938321 |
| P68104 | Elongation factor 1-alpha 1 | 50483.1 | 24 | 58.7 | 10 | 1028420 |
| P61106 | Ras-related protein Rab-14 | 24125.1 | 12 | 58.6 | 10 | 33923 |
| P40926 | Malate dehydrogenase, mitochondrial | 35959.6 | 17 | 58.6 | 10 | 633463 |
| P03246 | E1B protein, small T-antigen | 20785.5 | 9 | 58.5 | 10 | 210492 |
| P04908 | Histone H2A type 1-B/E | 14135.5 | 7 | 58.5 | 10 | 4767602 |
| O00264 | Membrane-associated progesterone receptor component 1 | 21785.2 | 10 | 58.5 | 10 | 125877 |
| Q7L7L0 | Histone H2A type 3 | 14121.5 | 7 | 58.5 | 10 | 0 |
| Q93077 | Histone H2A type 1-C | 14105.5 | 7 | 58.5 | 10 | 0 |
| P34897 | Serine hydroxymethyltransferase, mitochondrial | 55207.5 | 23 | 58.4 | 10 | 255872 |
| P62888 | 60S ribosomal protein L30 | 12955.2 | 6 | 58.3 | 10 | 281964 |
| Q92945 | Far upstream element-binding protein 2 | 73400.6 | 28 | 58.2 | 10 | 236867 |
| P04350 | Tubulin beta-4A chain | 50042.1 | 21 | 58.1 | 10 | 48162 |
| P12004 | Proliferating cell nuclear antigen | 29111.0 | 11 | 57.9 | 10 | 151656 |
| P48047 | ATP synthase subunit O, mitochondrial | 23391.4 | 11 | 57.8 | 10 | 105915 |
| P06748 | Nucleophosmin | 30298.7 | 16 | 57.7 | 10 | 2326268 |
| P62244 | 40S ribosomal protein S15a | 14953.6 | 8 | 57.7 | 10 | 133667 |
| P78371 | T-complex protein 1 subunit beta | 55445.2 | 23 | 57.6 | 10 | 146360 |
| P61326 | Protein mago nashi homolog | 17220.7 | 7 | 57.5 | 10 | 102076.5 |
| P61204 | ADP-ribosylation factor 3 | 20657.8 | 10 | 57.5 | 10 | 0 |
| P54819 | Adenylate kinase 2, mitochondrial | 22754.4 | 14 | 57.3 | 10 | 139674 |
| P38646 | Stress-70 protein, mitochondrial | 73965.8 | 36 | 57.3 | 10 | 383168 |
| P62241 | 40S ribosomal protein S8 | 24490.3 | 10 | 57.2 | 10 | 318491 |
| Q9UQ80 | Proliferation-associated protein 2G4 | 44129.1 | 20 | 57.1 | 10 | 84697 |
| P09874 | Poly [ADP-ribose] polymerase 1 | 113882.4 | 46 | 57.0 | 10 | 593227 |
| P60842 | Eukaryotic initiation factor 4A-I | 43079.4 | 19 | 56.9 | 10 | 233346 |
| Q96A72 | Protein mago nashi homolog 2 | 17332.8 | 7 | 56.8 | 10 | 28669 |
| P14406 | Cytochrome c oxidase subunit 7A2, mitochondrial | 9396.0 | 3 | 56.6 | 10 | 149406 |
| P05141 | ADP/ATP translocase 2 | 33080.4 | 17 | 56.4 | 10 | 653149.1 |
| Q96KK5 | Histone H2A type 1-H | 13906.3 | 6 | 56.3 | 10 | 3525 |
| Q99878 | Histone H2A type 1-J | 13936.3 | 6 | 56.3 | 10 | 0 |
| P12236 | ADP/ATP translocase 3 | 33094.4 | 15 | 56.0 | 10 | 283704.5 |
| Q15233 | Non-POU domain-containing octamer-binding protein | 49163.1 | 23 | 56.0 | 10 | 344411 |
| P62316 | Small nuclear ribonucleoprotein Sm D2 | 13076.8 | 7 | 55.9 | 10 | 202066 |
| P12277 | Creatine kinase B-type | 42929.5 | 16 | 55.9 | 10 | 227338 |
| P37108 | Signal recognition particle 14 kDa protein | 14684.0 | 5 | 55.9 | 10 | 181806 |
| P51991 | Heterogeneous nuclear ribonucleoprotein A3 | 38540.2 | 20 | 55.8 | 10 | 539225 |
| Q16777 | Histone H2A type 2-C | 13988.4 | 7 | 55.8 | 10 | 14162340 |
| Q9BTM1 | Histone H2A.J | 15088.2 | 6 | 55.8 | 10 | 0 |
| Q13185 | Chromobox protein homolog 3 | 20982.5 | 10 | 55.7 | 10 | 272259 |

FIG. 17 (cont'd)

| | | | | | | |
|---|---|---|---|---|---|---|
| P48643 | T-complex protein 1 subunit epsilon | 60127.4 | 20 | 55.6 | 10 | 99198 |
| Q6FI13 | Histone H2A type 2-A | 14095.5 | 7 | 55.4 | 10 | 6878346 |
| P0C0S8 | Histone H2A type 1 | 14091.5 | 6 | 55.4 | 10 | 0 |
| P20671 | Histone H2A type 1-D | 14107.5 | 6 | 55.4 | 10 | 0 |
| P20674 | Cytochrome c oxidase subunit 5A, mitochondrial | 16933.3 | 6 | 55.3 | 10 | 79914 |
| P42704 | Leucine-rich PPR motif-containing protein, mitochondrial | 159102.9 | 59 | 55.2 | 10 | 125662 |
| P40939 | Trifunctional enzyme subunit alpha, mitochondrial | 83741.2 | 29 | 54.8 | 10 | 160354 |
| Q13838 | Spliceosome RNA helicase DDX39B | 50291.7 | 19 | 54.7 | 10 | 457715 |
| P62314 | Small nuclear ribonucleoprotein Sm D1 | 13281.6 | 4 | 54.6 | 10 | 279954 |
| P08865 | 40S ribosomal protein SA | 32968.2 | 12 | 54.6 | 10 | 315535 |
| P30050 | 60S ribosomal protein L12 | 16180.1 | 7 | 54.6 | 10 | 249512 |
| P62979 | Ubiquitin-40S ribosomal protein S27a | 18307.1 | 8 | 54.5 | 10 | 1121175 |
| P04406 | Glyceraldehyde-3-phosphate dehydrogenase | 36224.4 | 16 | 54.3 | 10 | 507437 |
| Q15181 | Inorganic pyrophosphatase | 33116.3 | 10 | 54.3 | 10 | 85077 |
| P43487 | Ran-specific GTPase-activating protein | 23481.2 | 7 | 54.2 | 10 | 216657 |
| P62826 | GTP-binding nuclear protein Ran | 24594.2 | 9 | 54.2 | 10 | 236830 |
| P61247 | 40S ribosomal protein S3a | 30173.1 | 16 | 54.2 | 10 | 209411 |
| P30041 | Peroxiredoxin-6 | 25149.1 | 11 | 54.0 | 10 | 80061 |
| O60361 | Putative nucleoside diphosphate kinase | 15700.2 | 8 | 54.0 | 10 | 0 |
| P35268 | 60S ribosomal protein L22 | 14844.0 | 5 | 53.9 | 10 | 218082 |
| P0C0S5 | Histone H2A.Z | 13552.8 | 5 | 53.9 | 10 | 0 |
| Q15366 | Poly(rC)-binding protein 2 | 37691.5 | 11 | 53.7 | 10 | 209767 |
| Q5VTE0 | Putative elongation factor 1-alpha-like 3 | 50527.3 | 23 | 53.7 | 10 | 0 |
| P02545 | Prelamin-A/C | 68713.7 | 29 | 53.2 | 10 | 94093 |
| P38919 | Eukaryotic initiation factor 4A-III | 47156.3 | 21 | 53.0 | 10 | 183078 |
| P52597 | Heterogeneous nuclear ribonucleoprotein F | 46014.1 | 14 | 53.0 | 10 | 388906.1 |
| P35244 | Replication protein A 14 kDa subunit | 13682.8 | 5 | 52.9 | 9 | 26685 |
| P31946 | 14-3-3 protein beta/alpha | 28080.4 | 11 | 52.9 | 10 | 60142 |
| P62701 | 40S ribosomal protein S4, X isoform | 29825.9 | 15 | 52.9 | 10 | 329836 |
| O75531 | Barrier-to-autointegration factor | 10286.7 | 5 | 52.8 | 10 | 273447 |
| O95292 | Vesicle-associated membrane protein-associated protein B/C | 21742.1 | 9 | 52.7 | 10 | 59949 |
| Q08211 | ATP-dependent RNA helicase A | 83331.9 | 43 | 52.6 | 10 | 354783 |
| P0CW22 | 40S ribosomal protein S17-like | 15607.2 | 10 | 52.6 | 10 | 180057 |
| P08708 | 40S ribosomal protein S17 | 15607.2 | 10 | 52.6 | 10 | 0 |
| P07355 | Annexin A2 | 39764.3 | 16 | 52.5 | 10 | 84628 |
| P16104 | Histone H2AX | 15144.6 | 6 | 52.5 | 10 | 165930 |
| Q9Y265 | RuvB-like 1 | 46548.2 | 19 | 52.4 | 10 | 97806 |
| Q8IUE6 | Histone H2A type 2-B | 13995.3 | 4 | 52.3 | 10 | 26206.5 |
| P62304 | Small nuclear ribonucleoprotein E | 10860.7 | 5 | 52.2 | 10 | 339177 |
| P67809 | Nuclease-sensitive element-binding protein 1 | 35924.2 | 9 | 52.2 | 10 | 255405 |

FIG. 17 (cont'd)

| | | | | | | |
|---|---|---|---|---|---|---|
| P13804 | Electron transfer flavoprotein subunit alpha, mitochondrial | 32837.8 | 10 | 52.1 | 10 | 126410 |
| P62081 | 40S ribosomal protein S7 | 22126.9 | 8 | 52.1 | 10 | 167836 |
| P05388 | 60S acidic ribosomal protein P0 | 34444.7 | 13 | 51.7 | 10 | 344218 |
| O43390 | Heterogeneous nuclear ribonucleoprotein R | 71364.0 | 25 | 51.7 | 10 | 292171 |
| P30101 | Protein disulfide-isomerase A3 | 57181.6 | 23 | 51.7 | 10 | 150648 |
| P62807 | Histone H2B type 1-C/E/F/G/I | 13906.2 | 12 | 51.6 | 10 | 20159700 |
| P33778 | Histone H2B type 1-B | 13950.2 | 12 | 51.6 | 10 | 5255009 |
| O60814 | Histone H2B type 1-K | 13890.2 | 12 | 51.6 | 10 | 0 |
| P06899 | Histone H2B type 1-J | 13904.2 | 12 | 51.6 | 10 | 0 |
| P23527 | Histone H2B type 1-O | 13906.2 | 12 | 51.6 | 10 | 0 |
| P58876 | Histone H2B type 1-D | 13936.2 | 12 | 51.6 | 10 | 0 |
| Q16778 | Histone H2B type 2-E | 13920.2 | 12 | 51.6 | 10 | 0 |
| Q5QNW6 | Histone H2B type 2-F | 14380.8 | 12 | 51.6 | 10 | 0 |
| Q93079 | Histone H2B type 1-H | 13892.1 | 12 | 51.6 | 10 | 0 |
| Q99877 | Histone H2B type 1-N | 13922.2 | 12 | 51.6 | 10 | 0 |
| Q99879 | Histone H2B type 1-M | 13989.3 | 12 | 51.6 | 10 | 0 |
| P42167 | Lamina-associated polypeptide 2, isoforms beta/gamma | 44761.1 | 15 | 51.5 | 10 | 239817 |
| Q13263 | Transcription intermediary factor 1-beta | 85494.5 | 26 | 51.4 | 10 | 107832 |
| P27695 | DNA-(apurinic or apyrimidinic site) lyase | 35953.7 | 11 | 51.3 | 10 | 72474 |
| P84085 | ADP-ribosylation factor 5 | 20643.8 | 7 | 51.1 | 10 | 86137.82 |
| Q9UHX1 | Poly(U)-binding-splicing factor PUF60 | 56888.5 | 19 | 51.1 | 10 | 96753 |
| Q9NR30 | Nucleolar RNA helicase 2 | 84013.9 | 36 | 51.1 | 10 | 261239 |
| O60506 | Heterogeneous nuclear ribonucleoprotein Q | 60817.8 | 24 | 51.0 | 10 | 203321 |
| Q86U42 | Polyadenylate-binding protein 2 | 32237.0 | 9 | 51.0 | 10 | 133635 |
| Q9NR31 | GTP-binding protein SAR1a | 22480.9 | 7 | 51.0 | 10 | 61936 |
| P17844 | Probable ATP-dependent RNA helicase DDX5 | 69661.4 | 27 | 51.0 | 10 | 443848 |
| P62873 | Guanine nucleotide-binding protein G(I)/G(S)/G(T) subunit beta-1 | 38175.4 | 11 | 50.9 | 10 | 140622 |
| P19105 | Myosin regulatory light chain 12A | 19851.2 | 8 | 50.9 | 10 | 59760 |
| P08559 | Pyruvate dehydrogenase E1 component subunit alpha, somatic form, mitochondrial | 44463.2 | 12 | 50.8 | 10 | 121047 |
| Q07955 | Serine/arginine-rich splicing factor 1 | 27591.3 | 14 | 50.8 | 10 | 325751 |
| Q13748 | Tubulin alpha-3C/D chain | 48720.3 | 16 | 50.7 | 10 | 0 |
| Q13242 | Serine/arginine-rich splicing factor 9 | 25656.3 | 13 | 50.7 | 10 | 142482 |
| P27348 | 14-3-3 protein theta | 28049.4 | 13 | 50.6 | 10 | 64464.23 |
| P16989 | Y-box-binding protein 3 | 36352.6 | 11 | 50.6 | 10 | 32224 |
| O14950 | Myosin regulatory light chain 12B | 19836.2 | 8 | 50.6 | 10 | 0 |
| Q99832 | T-complex protein 1 subunit eta | 50961.8 | 20 | 50.5 | 10 | 112575 |
| P30084 | Enoyl-CoA hydratase, mitochondrial | 31843.7 | 13 | 50.3 | 10 | 195422 |
| P04637 | Cellular tumor antigen p53 | 35393.1 | 12 | 50.3 | 10 | 67303 |
| P83916 | Chromobox protein homolog 1 | 21531.9 | 8 | 50.3 | 10 | 132377.1 |
| Q99497 | Protein DJ-1 | 20062.2 | 6 | 50.3 | 10 | 18648 |
| P37802 | Transgelin-2 | 22562.6 | 10 | 50.3 | 10 | 57082.5 |

FIG. 17 (cont'd)

| | | | | | | |
|---|---|---|---|---|---|---|
| Q9UMS4 | Pre-mRNA-processing factor 19 | 55637.1 | 14 | 50.2 | 10 | 174512 |
| P22234 | Multifunctional protein ADE2 | 48246.8 | 16 | 50.1 | 10 | 59268 |
| P62750 | 60S ribosomal protein L23a | 17695.1 | 9 | 50.0 | 10 | 373350 |
| Q9H9B4 | Sideroflexin-1 | 35904.6 | 12 | 50.0 | 10 | 135186 |
| P14625 | Endoplasmin | 92754.2 | 38 | 49.8 | 10 | 245779 |
| P11021 | 78 kDa glucose-regulated protein | 72447.1 | 29 | 49.7 | 10 | 319105.6 |
| P50991 | T-complex protein 1 subunit delta | 56835.2 | 21 | 49.5 | 10 | 110208 |
| O60220 | Mitochondrial import inner membrane translocase subunit Tim8 A | 11226.5 | 4 | 49.5 | 9 | 37542 |
| P18085 | ADP-ribosylation factor 4 | 20624.9 | 8 | 49.4 | 10 | 69412.18 |
| P18754 | Regulator of chromosome condensation | 47070.6 | 13 | 49.4 | 10 | 103179 |
| P10599 | Thioredoxin | 10957.9 | 4 | 49.4 | 10 | 50907 |
| P07195 | L-lactate dehydrogenase B chain | 36923.7 | 15 | 49.4 | 10 | 350583 |
| Q96EL3 | 39S ribosomal protein L53, mitochondrial | 12277.9 | 4 | 49.1 | 4 | 0 |
| P17987 | T-complex protein 1 subunit alpha | 60856.9 | 21 | 49.1 | 10 | 122182 |
| P52272 | Heterogeneous nuclear ribonucleoprotein M | 75853.8 | 34 | 49.1 | 10 | 256246 |
| P61019 | Ras-related protein Rab-2A | 22339.1 | 8 | 49.1 | 10 | 79446 |
| P98179 | Putative RNA-binding protein 3 | 17170.4 | 5 | 49.0 | 10 | 51972 |
| P22087 | rRNA 2'-O-methyltransferase fibrillarin | 33898.3 | 10 | 48.9 | 10 | 142182 |
| P00338 | L-lactate dehydrogenase A chain | 33019.5 | 15 | 48.8 | 10 | 281034 |
| P55795 | Heterogeneous nuclear ribonucleoprotein H2 | 49548.8 | 21 | 48.8 | 10 | 167604.4 |
| Q92979 | Ribosomal RNA small subunit methyltransferase NEP1 | 26948.3 | 8 | 48.8 | 9 | 48081 |
| Q96I24 | Far upstream element-binding protein 3 | 46934.9 | 14 | 48.7 | 10 | 50277 |
| P99999 | Cytochrome c | 11862.8 | 6 | 48.6 | 10 | 82315.5 |
| Q71DI3 | Histone H3.2 | 15445.1 | 7 | 48.5 | 10 | 1941783 |
| P84243 | Histone H3.3 | 15385.0 | 6 | 48.5 | 10 | 92197.59 |
| Q16629 | Serine/arginine-rich splicing factor 7 | 21280.4 | 7 | 48.5 | 10 | 281245 |
| P30048 | Thioredoxin-dependent peroxide reductase, mitochondrial | 28034.8 | 9 | 48.4 | 10 | 395106 |
| P12956 | X-ray repair cross-complementing protein 6 | 70128.3 | 25 | 48.4 | 10 | 152542 |
| P07919 | Cytochrome b-c1 complex subunit 6, mitochondrial | 11023.9 | 2 | 48.4 | 4 | 0 |
| Q96PK6 | RNA-binding protein 14 | 37785.1 | 13 | 48.3 | 10 | 121369 |
| Q9Y5J7 | Mitochondrial import inner membrane translocase subunit Tim9 | 10606.0 | 4 | 48.3 | 2 | 0 |
| P55084 | Trifunctional enzyme subunit beta, mitochondrial | 51579.7 | 18 | 48.1 | 10 | 98049 |
| P32119 | Peroxiredoxin-2 | 22063.0 | 10 | 48.0 | 10 | 0 |
| P61224 | Ras-related protein Rap-1b | 18000.5 | 9 | 47.8 | 10 | 61363 |
| P62333 | 26S protease regulatory subunit 10B | 44458.2 | 12 | 47.8 | 10 | 30516 |
| Q96I99 | Succinyl-CoA ligase [GDP-forming] subunit beta, mitochondrial | 47520.6 | 17 | 47.7 | 10 | 32311 |
| P14854 | Cytochrome c oxidase subunit 6B1 | 10420.5 | 3 | 47.7 | 7 | 17868 |
| P62318 | Small nuclear ribonucleoprotein Sm D3 | 14030.4 | 6 | 47.6 | 10 | 324862.5 |
| P57053 | Histone H2B type F-S | 13944.2 | 10 | 47.6 | 10 | 0 |

FIG. 17 (cont'd)

| | | | | | | |
|---|---|---|---|---|---|---|
| Q99880 | Histone H2B type 1-L | 13952.2 | 11 | 47.6 | 10 | 0 |
| P26641 | Elongation factor 1-gamma | 50461.0 | 18 | 47.6 | 10 | 170927 |
| P18124 | 60S ribosomal protein L7 | 29282.9 | 12 | 47.6 | 10 | 264360 |
| Q96AG4 | Leucine-rich repeat-containing protein 59 | 35329.7 | 13 | 47.6 | 10 | 180783 |
| Q7KZF4 | Staphylococcal nuclease domain-containing protein 1 | 102681.4 | 32 | 47.4 | 10 | 76791 |
| O43852 | Calumenin | 26798.8 | 8 | 47.3 | 10 | 37707 |
| O60828 | Polyglutamine-binding protein 1 | 24658.6 | 4 | 47.3 | 8 | 0 |
| P18669 | Phosphoglycerate mutase 1 | 28918.0 | 9 | 47.2 | 10 | 116832 |
| O00483 | NADH dehydrogenase [ubiquinone] 1 alpha subcomplex subunit 4 | 9426.9 | 4 | 46.9 | 10 | 118840.5 |
| P20290 | Transcription factor BTF3 | 19962.1 | 6 | 46.9 | 10 | 0 |
| Q13595 | Transformer-2 protein homolog alpha | 23195.5 | 7 | 46.9 | 10 | 73303 |
| Q9Y5S9 | RNA-binding protein 8A | 19881.5 | 6 | 46.8 | 10 | 107058 |
| Q9GZT3 | SRA stem-loop-interacting RNA-binding protein, mitochondrial | 12406.1 | 4 | 46.8 | 4 | 0 |
| P27797 | Calreticulin | 48312.7 | 14 | 46.8 | 10 | 255350 |
| Q86V81 | THO complex subunit 4 | 26887.9 | 10 | 46.7 | 10 | 321147 |
| P24534 | Elongation factor 1-beta | 24934.8 | 7 | 46.7 | 10 | 203209.5 |
| Q6PEY2 | Tubulin alpha-3E chain | 50600.0 | 12 | 46.7 | 10 | 0 |
| Q9Y230 | RuvB-like 2 | 51327.8 | 20 | 46.7 | 10 | 77186 |
| P00558 | Phosphoglycerate kinase 1 | 45014.0 | 13 | 46.5 | 10 | 94540 |
| P31930 | Cytochrome b-c1 complex subunit 1, mitochondrial | 53330.2 | 14 | 46.5 | 10 | 152049 |
| P62829 | 60S ribosomal protein L23 | 14979.5 | 6 | 46.4 | 10 | 281601 |
| P62857 | 40S ribosomal protein S28 | 7898.1 | 4 | 46.4 | 10 | 276387 |
| Q7RTV0 | PHD finger-like domain-containing protein 5A | 13146.8 | 4 | 46.4 | 5 | 26379 |
| O43707 | Alpha-actinin-4 | 105310.4 | 31 | 46.3 | 10 | 162915 |
| O00567 | Nucleolar protein 56 | 66449.2 | 19 | 46.3 | 10 | 113935 |
| P62995 | Transformer-2 protein homolog beta | 27914.5 | 7 | 46.3 | 10 | 219816 |
| P17980 | 26S protease regulatory subunit 6A | 49488.8 | 14 | 46.2 | 10 | 27193 |
| Q92841 | Probable ATP-dependent RNA helicase DDX17 | 75077.2 | 33 | 46.2 | 10 | 211467.8 |
| P38159 | RNA-binding motif protein, X chromosome | 35154.8 | 16 | 46.0 | 10 | 452996 |
| Q15836 | Vesicle-associated membrane protein 3 | 11366.1 | 3 | 46.0 | 8 | 0 |
| Q15029 | 116 kDa U5 small nuclear ribonucleoprotein component | 108379.4 | 27 | 46.0 | 10 | 116630 |
| Q9Y277 | Voltage-dependent anion-selective channel protein 3 | 31066.5 | 10 | 45.9 | 10 | 150127 |
| P68133 | Actin, alpha skeletal muscle | 42393.3 | 18 | 45.9 | 10 | 1707962 |
| P18621 | 60S ribosomal protein L17 | 19445.2 | 8 | 45.9 | 10 | 166130 |
| P30405 | Peptidyl-prolyl cis-trans isomerase F, mitochondrial | 22382.4 | 7 | 45.9 | 8 | 0 |
| Q12931 | Heat shock protein 75 kDa, mitochondrial | 80395.3 | 24 | 45.9 | 10 | 272558 |
| P28331 | NADH-ubiquinone oxidoreductase 75 kDa subunit, mitochondrial | 76268.0 | 23 | 45.8 | 10 | 78308 |
| Q02790 | Peptidyl-prolyl cis-trans isomerase FKBP4 | 52089.8 | 18 | 45.8 | 10 | 58560 |

FIG. 17 (cont'd)

| P21964 | Catechol O-methyltransferase | 27670.8 | 8 | 45.7 | 10 | 21774 |
|---|---|---|---|---|---|---|
| P55209 | Nucleosome assembly protein 1-like 1 | 45659.3 | 11 | 45.5 | 10 | 134732 |
| P13010 | X-ray repair cross-complementing protein 5 | 83275.0 | 23 | 45.5 | 10 | 149036 |
| P13639 | Elongation factor 2 | 96307.8 | 33 | 45.5 | 10 | 218889 |
| P00387 | NADH-cytochrome b5 reductase 3 | 34962.8 | 9 | 45.3 | 10 | 81192 |
| P56537 | Eukaryotic translation initiation factor 6 | 27112.4 | 7 | 45.3 | 10 | 102975 |
| P23246 | Splicing factor, proline- and glutamine-rich | 74320.5 | 23 | 45.3 | 10 | 451035 |
| O75367 | Core histone macro-H2A.1 | 39600.9 | 13 | 45.3 | 10 | 155967 |
| P62424 | 60S ribosomal protein L7a | 30166.7 | 13 | 45.1 | 10 | 213545 |
| P14314 | Glucosidase 2 subunit beta | 60271.3 | 16 | 45.1 | 10 | 108670 |
| P62277 | 40S ribosomal protein S13 | 17222.3 | 8 | 45.0 | 10 | 210693 |
| P56385 | ATP synthase subunit e, mitochondrial | 7933.2 | 3 | 44.9 | 8 | 23208 |
| Q13151 | Heterogeneous nuclear ribonucleoprotein A0 | 31011.7 | 10 | 44.9 | 10 | 226157 |
| P39019 | 40S ribosomal protein S19 | 16060.5 | 10 | 44.8 | 10 | 164628 |
| Q02878 | 60S ribosomal protein L6 | 32785.0 | 13 | 44.8 | 10 | 172539 |
| P07237 | Protein disulfide-isomerase | 57515.6 | 19 | 44.7 | 10 | 168164 |
| P46782 | 40S ribosomal protein S5 | 23047.5 | 9 | 44.6 | 10 | 313488 |
| P63220 | 40S ribosomal protein S21 | 9225.5 | 5 | 44.6 | 10 | 95286 |
| P03247 | E1B protein, small T-antigen | 20685.4 | 7 | 44.6 | 10 | 0 |
| O43169 | Cytochrome b5 type B | 16446.2 | 4 | 44.5 | 10 | 224454 |
| P42166 | Lamina-associated polypeptide 2, isoform alpha | 76062.4 | 19 | 44.5 | 10 | 144777 |
| O00148 | ATP-dependent RNA helicase DDX39A | 49642.9 | 14 | 44.5 | 10 | 379707 |
| Q15717 | ELAV-like protein 1 | 36263.0 | 11 | 44.5 | 10 | 175207 |
| P18859 | ATP synthase-coupling factor 6, mitochondrial | 13016.5 | 5 | 44.4 | 6 | 0 |
| P07910 | Heterogeneous nuclear ribonucleoproteins C1/C2 | 29876.0 | 15 | 44.4 | 10 | 1589745 |
| O75533 | Splicing factor 3B subunit 1 | 146572.0 | 38 | 44.3 | 10 | 137433 |
| Q53H12 | Acylglycerol kinase, mitochondrial | 47593.4 | 14 | 44.3 | 10 | 69477 |
| Q9Y5M8 | Signal recognition particle receptor subunit beta | 29930.4 | 8 | 44.3 | 8 | 33049 |
| Q9Y3E5 | Peptidyl-tRNA hydrolase 2, mitochondrial | 19478.7 | 5 | 44.1 | 8 | 0 |
| P50990 | T-complex protein 1 subunit theta | 60191.0 | 23 | 44.0 | 10 | 128711 |
| P09211 | Glutathione S-transferase P | 23584.0 | 7 | 43.8 | 10 | 115014 |
| Q96DI7 | U5 small nuclear ribonucleoprotein 40 kDa protein | 39766.8 | 9 | 43.7 | 10 | 52647 |
| Q16836 | Hydroxyacyl-coenzyme A dehydrogenase, mitochondrial | 38416.2 | 7 | 43.6 | 10 | 78489 |
| P62917 | 60S ribosomal protein L8 | 28252.8 | 8 | 43.6 | 10 | 175299 |
| Q15056 | Eukaryotic translation initiation factor 4H | 26349.5 | 7 | 43.6 | 10 | 0 |
| P68032 | Actin, alpha cardiac muscle 1 | 42361.2 | 17 | 43.5 | 10 | 1638927 |
| P62834 | Ras-related protein Rap-1A | 21329.4 | 7 | 43.5 | 10 | 61122 |
| Q8NC51 | Plasminogen activator inhibitor 1 RNA-binding protein | 43753.1 | 13 | 43.4 | 10 | 195707 |
| Q00610 | Clathrin heavy chain 1 | 191520.7 | 57 | 43.4 | 10 | 149175 |

FIG. 17 (cont'd)

| | | | | | | |
|---|---|---|---|---|---|---|
| P49368 | T-complex protein 1 subunit gamma | 59024.3 | 19 | 43.3 | 10 | 125968 |
| P68366 | Tubulin alpha-4A chain | 50665.8 | 16 | 43.3 | 10 | 0 |
| P14927 | Cytochrome b-c1 complex subunit 7 | 14718.1 | 6 | 43.2 | 10 | 69797 |
| Q9Y2X3 | Nucleolar protein 58 | 60091.5 | 18 | 43.1 | 10 | 114263 |
| Q96IX5 | Up-regulated during skeletal muscle growth protein 5 | 6514.6 | 2 | 43.1 | 8 | 83880 |
| Q13347 | Eukaryotic translation initiation factor 3 subunit I | 36901.1 | 11 | 43.1 | 6 | 16366.5 |
| P23284 | Peptidyl-prolyl cis-trans isomerase B | 23799.6 | 11 | 43.1 | 10 | 215733 |
| P51148 | Ras-related protein Rab-5C | 25487.2 | 9 | 43.1 | 10 | 94568 |
| P62280 | 40S ribosomal protein S11 | 18601.8 | 7 | 43.0 | 10 | 326187 |
| Q03252 | Lamin-B2 | 67803.0 | 26 | 43.0 | 10 | 113659 |
| O43684 | Mitotic checkpoint protein BUB3 | 37482.4 | 10 | 42.9 | 10 | 45164 |
| P63208 | S-phase kinase-associated protein 1 | 18531.8 | 6 | 42.9 | 10 | 21654 |
| P35613 | Basigin | 28634.0 | 7 | 42.9 | 10 | 202386 |
| P00367 | Glutamate dehydrogenase 1, mitochondrial | 61740.1 | 19 | 42.8 | 10 | 80607 |
| P62269 | 40S ribosomal protein S18 | 17718.7 | 9 | 42.8 | 10 | 229377 |
| O75607 | Nucleoplasmin-3 | 19628.9 | 4 | 42.7 | 10 | 116862 |
| Q9UKD2 | mRNA turnover protein 4 homolog | 27674.6 | 10 | 42.7 | 10 | 144166.5 |
| P22307 | Non-specific lipid-transfer protein | 42967.2 | 13 | 42.7 | 10 | 34158 |
| P61353 | 60S ribosomal protein L27 | 15797.8 | 6 | 42.7 | 10 | 267358.5 |
| P43243 | Matrin-3 | 79027.5 | 26 | 42.6 | 10 | 272207 |
| P12235 | ADP/ATP translocase 1 | 33292.7 | 13 | 42.6 | 10 | 48821.61 |
| P13693 | Translationally-controlled tumor protein | 19709.5 | 4 | 42.4 | 10 | 44100 |
| P27824 | Calnexin | 68024.6 | 20 | 42.4 | 10 | 404790 |
| P62736 | Actin, aortic smooth muscle | 42408.3 | 16 | 42.2 | 10 | 787849 |
| P13667 | Protein disulfide-isomerase A4 | 73274.7 | 24 | 42.2 | 10 | 144490 |
| P61981 | 14-3-3 protein gamma | 28473.7 | 11 | 42.1 | 10 | 69814.73 |
| Q8N257 | Histone H2B type 3-B | 13908.1 | 10 | 42.1 | 10 | 0 |
| P34932 | Heat shock 70 kDa protein 4 | 95186.5 | 24 | 42.0 | 10 | 84870 |
| Q9Y3F4 | Serine-threonine kinase receptor-associated protein | 38780.5 | 13 | 42.0 | 9 | 42216 |
| Q53GQ0 | Estradiol 17-beta-dehydrogenase 12 | 34438.3 | 11 | 42.0 | 10 | 67896 |
| P09661 | U2 small nuclear ribonucleoprotein A' | 28529.7 | 9 | 42.0 | 10 | 82195 |
| O00299 | Chloride intracellular channel protein 1 | 27264.9 | 8 | 41.9 | 5 | 0 |
| Q6PI48 | Aspartate--tRNA ligase, mitochondrial | 74133.1 | 18 | 41.9 | 10 | 89813 |
| O43175 | D-3-phosphoglycerate dehydrogenase | 57392.0 | 17 | 41.8 | 10 | 134955 |
| O15371 | Eukaryotic translation initiation factor 3 subunit D | 64600.2 | 13 | 41.8 | 10 | 37314 |
| O95777 | N-alpha-acetyltransferase 38, NatC auxiliary subunit | 10402.7 | 2 | 41.7 | 8 | 0 |
| P52907 | F-actin-capping protein subunit alpha-1 | 33093.9 | 8 | 41.6 | 9 | 41490 |
| Q15393 | Splicing factor 3B subunit 3 | 70663.3 | 33 | 41.6 | 10 | 151768 |
| P08195 | 4F2 cell-surface antigen heavy chain | 64890.8 | 18 | 41.6 | 10 | 111277 |
| P08621 | U1 small nuclear ribonucleoprotein 70 kDa | 40467.9 | 14 | 41.6 | 10 | 135948 |
| Q9Y281 | Cofilin-2 | 18850.7 | 6 | 41.6 | 10 | 0 |

FIG. 17 (cont'd)

| | | | | | | |
|---|---|---|---|---|---|---|
| Q00839 | Heterogeneous nuclear ribonucleoprotein U | 90523.5 | 29 | 41.6 | 10 | 1241148 |
| P62987 | Ubiquitin-60S ribosomal protein L40 | 15013.5 | 6 | 41.4 | 10 | 0 |
| P00505 | Aspartate aminotransferase, mitochondrial | 47916.9 | 15 | 41.4 | 10 | 211558 |
| P25789 | Proteasome subunit alpha type-4 | 27539.1 | 7 | 41.4 | 10 | 0 |
| P15880 | 40S ribosomal protein S2 | 31609.6 | 12 | 41.3 | 10 | 188868 |
| P61513 | 60S ribosomal protein L37a | 10503.4 | 4 | 41.3 | 10 | 83443.5 |
| A6NMY6 | Putative annexin A2-like protein | 38830.2 | 14 | 41.3 | 10 | 0 |
| O75489 | NADH dehydrogenase [ubiquinone] iron-sulfur protein 3, mitochondrial | 30355.6 | 10 | 41.3 | 10 | 62482 |
| Q07065 | Cytoskeleton-associated protein 4 | 66136.6 | 19 | 41.2 | 10 | 79818 |
| Q7L0Y3 | Mitochondrial ribonuclease P protein 1 | 47632.2 | 14 | 41.2 | 10 | 12333 |
| P38117 | Electron transfer flavoprotein subunit beta | 32924.2 | 10 | 41.2 | 10 | 103627 |
| Q9NX24 | H/ACA ribonucleoprotein complex subunit 2 | 17543.2 | 3 | 41.2 | 9 | 0 |
| Q15084 | Protein disulfide-isomerase A6 | 51467.4 | 15 | 41.1 | 10 | 165244 |
| Q9BZZ5 | Apoptosis inhibitor 5 | 53583.8 | 15 | 41.1 | 10 | 84034 |
| P62249 | 40S ribosomal protein S16 | 16559.4 | 7 | 41.1 | 10 | 163437 |
| Q7Z7K6 | Centromere protein V | 26750.9 | 6 | 41.1 | 10 | 62341.5 |
| P19338 | Nucleolin | 76671.5 | 28 | 41.0 | 10 | 816018 |
| O14979 | Heterogeneous nuclear ribonucleoprotein D-like | 35910.4 | 13 | 41.0 | 10 | 164042 |
| P62140 | Serine/threonine-protein phosphatase PP1-beta catalytic subunit | 37985.3 | 13 | 41.0 | 10 | 136545 |
| P28838 | Cytosol aminopeptidase | 54919.5 | 18 | 41.0 | 10 | 42561 |
| Q13509 | Tubulin beta-3 chain | 50889.0 | 16 | 40.9 | 10 | 21054.37 |
| O95831 | Apoptosis-inducing factor 1, mitochondrial | 46729.6 | 18 | 40.8 | 10 | 172714 |
| P36578 | 60S ribosomal protein L4 | 47982.5 | 15 | 40.8 | 10 | 246531 |
| Q9GZZ1 | N-alpha-acetyltransferase 50 | 14545.7 | 4 | 40.7 | 2 | 0 |
| O00571 | ATP-dependent RNA helicase DDX3X | 72698.6 | 26 | 40.7 | 10 | 109486 |
| P63267 | Actin, gamma-enteric smooth muscle | 39879.4 | 16 | 40.7 | 10 | 0 |
| O43504 | Ragulator complex protein LAMTOR5 | 9785.0 | 3 | 40.7 | 2 | 0 |
| Q99798 | Aconitate hydratase, mitochondrial | 86166.9 | 23 | 40.6 | 10 | 82553 |
| Q14103 | Heterogeneous nuclear ribonucleoprotein D0 | 34724.4 | 16 | 40.5 | 10 | 750997 |
| Q12788 | Transducin beta-like protein 3 | 90403.4 | 22 | 40.5 | 10 | 34687 |
| O75934 | Pre-mRNA-splicing factor SPF27 | 26245.6 | 6 | 40.4 | 8 | 0 |
| P00492 | Hypoxanthine-guanine phosphoribosyltransferase | 24807.5 | 8 | 40.4 | 10 | 54399 |
| Q9HB71 | Calcyclin-binding protein | 26324.0 | 9 | 40.4 | 8 | 84390 |
| Q32P51 | Heterogeneous nuclear ribonucleoprotein A1-like 2 | 34396.5 | 16 | 40.3 | 10 | 0 |
| Q16891 | Mitochondrial inner membrane protein | 82509.2 | 23 | 40.3 | 10 | 105552 |
| P04844 | Dolichyl-diphosphooligosaccharide--protein glycosyltransferase subunit 2 | 68560.8 | 18 | 40.3 | 10 | 154450 |
| P26583 | High mobility group protein B2 | 24204.9 | 10 | 40.2 | 10 | 357762 |
| Q02978 | Mitochondrial 2-oxoglutarate/malate carrier protein | 34232.9 | 11 | 40.1 | 10 | 97788 |
| P03243 | E1B protein, large T-antigen | 36737.2 | 14 | 40.1 | 10 | 263160 |

FIG. 17 (cont'd)

| | | | | | | |
|---|---|---|---|---|---|---|
| P04843 | Dolichyl-diphosphooligosaccharide--protein glycosyltransferase subunit 1 | 68683.6 | 20 | 40.0 | 10 | 144842 |
| O75643 | U5 small nuclear ribonucleoprotein 200 kDa helicase | 159045.1 | 53 | 40.0 | 10 | 98207 |
| P05455 | Lupus La protein | 47008.2 | 17 | 40.0 | 10 | 91736 |
| Q15907 | Ras-related protein Rab-11B | 24602.6 | 8 | 39.9 | 10 | 56882 |
| Q9Y3L5 | Ras-related protein Rap-2c | 20972.9 | 7 | 39.9 | 2 | 0 |
| Q15459 | Splicing factor 3A subunit 1 | 88943.4 | 24 | 39.9 | 10 | 95595 |
| P55769 | NHP2-like protein 1 | 14401.7 | 5 | 39.8 | 10 | 200719.5 |
| P51659 | Peroxisomal multifunctional enzyme type 2 | 80764.4 | 20 | 39.8 | 10 | 93210 |
| P31948 | Stress-induced-phosphoprotein 1 | 63266.7 | 21 | 39.8 | 10 | 144263 |
| P54886 | Delta-1-pyrroline-5-carboxylate synthase | 87937.2 | 26 | 39.8 | 10 | 136902 |
| P46781 | 40S ribosomal protein S9 | 22648.5 | 11 | 39.7 | 10 | 103515 |
| P13073 | Cytochrome c oxidase subunit 4 isoform 1, mitochondrial | 19633.8 | 7 | 39.6 | 10 | 169116 |
| P04899 | Guanine nucleotide-binding protein G(i) subunit alpha-2 | 40374.0 | 12 | 39.6 | 10 | 0 |
| Q9Y3Y2 | Chromatin target of PRMT1 protein | 24946.6 | 8 | 39.6 | 10 | 86550 |
| P09429 | High mobility group protein B1 | 25064.9 | 9 | 39.5 | 10 | 0 |
| P62633 | Cellular nucleic acid-binding protein | 20127.0 | 5 | 39.5 | 6 | 0 |
| P62136 | Serine/threonine-protein phosphatase PP1-alpha catalytic subunit | 38841.7 | 12 | 39.4 | 10 | 79475 |
| Q96A08 | Histone H2B type 1-A | 14167.5 | 5 | 39.4 | 10 | 1265668 |
| P42677 | 40S ribosomal protein S27 | 9803.3 | 4 | 39.3 | 10 | 211413 |
| P21912 | Succinate dehydrogenase [ubiquinone] iron-sulfur subunit, mitochondrial | 32428.2 | 8 | 39.3 | 10 | 86108 |
| P26368 | Splicing factor U2AF 65 kDa subunit | 53653.0 | 11 | 39.3 | 10 | 228992 |
| Q9BQ67 | Glutamate-rich WD repeat-containing protein 1 | 49818.4 | 10 | 39.2 | 10 | 51463 |
| Q15691 | Microtubule-associated protein RP/EB family member 1 | 30170.2 | 8 | 39.2 | 5 | 0 |
| P29692 | Elongation factor 1-delta | 40404.2 | 9 | 39.2 | 10 | 135247 |
| P05023 | Sodium/potassium-transporting ATPase subunit alpha-1 | 100059.8 | 31 | 39.1 | 10 | 153692 |
| Q05639 | Elongation factor 1-alpha 2 | 50812.4 | 12 | 39.1 | 10 | 215978 |
| O75940 | Survival of motor neuron-related-splicing factor 30 | 26882.2 | 5 | 39.1 | 4 | 0 |
| P16152 | Carbonyl reductase [NADPH] 1 | 30660.1 | 9 | 39.0 | 4 | 0 |
| Q9NY65 | Tubulin alpha-8 chain | 47122.5 | 12 | 38.9 | 10 | 0 |
| Q99729 | Heterogeneous nuclear ribonucleoprotein A/B | 33484.5 | 13 | 38.9 | 10 | 721232 |
| P27635 | 60S ribosomal protein L10 | 25060.2 | 8 | 38.8 | 10 | 185573 |
| Q6P2Q9 | Pre-mRNA-processing-splicing factor 8 | 274912.5 | 65 | 38.8 | 10 | 121651 |
| P11177 | Pyruvate dehydrogenase E1 component subunit beta, mitochondrial | 38324.9 | 12 | 38.7 | 10 | 170256 |
| P31939 | Bifunctional purine biosynthesis protein PURH | 65129.2 | 18 | 38.7 | 9 | 35293.5 |
| P28066 | Proteasome subunit alpha type-5 | 23873.4 | 6 | 38.6 | 10 | 57516 |
| Q14974 | Importin subunit beta-1 | 98482.0 | 24 | 38.6 | 10 | 129410 |
| P84090 | Enhancer of rudimentary homolog | 12430.0 | 5 | 38.5 | 10 | 111066 |

FIG. 17 (cont'd)

| | | | | | | |
|---|---|---|---|---|---|---|
| Q9Y2Q5 | Ragulator complex protein LAMTOR2 | 14729.3 | 6 | 38.4 | 4 | 0 |
| Q14240 | Eukaryotic initiation factor 4A-II | 46674.0 | 13 | 38.3 | 10 | 0 |
| Q9H2U2 | Inorganic pyrophosphatase 2, mitochondrial | 33632.1 | 11 | 38.3 | 10 | 61155 |
| Q9Y2Q3 | Glutathione S-transferase kappa 1 | 25562.2 | 6 | 38.3 | 10 | 62424 |
| P22102 | Trifunctional purine biosynthetic protein adenosine-3 | 83038.0 | 16 | 38.1 | 10 | 31076 |
| Q71UM5 | 40S ribosomal protein S27-like | 9819.3 | 3 | 38.1 | 10 | 86310 |
| P31040 | Succinate dehydrogenase [ubiquinone] flavoprotein subunit, mitochondrial | 73718.1 | 15 | 38.0 | 10 | 98997 |
| P62195 | 26S protease regulatory subunit 8 | 45376.2 | 12 | 37.9 | 10 | 36980 |
| P28070 | Proteasome subunit beta type-4 | 29261.4 | 7 | 37.9 | 10 | 72669 |
| O75521 | Enoyl-CoA delta isomerase 2, mitochondrial | 41968.0 | 10 | 37.9 | 10 | 28035 |
| Q9Y617 | Phosphoserine aminotransferase | 38396.8 | 11 | 37.8 | 10 | 51059 |
| Q12904 | Aminoacyl tRNA synthase complex-interacting multifunctional protein 1 | 36009.6 | 8 | 37.8 | 10 | 0 |
| P84103 | Serine/arginine-rich splicing factor 3 | 19557.7 | 8 | 37.8 | 10 | 495434 |
| P53999 | Activated RNA polymerase II transcriptional coactivator p15 | 14395.4 | 5 | 37.8 | 10 | 124029 |
| Q99459 | Cell division cycle 5-like protein | 92478.9 | 22 | 37.8 | 10 | 54633 |
| P62263 | 40S ribosomal protein S14 | 16443.8 | 7 | 37.8 | 10 | 207925 |
| P82930 | 28S ribosomal protein S34, mitochondrial | 25707.5 | 5 | 37.6 | 10 | 18261 |
| P40616 | ADP-ribosylation factor-like protein 1 | 20531.6 | 4 | 37.6 | 7 | 22098 |
| P61026 | Ras-related protein Rab-10 | 22769.1 | 6 | 37.5 | 10 | 138828 |
| P50213 | Isocitrate dehydrogenase [NAD] subunit alpha, mitochondrial | 35942.8 | 12 | 37.5 | 10 | 82793 |
| P06493 | Cyclin-dependent kinase 1 | 30827.7 | 10 | 37.5 | 10 | 32195 |
| Q15369 | Transcription elongation factor B polypeptide 1 | 12078.4 | 3 | 37.5 | 6 | 0 |
| P36873 | Serine/threonine-protein phosphatase PP1-gamma catalytic subunit | 38492.5 | 11 | 37.5 | 10 | 107700 |
| Q9BX68 | Histidine triad nucleotide-binding protein 2, mitochondrial | 17218.8 | 4 | 37.4 | 7 | 0 |
| P61586 | Transforming protein RhoA | 22110.3 | 7 | 37.3 | 10 | 72332 |
| P08754 | Guanine nucleotide-binding protein G(k) subunit alpha | 41102.5 | 12 | 37.3 | 10 | 43782 |
| P39023 | 60S ribosomal protein L3 | 46394.1 | 15 | 37.2 | 10 | 188885 |
| Q9UJS0 | Calcium-binding mitochondrial carrier protein Aralar2 | 74638.9 | 18 | 37.2 | 10 | 45564 |
| P30153 | Serine/threonine-protein phosphatase 2A 65 kDa regulatory subunit A alpha isoform | 66107.1 | 20 | 37.2 | 10 | 54942 |
| P03244 | E1B 55 kDa protein | 56334.5 | 13 | 37.2 | 10 | 0 |
| Q15019 | Septin-2 | 43730.9 | 11 | 37.1 | 10 | 39516 |
| P63167 | Dynein light chain 1, cytoplasmic | 10537.0 | 3 | 37.1 | 10 | 188058 |
| P60900 | Proteasome subunit alpha type-6 | 27855.7 | 8 | 37.0 | 10 | 39036 |
| O95202 | LETM1 and EF-hand domain-containing protein 1, mitochondrial | 58660.4 | 21 | 36.9 | 10 | 72336 |
| P05091 | Aldehyde dehydrogenase, mitochondrial | 56894.6 | 17 | 36.9 | 10 | 65411 |
| Q02543 | 60S ribosomal protein L18a | 21047.5 | 8 | 36.9 | 10 | 182385 |

FIG. 17 (cont'd)

| | | | | | | |
|---|---|---|---|---|---|---|
| Q9Y3B4 | Pre-mRNA branch site protein p14 | 14699.0 | 4 | 36.8 | 10 | 117678 |
| Q96AE4 | Far upstream element-binding protein 1 | 68282.2 | 20 | 36.8 | 10 | 113676 |
| Q99873 | Protein arginine N-methyltransferase 1 | 40983.4 | 12 | 36.7 | 10 | 39372 |
| Q9GZL7 | Ribosome biogenesis protein WDR12 | 48221.3 | 11 | 36.6 | 10 | 43962 |
| P43897 | Elongation factor Ts, mitochondrial | 36038.6 | 8 | 36.6 | 10 | 56373 |
| Q8TDN6 | Ribosome biogenesis protein BRX1 homolog | 41686.6 | 12 | 36.5 | 10 | 0 |
| Q9Y224 | UPF0568 protein C14orf166 | 28182.2 | 9 | 36.5 | 10 | 33130.5 |
| Q12849 | G-rich sequence factor 1 | 45212.1 | 13 | 36.5 | 10 | 0 |
| P32969 | 60S ribosomal protein L9 | 21977.5 | 6 | 36.5 | 10 | 218925 |
| Q8NBS9 | Thioredoxin domain-containing protein 5 | 42530.7 | 11 | 36.4 | 10 | 48192 |
| Q99986 | Serine/threonine-protein kinase VRK1 | 45818.3 | 10 | 36.4 | 9 | 0 |
| O00116 | Alkyldihydroxyacetonephosphate synthase, peroxisomal | 73710.3 | 16 | 36.3 | 10 | 50101.5 |
| Q9BTV4 | Transmembrane protein 43 | 44932.7 | 13 | 36.3 | 4 | 0 |
| P54709 | Sodium/potassium-transporting ATPase subunit beta-3 | 31854.8 | 7 | 36.2 | 10 | 135741 |
| P22695 | Cytochrome b-c1 complex subunit 2, mitochondrial | 48614.2 | 13 | 36.2 | 10 | 119106 |
| P54577 | Tyrosine--tRNA ligase, cytoplasmic | 59485.7 | 17 | 36.2 | 10 | 43046 |
| Q9P0L0 | Vesicle-associated membrane protein-associated protein A | 30481.6 | 8 | 36.1 | 10 | 13030.5 |
| P20618 | Proteasome subunit beta type-1 | 26717.5 | 9 | 36.1 | 10 | 46018.5 |
| P55036 | 26S proteasome non-ATPase regulatory subunit 4 | 35286.2 | 9 | 36.1 | 10 | 32247 |
| P20042 | Eukaryotic translation initiation factor 2 subunit 2 | 38730.6 | 9 | 36.0 | 10 | 35292 |
| Q08945 | FACT complex subunit SSRP1 | 81417.1 | 22 | 36.0 | 10 | 171342 |
| P29401 | Transketolase | 69030.1 | 14 | 36.0 | 10 | 69800 |
| Q9Y2R9 | 28S ribosomal protein S7, mitochondrial | 28248.2 | 10 | 36.0 | 7 | 0 |
| O75964 | ATP synthase subunit g, mitochondrial | 11428.5 | 3 | 35.9 | 6 | 41163 |
| P49207 | 60S ribosomal protein L34 | 13521.1 | 5 | 35.9 | 10 | 55444.5 |
| P46779 | 60S ribosomal protein L28 | 18022.5 | 5 | 35.8 | 10 | 88428 |
| O96008 | Mitochondrial import receptor subunit TOM40 homolog | 36935.6 | 9 | 35.7 | 10 | 86037 |
| Q96CS3 | FAS-associated factor 2 | 52965.7 | 11 | 35.7 | 10 | 65675 |
| Q6IS14 | Eukaryotic translation initiation factor 5A-1-like | 17001.3 | 6 | 35.7 | 10 | 0 |
| P14174 | Macrophage migration inhibitory factor | 12647.4 | 3 | 35.7 | 10 | 306162 |
| P46060 | Ran GTPase-activating protein 1 | 63998.3 | 16 | 35.6 | 10 | 43963.5 |
| A8MWD9 | Small nuclear ribonucleoprotein G-like protein | 8601.1 | 3 | 35.5 | 10 | 105177 |
| Q9NVP1 | ATP-dependent RNA helicase DDX18 | 75749.1 | 19 | 35.4 | 10 | 110074 |
| Q07812 | Apoptosis regulator BAX | 20661.0 | 6 | 35.4 | 10 | 13824 |
| P52815 | 39S ribosomal protein L12, mitochondrial | 21576.3 | 6 | 35.4 | 10 | 250710 |
| A6NIZ1 | Ras-related protein Rap-1b-like protein | 21153.0 | 6 | 35.3 | 10 | 0 |
| O76021 | Ribosomal L1 domain-containing protein 1 | 55200.7 | 16 | 35.3 | 10 | 147493 |

FIG. 17 (cont'd)

| | | | | | | |
|---|---|---|---|---|---|---|
| Q14697 | Neutral alpha-glucosidase AB | 108612.4 | 26 | 35.3 | 10 | 131335 |
| P61006 | Ras-related protein Rab-8A | 23839.3 | 7 | 35.3 | 10 | 25407.88 |
| P24539 | ATP synthase F(0) complex subunit B1, mitochondrial | 28965.7 | 8 | 35.2 | 10 | 70389 |
| O75494 | Serine/arginine-rich splicing factor 10 | 25250.6 | 6 | 35.2 | 10 | 113805 |
| Q96QV6 | Histone H2A type 1-A | 14233.5 | 5 | 35.1 | 10 | 105594 |
| P60604 | Ubiquitin-conjugating enzyme E2 G2 | 17261.2 | 3 | 35.0 | 2 | 0 |
| P62913 | 60S ribosomal protein L11 | 20416.5 | 5 | 35.0 | 10 | 190831.5 |
| P35250 | Replication factor C subunit 2 | 38048.1 | 7 | 35.0 | 5 | 22830 |
| P62906 | 60S ribosomal protein L10a | 25002.4 | 9 | 35.0 | 10 | 149508 |
| O14579 | Coatomer subunit epsilon | 31828.9 | 10 | 35.0 | 8 | 0 |
| P28074 | Proteasome subunit beta type-5 | 24149.0 | 8 | 35.0 | 10 | 19476 |
| Q13813 | Spectrin alpha chain, non-erythrocytic 1 | 284770.5 | 71 | 35.0 | 10 | 76179 |
| P62266 | 40S ribosomal protein S23 | 15978.7 | 4 | 35.0 | 10 | 147147 |
| P61225 | Ras-related protein Rap-2b | 20732.5 | 5 | 35.0 | 2 | 0 |
| P34931 | Heat shock 70 kDa protein 1-like | 70774.3 | 17 | 35.0 | 10 | 33876.34 |
| P11940 | Polyadenylate-binding protein 1 | 66154.2 | 22 | 34.9 | 10 | 132868 |
| P11310 | Medium-chain specific acyl-CoA dehydrogenase, mitochondrial | 47288.9 | 13 | 34.9 | 10 | 64702 |
| P49458 | Signal recognition particle 9 kDa protein | 9892.9 | 4 | 34.9 | 10 | 135312 |
| P30040 | Endoplasmic reticulum resident protein 29 | 25682.8 | 7 | 34.9 | 10 | 68144 |
| Q15738 | Sterol-4-alpha-carboxylate 3-dehydrogenase, decarboxylating | 42185.5 | 10 | 34.9 | 10 | 41651 |
| P78527 | DNA-dependent protein kinase catalytic subunit | 472257.0 | 111 | 34.8 | 10 | 141583 |
| P22061 | Protein-L-isoaspartate(D-aspartate) O-methyltransferase | 24829.0 | 8 | 34.8 | 10 | 50952 |
| O75937 | DnaJ homolog subfamily C member 8 | 29841.7 | 7 | 34.8 | 8 | 0 |
| P12532 | Creatine kinase U-type, mitochondrial | 49185.0 | 11 | 34.8 | 10 | 92481 |
| P47813 | Eukaryotic translation initiation factor 1A, X-chromosomal | 16574.5 | 5 | 34.7 | 10 | 0 |
| P00167 | Cytochrome b5 | 13589.1 | 3 | 34.7 | 10 | 0 |
| P50395 | Rab GDP dissociation inhibitor beta | 48807.8 | 12 | 34.6 | 10 | 53428 |
| Q07020 | 60S ribosomal protein L18 | 21748.6 | 6 | 34.6 | 10 | 431140.5 |
| Q9Y5B9 | FACT complex subunit SPT16 | 120484.3 | 30 | 34.6 | 10 | 195707 |
| P41091 | Eukaryotic translation initiation factor 2 subunit 3 | 51679.8 | 12 | 34.5 | 10 | 95890 |
| Q9UKM9 | RNA-binding protein Raly | 31470.6 | 8 | 34.5 | 10 | 98412 |
| Q9BYG3 | MKI67 FHA domain-interacting nucleolar phosphoprotein | 34393.3 | 9 | 34.5 | 10 | 36721.5 |
| Q9Y3I0 | tRNA-splicing ligase RtcB homolog | 55723.7 | 14 | 34.5 | 10 | 89133 |
| P13861 | cAMP-dependent protein kinase type II-alpha regulatory subunit | 45860.6 | 11 | 34.4 | 10 | 18060 |
| Q01082 | Spectrin beta chain, non-erythrocytic 1 | 260422.1 | 64 | 34.4 | 10 | 49303 |
| Q01780 | Exosome component 10 | 100339.3 | 20 | 34.3 | 10 | 17288 |
| O75347 | Tubulin-specific chaperone A | 12911.9 | 5 | 34.3 | 6 | 17007 |
| P52292 | Importin subunit alpha-1 | 58204.2 | 11 | 34.2 | 10 | 87747 |
| O14880 | Microsomal glutathione S-transferase 3 | 16744.4 | 6 | 34.2 | 10 | 92892 |

FIG. 17 (cont'd)

| | | | | | | |
|---|---|---|---|---|---|---|
| Q5JTJ3 | Cytochrome c oxidase assembly factor 6 homolog | 15275.0 | 3 | 34.2 | 4 | 0 |
| Q96CX2 | BTB/POZ domain-containing protein KCTD12 | 35986.0 | 8 | 34.2 | 8 | 22554 |
| Q9BXW7 | Cat eye syndrome critical region protein 5 | 45325.6 | 7 | 34.1 | 10 | 33182 |
| P35222 | Catenin beta-1 | 75194.2 | 8 | 34.1 | 7 | 0 |
| P49821 | NADH dehydrogenase [ubiquinone] flavoprotein 1, mitochondrial | 51027.0 | 12 | 34.1 | 10 | 34645.5 |
| Q96C36 | Pyrroline-5-carboxylate reductase 2 | 33979.4 | 10 | 34.1 | 10 | 68181 |
| P46777 | 60S ribosomal protein L5 | 34590.8 | 11 | 34.0 | 10 | 196395 |
| P05114 | Non-histone chromosomal protein HMG-14 | 10658.9 | 3 | 34.0 | 2 | 0 |
| P55884 | Eukaryotic translation initiation factor 3 subunit B | 96325.9 | 22 | 33.9 | 10 | 35667 |
| Q9P0M6 | Core histone macro-H2A.2 | 40286.4 | 11 | 33.9 | 10 | 79666 |
| P32322 | Pyrroline-5-carboxylate reductase 1, mitochondrial | 33578.8 | 8 | 33.9 | 10 | 74339 |
| P61313 | 60S ribosomal protein L15 | 20545.8 | 7 | 33.8 | 10 | 177342 |
| Q13148 | TAR DNA-binding protein 43 | 39983.9 | 10 | 33.8 | 10 | 136170 |
| P36776 | Lon protease homolog, mitochondrial | 107002.7 | 22 | 33.8 | 10 | 63614 |
| Q9Y6H1 | Coiled-coil-helix-coiled-coil-helix domain-containing protein 2, mitochondrial | 15740.7 | 4 | 33.8 | 2 | 10623 |
| P04080 | Cystatin-B | 11196.6 | 2 | 33.7 | 5 | 41232 |
| P07814 | Bifunctional glutamate/proline--tRNA ligase | 172187.9 | 41 | 33.6 | 10 | 54462 |
| Q8N1F7 | Nuclear pore complex protein Nup93 | 87198.6 | 20 | 33.6 | 10 | 54166 |
| O75396 | Vesicle-trafficking protein SEC22b | 24821.5 | 8 | 33.5 | 10 | 59637 |
| P13995 | Bifunctional methylenetetrahydrofolate dehydrogenase/cyclohydrolase, mitochondrial | 38066.2 | 9 | 33.4 | 10 | 121531.5 |
| Q16576 | Histone-binding protein RBBP7 | 50437.9 | 9 | 33.4 | 10 | 130977 |
| O43615 | Mitochondrial import inner membrane translocase subunit TIM44 | 51698.0 | 17 | 33.4 | 10 | 78109 |
| Q96EP5 | DAZ-associated protein 1 | 42213.2 | 10 | 33.3 | 10 | 185127 |
| P62910 | 60S ribosomal protein L32 | 15973.9 | 5 | 33.3 | 10 | 153669 |
| P67775 | Serine/threonine-protein phosphatase 2A catalytic subunit alpha isoform | 33502.1 | 7 | 33.3 | 10 | 49413 |
| P24941 | Cyclin-dependent kinase 2 | 32096.3 | 8 | 33.3 | 8 | 0 |
| Q9NWU5 | 39S ribosomal protein L22, mitochondrial | 17427.6 | 6 | 33.3 | 9 | 0 |
| Q9NZI8 | Insulin-like growth factor 2 mRNA-binding protein 1 | 56324.3 | 16 | 33.3 | 10 | 140135 |
| P49419 | Alpha-aminoadipic semialdehyde dehydrogenase | 52377.1 | 13 | 33.3 | 10 | 39249 |
| O75390 | Citrate synthase, mitochondrial | 51940.7 | 13 | 33.3 | 10 | 193641 |
| Q96HS1 | Serine/threonine-protein phosphatase PGAM5, mitochondrial | 30240.3 | 7 | 33.2 | 10 | 36630 |
| Q14165 | Malectin | 32405.0 | 8 | 33.2 | 4 | 0 |
| Q9BVK6 | Transmembrane emp24 domain-containing protein 9 | 27391.5 | 7 | 33.2 | 10 | 86146 |
| P26373 | 60S ribosomal protein L13 | 21610.4 | 8 | 33.2 | 10 | 210794 |
| Q9NY12 | H/ACA ribonucleoprotein complex subunit 1 | 21762.2 | 6 | 33.2 | 10 | 57664.5 |

FIG. 17 (cont'd)

| | | | | | | |
|---|---|---|---|---|---|---|
| P78406 | mRNA export factor | 41595.5 | 9 | 33.2 | 9 | 24285 |
| Q04760 | Lactoylglutathione lyase | 20138.5 | 6 | 33.1 | 10 | 38664 |
| Q9P258 | Protein RCC2 | 56826.0 | 13 | 33.1 | 10 | 35136 |
| P24844 | Myosin regulatory light polypeptide 9 | 17734.7 | 5 | 33.1 | 10 | 0 |
| Q9Y3C6 | Peptidyl-prolyl cis-trans isomerase-like 1 | 18350.9 | 5 | 33.1 | 4 | 63282 |
| Q13526 | Peptidyl-prolyl cis-trans isomerase NIMA-interacting 1 | 18357.4 | 4 | 33.1 | 5 | 0 |
| Q86W42 | THO complex subunit 6 homolog | 35623.8 | 8 | 33.1 | 6 | 0 |
| Q96E39 | RNA binding motif protein, X-linked-like-1 | 42198.7 | 12 | 33.1 | 10 | 0 |
| P62899 | 60S ribosomal protein L31 | 14363.5 | 4 | 33.1 | 10 | 120243 |
| Q9Y2B0 | Protein canopy homolog 2 | 20994.4 | 5 | 33.0 | 3 | 0 |
| P08758 | Annexin A5 | 35993.9 | 12 | 32.8 | 10 | 0 |
| P14868 | Aspartate--tRNA ligase, cytoplasmic | 57535.5 | 15 | 32.7 | 10 | 53280 |
| Q9HAV7 | GrpE protein homolog 1, mitochondrial | 24507.2 | 6 | 32.7 | 10 | 77310 |
| P06753 | Tropomyosin alpha-3 chain | 30421.1 | 10 | 32.7 | 10 | 126079 |
| Q9Y383 | Putative RNA-binding protein Luc7-like 2 | 46859.3 | 12 | 32.7 | 10 | 57078 |
| Q13435 | Splicing factor 3B subunit 2 | 100341.8 | 21 | 32.6 | 10 | 156837 |
| P62330 | ADP-ribosylation factor 6 | 20196.3 | 6 | 32.6 | 3 | 0 |
| Q13765 | Nascent polypeptide-associated complex subunit alpha | 59224.4 | 9 | 32.6 | 10 | 149910 |
| P62753 | 40S ribosomal protein S6 | 28851.8 | 8 | 32.5 | 10 | 248743 |
| Q00059 | Transcription factor A, mitochondrial | 29324.8 | 10 | 32.5 | 10 | 77317 |
| Q9Y3U8 | 60S ribosomal protein L36 | 12310.8 | 4 | 32.4 | 10 | 143646 |
| P36551 | Coproporphyrinogen-III oxidase, mitochondrial | 50950.4 | 13 | 32.4 | 10 | 32901 |
| P62714 | Serine/threonine-protein phosphatase 2A catalytic subunit beta isoform | 36145.4 | 7 | 32.4 | 10 | 0 |
| P07954 | Fumarate hydratase, mitochondrial | 52596.1 | 11 | 32.3 | 10 | 70460 |
| P55265 | Double-stranded RNA-specific adenosine deaminase | 130207.2 | 25 | 32.3 | 10 | 49872 |
| P00918 | Carbonic anhydrase 2 | 29303.1 | 6 | 32.3 | 10 | 66698 |
| O75340 | Programmed cell death protein 6 | 21823.4 | 4 | 32.3 | 10 | 0 |
| P82970 | High mobility group nucleosome-binding domain-containing protein 5 | 31524.6 | 8 | 32.3 | 9 | 32187 |
| P40925 | Malate dehydrogenase, cytoplasmic | 34607.3 | 8 | 32.2 | 10 | 96162 |
| Q8IY81 | pre-rRNA processing protein FTSJ3 | 96957.8 | 18 | 32.2 | 10 | 89804 |
| Q14257 | Reticulocalbin-2 | 36933.5 | 8 | 32.2 | 10 | 50488.5 |
| O43809 | Cleavage and polyadenylation specificity factor subunit 5 | 26284.3 | 6 | 32.2 | 10 | 183237 |
| Q9H0D6 | 5'-3' exoribonuclease 2 | 105099.1 | 19 | 32.2 | 10 | 58555 |
| O94826 | Mitochondrial import receptor subunit TOM70 | 68139.3 | 16 | 32.1 | 10 | 46659 |
| Q99536 | Synaptic vesicle membrane protein VAT-1 homolog | 42148.5 | 11 | 32.1 | 10 | 56940 |
| P50454 | Serpin H1 | 46554.7 | 12 | 32.1 | 10 | 52623 |
| P54727 | UV excision repair protein RAD23 homolog B | 39961.7 | 7 | 32.1 | 10 | 37425 |
| P25787 | Proteasome subunit alpha type-2 | 26012.7 | 7 | 32.1 | 7 | 0 |
| Q9Y6C9 | Mitochondrial carrier homolog 2 | 33958.3 | 9 | 32.0 | 4 | 0 |

FIG. 17 (cont'd)

| | | | | | | |
|---|---|---|---|---|---|---|
| Q14011 | Cold-inducible RNA-binding protein | 18648.0 | 6 | 32.0 | 10 | 66016 |
| Q13283 | Ras GTPase-activating protein-binding protein 1 | 52221.4 | 9 | 32.0 | 9 | 74112 |
| Q9HCU5 | Prolactin regulatory element-binding protein | 46038.5 | 7 | 31.9 | 3 | 0 |
| P46778 | 60S ribosomal protein L21 | 18621.9 | 5 | 31.9 | 10 | 97878 |
| P62070 | Ras-related protein R-Ras2 | 23627.7 | 5 | 31.9 | 1 | 0 |
| Q8NHW5 | 60S acidic ribosomal protein P0-like | 34535.6 | 9 | 31.9 | 10 | 0 |
| P83731 | 60S ribosomal protein L24 | 17893.0 | 7 | 31.9 | 10 | 168694 |
| Q92928 | Putative Ras-related protein Rab-1C | 22245.1 | 7 | 31.8 | 10 | 0 |
| P40227 | T-complex protein 1 subunit zeta | 56112.8 | 13 | 31.8 | 10 | 103458 |
| P39656 | Dolichyl-diphosphooligosaccharide--protein glycosyltransferase 48 kDa subunit | 50972.0 | 11 | 31.8 | 10 | 102223 |
| P08133 | Annexin A6 | 74490.7 | 15 | 31.8 | 10 | 50151 |
| P22314 | Ubiquitin-like modifier-activating enzyme 1 | 118932.7 | 24 | 31.8 | 10 | 101201 |
| Q9BU76 | Multiple myeloma tumor-associated protein 2 | 22013.0 | 6 | 31.8 | 10 | 0 |
| Q9NX63 | Coiled-coil-helix-coiled-coil-helix domain-containing protein 3, mitochondrial | 26437.5 | 8 | 31.7 | 10 | 71022 |
| O15523 | ATP-dependent RNA helicase DDX3Y | 73610.0 | 22 | 31.7 | 10 | 0 |
| Q9Y4Z0 | U6 snRNA-associated Sm-like protein LSm4 | 15520.8 | 3 | 31.7 | 4 | 0 |
| Q9Y5K5 | Ubiquitin carboxyl-terminal hydrolase isozyme L5 | 37414.3 | 7 | 31.7 | 8 | 0 |
| P13797 | Plastin-3 | 71324.4 | 14 | 31.6 | 10 | 53172 |
| Q6YN16 | Hydroxysteroid dehydrogenase-like protein 2 | 41585.7 | 12 | 31.6 | 10 | 38755.5 |
| Q92804 | TATA-binding protein-associated factor 2N | 61922.0 | 11 | 31.6 | 10 | 96205 |
| P19367 | Hexokinase-1 | 103311.2 | 23 | 31.5 | 10 | 49465 |
| O14818 | Proteasome subunit alpha type-7 | 24154.0 | 7 | 31.5 | 10 | 116496 |
| O15260 | Surfeit locus protein 4 | 24410.2 | 4 | 31.5 | 10 | 27207 |
| P62306 | Small nuclear ribonucleoprotein F | 9782.3 | 4 | 31.4 | 6 | 63735 |
| Q9UBX3 | Mitochondrial dicarboxylate carrier | 32170.2 | 7 | 31.4 | 10 | 35781 |
| O43678 | NADH dehydrogenase [ubiquinone] 1 alpha subcomplex subunit 2 | 11035.6 | 2 | 31.3 | 1 | 0 |
| O94905 | Erlin-2 | 29684.9 | 10 | 31.3 | 10 | 70118.47 |
| Q15185 | Prostaglandin E synthase 3 | 18982.6 | 5 | 31.3 | 10 | 109677 |
| P33991 | DNA replication licensing factor MCM4 | 97128.4 | 19 | 31.2 | 10 | 58950 |
| Q14498 | RNA-binding protein 39 | 58660.6 | 12 | 31.1 | 10 | 105869 |
| P33316 | Deoxyuridine 5'-triphosphate nucleotidohydrolase, mitochondrial | 22383.8 | 7 | 31.1 | 10 | 21258 |
| Q16822 | Phosphoenolpyruvate carboxykinase [GTP], mitochondrial | 60989.0 | 15 | 31.1 | 10 | 49090 |
| P49321 | Nuclear autoantigenic sperm protein | 80305.4 | 19 | 31.1 | 10 | 26508 |
| P46776 | 60S ribosomal protein L27a | 16675.5 | 5 | 31.1 | 10 | 203478 |
| Q6IAA8 | Ragulator complex protein LAMTOR1 | 17858.9 | 4 | 31.1 | 6 | 26448 |
| P16615 | Sarcoplasmic/endoplasmic reticulum calcium ATPase 2 | 112735.9 | 27 | 31.0 | 10 | 105235 |
| P61956 | Small ubiquitin-related modifier 2 | 9548.2 | 3 | 31.0 | 10 | 263136 |

FIG. 17 (cont'd)

| | | | | | | |
|---|---|---|---|---|---|---|
| Q01085 | Nucleolysin TIAR | 42862.0 | 8 | 30.9 | 10 | 0 |
| Q9UKX7 | Nuclear pore complex protein Nup50 | 48902.7 | 12 | 30.9 | 10 | 0 |
| O60264 | SWI/SNF-related matrix-associated actin-dependent regulator of chromatin subfamily A member 5 | 122589.9 | 30 | 30.9 | 10 | 69114 |
| P54920 | Alpha-soluble NSF attachment protein | 33689.0 | 10 | 30.9 | 9 | 15858 |
| Q01081 | Splicing factor U2AF 35 kDa subunit | 24622.3 | 6 | 30.8 | 10 | 66108 |
| P39748 | Flap endonuclease 1 | 42935.2 | 9 | 30.8 | 10 | 15681 |
| P11388 | DNA topoisomerase 2-alpha | 179118.6 | 37 | 30.8 | 10 | 92672 |
| P49720 | Proteasome subunit beta type-3 | 23234.1 | 6 | 30.7 | 10 | 40108.5 |
| Q01105 | Protein SET | 32194.9 | 7 | 30.7 | 10 | 212484 |
| Q96DH6 | RNA-binding protein Musashi homolog 2 | 28130.4 | 7 | 30.7 | 10 | 0 |
| Q9NQG5 | Regulation of nuclear pre-mRNA domain-containing protein 1B | 37013.8 | 10 | 30.7 | 10 | 0 |
| P51571 | Translocon-associated protein subunit delta | 19169.7 | 5 | 30.6 | 10 | 239676 |
| Q9Y4L1 | Hypoxia up-regulated protein 1 | 111563.7 | 21 | 30.5 | 10 | 45764 |
| P05198 | Eukaryotic translation initiation factor 2 subunit 1 | 36397.4 | 8 | 30.5 | 10 | 51603 |
| Q9H0A0 | N-acetyltransferase 10 | 116642.5 | 24 | 30.4 | 10 | 49278 |
| Q92930 | Ras-related protein Rab-8B | 23755.2 | 5 | 30.4 | 10 | 0 |
| P51858 | Hepatoma-derived growth factor | 26318.8 | 6 | 30.4 | 10 | 0 |
| Q00325 | Phosphate carrier protein, mitochondrial | 40483.1 | 11 | 30.4 | 10 | 182818 |
| Q16643 | Drebrin | 71998.7 | 15 | 30.4 | 10 | 57660 |
| P49736 | DNA replication licensing factor MCM2 | 102580.6 | 21 | 30.3 | 10 | 70758 |
| Q9H3P7 | Golgi resident protein GCP60 | 60878.6 | 11 | 30.3 | 7 | 28899 |
| Q92688 | Acidic leucine-rich nuclear phosphoprotein 32 family member B | 25703.3 | 5 | 30.3 | 10 | 42038 |
| P30042 | ES1 protein homolog, mitochondrial | 27178.0 | 5 | 30.2 | 10 | 0 |
| P30837 | Aldehyde dehydrogenase X, mitochondrial | 57662.6 | 12 | 30.2 | 10 | 51849 |
| P12268 | Inosine-5'-monophosphate dehydrogenase 2 | 56261.3 | 15 | 30.2 | 10 | 46440 |
| P49755 | Transmembrane emp24 domain-containing protein 10 | 25147.1 | 7 | 30.1 | 10 | 197397 |
| Q12874 | Splicing factor 3A subunit 3 | 59191.2 | 15 | 30.1 | 10 | 91862 |
| Q9Y3B7 | 39S ribosomal protein L11, mitochondrial | 19527.9 | 6 | 30.1 | 10 | 0 |
| Q04917 | 14-3-3 protein eta | 28389.9 | 7 | 30.1 | 10 | 40002.92 |
| P62847 | 40S ribosomal protein S24 | 19676.0 | 5 | 30.0 | 10 | 248277 |
| O43290 | U4/U6.U5 tri-snRNP-associated protein 1 | 90426.0 | 19 | 30.0 | 9 | 18473 |
| Q9Y3D9 | 28S ribosomal protein S23, mitochondrial | 21827.7 | 6 | 30.0 | 9 | 0 |
| P10515 | Dihydrolipoyllysine-residue acetyltransferase component of pyruvate dehydrogenase complex, mitochondrial | 69510.0 | 14 | 30.0 | 10 | 91167 |
| Q9BZE4 | Nucleolar GTP-binding protein 1 | 74363.9 | 19 | 30.0 | 10 | 43480 |
| Q9NPJ3 | Acyl-coenzyme A thioesterase 13 | 13777.6 | 4 | 29.9 | 6 | 46371 |
| P82921 | 28S ribosomal protein S21, mitochondrial | 10912.7 | 2 | 29.9 | 3 | 0 |

FIG. 17 (cont'd)

| | | | | | | |
|---|---|---|---|---|---|---|
| P41223 | Protein BUD31 homolog | 17570.0 | 5 | 29.9 | 3 | 0 |
| P29966 | Myristoylated alanine-rich C-kinase substrate | 31725.8 | 7 | 29.8 | 10 | 25089 |
| P11387 | DNA topoisomerase 1 | 91182.1 | 23 | 29.8 | 10 | 78990 |
| P30519 | Heme oxygenase 2 | 36204.0 | 9 | 29.8 | 10 | 22773 |
| Q8N5N7 | 39S ribosomal protein L50, mitochondrial | 18496.1 | 5 | 29.8 | 2 | 0 |
| Q9BQG0 | Myb-binding protein 1A | 150080.5 | 32 | 29.7 | 10 | 82468 |
| P35579 | Myosin-9 | 194339.1 | 48 | 29.7 | 10 | 76117 |
| Q99848 | Probable rRNA-processing protein EBP2 | 34909.0 | 11 | 29.7 | 10 | 43494 |
| P39687 | Acidic leucine-rich nuclear phosphoprotein 32 family member A | 28699.5 | 7 | 29.7 | 10 | 74193 |
| P19404 | NADH dehydrogenase [ubiquinone] flavoprotein 2, mitochondrial | 27676.7 | 6 | 29.7 | 10 | 29325 |
| Q6P161 | 39S ribosomal protein L54, mitochondrial | 15876.2 | 3 | 29.7 | 1 | 0 |
| Q13561 | Dynactin subunit 2 | 44622.1 | 9 | 29.7 | 10 | 0 |
| Q13573 | SNW domain-containing protein 1 | 61551.6 | 12 | 29.7 | 9 | 0 |
| Q96HY6 | DDRGK domain-containing protein 1 | 35625.0 | 5 | 29.6 | 5 | 0 |
| Q9BUF5 | Tubulin beta-6 chain | 50313.5 | 10 | 29.6 | 10 | 67242.28 |
| Q99720 | Sigma non-opioid intracellular receptor 1 | 22631.5 | 5 | 29.6 | 8 | 0 |
| Q9UNX4 | WD repeat-containing protein 3 | 107182.6 | 22 | 29.6 | 10 | 21415 |
| P16949 | Stathmin | 18620.1 | 4 | 29.5 | 10 | 65019 |
| P53582 | Methionine aminopeptidase 1 | 44127.7 | 7 | 29.5 | 3 | 0 |
| O15347 | High mobility group protein B3 | 23151.1 | 8 | 29.5 | 10 | 99349.5 |
| P62879 | Guanine nucleotide-binding protein G(I)/G(S)/G(T) subunit beta-2 | 38072.5 | 10 | 29.4 | 10 | 47427.61 |
| Q5JRX3 | Presequence protease, mitochondrial | 118529.0 | 20 | 29.4 | 10 | 23796 |
| P56381 | ATP synthase subunit epsilon, mitochondrial | 5836.8 | 3 | 29.4 | 1 | 0 |
| Q5VTU8 | ATP synthase subunit epsilon-like protein, mitochondrial | 5863.9 | 3 | 29.4 | 1 | 0 |
| Q5TC12 | ATP synthase mitochondrial F1 complex assembly factor 1 | 29315.6 | 7 | 29.4 | 8 | 0 |
| Q92598 | Heat shock protein 105 kDa | 94638.8 | 18 | 29.4 | 10 | 38120 |
| P25205 | DNA replication licensing factor MCM3 | 91608.3 | 19 | 29.3 | 10 | 52895 |
| Q9Y536 | Peptidyl-prolyl cis-trans isomerase A-like 4A/B/C | 18409.9 | 5 | 29.3 | 10 | 0 |
| Q8TAA3 | Proteasome subunit alpha type-7-like | 26824.7 | 5 | 29.3 | 10 | 34497 |
| Q9Y2R5 | 28S ribosomal protein S17, mitochondrial | 14616.1 | 3 | 29.2 | 4 | 40071 |
| Q8N0Y7 | Probable phosphoglycerate mutase 4 | 28948.0 | 7 | 29.1 | 10 | 0 |
| P62191 | 26S protease regulatory subunit 4 | 49355.7 | 11 | 29.1 | 8 | 0 |
| O75380 | NADH dehydrogenase [ubiquinone] iron-sulfur protein 6, mitochondrial | 14053.8 | 3 | 29.0 | 2 | 0 |
| O43660 | Pleiotropic regulator 1 | 57084.1 | 12 | 29.0 | 8 | 0 |
| Q3ZCQ8 | Mitochondrial import inner membrane translocase subunit TIM50 | 45426.2 | 9 | 28.9 | 10 | 73536 |
| P08579 | U2 small nuclear ribonucleoprotein B" | 25486.4 | 5 | 28.9 | 10 | 40167 |
| Q96AB3 | Isochorismatase domain-containing protein 2, mitochondrial | 20628.0 | 3 | 28.9 | 3 | 0 |

FIG. 17 (cont'd)

| | | | | | | |
|---|---|---|---|---|---|---|
| Q9NVI7 | ATPase family AAA domain-containing protein 3A | 65349.6 | 17 | 28.8 | 10 | 89258 |
| Q1KMD3 | Heterogeneous nuclear ribonucleoprotein U-like protein 2 | 85675.1 | 18 | 28.8 | 10 | 93799 |
| P60228 | Eukaryotic translation initiation factor 3 subunit E | 52620.1 | 12 | 28.8 | 10 | 28987 |
| O15173 | Membrane-associated progesterone receptor component 2 | 23875.5 | 7 | 28.7 | 10 | 39827.8 |
| Q5QJE6 | Deoxynucleotidyltransferase terminal-interacting protein 2 | 84868.3 | 18 | 28.7 | 10 | 23667 |
| Q8WUD1 | Ras-related protein Rab-2B | 24442.5 | 8 | 28.7 | 10 | 0 |
| Q16181 | Septin-7 | 50915.6 | 11 | 28.7 | 10 | 0 |
| Q13011 | Delta(3,5)-Delta(2,4)-dienoyl-CoA isomerase, mitochondrial | 36158.4 | 9 | 28.7 | 10 | 57471 |
| Q8NCW5 | NAD(P)H-hydrate epimerase | 26337.8 | 3 | 28.7 | 6 | 0 |
| P54136 | Arginine--tRNA ligase, cytoplasmic | 71972.7 | 17 | 28.6 | 10 | 41767 |
| Q9BQ39 | ATP-dependent RNA helicase DDX50 | 83135.4 | 17 | 28.6 | 10 | 67062.25 |
| P60866 | 40S ribosomal protein S20 | 14831.7 | 5 | 28.6 | 10 | 102444 |
| Q9BPW8 | Protein NipSnap homolog 1 | 33481.1 | 6 | 28.5 | 10 | 32841 |
| Q9UHG3 | Prenylcysteine oxidase 1 | 57039.5 | 12 | 28.5 | 9 | 19569 |
| Q9Y6M9 | NADH dehydrogenase [ubiquinone] 1 beta subcomplex subunit 9 | 22059.1 | 5 | 28.5 | 3 | 0 |
| P12814 | Alpha-actinin-1 | 104368.0 | 20 | 28.5 | 10 | 18965 |
| Q8IXM3 | 39S ribosomal protein L41, mitochondrial | 15439.8 | 4 | 28.5 | 3 | 0 |
| Q9Y3D3 | 28S ribosomal protein S16, mitochondrial | 15573.0 | 4 | 28.5 | 1 | 0 |
| P63027 | Vesicle-associated membrane protein 2 | 12719.8 | 3 | 28.5 | 8 | 71673 |
| Q9UL25 | Ras-related protein Rab-21 | 24746.8 | 8 | 28.4 | 6 | 30900 |
| Q9Y333 | U6 snRNA-associated Sm-like protein LSm2 | 10948.6 | 3 | 28.4 | 6 | 0 |
| P31150 | Rab GDP dissociation inhibitor alpha | 51210.1 | 9 | 28.4 | 5 | 40635 |
| P07339 | Cathepsin D | 45065.5 | 11 | 28.4 | 10 | 38425.5 |
| Q15293 | Reticulocalbin-1 | 38890.0 | 9 | 28.4 | 7 | 0 |
| Q92499 | ATP-dependent RNA helicase DDX1 | 83401.7 | 16 | 28.4 | 10 | 40528 |
| P49721 | Proteasome subunit beta type-2 | 23007.4 | 7 | 28.4 | 9 | 40501.5 |
| P19387 | DNA-directed RNA polymerase II subunit RPB3 | 31783.4 | 5 | 28.4 | 3 | 17223 |
| Q9Y676 | 28S ribosomal protein S18b, mitochondrial | 29737.8 | 8 | 28.3 | 4 | 0 |
| P62841 | 40S ribosomal protein S15 | 17040.2 | 3 | 28.3 | 10 | 146136 |
| Q14568 | Putative heat shock protein HSP 90-alpha A2 | 39478.9 | 8 | 28.3 | 10 | 0 |
| Q86Y82 | Syntaxin-12 | 31756.0 | 7 | 28.3 | 9 | 29398.5 |
| Q14684 | Ribosomal RNA processing protein 1 homolog B | 83672.5 | 19 | 28.2 | 10 | 52462 |
| Q8IWS0 | PHD finger protein 6 | 39393.4 | 9 | 28.2 | 8 | 0 |
| Q8TD30 | Alanine aminotransferase 2 | 53213.3 | 9 | 28.1 | 2 | 0 |
| O43172 | U4/U6 small nuclear ribonucleoprotein Prp4 | 59069.5 | 11 | 28.0 | 10 | 28365 |
| O00629 | Importin subunit alpha-3 | 58400.1 | 9 | 28.0 | 9 | 0 |
| P62851 | 40S ribosomal protein S25 | 13799.2 | 4 | 28.0 | 10 | 184648.5 |

FIG. 17 (cont'd)

| | | | | | | |
|---|---|---|---|---|---|---|
| O14737 | Programmed cell death protein 5 | 14285.1 | 4 | 28.0 | 7 | 0 |
| Q8WXF1 | Paraspeckle component 1 | 52299.9 | 10 | 28.0 | 10 | 69666 |
| Q13868 | Exosome complex component RRP4 | 33017.2 | 7 | 28.0 | 7 | 11820 |
| P31689 | DnaJ homolog subfamily A member 1 | 45609.6 | 7 | 28.0 | 10 | 57031.5 |
| P42765 | 3-ketoacyl-CoA thiolase, mitochondrial | 42380.4 | 7 | 28.0 | 7 | 0 |
| P61289 | Proteasome activator complex subunit 3 | 30339.0 | 7 | 28.0 | 10 | 14709 |
| Q86UP2 | Kinectin | 152364.9 | 27 | 27.9 | 10 | 36339 |
| Q9BWJ5 | Splicing factor 3B subunit 5 | 10249.4 | 2 | 27.9 | 1 | 0 |
| O00410 | Importin-5 | 123643.4 | 21 | 27.9 | 10 | 43738 |
| P68400 | Casein kinase II subunit alpha | 41001.1 | 10 | 27.9 | 10 | 42714 |
| O14602 | Eukaryotic translation initiation factor 1A, Y-chromosomal | 16556.4 | 3 | 27.8 | 9 | 0 |
| Q9UQE7 | Structural maintenance of chromosomes protein 3 | 141941.1 | 29 | 27.8 | 10 | 34577 |
| Q9BYX7 | Putative beta-actin-like protein 3 | 42358.5 | 7 | 27.7 | 10 | 0 |
| P16403 | Histone H1.2 | 21364.8 | 8 | 27.7 | 10 | 3343983 |
| P54652 | Heat shock-related 70 kDa protein 2 | 70306.2 | 16 | 27.7 | 10 | 9245.247 |
| P09012 | U1 small nuclear ribonucleoprotein A | 31279.6 | 6 | 27.7 | 10 | 96672 |
| P61163 | Alpha-centractin | 42727.9 | 10 | 27.7 | 8 | 0 |
| P12270 | Nucleoprotein TPR | 267692.3 | 49 | 27.6 | 10 | 70651 |
| Q58FF8 | Putative heat shock protein HSP 90-beta 2 | 44520.1 | 12 | 27.6 | 10 | 0 |
| Q9BU61 | NADH dehydrogenase [ubiquinone] 1 alpha subcomplex assembly factor 3 | 17952.2 | 4 | 27.6 | 5 | 0 |
| Q9BQ52 | Zinc phosphodiesterase ELAC protein 2 | 77884.7 | 13 | 27.5 | 10 | 0 |
| P36542 | ATP synthase subunit gamma, mitochondrial | 32995.6 | 8 | 27.5 | 10 | 137214 |
| P43686 | 26S protease regulatory subunit 6B | 45765.6 | 7 | 27.5 | 10 | 0 |
| Q9Y512 | Sorting and assembly machinery component 50 homolog | 52375.4 | 9 | 27.5 | 6 | 0 |
| P09622 | Dihydrolipoyl dehydrogenase, mitochondrial | 54747.6 | 13 | 27.5 | 10 | 117787 |
| P82650 | 28S ribosomal protein S22, mitochondrial | 41451.5 | 8 | 27.5 | 9 | 40224 |
| P13929 | Beta-enolase | 44792.2 | 8 | 27.4 | 10 | 94913 |
| Q562R1 | Beta-actin-like protein 2 | 42345.5 | 12 | 27.4 | 10 | 0 |
| Q01518 | Adenylyl cyclase-associated protein 1 | 52322.2 | 10 | 27.4 | 10 | 46341 |
| Q02880 | DNA topoisomerase 2-beta | 183934.6 | 36 | 27.3 | 10 | 62574 |
| Q14683 | Structural maintenance of chromosomes protein 1A | 143860.4 | 28 | 27.3 | 10 | 51345 |
| P52434 | DNA-directed RNA polymerases I, II, and III subunit RPABC3 | 17200.4 | 4 | 27.3 | 3 | 0 |
| Q8IXM2 | Chromatin complexes subunit BAP18 | 16139.4 | 3 | 27.3 | 10 | 0 |
| Q13123 | Protein Red | 65716.4 | 12 | 27.3 | 10 | 13644 |
| P49327 | Fatty acid synthase | 276050.2 | 50 | 27.3 | 10 | 50733 |
| P56134 | ATP synthase subunit f, mitochondrial | 10726.1 | 3 | 27.3 | 10 | 174952.5 |
| Q15006 | ER membrane protein complex subunit 2 | 35004.7 | 6 | 27.3 | 8 | 23146.5 |
| P53701 | Cytochrome c-type heme lyase | 31000.8 | 6 | 27.2 | 9 | 29826 |
| Q9H307 | Pinin | 74423.7 | 14 | 27.2 | 10 | 59416.5 |

FIG. 17 (cont'd)

| | | | | | | |
|---|---|---|---|---|---|---|
| O75131 | Copine-3 | 60986.1 | 11 | 27.2 | 9 | 32256 |
| P55060 | Exportin-2 | 84488.1 | 21 | 27.2 | 10 | 71091 |
| P35606 | Coatomer subunit beta' | 103342.8 | 19 | 27.2 | 10 | 29464 |
| Q5T1J5 | Putative coiled-coil-helix-coiled-coil-helix domain-containing protein CHCHD2P9, mitochondrial | 15717.7 | 2 | 27.2 | 2 | 0 |
| Q9BRJ2 | 39S ribosomal protein L45, mitochondrial | 35636.1 | 5 | 27.1 | 1 | 0 |
| Q9H9J2 | 39S ribosomal protein L44, mitochondrial | 37877.6 | 9 | 27.1 | 9 | 17676 |
| O14828 | Secretory carrier-associated membrane protein 3 | 37657.8 | 6 | 27.1 | 9 | 26598 |
| P08574 | Cytochrome c1, heme protein, mitochondrial | 35764.2 | 6 | 27.1 | 10 | 25855.5 |
| P78347 | General transcription factor II-I | 110706.5 | 20 | 27.1 | 10 | 45425 |
| Q5T2N8 | ATPase family AAA domain-containing protein 3C | 46664.8 | 8 | 27.0 | 10 | 0 |
| Q9UDW1 | Cytochrome b-c1 complex subunit 9 | 7308.5 | 2 | 27.0 | 9 | 52728 |
| O14929 | Histone acetyltransferase type B catalytic subunit | 46459.0 | 9 | 27.0 | 10 | 56136 |
| Q58FF7 | Putative heat shock protein HSP 90-beta-3 | 68667.1 | 19 | 27.0 | 10 | 0 |
| P53396 | ATP-citrate synthase | 121218.3 | 25 | 27.0 | 10 | 66554 |
| P23368 | NAD-dependent malic enzyme, mitochondrial | 60400.1 | 13 | 26.9 | 10 | 51786 |
| Q96I25 | Splicing factor 45 | 45189.7 | 11 | 26.9 | 10 | 19077 |
| P20340 | Ras-related protein Rab-6A | 20721.0 | 4 | 26.9 | 10 | 275880 |
| Q14566 | DNA replication licensing factor MCM6 | 93858.9 | 21 | 26.9 | 10 | 43933 |
| P06744 | Glucose-6-phosphate isomerase | 63992.6 | 11 | 26.9 | 10 | 77025 |
| Q7Z7H5 | Transmembrane emp24 domain-containing protein 4 | 23759.4 | 5 | 26.9 | 10 | 6720 |
| Q9H2W6 | 39S ribosomal protein L46, mitochondrial | 31819.2 | 8 | 26.9 | 4 | 0 |
| P07741 | Adenine phosphoribosyltransferase | 18057.2 | 4 | 26.9 | 3 | 0 |
| P62491 | Ras-related protein Rab-11A | 24507.6 | 7 | 26.9 | 10 | 75693 |
| Q7Z2W9 | 39S ribosomal protein L21, mitochondrial | 22985.8 | 4 | 26.8 | 1 | 0 |
| P45973 | Chromobox protein homolog 5 | 22396.1 | 5 | 26.7 | 10 | 0 |
| P84095 | Rho-related GTP-binding protein RhoG | 21764.7 | 3 | 26.7 | 1 | 0 |
| P46783 | 40S ribosomal protein S10 | 18897.8 | 6 | 26.7 | 10 | 183621 |
| P35659 | Protein DEK | 40974.7 | 11 | 26.7 | 10 | 161739 |
| Q9Y266 | Nuclear migration protein nudC | 38300.0 | 8 | 26.6 | 6 | 0 |
| Q14980 | Nuclear mitotic apparatus protein 1 | 220122.3 | 46 | 26.6 | 10 | 27256 |
| Q9Y5J9 | Mitochondrial import inner membrane translocase subunit Tim8 B | 9571.7 | 2 | 26.5 | 5 | 0 |
| P27694 | Replication protein A 70 kDa DNA-binding subunit | 68765.6 | 14 | 26.5 | 10 | 42576 |
| Q92520 | Protein FAM3C | 24965.7 | 6 | 26.4 | 2 | 0 |
| Q09028 | Histone-binding protein RBBP4 | 46505.4 | 9 | 26.4 | 10 | 196683 |
| P53621 | Coatomer subunit alpha | 140403.3 | 25 | 26.3 | 10 | 34611 |
| O95573 | Long-chain-fatty-acid--CoA ligase 3 | 81389.7 | 15 | 26.3 | 10 | 46386 |
| Q7Z4W1 | L-xylulose reductase | 26198.2 | 5 | 26.2 | 2 | 0 |

FIG. 17 (cont'd)

| | | | | | | |
|---|---|---|---|---|---|---|
| P43307 | Translocon-associated protein subunit alpha | 30952.4 | 4 | 26.2 | 10 | 97239 |
| P49756 | RNA-binding protein 25 | 59806.2 | 9 | 26.2 | 10 | 34176 |
| O96000 | NADH dehydrogenase [ubiquinone] 1 beta subcomplex subunit 10 | 21061.9 | 6 | 26.2 | 9 | 0 |
| O75475 | PC4 and SFRS1-interacting protein | 48534.6 | 11 | 26.1 | 10 | 48015 |
| O96019 | Actin-like protein 6A | 45833.5 | 9 | 26.1 | 10 | 0 |
| P62854 | 40S ribosomal protein S26 | 13300.6 | 3 | 26.1 | 10 | 215484 |
| Q96P16 | Regulation of nuclear pre-mRNA domain-containing protein 1A | 33929.0 | 6 | 26.1 | 10 | 47601 |
| O43776 | Asparagine--tRNA ligase, cytoplasmic | 63798.4 | 13 | 26.1 | 10 | 17502 |
| Q9P2R7 | Succinyl-CoA ligase [ADP-forming] subunit beta, mitochondrial | 49520.8 | 11 | 26.1 | 10 | 34069 |
| Q9UNM6 | 26S proteasome non-ATPase regulatory subunit 13 | 43257.7 | 10 | 26.1 | 10 | 17143.5 |
| P60468 | Protein transport protein Sec61 subunit beta | 10031.5 | 2 | 26.0 | 3 | 0 |
| P09936 | Ubiquitin carboxyl-terminal hydrolase isozyme L1 | 25166.6 | 6 | 26.0 | 6 | 0 |
| Q5U5X0 | Complex III assembly factor LYRM7 | 12011.9 | 3 | 26.0 | 3 | 31503 |
| P55809 | Succinyl-CoA:3-ketoacid coenzyme A transferase 1, mitochondrial | 56614.0 | 9 | 26.0 | 10 | 7587 |
| Q15008 | 26S proteasome non-ATPase regulatory subunit 6 | 45816.6 | 10 | 26.0 | 6 | 0 |
| Q9Y394 | Dehydrogenase/reductase SDR family member 7 | 35653.9 | 5 | 26.0 | 4 | 0 |
| Q7L2H7 | Eukaryotic translation initiation factor 3 subunit M | 42959.2 | 7 | 25.9 | 8 | 10050 |
| Q9NZ45 | CDGSH iron-sulfur domain-containing protein 1 | 12370.2 | 2 | 25.9 | 5 | 0 |
| P35580 | Myosin-10 | 231888.5 | 40 | 25.9 | 10 | 69769 |
| P61158 | Actin-related protein 3 | 47827.5 | 8 | 25.8 | 10 | 0 |
| Q92522 | Histone H1x | 22487.1 | 6 | 25.8 | 10 | 134349 |
| Q92665 | 28S ribosomal protein S31, mitochondrial | 45432.6 | 10 | 25.8 | 10 | 47217 |
| P09104 | Gamma-enolase | 47610.8 | 8 | 25.8 | 10 | 0 |
| P60891 | Ribose-phosphate pyrophosphokinase 1 | 35347.5 | 6 | 25.8 | 10 | 117606 |
| P41252 | Isoleucine--tRNA ligase, cytoplasmic | 145810.0 | 26 | 25.8 | 10 | 51312 |
| P47756 | F-actin-capping protein subunit beta | 31303.3 | 8 | 25.7 | 10 | 0 |
| Q2TAY7 | WD40 repeat-containing protein SMU1 | 58171.3 | 10 | 25.7 | 10 | 40734 |
| Q9NQ50 | 39S ribosomal protein L40, mitochondrial | 24490.4 | 4 | 25.7 | 4 | 0 |
| O75477 | Erlin-1 | 39097.0 | 8 | 25.7 | 10 | 36504.13 |
| P51809 | Vesicle-associated membrane protein 7 | 26089.9 | 6 | 25.7 | 8 | 0 |
| P49257 | Protein ERGIC-53 | 57834.2 | 7 | 25.7 | 7 | 0 |
| Q9P2J5 | Leucine--tRNA ligase, cytoplasmic | 135664.0 | 25 | 25.7 | 10 | 43487 |
| Q15005 | Signal peptidase complex subunit 2 | 25288.0 | 5 | 25.7 | 9 | 66177 |
| P61088 | Ubiquitin-conjugating enzyme E2 N | 17194.9 | 4 | 25.7 | 2 | 0 |
| Q7L2E3 | Putative ATP-dependent RNA helicase DHX30 | 134190.5 | 26 | 25.6 | 10 | 29799 |
| B2RPK0 | Putative high mobility group protein B1-like 1 | 24409.1 | 7 | 25.6 | 10 | 208458 |

FIG. 17 (cont'd)

| | | | | | | |
|---|---|---|---|---|---|---|
| P25325 | 3-mercaptopyruvate sulfurtransferase | 33463.6 | 4 | 25.6 | 3 | 0 |
| P21333 | Filamin-A | 283116.2 | 43 | 25.6 | 10 | 55298 |
| Q9H078 | Caseinolytic peptidase B protein homolog | 75850.4 | 15 | 25.6 | 10 | 41289 |
| O14980 | Exportin-1 | 124526.7 | 25 | 25.5 | 10 | 50473 |
| P49591 | Serine--tRNA ligase, cytoplasmic | 59290.6 | 13 | 25.5 | 7 | 0 |
| Q96A33 | Coiled-coil domain-containing protein 47 | 55995.2 | 9 | 25.4 | 10 | 48435 |
| Q9BVI4 | Nucleolar complex protein 4 homolog | 58867.0 | 12 | 25.4 | 7 | 24508.5 |
| O00231 | 26S proteasome non-ATPase regulatory subunit 11 | 47784.5 | 9 | 25.4 | 10 | 82109 |
| Q15050 | Ribosome biogenesis regulatory protein homolog | 41250.4 | 11 | 25.2 | 10 | 49358 |
| Q92769 | Histone deacetylase 2 | 55934.6 | 10 | 25.2 | 10 | 85875 |
| P33993 | DNA replication licensing factor MCM7 | 63955.8 | 15 | 25.2 | 10 | 27706 |
| P60953 | Cell division control protein 42 homolog | 21600.8 | 3 | 25.1 | 1 | 0 |
| P51153 | Ras-related protein Rab-13 | 23002.3 | 6 | 25.1 | 10 | 22574.75 |
| Q8N684 | Cleavage and polyadenylation specificity factor subunit 7 | 53325.8 | 10 | 25.1 | 10 | 28998 |
| Q14137 | Ribosome biogenesis protein BOP1 | 84314.0 | 14 | 25.1 | 10 | 10242 |
| Q14320 | Protein FAM50A | 40241.7 | 6 | 25.1 | 7 | 8433 |
| P61421 | V-type proton ATPase subunit d 1 | 40785.4 | 7 | 25.1 | 2 | 0 |
| Q07666 | KH domain-containing, RNA-binding, signal transduction-associated protein 1 | 46152.6 | 10 | 25.1 | 10 | 342720 |
| O75306 | NADH dehydrogenase [ubiquinone] iron-sulfur protein 2, mitochondrial | 52945.0 | 10 | 25.1 | 10 | 30690 |
| Q16695 | Histone H3.1t | 15622.3 | 6 | 25.0 | 10 | 1554896 |
| Q13243 | Serine/arginine-rich splicing factor 5 | 27107.0 | 7 | 25.0 | 10 | 76206 |
| P60033 | CD81 antigen | 26493.8 | 5 | 25.0 | 2 | 0 |
| P62308 | Small nuclear ribonucleoprotein G | 8553.1 | 2 | 25.0 | 10 | 0 |
| P68431 | Histone H3.1 | 15518.2 | 6 | 25.0 | 10 | 0 |
| P51553 | Isocitrate dehydrogenase [NAD] subunit gamma, mitochondrial | 43193.6 | 8 | 24.9 | 6 | 0 |
| Q9HDC9 | Adipocyte plasma membrane-associated protein | 39463.3 | 9 | 24.9 | 10 | 34986 |
| Q6NUK1 | Calcium-binding mitochondrial carrier protein SCaMC-1 | 52554.0 | 11 | 24.9 | 10 | 53805 |
| Q96GQ7 | Probable ATP-dependent RNA helicase DDX27 | 90348.7 | 19 | 24.9 | 10 | 35636 |
| P02786 | Transferrin receptor protein 1 | 85327.7 | 18 | 24.9 | 10 | 22629 |
| Q8N183 | Mimitin, mitochondrial | 19856.4 | 3 | 24.9 | 5 | 0 |
| Q9GZV4 | Eukaryotic translation initiation factor 5A-2 | 17135.4 | 5 | 24.8 | 10 | 0 |
| P51572 | B-cell receptor-associated protein 31 | 31486.0 | 8 | 24.8 | 10 | 84138 |
| Q13247 | Serine/arginine-rich splicing factor 6 | 34004.6 | 9 | 24.8 | 10 | 344139 |
| P13637 | Sodium/potassium-transporting ATPase subunit alpha-3 | 113174.4 | 19 | 24.8 | 10 | 85064 |
| Q3ZCM7 | Tubulin beta-8 chain | 50289.4 | 12 | 24.8 | 10 | 236215.7 |
| Q8IWA0 | WD repeat-containing protein 75 | 95981.6 | 17 | 24.7 | 8 | 0 |
| P00403 | Cytochrome c oxidase subunit 2 | 25736.2 | 5 | 24.7 | 10 | 117927 |
| P10412 | Histone H1.4 | 21865.3 | 9 | 24.7 | 10 | 4346096 |

FIG. 17 (cont'd)

| | | | | | | |
|---|---|---|---|---|---|---|
| P27144 | Adenylate kinase 4, mitochondrial | 25382.1 | 6 | 24.7 | 1 | 0 |
| Q6UB35 | Monofunctional C1-tetrahydrofolate synthase, mitochondrial | 98644.0 | 19 | 24.6 | 10 | 47171 |
| P30086 | Phosphatidylethanolamine-binding protein 1 | 21170.9 | 4 | 24.6 | 6 | 0 |
| Q9UBS4 | DnaJ homolog subfamily B member 11 | 40799.1 | 8 | 24.6 | 9 | 0 |
| Q9P032 | NADH dehydrogenase [ubiquinone] 1 alpha subcomplex assembly factor 4 | 20323.5 | 5 | 24.6 | 1 | 0 |
| O75439 | Mitochondrial-processing peptidase subunit beta | 55107.6 | 9 | 24.5 | 10 | 27052 |
| P09234 | U1 small nuclear ribonucleoprotein C | 17564.9 | 3 | 24.5 | 10 | 151770 |
| P47985 | Cytochrome b-c1 complex subunit Rieske, mitochondrial | 29953.2 | 6 | 24.5 | 10 | 95277 |
| Q9HAV0 | Guanine nucleotide-binding protein subunit beta-4 | 38308.6 | 9 | 24.4 | 10 | 0 |
| P50502 | Hsc70-interacting protein | 41502.9 | 8 | 24.4 | 10 | 117245 |
| Q9BVP2 | Guanine nucleotide-binding protein-like 3 | 61780.1 | 11 | 24.4 | 10 | 0 |
| Q9NUP9 | Protein lin-7 homolog C | 21948.1 | 4 | 24.4 | 3 | 0 |
| Q15637 | Splicing factor 1 | 67657.2 | 10 | 24.3 | 10 | 73722 |
| Q9GZS3 | WD repeat-containing protein 61 | 33751.7 | 6 | 24.3 | 2 | 0 |
| Q9BUJ2 | Heterogeneous nuclear ribonucleoprotein U-like protein 1 | 89372.8 | 19 | 24.3 | 10 | 50917 |
| O60812 | Heterogeneous nuclear ribonucleoprotein C-like 1 | 32199.5 | 8 | 24.2 | 10 | 148170 |
| Q9Y4W2 | Ribosomal biogenesis protein LAS1L | 69795.8 | 13 | 24.1 | 10 | 28722 |
| Q96A35 | 39S ribosomal protein L24, mitochondrial | 25028.9 | 4 | 24.1 | 8 | 13668 |
| P59190 | Ras-related protein Rab-15 | 24210.9 | 5 | 24.1 | 10 | 149943 |
| P49448 | Glutamate dehydrogenase 2, mitochondrial | 61776.3 | 15 | 24.0 | 10 | 0 |
| Q9UBE0 | SUMO-activating enzyme subunit 1 | 36089.5 | 6 | 24.0 | 5 | 0 |
| Q96C01 | Protein FAM136A | 16154.5 | 4 | 23.9 | 2 | 0 |
| Q8TC12 | Retinol dehydrogenase 11 | 35509.0 | 6 | 23.9 | 10 | 30924 |
| Q8TEM1 | Nuclear pore membrane glycoprotein 210 | 166189.3 | 18 | 23.9 | 10 | 17808 |
| P20338 | Ras-related protein Rab-4A | 24674.8 | 5 | 23.9 | 10 | 0 |
| P51970 | NADH dehydrogenase [ubiquinone] 1 alpha subcomplex subunit 8 | 20561.3 | 5 | 23.8 | 3 | 0 |
| O00217 | NADH dehydrogenase [ubiquinone] iron-sulfur protein 8, mitochondrial | 24218.4 | 6 | 23.8 | 10 | 45303 |
| P51398 | 28S ribosomal protein S29, mitochondrial | 43103.6 | 8 | 23.8 | 10 | 33051 |
| Q16543 | Hsp90 co-chaperone Cdc37 | 44981.6 | 8 | 23.8 | 9 | 0 |
| P62312 | U6 snRNA-associated Sm-like protein LSm6 | 9184.6 | 4 | 23.8 | 2 | 0 |
| P15311 | Ezrin | 69527.0 | 16 | 23.7 | 10 | 68152 |
| P07305 | Histone H1.0 | 20015.0 | 4 | 23.7 | 10 | 96846 |
| Q86UE4 | Protein LYRIC | 63894.1 | 13 | 23.7 | 10 | 0 |
| O95816 | BAG family molecular chaperone regulator 2 | 23943.1 | 4 | 23.7 | 4 | 0 |
| Q9BSD7 | Cancer-related nucleoside-triphosphatase | 20941.2 | 3 | 23.7 | 3 | 29409 |
| Q9Y3D6 | Mitochondrial fission 1 protein | 16994.8 | 3 | 23.7 | 2 | 0 |

FIG. 17 (cont'd)

| | | | | | | |
|---|---|---|---|---|---|---|
| P61970 | Nuclear transport factor 2 | 14649.6 | 3 | 23.6 | 7 | 0 |
| Q9P0J0 | NADH dehydrogenase [ubiquinone] 1 alpha subcomplex subunit 13 | 16698.4 | 3 | 23.6 | 8 | 0 |
| Q14839 | Chromodomain-helicase-DNA-binding protein 4 | 220994.9 | 33 | 23.6 | 10 | 54435 |
| Q6DKI1 | 60S ribosomal protein L7-like 1 | 28775.1 | 4 | 23.6 | 4 | 51454.5 |
| Q86YS6 | Ras-related protein Rab-43 | 23567.5 | 4 | 23.6 | 10 | 26891.91 |
| P09110 | 3-ketoacyl-CoA thiolase, peroxisomal | 40558.2 | 10 | 23.6 | 9 | 0 |
| Q9H3N1 | Thioredoxin-related transmembrane protein 1 | 32190.5 | 7 | 23.6 | 10 | 91884 |
| P26038 | Moesin | 67934.2 | 14 | 23.6 | 10 | 0 |
| O75369 | Filamin-B | 266073.9 | 47 | 23.6 | 10 | 21942 |
| P42696 | RNA-binding protein 34 | 37185.0 | 9 | 23.6 | 6 | 0 |
| P11586 | C-1-tetrahydrofolate synthase, cytoplasmic | 102243.7 | 18 | 23.5 | 10 | 58899 |
| Q9H7B2 | Ribosome production factor 2 homolog | 35754.0 | 6 | 23.5 | 10 | 30411 |
| Q9NUJ1 | Mycophenolic acid acyl-glucuronide esterase, mitochondrial | 34274.7 | 7 | 23.5 | 10 | 23559 |
| Q13405 | 39S ribosomal protein L49, mitochondrial | 19255.1 | 5 | 23.5 | 9 | 0 |
| O60762 | Dolichol-phosphate mannosyltransferase | 29691.3 | 7 | 23.5 | 10 | 27669 |
| Q5T9A4 | ATPase family AAA domain-containing protein 3B | 59423.7 | 15 | 23.5 | 10 | 3433 |
| Q9NSE4 | Isoleucine--tRNA ligase, mitochondrial | 114761.2 | 17 | 23.4 | 10 | 58040 |
| A6NNZ2 | Tubulin beta-8 chain-like protein LOC260334 | 50200.0 | 8 | 23.4 | 10 | 0 |
| O43143 | Putative pre-mRNA-splicing factor ATP-dependent RNA helicase DHX15 | 91731.4 | 16 | 23.4 | 10 | 78764 |
| Q9Y3B3 | Transmembrane emp24 domain-containing protein 7 | 23544.5 | 4 | 23.4 | 6 | 0 |
| P82664 | 28S ribosomal protein S10, mitochondrial | 23113.6 | 4 | 23.4 | 2 | 0 |
| Q12907 | Vesicular integral-membrane protein VIP36 | 40570.9 | 8 | 23.3 | 10 | 21705 |
| Q2VIR3 | Putative eukaryotic translation initiation factor 2 subunit 3-like protein | 51525.0 | 8 | 23.3 | 10 | 0 |
| P35221 | Catenin alpha-1 | 102018.2 | 18 | 23.3 | 10 | 23113.5 |
| Q13200 | 26S proteasome non-ATPase regulatory subunit 2 | 100941.3 | 17 | 23.2 | 10 | 22029 |
| Q9P2E9 | Ribosome-binding protein 1 | 138163.6 | 19 | 23.2 | 10 | 25298 |
| P13489 | Ribonuclease inhibitor | 51798.4 | 8 | 23.2 | 2 | 0 |
| P42126 | Enoyl-CoA delta isomerase 1, mitochondrial | 32112.5 | 6 | 23.2 | 10 | 154276.5 |
| P33992 | DNA replication licensing factor MCM5 | 83084.1 | 13 | 23.2 | 10 | 37949 |
| P48741 | Putative heat shock 70 kDa protein 7 | 40472.6 | 8 | 23.2 | 10 | 0 |
| P0CG47 | Polyubiquitin-B | 25818.7 | 6 | 23.1 | 10 | 0 |
| P19784 | Casein kinase II subunit alpha' | 41384.4 | 7 | 23.1 | 8 | 0 |
| P35249 | Replication factor C subunit 4 | 40195.0 | 7 | 23.1 | 6 | 0 |
| Q15287 | RNA-binding protein with serine-rich domain 1 | 32090.6 | 6 | 23.1 | 10 | 105624 |
| Q15046 | Lysine--tRNA ligase | 70228.9 | 10 | 23.1 | 10 | 13302 |
| Q13895 | Bystin | 49829.5 | 10 | 23.1 | 3 | 10719 |
| Q8WXX5 | DnaJ homolog subfamily C member 9 | 30080.9 | 5 | 23.1 | 6 | 0 |

FIG. 17 (cont'd)

| | | | | | | |
|---|---|---|---|---|---|---|
| Q9UFN0 | Protein NipSnap homolog 3A | 28580.7 | 6 | 23.1 | 5 | 0 |
| Q9Y262 | Eukaryotic translation initiation factor 3 subunit L | 64070.0 | 9 | 23.1 | 10 | 41950.5 |
| P10768 | S-formylglutathione hydrolase | 31976.1 | 4 | 23.1 | 2 | 0 |
| Q9BRT2 | Ubiquinol-cytochrome-c reductase complex assembly factor 2 | 14988.9 | 3 | 23.0 | 1 | 0 |
| P07108 | Acyl-CoA-binding protein | 12614.5 | 1 | 23.0 | 5 | 0 |
| Q9Y2Q9 | 28S ribosomal protein S28, mitochondrial | 21013.9 | 3 | 23.0 | 4 | 0 |
| Q9UNP9 | Peptidyl-prolyl cis-trans isomerase E | 33514.8 | 7 | 23.0 | 6 | 0 |
| O00422 | Histone deacetylase complex subunit SAP18 | 17618.1 | 5 | 22.9 | 1 | 0 |
| P46940 | Ras GTPase-activating-like protein IQGAP1 | 189879.6 | 30 | 22.9 | 10 | 42002 |
| Q9UBQ7 | Glyoxylate reductase/hydroxypyruvate reductase | 36067.5 | 7 | 22.9 | 6 | 0 |
| P35637 | RNA-binding protein FUS | 53618.5 | 11 | 22.9 | 10 | 269140 |
| Q96E11 | Ribosome-recycling factor, mitochondrial | 25729.3 | 5 | 22.9 | 3 | 0 |
| P11233 | Ras-related protein Ral-A | 23737.9 | 4 | 22.8 | 3 | 0 |
| Q16630 | Cleavage and polyadenylation specificity factor subunit 6 | 58506.7 | 8 | 22.8 | 10 | 62313 |
| Q9UNX3 | 60S ribosomal protein L26-like 1 | 17256.3 | 5 | 22.8 | 10 | 177648 |
| P61254 | 60S ribosomal protein L26 | 17258.2 | 5 | 22.8 | 10 | 0 |
| Q6UN15 | Pre-mRNA 3'-end-processing factor FIP1 | 57965.9 | 6 | 22.8 | 10 | 48495 |
| P18077 | 60S ribosomal protein L35a | 12594.7 | 5 | 22.7 | 7 | 106428 |
| Q13642 | Four and a half LIM domains protein 1 | 34270.3 | 6 | 22.7 | 6 | 0 |
| Q15024 | Exosome complex component RRP42 | 32448.8 | 5 | 22.7 | 2 | 0 |
| Q9HCC0 | Methylcrotonoyl-CoA carboxylase beta chain, mitochondrial | 59910.8 | 9 | 22.7 | 10 | 0 |
| Q09161 | Nuclear cap-binding protein subunit 1 | 92923.1 | 14 | 22.7 | 10 | 0 |
| Q9H0S4 | Probable ATP-dependent RNA helicase DDX47 | 46785.8 | 10 | 22.6 | 10 | 50778 |
| Q16531 | DNA damage-binding protein 1 | 128222.7 | 22 | 22.6 | 10 | 28856 |
| P61923 | Coatomer subunit zeta-1 | 20255.3 | 5 | 22.6 | 3 | 0 |
| O15042 | U2 snRNP-associated SURP motif-containing protein | 104129.9 | 16 | 22.6 | 10 | 11205 |
| Q9UHA4 | Ragulator complex protein LAMTOR3 | 13679.8 | 1 | 22.6 | 1 | 0 |
| P04179 | Superoxide dismutase [Mn], mitochondrial | 22944.9 | 7 | 22.5 | 10 | 94060.5 |
| P17174 | Aspartate aminotransferase, cytoplasmic | 46475.7 | 11 | 22.5 | 2 | 0 |
| Q13310 | Polyadenylate-binding protein 4 | 71221.7 | 14 | 22.5 | 10 | 28978 |
| Q8IZP2 | Putative protein FAM10A4 | 27577.9 | 4 | 22.5 | 10 | 0 |
| P00491 | Purine nucleoside phosphorylase | 32346.1 | 7 | 22.5 | 6 | 0 |
| P41250 | Glycine--tRNA ligase | 83907.1 | 15 | 22.5 | 10 | 38355 |
| Q9NQ29 | Putative RNA-binding protein Luc7-like 1 | 41657.5 | 8 | 22.5 | 10 | 0 |
| P23526 | Adenosylhomocysteinase | 46838.2 | 8 | 22.5 | 10 | 53963 |
| O94906 | Pre-mRNA-processing factor 6 | 105475.5 | 21 | 22.4 | 10 | 30945 |
| Q16718 | NADH dehydrogenase [ubiquinone] 1 alpha subcomplex subunit 5 | 13515.7 | 2 | 22.4 | 2 | 0 |

FIG. 17 (cont'd)

| | | | | | | |
|---|---|---|---|---|---|---|
| Q15758 | Neutral amino acid transporter B(0) | 57054.6 | 9 | 22.4 | 10 | 117949.5 |
| Q9P0I2 | ER membrane protein complex subunit 3 | 27433.8 | 3 | 22.4 | 2 | 0 |
| Q15269 | Periodic tryptophan protein 2 homolog | 103421.7 | 18 | 22.3 | 10 | 32629 |
| Q9P015 | 39S ribosomal protein L15, mitochondrial | 33590.9 | 7 | 22.3 | 6 | 0 |
| O95299 | NADH dehydrogenase [ubiquinone] 1 alpha subcomplex subunit 10, mitochondrial | 41092.8 | 7 | 22.3 | 9 | 0 |
| Q13547 | Histone deacetylase 1 | 55673.4 | 10 | 22.2 | 10 | 34119 |
| P62495 | Eukaryotic peptide chain release factor subunit 1 | 49259.1 | 10 | 22.2 | 4 | 0 |
| Q01130 | Serine/arginine-rich splicing factor 2 | 25476.4 | 6 | 22.2 | 10 | 181072.5 |
| P05787 | Keratin, type II cytoskeletal 8 | 55156.4 | 15 | 22.2 | 10 | 8014.5 |
| Q9Y3A4 | Ribosomal RNA-processing protein 7 homolog A | 32505.2 | 4 | 22.1 | 1 | 0 |
| Q9H8H0 | Nucleolar protein 11 | 82093.2 | 11 | 22.1 | 9 | 12603 |
| O43242 | 26S proteasome non-ATPase regulatory subunit 3 | 61091.7 | 12 | 22.1 | 10 | 4950 |
| Q16698 | 2,4-dienoyl-CoA reductase, mitochondrial | 36352.9 | 7 | 22.1 | 5 | 0 |
| Q53GS9 | U4/U6.U5 tri-snRNP-associated protein 2 | 59759.2 | 13 | 22.1 | 10 | 19152 |
| Q16740 | Putative ATP-dependent Clp protease proteolytic subunit, mitochondrial | 30465.3 | 6 | 22.0 | 8 | 16584 |
| P31937 | 3-hydroxyisobutyrate dehydrogenase, mitochondrial | 35728.2 | 7 | 22.0 | 7 | 0 |
| P82933 | 28S ribosomal protein S9, mitochondrial | 46063.0 | 8 | 22.0 | 10 | 37455 |
| Q9BXP5 | Serrate RNA effector molecule homolog | 100066.0 | 15 | 21.9 | 10 | 62339 |
| O00425 | Insulin-like growth factor 2 mRNA-binding protein 3 | 43550.3 | 10 | 21.9 | 10 | 22328.91 |
| P46087 | Putative ribosomal RNA methyltransferase NOP2 | 85558.2 | 14 | 21.9 | 10 | 80035 |
| Q10713 | Mitochondrial-processing peptidase subunit alpha | 58766.3 | 10 | 21.9 | 9 | 0 |
| Q9NYL9 | Tropomodulin-3 | 39765.9 | 6 | 21.9 | 1 | 0 |
| P06454 | Prothymosin alpha | 12138.4 | 3 | 21.8 | 4 | 0 |
| P56545 | C-terminal-binding protein 2 | 81577.6 | 10 | 21.8 | 10 | 60744 |
| O15400 | Syntaxin-7 | 28722.1 | 7 | 21.8 | 4 | 0 |
| Q16795 | NADH dehydrogenase [ubiquinone] 1 alpha subcomplex subunit 9, mitochondrial | 42680.7 | 6 | 21.8 | 9 | 23386.5 |
| Q7L014 | Probable ATP-dependent RNA helicase DDX46 | 117875.5 | 23 | 21.7 | 10 | 34290 |
| Q9BW92 | Threonine--tRNA ligase, mitochondrial | 81891.6 | 13 | 21.7 | 7 | 0 |
| Q9UHD1 | Cysteine and histidine-rich domain-containing protein 1 | 38288.2 | 5 | 21.7 | 1 | 0 |
| P22090 | 40S ribosomal protein S4, Y isoform 1 | 29683.8 | 7 | 21.7 | 10 | 0 |
| Q96EE3 | Nucleoporin SEH1 | 43655.3 | 7 | 21.7 | 10 | 0 |
| P14678 | Small nuclear ribonucleoprotein-associated proteins B and B' | 26365.7 | 5 | 21.7 | 10 | 0 |
| Q92843 | Bcl-2-like protein 2 | 37399.0 | 7 | 21.6 | 10 | 70083 |
| P17066 | Heat shock 70 kDa protein 6 | 71484.5 | 14 | 21.6 | 10 | 32698 |

FIG. 17 (cont'd)

| | | | | | | |
|---|---|---|---|---|---|---|
| Q99733 | Nucleosome assembly protein 1-like 4 | 42994.6 | 6 | 21.6 | 7 | 0 |
| Q9Y2Z4 | Tyrosine--tRNA ligase, mitochondrial | 53427.2 | 10 | 21.6 | 6 | 0 |
| P09496 | Clathrin light chain A | 25166.2 | 4 | 21.6 | 10 | 0 |
| P53007 | Tricarboxylate transport protein, mitochondrial | 34354.9 | 7 | 21.5 | 10 | 41814 |
| P08243 | Asparagine synthetase [glutamine-hydrolyzing] | 61379.1 | 11 | 21.5 | 10 | 39906 |
| P57088 | Transmembrane protein 33 | 28320.4 | 4 | 21.5 | 10 | 73242 |
| P48735 | Isocitrate dehydrogenase [NADP], mitochondrial | 51365.6 | 9 | 21.5 | 10 | 0 |
| O60716 | Catenin delta-1 | 92842.1 | 17 | 21.5 | 10 | 6072 |
| O60508 | Pre-mRNA-processing factor 17 | 66205.7 | 9 | 21.4 | 2 | 0 |
| O94925 | Glutaminase kidney isoform, mitochondrial | 66788.1 | 10 | 21.4 | 10 | 28596 |
| P25788 | Proteasome subunit alpha type-3 | 28268.4 | 6 | 21.4 | 10 | 0 |
| Q5J8M3 | ER membrane protein complex subunit 4 | 17439.6 | 2 | 21.3 | 3 | 0 |
| P42285 | Superkiller viralicidic activity 2-like 2 | 118831.5 | 17 | 21.3 | 10 | 35624 |
| Q9NQ55 | Suppressor of SWI 1 homolog | 52832.4 | 6 | 21.3 | 10 | 0 |
| Q9H857 | 5'-nucleotidase domain-containing protein 2 | 54852.5 | 9 | 21.3 | 10 | 0 |
| O43681 | ATPase ASNA1 | 39249.1 | 5 | 21.3 | 8 | 0 |
| Q8N163 | Cell cycle and apoptosis regulator protein 2 | 103649.7 | 14 | 21.2 | 10 | 39390 |
| O95758 | Polypyrimidine tract-binding protein 3 | 58913.8 | 6 | 21.2 | 10 | 0 |
| Q9BYD6 | 39S ribosomal protein L1, mitochondrial | 37136.9 | 6 | 21.2 | 10 | 0 |
| Q9P2I0 | Cleavage and polyadenylation specificity factor subunit 2 | 89342.3 | 14 | 21.2 | 4 | 0 |
| Q9UQ35 | Serine/arginine repetitive matrix protein 2 | 214066.1 | 24 | 21.2 | 10 | 54522 |
| P15121 | Aldose reductase | 36252.6 | 6 | 21.2 | 9 | 0 |
| Q14108 | Lysosome membrane protein 2 | 47665.3 | 6 | 21.2 | 7 | 0 |
| Q8WVM8 | Sec1 family domain-containing protein 1 | 72722.2 | 10 | 21.2 | 9 | 22102.5 |
| Q99460 | 26S proteasome non-ATPase regulatory subunit 1 | 105045.4 | 19 | 21.2 | 10 | 23028 |
| Q9BSJ8 | Extended synaptotagmin-1 | 123943.0 | 18 | 21.1 | 10 | 31281 |
| Q9BRX8 | Redox-regulatory protein FAM213A | 25227.5 | 5 | 21.1 | 6 | 0 |
| Q92575 | UBX domain-containing protein 4 | 57062.7 | 6 | 21.1 | 3 | 0 |
| Q9Y285 | Phenylalanine--tRNA ligase alpha subunit | 57620.8 | 10 | 21.1 | 5 | 0 |
| Q6RFH5 | WD repeat-containing protein 74 | 41866.2 | 6 | 21.0 | 4 | 0 |
| Q86SX6 | Glutaredoxin-related protein 5, mitochondrial | 16741.9 | 3 | 21.0 | 9 | 26679 |
| Q8N9F7 | Glycerophosphodiester phosphodiesterase domain-containing protein 1 | 35043.0 | 6 | 21.0 | 8 | 0 |
| P10155 | 60 kDa SS-A/Ro ribonucleoprotein | 57679.2 | 9 | 21.0 | 10 | 0 |
| Q9NR28 | Diablo homolog, mitochondrial | 23701.4 | 4 | 21.0 | 10 | 50163 |
| Q58FG0 | Putative heat shock protein HSP 90-alpha A5 | 38966.2 | 8 | 21.0 | 10 | 0 |
| P28288 | ATP-binding cassette sub-family D member 3 | 66192.1 | 11 | 21.0 | 10 | 60903 |

FIG. 17 (cont'd)

| | | | | | | |
|---|---|---|---|---|---|---|
| P50914 | 60S ribosomal protein L14 | 23545.9 | 4 | 20.9 | 10 | 257359 |
| Q9UKV3 | Apoptotic chromatin condensation inducer in the nucleus | 111976.4 | 20 | 20.9 | 10 | 77856 |
| Q9Y2S7 | Polymerase delta-interacting protein 2 | 42261.4 | 8 | 20.9 | 7 | 0 |
| Q9Y2P8 | RNA 3'-terminal phosphate cyclase-like protein | 41298.9 | 6 | 20.9 | 5 | 31677 |
| Q92973 | Transportin-1 | 101652.5 | 15 | 20.9 | 10 | 52434 |
| P09972 | Fructose-bisphosphate aldolase C | 39855.1 | 9 | 20.9 | 10 | 0 |
| P57721 | Poly(rC)-binding protein 3 | 38266.4 | 7 | 20.9 | 10 | 0 |
| Q9UHA3 | Probable ribosome biogenesis protein RLP24 | 19906.3 | 4 | 20.9 | 5 | 0 |
| P45954 | Short/branched chain specific acyl-CoA dehydrogenase, mitochondrial | 47827.7 | 8 | 20.8 | 4 | 0 |
| P63162 | Small nuclear ribonucleoprotein-associated protein N | 24785.2 | 5 | 20.8 | 3 | 0 |
| P01892 | HLA class I histocompatibility antigen, A-2 alpha chain | 41207.1 | 6 | 20.8 | 9 | 0 |
| P10316 | HLA class I histocompatibility antigen, A-69 alpha chain | 41262.0 | 6 | 20.8 | 9 | 0 |
| P83881 | 60S ribosomal protein L36a | 12726.0 | 2 | 20.8 | 10 | 101103 |
| Q969Q0 | 60S ribosomal protein L36a-like | 12754.0 | 2 | 20.8 | 10 | 0 |
| P15927 | Replication protein A 32 kDa subunit | 32870.6 | 4 | 20.7 | 10 | 0 |
| P08134 | Rho-related GTP-binding protein RhoC | 22348.6 | 5 | 20.7 | 10 | 0 |
| P40429 | 60S ribosomal protein L13a | 23634.3 | 5 | 20.7 | 10 | 218481 |
| P40937 | Replication factor C subunit 5 | 37585.9 | 11 | 20.7 | 6 | 0 |
| Q7Z3B4 | Nucleoporin p54 | 44364.7 | 6 | 20.6 | 6 | 0 |
| Q9Y2L1 | Exosome complex exonuclease RRP44 | 108303.4 | 14 | 20.6 | 10 | 26400 |
| P36957 | Dihydrolipoyllysine-residue succinyltransferase component of 2-oxoglutarate dehydrogenase complex, mitochondrial | 49097.6 | 9 | 20.5 | 10 | 78517 |
| Q6DD88 | Atlastin-3 | 60998.3 | 10 | 20.5 | 1 | 0 |
| Q92734 | Protein TFG | 43505.0 | 5 | 20.5 | 1 | 0 |
| P49189 | 4-trimethylaminobutyraldehyde dehydrogenase | 54714.5 | 10 | 20.5 | 10 | 20982 |
| P09543 | 2',3'-cyclic-nucleotide 3'-phosphodiesterase | 46737.9 | 10 | 20.5 | 4 | 0 |
| Q9Y295 | Developmentally-regulated GTP-binding protein 1 | 40827.3 | 7 | 20.4 | 10 | 0 |
| Q9Y2Z0 | Suppressor of G2 allele of SKP1 homolog | 39699.5 | 6 | 20.4 | 4 | 0 |
| Q9UHB9 | Signal recognition particle subunit SRP68 | 61131.3 | 12 | 20.4 | 10 | 53013 |
| Q96DB5 | Regulator of microtubule dynamics protein 1 | 36036.2 | 6 | 20.4 | 3 | 11805 |
| Q9NPE3 | H/ACA ribonucleoprotein complex subunit 3 | 7763.0 | 2 | 20.3 | 2 | 34698 |
| Q92552 | 28S ribosomal protein S27, mitochondrial | 47953.6 | 8 | 20.3 | 10 | 34551 |
| P80723 | Brain acid soluble protein 1 | 20178.7 | 5 | 20.2 | 2 | 0 |
| Q9BSH4 | Translational activator of cytochrome c oxidase 1 | 32933.4 | 4 | 20.2 | 9 | 0 |
| P55010 | Eukaryotic translation initiation factor 5 | 49679.0 | 9 | 20.2 | 8 | 0 |

FIG. 17 (cont'd)

| | | | | | | |
|---|---|---|---|---|---|---|
| P43246 | DNA mismatch repair protein Msh2 | 101894.1 | 14 | 20.2 | 10 | 36408 |
| O60884 | DnaJ homolog subfamily A member 2 | 46373.0 | 6 | 20.2 | 9 | 0 |
| Q9BYD3 | 39S ribosomal protein L4, mitochondrial | 32296.2 | 5 | 20.2 | 10 | 0 |
| P55735 | Protein SEC13 homolog | 35289.5 | 5 | 20.1 | 8 | 0 |
| O43491 | Band 4.1-like protein 2 | 92758.7 | 18 | 20.1 | 10 | 31561 |
| P35998 | 26S protease regulatory subunit 7 | 49033.1 | 7 | 20.1 | 9 | 8724 |
| Q00688 | Peptidyl-prolyl cis-trans isomerase FKBP3 | 25233.9 | 5 | 20.1 | 4 | 0 |
| Q9UNZ2 | NSFL1 cofactor p47 | 36637.1 | 4 | 20.1 | 6 | 0 |
| O60832 | H/ACA ribonucleoprotein complex subunit 4 | 53094.7 | 11 | 20.0 | 10 | 0 |
| P31483 | Nucleolysin TIA-1 isoform p40 | 42699.0 | 8 | 20.0 | 10 | 0 |
| Q5T653 | 39S ribosomal protein L2, mitochondrial | 33586.0 | 3 | 20.0 | 5 | 0 |
| Q6P1L8 | 39S ribosomal protein L14, mitochondrial | 16175.8 | 4 | 20.0 | 2 | 0 |
| Q9BUB7 | Transmembrane protein 70, mitochondrial | 29140.5 | 5 | 20.0 | 1 | 0 |
| Q9BUR5 | Apolipoprotein O | 21356.2 | 5 | 20.0 | 10 | 0 |
| Q8WUM0 | Nuclear pore complex protein Nup133 | 130005.7 | 16 | 20.0 | 9 | 0 |
| P17812 | CTP synthase 1 | 67374.8 | 9 | 20.0 | 6 | 0 |
| Q9BQ95 | Evolutionarily conserved signaling intermediate in Toll pathway, mitochondrial | 49490.4 | 5 | 20.0 | 1 | 0 |
| Q9P035 | Very-long-chain (3R)-3-hydroxyacyl-[acyl-carrier protein] dehydratase 3 | 43387.7 | 7 | 19.9 | 10 | 111093 |
| O95433 | Activator of 90 kDa heat shock protein ATPase homolog 1 | 38445.5 | 5 | 19.8 | 6 | 0 |
| Q16850 | Lanosterol 14-alpha demethylase | 51929.8 | 7 | 19.8 | 10 | 0 |
| P16188 | HLA class I histocompatibility antigen, A-30 alpha chain | 41190.0 | 5 | 19.7 | 7 | 0 |
| P50993 | Sodium/potassium-transporting ATPase subunit alpha-2 | 113577.3 | 17 | 19.7 | 10 | 0 |
| O75915 | PRA1 family protein 3 | 21614.8 | 3 | 19.7 | 6 | 0 |
| Q96EY7 | Pentatricopeptide repeat domain-containing protein 3, mitochondrial | 75310.4 | 11 | 19.6 | 10 | 11214 |
| Q6NVV1 | Putative 60S ribosomal protein L13a-like MGC87657 | 12191.7 | 3 | 19.6 | 10 | 210138 |
| P27816 | Microtubule-associated protein 4 | 112832.7 | 18 | 19.6 | 10 | 14724 |
| Q7Z7H8 | 39S ribosomal protein L10, mitochondrial | 30051.7 | 4 | 19.5 | 6 | 0 |
| P05783 | Keratin, type I cytoskeletal 18 | 48057.9 | 7 | 19.5 | 3 | 0 |
| Q9NX58 | Cell growth-regulating nucleolar protein | 44071.1 | 6 | 19.5 | 3 | 0 |
| O00232 | 26S proteasome non-ATPase regulatory subunit 12 | 52307.0 | 9 | 19.5 | 10 | 0 |
| P61803 | Dolichyl-diphosphooligosaccharide--protein glycosyltransferase subunit DAD1 | 12667.8 | 2 | 19.5 | 2 | 15450 |
| Q15424 | Scaffold attachment factor B1 | 99339.0 | 14 | 19.5 | 10 | 173648 |
| P26196 | Probable ATP-dependent RNA helicase DDX6 | 54816.1 | 8 | 19.5 | 10 | 18096 |
| Q8NI36 | WD repeat-containing protein 36 | 106348.8 | 20 | 19.5 | 10 | 16164 |
| Q14676 | Mediator of DNA damage checkpoint | 197572.4 | 22 | 19.5 | 10 | 4962 |

FIG. 17 (cont'd)

| | | | | | | |
|---|---|---|---|---|---|---|
| | protein 1 | | | | | |
| Q9NYH9 | U3 small nucleolar RNA-associated protein 6 homolog | 70821.3 | 13 | 19.4 | 4 | 0 |
| Q99417 | C-Myc-binding protein | 11966.7 | 4 | 19.4 | 3 | 0 |
| Q9NTK5 | Obg-like ATPase 1 | 39235.5 | 6 | 19.4 | 10 | 0 |
| P25786 | Proteasome subunit alpha type-1 | 30182.7 | 9 | 19.4 | 8 | 0 |
| Q13155 | Aminoacyl tRNA synthase complex-interacting multifunctional protein 2 | 35691.0 | 4 | 19.4 | 5 | 0 |
| P67936 | Tropomyosin alpha-4 chain | 30764.9 | 5 | 19.4 | 10 | 0 |
| O76094 | Signal recognition particle subunit SRP72 | 71813.2 | 9 | 19.3 | 10 | 17088 |
| Q01844 | RNA-binding protein EWS | 63763.4 | 9 | 19.3 | 10 | 120197 |
| Q29960 | HLA class I histocompatibility antigen, Cw-16 alpha chain | 39260.0 | 4 | 19.3 | 10 | 0 |
| P43304 | Glycerol-3-phosphate dehydrogenase, mitochondrial | 75992.0 | 12 | 19.3 | 10 | 0 |
| Q8N5K1 | CDGSH iron-sulfur domain-containing protein 2 | 15506.3 | 4 | 19.3 | 8 | 78993 |
| P04264 | Keratin, type II cytoskeletal 1 | 66209.9 | 13 | 19.3 | 10 | 64740 |
| Q5T8P6 | RNA-binding protein 26 | 86231.2 | 11 | 19.2 | 10 | 19593 |
| P51610 | Host cell factor 1 | 191849.1 | 18 | 19.2 | 10 | 21588 |
| Q13601 | KRR1 small subunit processome component homolog | 40454.6 | 8 | 19.2 | 10 | 0 |
| Q12824 | SWI/SNF-related matrix-associated actin-dependent regulator of chromatin subfamily B member 1 | 43934.9 | 5 | 19.2 | 2 | 0 |
| Q9BY77 | Polymerase delta-interacting protein 3 | 44720.1 | 7 | 19.1 | 10 | 0 |
| Q9BYD1 | 39S ribosomal protein L13, mitochondrial | 20749.0 | 5 | 19.1 | 1 | 0 |
| Q6S8J3 | POTE ankyrin domain family member E | 122960.5 | 16 | 19.1 | 10 | 2345653 |
| Q14157 | Ubiquitin-associated protein 2-like | 110307.6 | 11 | 19.1 | 10 | 17703 |
| P35520 | Cystathionine beta-synthase | 61852.1 | 8 | 19.1 | 8 | 0 |
| Q99496 | E3 ubiquitin-protein ligase RING2 | 38111.7 | 7 | 19.1 | 8 | 0 |
| P63096 | Guanine nucleotide-binding protein G(i) subunit alpha-1 | 39520.6 | 9 | 18.9 | 8 | 26943 |
| Q14197 | Peptidyl-tRNA hydrolase ICT1, mitochondrial | 23858.2 | 5 | 18.9 | 7 | 0 |
| Q96B49 | Mitochondrial import receptor subunit TOM6 homolog | 8002.0 | 1 | 18.9 | 4 | 0 |
| Q9HB40 | Retinoid-inducible serine carboxypeptidase | 42122.0 | 5 | 18.9 | 4 | 0 |
| Q06265 | Exosome complex component RRP45 | 45532.3 | 8 | 18.9 | 10 | 26703 |
| P07099 | Epoxide hydrolase 1 | 53177.1 | 8 | 18.9 | 6 | 0 |
| P28482 | Mitogen-activated protein kinase 1 | 41789.0 | 7 | 18.9 | 2 | 0 |
| P84098 | 60S ribosomal protein L19 | 23580.1 | 4 | 18.9 | 10 | 286488 |
| O43837 | Isocitrate dehydrogenase [NAD] subunit beta, mitochondrial | 40007.1 | 5 | 18.9 | 10 | 25266 |
| Q08J23 | tRNA (cytosine(34)-C(5))-methyltransferase | 85201.9 | 11 | 18.9 | 10 | 0 |
| O00267 | Transcription elongation factor SPT5 | 121148.7 | 15 | 18.8 | 10 | 0 |
| Q9H845 | Acyl-CoA dehydrogenase family member 9, mitochondrial | 69387.7 | 12 | 18.8 | 3 | 0 |
| P21281 | V-type proton ATPase subunit B, brain | 56843.0 | 7 | 18.8 | 1 | 0 |

FIG. 17 (cont'd)

| | isoform | | | | | |
|---|---|---|---|---|---|---|
| P07197 | Neurofilament medium polypeptide | 80998.5 | 14 | 18.8 | 10 | 35819.19 |
| Q00341 | Vigilin | 140499.1 | 17 | 18.8 | 10 | 20337 |
| P63000 | Ras-related C3 botulinum toxin substrate 1 | 22858.0 | 3 | 18.8 | 10 | 40407 |
| P14649 | Myosin light chain 6B | 22878.1 | 5 | 18.8 | 10 | 0 |
| P42766 | 60S ribosomal protein L35 | 14551.5 | 2 | 18.7 | 10 | 280665 |
| O75608 | Acyl-protein thioesterase 1 | 24114.7 | 3 | 18.7 | 4 | 0 |
| Q9Y2W1 | Thyroid hormone receptor-associated protein 3 | 108722.9 | 16 | 18.6 | 10 | 64249 |
| P04439 | HLA class I histocompatibility antigen, A-3 alpha chain | 41125.9 | 4 | 18.6 | 5 | 0 |
| P13746 | HLA class I histocompatibility antigen, A-11 alpha chain | 41485.8 | 4 | 18.6 | 10 | 0 |
| P30443 | HLA class I histocompatibility antigen, A-1 alpha chain | 41131.0 | 4 | 18.6 | 5 | 0 |
| P30455 | HLA class I histocompatibility antigen, A-36 alpha chain | 41219.1 | 4 | 18.6 | 5 | 0 |
| Q8TDD1 | ATP-dependent RNA helicase DDX54 | 98915.6 | 15 | 18.6 | 10 | 22371 |
| Q58FF6 | Putative heat shock protein HSP 90-beta 4 | 58891.8 | 10 | 18.6 | 10 | 11232.98 |
| P49915 | GMP synthase [glutamine-hydrolyzing] | 77456.9 | 9 | 18.6 | 8 | 0 |
| Q03701 | CCAAT/enhancer-binding protein zeta | 121601.4 | 18 | 18.6 | 7 | 0 |
| P53618 | Coatomer subunit beta | 108283.0 | 15 | 18.6 | 10 | 33148 |
| P49959 | Double-strand break repair protein MRE11A | 79460.0 | 12 | 18.5 | 10 | 19173 |
| O00303 | Eukaryotic translation initiation factor 3 subunit F | 37678.0 | 8 | 18.5 | 10 | 0 |
| P38606 | V-type proton ATPase catalytic subunit A | 68703.4 | 11 | 18.5 | 2 | 0 |
| P23381 | Tryptophan--tRNA ligase, cytoplasmic | 51014.8 | 6 | 18.5 | 4 | 0 |
| Q8TAE8 | Growth arrest and DNA damage-inducible proteins-interacting protein 1 | 25440.9 | 3 | 18.5 | 2 | 0 |
| Q14318 | Peptidyl-prolyl cis-trans isomerase FKBP8 | 45061.6 | 6 | 18.5 | 10 | 58011 |
| P52209 | 6-phosphogluconate dehydrogenase, decarboxylating | 53653.3 | 9 | 18.4 | 8 | 0 |
| Q9BVJ6 | U3 small nucleolar RNA-associated protein 14 homolog A | 79415.8 | 13 | 18.4 | 10 | 16572 |
| Q15286 | Ras-related protein Rab-35 | 20269.8 | 3 | 18.4 | 10 | 90309 |
| Q8NFH5 | Nucleoporin NUP53 | 34887.9 | 5 | 18.4 | 2 | 0 |
| Q10567 | AP-1 complex subunit beta-1 | 104279.9 | 16 | 18.4 | 10 | 34953 |
| Q14696 | LDLR chaperone MESD | 26247.8 | 3 | 18.4 | 4 | 0 |
| P30512 | HLA class I histocompatibility antigen, A-29 alpha chain | 41148.0 | 4 | 18.4 | 7 | 0 |
| P63010 | AP-2 complex subunit beta | 106034.8 | 16 | 18.4 | 10 | 0 |
| Q9BSC4 | Nucleolar protein 10 | 77851.8 | 11 | 18.3 | 10 | 0 |
| Q9Y3A6 | Transmembrane emp24 domain-containing protein 5 | 26119.0 | 4 | 18.3 | 7 | 0 |
| Q8N4V1 | Membrane magnesium transporter 1 | 18426.1 | 2 | 18.3 | 6 | 0 |
| O15381 | Nuclear valosin-containing protein-like | 84496.1 | 12 | 18.3 | 10 | 0 |
| Q8NBU5 | ATPase family AAA domain-containing protein 1 | 38959.5 | 6 | 18.3 | 8 | 0 |
| Q08257 | Quinone oxidoreductase | 27956.2 | 3 | 18.2 | 2 | 0 |

FIG. 17 (cont'd)

| | | | | | | |
|---|---|---|---|---|---|---|
| Q9BT78 | COP9 signalosome complex subunit 4 | 43518.1 | 8 | 18.2 | 4 | 0 |
| P56182 | Ribosomal RNA processing protein 1 homolog A | 53067.4 | 8 | 18.2 | 7 | 63720 |
| Q14739 | Lamin-B receptor | 71102.5 | 9 | 18.2 | 10 | 132048 |
| Q8TCT9 | Minor histocompatibility antigen H13 | 41317.4 | 5 | 18.2 | 10 | 53433 |
| O00170 | AH receptor-interacting protein | 38092.3 | 4 | 18.2 | 2 | 0 |
| P00374 | Dihydrofolate reductase | 21509.8 | 5 | 18.2 | 1 | 0 |
| Q12972 | Nuclear inhibitor of protein phosphatase 1 | 31404.8 | 7 | 18.2 | 10 | 0 |
| Q9Y6M1 | Insulin-like growth factor 2 mRNA-binding protein 2 | 60131.1 | 10 | 18.2 | 10 | 3840 |
| P18031 | Tyrosine-protein phosphatase non-receptor type 1 | 50537.2 | 11 | 18.2 | 9 | 26748 |
| Q8NFI4 | Putative protein FAM10A5 | 41605.9 | 7 | 18.2 | 10 | 0 |
| O95983 | Methyl-CpG-binding domain protein 3 | 31128.6 | 4 | 18.2 | 4 | 0 |
| Q12996 | Cleavage stimulation factor subunit 3 | 83377.9 | 12 | 18.1 | 10 | 22407 |
| Q9NRN7 | L-aminoadipate-semialdehyde dehydrogenase-phosphopantetheinyl transferase | 36004.1 | 7 | 18.1 | 1 | 0 |
| Q8NFH4 | Nucleoporin Nup37 | 37163.9 | 5 | 18.1 | 2 | 0 |
| Q9NW64 | Pre-mRNA-splicing factor RBM22 | 45589.3 | 6 | 18.1 | 6 | 0 |
| Q7Z434 | Mitochondrial antiviral-signaling protein | 48897.3 | 5 | 18.1 | 4 | 0 |
| Q04637 | Eukaryotic translation initiation factor 4 gamma 1 | 166255.4 | 20 | 18.0 | 10 | 29974.5 |
| O14910 | Protein lin-7 homolog A | 26110.8 | 4 | 18.0 | 1 | 0 |
| Q14204 | Cytoplasmic dynein 1 heavy chain 1 | 535146.0 | 71 | 18.0 | 10 | 32067 |
| Q00577 | Transcriptional activator protein Pur-alpha | 35024.9 | 3 | 18.0 | 1 | 0 |
| A6NEC2 | Puromycin-sensitive aminopeptidase-like protein | 54260.6 | 7 | 18.0 | 4 | 0 |
| O94973 | AP-2 complex subunit alpha-2 | 96746.8 | 13 | 18.0 | 10 | 0 |
| P28072 | Proteasome subunit beta type-6 | 25585.9 | 6 | 18.0 | 6 | 0 |
| Q9NX47 | E3 ubiquitin-protein ligase MARCH5 | 31802.0 | 6 | 18.0 | 3 | 0 |
| Q13505 | Metaxin-1 | 43855.2 | 7 | 18.0 | 4 | 0 |
| O94776 | Metastasis-associated protein MTA2 | 75764.6 | 12 | 18.0 | 10 | 0 |
| Q9H4L4 | Sentrin-specific protease 3 | 65637.2 | 6 | 17.9 | 3 | 0 |
| O15372 | Eukaryotic translation initiation factor 3 subunit H | 40101.5 | 7 | 17.9 | 2 | 0 |
| O60493 | Sorting nexin-3 | 16988.4 | 4 | 17.9 | 7 | 0 |
| Q86VP6 | Cullin-associated NEDD8-dissociated protein 1 | 126241.7 | 20 | 17.9 | 10 | 15981 |
| O95400 | CD2 antigen cytoplasmic tail-binding protein 2 | 37760.6 | 6 | 17.9 | 4 | 0 |
| Q9UBQ5 | Eukaryotic translation initiation factor 3 subunit K | 25344.9 | 4 | 17.9 | 4 | 0 |
| Q8WTT2 | Nucleolar complex protein 3 homolog | 93004.1 | 13 | 17.9 | 10 | 54058 |
| Q14152 | Eukaryotic translation initiation factor 3 subunit A | 166968.8 | 24 | 17.9 | 10 | 79584 |
| P35080 | Profilin-2 | 15409.5 | 3 | 17.9 | 2 | 0 |
| Q8WU90 | Zinc finger CCCH domain-containing protein 15 | 49001.7 | 6 | 17.8 | 6 | 0 |
| P46013 | Antigen KI-67 | 341805.1 | 40 | 17.8 | 10 | 50783 |

FIG. 17 (cont'd)

| | | | | | | |
|---|---|---|---|---|---|---|
| Q9BRL6 | Serine/arginine-rich splicing factor 8 | 31970.1 | 5 | 17.8 | 10 | 0 |
| Q08170 | Serine/arginine-rich splicing factor 4 | 56792.5 | 9 | 17.8 | 10 | 123236 |
| P61009 | Signal peptidase complex subunit 3 | 20370.5 | 4 | 17.8 | 8 | 0 |
| Q9UHD8 | Septin-9 | 61235.7 | 8 | 17.8 | 5 | 0 |
| O95757 | Heat shock 70 kDa protein 4L | 95539.2 | 13 | 17.8 | 10 | 0 |
| Q6NVY1 | 3-hydroxyisobutyryl-CoA hydrolase, mitochondrial | 41089.5 | 6 | 17.8 | 10 | 0 |
| Q8TCS8 | Polyribonucleotide nucleotidyltransferase 1, mitochondrial | 86578.1 | 13 | 17.8 | 10 | 0 |
| O00487 | 26S proteasome non-ATPase regulatory subunit 14 | 34748.2 | 4 | 17.7 | 9 | 35802 |
| Q14690 | Protein RRP5 homolog | 210069.7 | 30 | 17.7 | 10 | 21803 |
| Q96AX2 | Ras-related protein Rab-37 | 24070.8 | 2 | 17.7 | 10 | 0 |
| O14925 | Mitochondrial import inner membrane translocase subunit Tim23 | 22114.3 | 2 | 17.7 | 4 | 45531 |
| Q13330 | Metastasis-associated protein MTA1 | 71140.9 | 12 | 17.7 | 10 | 20442 |
| O95251 | Histone acetyltransferase KAT7 | 60910.6 | 8 | 17.7 | 10 | 0 |
| O43719 | HIV Tat-specific factor 1 | 86423.2 | 12 | 17.6 | 8 | 30978 |
| Q9NQC3 | Reticulon-4 | 81797.5 | 9 | 17.6 | 10 | 10056 |
| O95232 | Luc7-like protein 3 | 51865.4 | 7 | 17.6 | 7 | 0 |
| Q49A26 | Putative oxidoreductase GLYR1 | 57144.3 | 8 | 17.6 | 10 | 0 |
| Q6P2E9 | Enhancer of mRNA-decapping protein 4 | 131778.2 | 13 | 17.6 | 10 | 0 |
| Q96ER9 | Coiled-coil domain-containing protein 51 | 39933.9 | 6 | 17.6 | 4 | 0 |
| Q9UBB4 | Ataxin-10 | 50486.5 | 8 | 17.5 | 4 | 0 |
| P33240 | Cleavage stimulation factor subunit 2 | 60219.8 | 10 | 17.5 | 10 | 23874 |
| Q8TD47 | 40S ribosomal protein S4, Y isoform 2 | 29637.6 | 6 | 17.5 | 10 | 0 |
| Q9BS26 | Endoplasmic reticulum resident protein 44 | 47370.5 | 6 | 17.5 | 4 | 0 |
| O75694 | Nuclear pore complex protein Nup155 | 153798.4 | 15 | 17.5 | 10 | 31903 |
| Q14978 | Nucleolar and coiled-body phosphoprotein 1 | 74031.8 | 11 | 17.4 | 10 | 100179 |
| O75436 | Vacuolar protein sorting-associated protein 26A | 35206.8 | 5 | 17.4 | 6 | 0 |
| P55786 | Puromycin-sensitive aminopeptidase | 103960.8 | 15 | 17.4 | 9 | 16347 |
| Q9Y696 | Chloride intracellular channel protein 4 | 29000.3 | 2 | 17.4 | 1 | 0 |
| P23434 | Glycine cleavage system H protein, mitochondrial | 19112.7 | 3 | 17.3 | 4 | 60156 |
| P98175 | RNA-binding protein 10 | 99293.6 | 11 | 17.3 | 10 | 0 |
| Q9BXK5 | Bcl-2-like protein 13 | 52837.3 | 5 | 17.3 | 2 | 0 |
| Q9UMX0 | Ubiquilin-1 | 60966.7 | 7 | 17.3 | 10 | 32766 |
| Q96T88 | E3 ubiquitin-protein ligase UHRF1 | 92005.0 | 15 | 17.3 | 10 | 0 |
| Q9Y5J1 | U3 small nucleolar RNA-associated protein 18 homolog | 62459.9 | 11 | 17.3 | 8 | 20565 |
| P01891 | HLA class I histocompatibility antigen, A-68 alpha chain | 41194.0 | 4 | 17.3 | 7 | 0 |
| P10321 | HLA class I histocompatibility antigen, Cw-7 alpha chain | 41161.8 | 4 | 17.2 | 9 | 55021.5 |
| Q29963 | HLA class I histocompatibility antigen, Cw-6 alpha chain | 41425.1 | 4 | 17.2 | 5 | 3247 |
| P30508 | HLA class I histocompatibility antigen, Cw-12 alpha chain | 41342.0 | 4 | 17.2 | 7 | 0 |

FIG. 17 (cont'd)

| | | | | | | |
|---|---|---|---|---|---|---|
| Q9H8H3 | Methyltransferase-like protein 7A | 28832.4 | 3 | 17.2 | 1 | 0 |
| P16402 | Histone H1.3 | 22349.9 | 7 | 17.2 | 10 | 0 |
| Q9NYK5 | 39S ribosomal protein L39, mitochondrial | 40069.7 | 6 | 17.2 | 8 | 0 |
| Q93009 | Ubiquitin carboxyl-terminal hydrolase 7 | 129385.9 | 18 | 17.2 | 10 | 15360 |
| Q9UN86 | Ras GTPase-activating protein-binding protein 2 | 52526.4 | 6 | 17.2 | 2 | 0 |
| P63173 | 60S ribosomal protein L38 | 8274.9 | 1 | 17.1 | 9 | 57987 |
| Q9BV38 | WD repeat-containing protein 18 | 48089.6 | 8 | 17.1 | 5 | 26019 |
| Q13442 | 28 kDa heat- and acid-stable phosphoprotein | 20630.0 | 3 | 17.1 | 2 | 0 |
| O60216 | Double-strand-break repair protein rad21 homolog | 71974.8 | 9 | 17.1 | 8 | 0 |
| Q99615 | DnaJ homolog subfamily C member 7 | 54394.5 | 10 | 17.1 | 9 | 0 |
| Q9BY67 | Cell adhesion molecule 1 | 43139.9 | 4 | 17.1 | 4 | 0 |
| Q6NXT2 | Histone H3.3C | 15327.8 | 4 | 17.0 | 10 | 0 |
| P53041 | Serine/threonine-protein phosphatase 5 | 57449.0 | 8 | 17.0 | 2 | 0 |
| O00151 | PDZ and LIM domain protein 1 | 36528.0 | 5 | 17.0 | 2 | 0 |
| Q92820 | Gamma-glutamyl hydrolase | 36363.6 | 5 | 17.0 | 1 | 0 |
| P62861 | 40S ribosomal protein S30 | 6647.9 | 1 | 17.0 | 10 | 143220 |
| Q15363 | Transmembrane emp24 domain-containing protein 2 | 22875.3 | 6 | 16.9 | 4 | 96240 |
| Q8N4Q1 | Mitochondrial intermembrane space import and assembly protein 40 | 17061.3 | 1 | 16.9 | 2 | 0 |
| O15213 | WD repeat-containing protein 46 | 68527.4 | 9 | 16.9 | 7 | 0 |
| Q9UKK9 | ADP-sugar pyrophosphatase | 24612.8 | 3 | 16.9 | 2 | 0 |
| Q15155 | Nodal modulator 1 | 135293.6 | 17 | 16.9 | 10 | 17402 |
| P69849 | Nodal modulator 3 | 135103.2 | 16 | 16.9 | 10 | 0 |
| Q5JPE7 | Nodal modulator 2 | 137842.0 | 16 | 16.9 | 10 | 0 |
| Q9UMX5 | Neudesin | 18856.4 | 3 | 16.9 | 1 | 0 |
| Q9NV31 | U3 small nucleolar ribonucleoprotein protein IMP3 | 21964.2 | 4 | 16.9 | 6 | 0 |
| P48444 | Coatomer subunit delta | 53523.2 | 11 | 16.8 | 10 | 38277 |
| Q53EL6 | Programmed cell death protein 4 | 51554.9 | 8 | 16.8 | 10 | 0 |
| Q969G3 | SWI/SNF-related matrix-associated actin-dependent regulator of chromatin subfamily E member 1 | 44328.8 | 6 | 16.8 | 4 | 0 |
| P02768 | Serum albumin | 62635.6 | 10 | 16.8 | 10 | 60542 |
| P49406 | 39S ribosomal protein L19, mitochondrial | 33820.2 | 6 | 16.8 | 6 | 0 |
| P20339 | Ras-related protein Rab-5A | 23886.8 | 5 | 16.7 | 9 | 0 |
| Q9UGP8 | Translocation protein SEC63 homolog | 88396.3 | 13 | 16.7 | 8 | 0 |
| O43395 | U4/U6 small nuclear ribonucleoprotein Prp3 | 77700.2 | 8 | 16.7 | 4 | 0 |
| Q9UBU9 | Nuclear RNA export factor 1 | 62126.6 | 10 | 16.6 | 7 | 0 |
| Q9NP92 | 28S ribosomal protein S30, mitochondrial | 50992.1 | 5 | 16.6 | 3 | 0 |
| P37837 | Transaldolase | 37711.3 | 6 | 16.6 | 7 | 46815 |
| Q8WU68 | Splicing factor U2AF 26 kDa subunit | 23848.7 | 3 | 16.6 | 10 | 0 |
| Q8WVV9 | Heterogeneous nuclear ribonucleoprotein L-like | 60720.9 | 8 | 16.6 | 10 | 0 |

FIG. 17 (cont'd)

| | | | | | | |
|---|---|---|---|---|---|---|
| O60869 | Endothelial differentiation-related factor 1 | 15953.1 | 3 | 16.6 | 4 | 0 |
| P57105 | Synaptojanin-2-binding protein | 15928.1 | 2 | 16.6 | 2 | 0 |
| Q9BQ75 | Protein CMSS1 | 32169.5 | 4 | 16.5 | 1 | 0 |
| Q9BWF3 | RNA-binding protein 4 | 32923.0 | 7 | 16.5 | 10 | 58629 |
| Q9NRG9 | Aladin | 58839.1 | 11 | 16.5 | 10 | 0 |
| P05534 | HLA class I histocompatibility antigen, A-24 alpha chain | 40973.8 | 4 | 16.4 | 5 | 0 |
| P30447 | HLA class I histocompatibility antigen, A-23 alpha chain | 41017.8 | 4 | 16.4 | 5 | 0 |
| P23193 | Transcription elongation factor A protein 1 | 33657.3 | 5 | 16.4 | 3 | 0 |
| P52701 | DNA mismatch repair protein Msh6 | 138157.0 | 18 | 16.4 | 10 | 21094 |
| Q9NRW1 | Ras-related protein Rab-6B | 23575.8 | 3 | 16.4 | 9 | 0 |
| O00541 | Pescadillo homolog | 68183.3 | 9 | 16.3 | 10 | 0 |
| P18206 | Vinculin | 116271.6 | 19 | 16.3 | 10 | 25131 |
| Q5VT66 | MOSC domain-containing protein 1, mitochondrial | 39018.4 | 5 | 16.3 | 4 | 0 |
| P18463 | HLA class I histocompatibility antigen, B-37 alpha chain | 40741.2 | 4 | 16.3 | 5 | 0 |
| P30460 | HLA class I histocompatibility antigen, B-8 alpha chain | 40673.1 | 4 | 16.3 | 5 | 0 |
| P30462 | HLA class I histocompatibility antigen, B-14 alpha chain | 40700.2 | 4 | 16.3 | 5 | 0 |
| P30480 | HLA class I histocompatibility antigen, B-42 alpha chain | 40675.1 | 4 | 16.3 | 5 | 0 |
| P30492 | HLA class I histocompatibility antigen, B-54 alpha chain | 40665.2 | 4 | 16.3 | 7 | 0 |
| P30493 | HLA class I histocompatibility antigen, B-55 alpha chain | 40781.3 | 4 | 16.3 | 7 | 0 |
| Q29940 | HLA class I histocompatibility antigen, B-59 alpha chain | 40869.6 | 4 | 16.3 | 7 | 0 |
| Q14444 | Caprin-1 | 77785.1 | 11 | 16.3 | 10 | 53437 |
| O75822 | Eukaryotic translation initiation factor 3 subunit J | 29176.5 | 7 | 16.3 | 2 | 0 |
| P61758 | Prefoldin subunit 3 | 22829.1 | 5 | 16.2 | 3 | 0 |
| Q05048 | Cleavage stimulation factor subunit 1 | 49156.1 | 7 | 16.2 | 3 | 0 |
| P67812 | Signal peptidase complex catalytic subunit SEC11A | 20625.4 | 5 | 16.2 | 8 | 12621 |
| P26639 | Threonine--tRNA ligase, cytoplasmic | 86089.2 | 10 | 16.2 | 10 | 0 |
| P10314 | HLA class I histocompatibility antigen, A-32 alpha chain | 41333.3 | 4 | 16.2 | 7 | 0 |
| P16189 | HLA class I histocompatibility antigen, A-31 alpha chain | 41289.1 | 4 | 16.2 | 7 | 0 |
| P16190 | HLA class I histocompatibility antigen, A-33 alpha chain | 41177.0 | 4 | 16.2 | 7 | 0 |
| P30453 | HLA class I histocompatibility antigen, A-34 alpha chain | 41340.1 | 4 | 16.2 | 7 | 0 |
| P30459 | HLA class I histocompatibility antigen, A-74 alpha chain | 41176.0 | 4 | 16.2 | 7 | 0 |
| Q13423 | NAD(P) transhydrogenase, mitochondrial | 114637.2 | 13 | 16.1 | 10 | 25118 |
| O15160 | DNA-directed RNA polymerases I and III subunit RPAC1 | 39204.9 | 4 | 16.1 | 8 | 0 |
| P22830 | Ferrochelatase, mitochondrial | 48814.0 | 6 | 16.1 | 2 | 0 |

FIG. 17 (cont'd)

| | | | | | | |
|---|---|---|---|---|---|---|
| Q9BTT0 | Acidic leucine-rich nuclear phosphoprotein 32 family member E | 30920.6 | 5 | 16.0 | 3 | 0 |
| Q7KZN9 | Cytochrome c oxidase assembly protein COX15 homolog | 45275.1 | 4 | 16.0 | 10 | 0 |
| Q5JTH9 | RRP12-like protein | 139248.8 | 17 | 16.0 | 10 | 28996 |
| O75955 | Flotillin-1 | 47583.5 | 7 | 15.9 | 5 | 0 |
| O75534 | Cold shock domain-containing protein E1 | 89407.1 | 14 | 15.9 | 10 | 0 |
| P16220 | Cyclic AMP-responsive element-binding protein 1 | 32632.1 | 3 | 15.9 | 6 | 0 |
| P18583 | Protein SON | 246141.9 | 18 | 15.9 | 10 | 17007 |
| P22033 | Methylmalonyl-CoA mutase, mitochondrial | 83590.9 | 13 | 15.9 | 4 | 14853 |
| P61964 | WD repeat-containing protein 5 | 37158.8 | 5 | 15.9 | 3 | 0 |
| Q9NZJ7 | Mitochondrial carrier homolog 1 | 41074.2 | 6 | 15.9 | 4 | 0 |
| Q13363 | C-terminal-binding protein 1 | 47426.4 | 5 | 15.9 | 10 | 0 |
| Q96KR1 | Zinc finger RNA-binding protein | 118152.8 | 16 | 15.8 | 4 | 0 |
| Q10471 | Polypeptide N-acetylgalactosaminyltransferase 2 | 65474.2 | 10 | 15.8 | 7 | 0 |
| P46459 | Vesicle-fusing ATPase | 83107.8 | 13 | 15.7 | 10 | 28464 |
| O95793 | Double-stranded RNA-binding protein Staufen homolog 1 | 58164.3 | 9 | 15.7 | 6 | 0 |
| Q9H361 | Polyadenylate-binding protein 3 | 70259.2 | 10 | 15.7 | 10 | 0 |
| O75152 | Zinc finger CCCH domain-containing protein 11A | 89986.6 | 13 | 15.7 | 3 | 0 |
| P57740 | Nuclear pore complex protein Nup107 | 107115.6 | 14 | 15.7 | 8 | 0 |
| Q9H583 | HEAT repeat-containing protein 1 | 244537.7 | 33 | 15.7 | 10 | 22725 |
| P15170 | Eukaryotic peptide chain release factor GTP-binding subunit ERF3A | 62891.2 | 7 | 15.6 | 6 | 0 |
| O00767 | Acyl-CoA desaturase | 41693.8 | 4 | 15.6 | 6 | 64731 |
| P53675 | Clathrin heavy chain 2 | 185716.4 | 26 | 15.6 | 10 | 0 |
| Q6PJT7 | Zinc finger CCCH domain-containing protein 14 | 77274.0 | 9 | 15.6 | 10 | 7665 |
| Q9C0J8 | pre-mRNA 3' end processing protein WDR33 | 107737.1 | 6 | 15.6 | 3 | 0 |
| Q9HCS7 | Pre-mRNA-splicing factor SYF1 | 100808.2 | 11 | 15.6 | 2 | 0 |
| O95716 | Ras-related protein Rab-3D | 24495.3 | 4 | 15.5 | 10 | 0 |
| P36871 | Phosphoglucomutase-1 | 62933.6 | 10 | 15.5 | 2 | 0 |
| Q96I51 | Williams-Beuren syndrome chromosomal region 16 protein | 50738.2 | 6 | 15.5 | 4 | 0 |
| P11171 | Protein 4.1 | 81228.7 | 10 | 15.5 | 10 | 0 |
| Q8N8A6 | ATP-dependent RNA helicase DDX51 | 73027.7 | 8 | 15.5 | 6 | 0 |
| P49790 | Nuclear pore complex protein Nup153 | 155535.3 | 17 | 15.5 | 10 | 18180 |
| P41227 | N-alpha-acetyltransferase 10 | 25792.2 | 2 | 15.5 | 2 | 0 |
| P17480 | Nucleolar transcription factor 1 | 87513.7 | 13 | 15.4 | 10 | 55599 |
| Q8IWX8 | Calcium homeostasis endoplasmic reticulum protein | 104215.6 | 11 | 15.4 | 9 | 0 |
| P17858 | 6-phosphofructokinase, liver type | 88523.4 | 10 | 15.4 | 6 | 0 |
| P47755 | F-actin-capping protein subunit alpha-2 | 33177.2 | 4 | 15.4 | 5 | 0 |
| Q969Z0 | Protein TBRG4 | 66230.5 | 9 | 15.4 | 10 | 34812 |
| O43818 | U3 small nucleolar RNA-interacting protein 2 | 52468.0 | 7 | 15.4 | 4 | 0 |

FIG. 17 (cont'd)

| | | | | | | |
|---|---|---|---|---|---|---|
| Q9H3K2 | Growth hormone-inducible transmembrane protein | 37376.4 | 6 | 15.4 | 7 | 0 |
| Q00765 | Receptor expression-enhancing protein 5 | 21721.3 | 3 | 15.3 | 2 | 0 |
| Q58FF3 | Putative endoplasmin-like protein | 46372.3 | 7 | 15.3 | 9 | 0 |
| Q12769 | Nuclear pore complex protein Nup160 | 149024.0 | 16 | 15.3 | 10 | 21222 |
| O43447 | Peptidyl-prolyl cis-trans isomerase H | 19493.3 | 4 | 15.3 | 4 | 0 |
| P08240 | Signal recognition particle receptor subunit alpha | 68641.2 | 8 | 15.3 | 2 | 0 |
| Q9H0C2 | ADP/ATP translocase 4 | 35307.1 | 6 | 15.2 | 10 | 0 |
| O15226 | NF-kappa-B-repressing factor | 78357.3 | 10 | 15.2 | 3 | 16126.5 |
| P16435 | NADPH--cytochrome P450 reductase | 77146.1 | 11 | 15.2 | 7 | 28554 |
| P62993 | Growth factor receptor-bound protein 2 | 25320.4 | 6 | 15.2 | 2 | 0 |
| P52565 | Rho GDP-dissociation inhibitor 1 | 23264.2 | 3 | 15.2 | 8 | 59511 |
| Q86TX2 | Acyl-coenzyme A thioesterase 1 | 46676.6 | 5 | 15.2 | 3 | 0 |
| Q9UIG0 | Tyrosine-protein kinase BAZ1B | 172272.1 | 19 | 15.2 | 10 | 30522 |
| P37198 | Nuclear pore glycoprotein p62 | 53426.1 | 6 | 15.1 | 9 | 0 |
| P51665 | 26S proteasome non-ATPase regulatory subunit 7 | 37082.5 | 5 | 15.1 | 6 | 0 |
| P17661 | Desmin | 53592.9 | 10 | 15.1 | 10 | 0 |
| Q9Y697 | Cysteine desulfurase, mitochondrial | 46552.9 | 9 | 15.1 | 6 | 0 |
| Q9NQW7 | Xaa-Pro aminopeptidase 1 | 71332.1 | 8 | 15.1 | 6 | 0 |
| Q9UJX3 | Anaphase-promoting complex subunit 7 | 65198.6 | 8 | 15.1 | 3 | 0 |
| Q96BM9 | ADP-ribosylation factor-like protein 8A | 21644.1 | 4 | 15.1 | 2 | 50259 |
| P61221 | ATP-binding cassette sub-family E member 1 | 68283.9 | 9 | 15.0 | 10 | 0 |
| O14735 | CDP-diacylglycerol--inositol 3-phosphatidyltransferase | 23881.0 | 3 | 15.0 | 6 | 0 |
| Q99613 | Eukaryotic translation initiation factor 3 subunit C | 106028.3 | 11 | 15.0 | 10 | 31312.5 |
| Q9NYF8 | Bcl-2-associated transcription factor 1 | 99673.9 | 14 | 15.0 | 10 | 136926 |
| P60510 | Serine/threonine-protein phosphatase 4 catalytic subunit | 35650.2 | 6 | 15.0 | 4 | 0 |
| P51649 | Succinate-semialdehyde dehydrogenase, mitochondrial | 58789.6 | 6 | 15.0 | 8 | 0 |
| Q96L21 | 60S ribosomal protein L10-like | 24975.0 | 3 | 15.0 | 6 | 0 |
| P56192 | Methionine--tRNA ligase, cytoplasmic | 102313.5 | 11 | 14.9 | 10 | 30231 |
| A1L0T0 | Acetolactate synthase-like protein | 68495.1 | 6 | 14.9 | 4 | 0 |
| Q96JJ7 | Protein disulfide-isomerase TMX3 | 37366.6 | 4 | 14.9 | 2 | 0 |
| O75787 | Renin receptor | 39008.1 | 4 | 14.9 | 1 | 0 |
| P47897 | Glutamine--tRNA ligase | 88711.3 | 13 | 14.8 | 6 | 0 |
| Q8WUA2 | Peptidyl-prolyl cis-trans isomerase-like 4 | 57738.4 | 9 | 14.8 | 2 | 0 |
| O00273 | DNA fragmentation factor subunit alpha | 36921.1 | 5 | 14.8 | 2 | 0 |
| O15258 | Protein RER1 | 23072.1 | 2 | 14.8 | 2 | 0 |
| O95782 | AP-2 complex subunit alpha-1 | 107537.3 | 13 | 14.8 | 10 | 0 |
| Q96FW1 | Ubiquitin thioesterase OTUB1 | 33598.3 | 4 | 14.8 | 2 | 0 |
| Q9BUQ8 | Probable ATP-dependent RNA helicase DDX23 | 95924.8 | 14 | 14.8 | 9 | 0 |
| Q9BZF1 | Oxysterol-binding protein-related | 99915.9 | 10 | 14.8 | 3 | 0 |

FIG. 17 (cont'd)

| | protein 8 | | | | | |
|---|---|---|---|---|---|---|
| P13645 | Keratin, type I cytoskeletal 10 | 59055.3 | 11 | 14.7 | 5 | 51009 |
| Q9NVH0 | Exonuclease 3'-5' domain-containing protein 2 | 62826.7 | 8 | 14.7 | 5 | 0 |
| P41219 | Peripherin | 53829.1 | 7 | 14.7 | 10 | 0 |
| Q9BRK5 | 45 kDa calcium-binding protein | 32619.4 | 6 | 14.7 | 10 | 0 |
| Q9BZE1 | 39S ribosomal protein L37, mitochondrial | 48630.8 | 7 | 14.7 | 4 | 0 |
| P01889 | HLA class I histocompatibility antigen, B-7 alpha chain | 40802.3 | 5 | 14.6 | 3 | 0 |
| Q14807 | Kinesin-like protein KIF22 | 73661.5 | 10 | 14.6 | 3 | 15777 |
| Q96SI9 | Spermatid perinuclear RNA-binding protein | 73494.1 | 14 | 14.6 | 10 | 3178 |
| Q96KP4 | Cytosolic non-specific dipeptidase | 48669.6 | 6 | 14.6 | 2 | 0 |
| Q9NW13 | RNA-binding protein 28 | 78229.5 | 10 | 14.6 | 10 | 0 |
| O14745 | Na(+)/H(+) exchange regulatory cofactor NHE-RF1 | 39153.6 | 7 | 14.5 | 2 | 29466 |
| Q9BQP7 | Mitochondrial genome maintenance exonuclease 1 | 39820.2 | 4 | 14.5 | 1 | 0 |
| P30504 | HLA class I histocompatibility antigen, Cw-4 alpha chain | 41394.2 | 4 | 14.5 | 7 | 0 |
| P30510 | HLA class I histocompatibility antigen, Cw-14 alpha chain | 41293.9 | 4 | 14.5 | 7 | 0 |
| P61011 | Signal recognition particle 54 kDa protein | 53293.9 | 9 | 14.5 | 4 | 0 |
| Q29865 | HLA class I histocompatibility antigen, Cw-18 alpha chain | 41389.2 | 4 | 14.5 | 5 | 0 |
| P47914 | 60S ribosomal protein L29 | 17809.1 | 2 | 14.5 | 10 | 221961 |
| Q9NY61 | Protein AATF | 63247.1 | 7 | 14.5 | 9 | 16350 |
| Q9Y247 | Protein FAM50B | 38765.8 | 5 | 14.5 | 7 | 0 |
| Q96QK1 | Vacuolar protein sorting-associated protein 35 | 92505.6 | 12 | 14.5 | 9 | 22176 |
| Q15428 | Splicing factor 3A subunit 2 | 49369.7 | 7 | 14.4 | 7 | 0 |
| Q14247 | Src substrate cortactin | 62683.9 | 7 | 14.4 | 8 | 0 |
| P58546 | Myotrophin | 13065.9 | 2 | 14.4 | 1 | 0 |
| Q96EY8 | Cob(I)yrinic acid a,c-diamide adenosyltransferase, mitochondrial | 27730.5 | 3 | 14.4 | 3 | 19104 |
| Q5SRD1 | Putative mitochondrial import inner membrane translocase subunit Tim23B | 28333.6 | 3 | 14.4 | 4 | 0 |
| Q9P003 | Protein cornichon homolog 4 | 16435.6 | 2 | 14.4 | 7 | 52434 |
| P09001 | 39S ribosomal protein L3, mitochondrial | 38917.8 | 5 | 14.4 | 1 | 0 |
| P29372 | DNA-3-methyladenine glycosylase | 32923.9 | 4 | 14.3 | 8 | 0 |
| Q8NHH9 | Atlastin-2 | 61658.5 | 5 | 14.3 | 4 | 0 |
| Q9UHV9 | Prefoldin subunit 2 | 16704.9 | 2 | 14.3 | 1 | 0 |
| A6NKZ8 | Putative tubulin beta chain-like protein ENSP00000290377 | 42231.4 | 7 | 14.3 | 10 | 0 |
| Q14254 | Flotillin-2 | 47463.4 | 7 | 14.3 | 3 | 0 |
| P35241 | Radixin | 63113.4 | 9 | 14.2 | 10 | 0 |
| Q5JTV8 | Torsin-1A-interacting protein 1 | 66419.6 | 8 | 14.2 | 2 | 0 |
| Q5JTZ9 | Alanine--tRNA ligase, mitochondrial | 108367.1 | 13 | 14.2 | 4 | 0 |
| P14209 | CD99 antigen | 18045.0 | 2 | 14.2 | 2 | 0 |

FIG. 17 (cont'd)

| | | | | | | |
|---|---|---|---|---|---|---|
| Q8IX12 | Cell division cycle and apoptosis regulator protein 1 | 132616.6 | 13 | 14.2 | 10 | 34366.5 |
| Q9P0M9 | 39S ribosomal protein L27, mitochondrial | 16129.9 | 2 | 14.2 | 2 | 0 |
| Q9Y2R4 | Probable ATP-dependent RNA helicase DDX52 | 67840.3 | 6 | 14.2 | 10 | 0 |
| Q14151 | Scaffold attachment factor B2 | 107986.8 | 13 | 14.2 | 10 | 126735 |
| Q8TAT6 | Nuclear protein localization protein 4 homolog | 69674.6 | 8 | 14.1 | 6 | 0 |
| Q9BQB6 | Vitamin K epoxide reductase complex subunit 1 | 15335.7 | 1 | 14.1 | 9 | 41205 |
| Q9Y228 | TRAF3-interacting JNK-activating modulator | 63213.4 | 8 | 14.1 | 2 | 0 |
| Q02818 | Nucleobindin-1 | 53879.4 | 8 | 14.1 | 1 | 0 |
| Q9UHQ9 | NADH-cytochrome b5 reductase 1 | 34266.0 | 6 | 14.1 | 2 | 0 |
| P01893 | Putative HLA class I histocompatibility antigen, alpha chain H | 41120.1 | 3 | 14.1 | 3 | 0 |
| P20645 | Cation-dependent mannose-6-phosphate receptor | 31506.6 | 2 | 14.1 | 1 | 0 |
| Q9Y3C1 | Nucleolar protein 16 | 24475.6 | 3 | 14.0 | 4 | 0 |
| Q01813 | 6-phosphofructokinase type C | 86508.7 | 8 | 14.0 | 2 | 0 |
| Q02252 | Methylmalonate-semialdehyde dehydrogenase [acylating], mitochondrial | 58296.1 | 6 | 14.0 | 2 | 0 |
| Q6DRA6 | Putative histone H2B type 2-D | 18417.3 | 4 | 14.0 | 10 | 0 |
| Q9Y490 | Talin-1 | 271934.6 | 30 | 14.0 | 10 | 7365 |
| O00505 | Importin subunit alpha-4 | 58324.2 | 5 | 14.0 | 7 | 0 |
| P63092 | Guanine nucleotide-binding protein G(s) subunit alpha isoforms short | 45159.6 | 8 | 14.0 | 10 | 0 |
| Q9H4B7 | Tubulin beta-1 chain | 50897.3 | 6 | 14.0 | 10 | 0 |
| Q6P1J9 | Parafibromin | 60690.7 | 7 | 13.9 | 2 | 0 |
| O60841 | Eukaryotic translation initiation factor 5B | 139283.3 | 14 | 13.9 | 10 | 24282 |
| O60763 | General vesicular transport factor p115 | 109457.5 | 14 | 13.9 | 10 | 0 |
| P53597 | Succinyl-CoA ligase [ADP/GDP-forming] subunit alpha, mitochondrial | 36649.0 | 4 | 13.9 | 2 | 0 |
| Q96RP9 | Elongation factor G, mitochondrial | 85245.9 | 13 | 13.9 | 10 | 11517 |
| Q9Y276 | Mitochondrial chaperone BCS1 | 47705.4 | 7 | 13.8 | 1 | 0 |
| P15259 | Phosphoglycerate mutase 2 | 28937.3 | 3 | 13.8 | 10 | 0 |
| Q02218 | 2-oxoglutarate dehydrogenase, mitochondrial | 110778.8 | 11 | 13.8 | 10 | 0 |
| Q8N766 | ER membrane protein complex subunit 1 | 111581.3 | 12 | 13.8 | 10 | 25043 |
| Q86XP3 | ATP-dependent RNA helicase DDX42 | 96807.0 | 14 | 13.8 | 10 | 20706 |
| Q15388 | Mitochondrial import receptor subunit TOM20 homolog | 16469.0 | 2 | 13.8 | 3 | 0 |
| O75530 | Polycomb protein EED | 50297.8 | 6 | 13.8 | 9 | 0 |
| P48651 | Phosphatidylserine synthase 1 | 56212.0 | 6 | 13.7 | 4 | 0 |
| Q95604 | HLA class I histocompatibility antigen, Cw-17 alpha chain | 41637.5 | 3 | 13.7 | 7 | 0 |
| P30049 | ATP synthase subunit delta, mitochondrial | 17490.0 | 3 | 13.7 | 10 | 163527 |
| Q6P1M0 | Long-chain fatty acid transport protein 4 | 72976.8 | 10 | 13.7 | 3 | 0 |

FIG. 17 (cont'd)

| | | | | | | |
|---|---|---|---|---|---|---|
| O75844 | CAAX prenyl protease 1 homolog | 55098.1 | 5 | 13.7 | 6 | 0 |
| Q96J01 | THO complex subunit 3 | 39456.1 | 3 | 13.7 | 1 | 0 |
| Q9BYN8 | 28S ribosomal protein S26, mitochondrial | 24268.8 | 5 | 13.7 | 1 | 0 |
| P06737 | Glycogen phosphorylase, liver form | 95512.2 | 15 | 13.7 | 8 | 0 |
| P07196 | Neurofilament light polypeptide | 61573.7 | 7 | 13.6 | 10 | 0 |
| Q8IZL8 | Proline-, glutamic acid- and leucine-rich protein 1 | 129467.4 | 12 | 13.6 | 10 | 0 |
| Q9Y678 | Coatomer subunit gamma-1 | 99030.1 | 12 | 13.6 | 2 | 0 |
| Q13733 | Sodium/potassium-transporting ATPase subunit alpha-4 | 115193.2 | 14 | 13.6 | 10 | 0 |
| P09493 | Tropomyosin alpha-1 chain | 31301.5 | 4 | 13.6 | 10 | 0 |
| Q15061 | WD repeat-containing protein 43 | 75860.2 | 9 | 13.6 | 8 | 31138.5 |
| P26232 | Catenin alpha-2 | 91763.3 | 15 | 13.6 | 10 | 0 |
| Q2NL82 | Pre-rRNA-processing protein TSR1 homolog | 92209.4 | 10 | 13.6 | 2 | 0 |
| P22492 | Histone H1t | 22019.0 | 4 | 13.5 | 10 | 0 |
| P06280 | Alpha-galactosidase A | 49508.2 | 5 | 13.5 | 5 | 0 |
| Q9Y399 | 28S ribosomal protein S2, mitochondrial | 33534.4 | 6 | 13.5 | 6 | 0 |
| Q9BXS5 | AP-1 complex subunit mu-1 | 49384.8 | 10 | 13.5 | 4 | 0 |
| Q9UHD9 | Ubiquilin-2 | 65696.3 | 5 | 13.5 | 2 | 0 |
| Q7Z2W4 | Zinc finger CCCH-type antiviral protein 1 | 81259.2 | 11 | 13.5 | 10 | 0 |
| Q9UNH7 | Sorting nexin-6 | 40394.8 | 4 | 13.5 | 2 | 0 |
| O76003 | Glutaredoxin-3 | 37717.2 | 5 | 13.4 | 3 | 0 |
| Q08043 | Alpha-actinin-3 | 103982.9 | 12 | 13.4 | 10 | 0 |
| P11413 | Glucose-6-phosphate 1-dehydrogenase | 62345.0 | 7 | 13.4 | 6 | 0 |
| P30505 | HLA class I histocompatibility antigen, Cw-8 alpha chain | 41229.0 | 3 | 13.4 | 5 | 0 |
| Q07000 | HLA class I histocompatibility antigen, Cw-15 alpha chain | 41319.1 | 3 | 13.4 | 5 | 0 |
| Q9TNN7 | HLA class I histocompatibility antigen, Cw-5 alpha chain | 41368.2 | 3 | 13.4 | 4 | 0 |
| P06730 | Eukaryotic translation initiation factor 4E | 27292.0 | 4 | 13.4 | 6 | 24519 |
| O94874 | E3 UFM1-protein ligase 1 | 79473.4 | 12 | 13.4 | 10 | 0 |
| Q14126 | Desmoglein-2 | 123092.5 | 11 | 13.3 | 4 | 0 |
| P07203 | Glutathione peroxidase 1 | 22223.3 | 3 | 13.3 | 2 | 0 |
| Q9ULV4 | Coronin-1C | 53933.5 | 7 | 13.3 | 10 | 56166 |
| P78417 | Glutathione S-transferase omega-1 | 26743.0 | 4 | 13.3 | 5 | 0 |
| O75526 | RNA-binding motif protein, X-linked-like-2 | 42985.4 | 7 | 13.3 | 10 | 0 |
| Q9P289 | Serine/threonine-protein kinase MST4 | 41566.1 | 5 | 13.3 | 3 | 0 |
| Q9BW27 | Nuclear pore complex protein Nup85 | 75875.0 | 10 | 13.3 | 5 | 0 |
| Q9H7Z7 | Prostaglandin E synthase 2 | 42114.3 | 5 | 13.3 | 2 | 0 |
| P49753 | Acyl-coenzyme A thioesterase 2, mitochondrial | 53617.8 | 5 | 13.3 | 3 | 0 |
| Q9BWM7 | Sideroflexin-3 | 36321.1 | 4 | 13.2 | 7 | 0 |
| Q5TH74 | O(6)-methylguanine-induced apoptosis 2 | 32112.2 | 3 | 13.2 | 3 | 0 |
| P35609 | Alpha-actinin-2 | 104424.3 | 17 | 13.2 | 10 | 0 |

FIG. 17 (cont'd)

| | | | | | | |
|---|---|---|---|---|---|---|
| P46977 | Dolichyl-diphosphooligosaccharide--protein glycosyltransferase subunit STT3A | 81157.1 | 9 | 13.2 | 10 | 61939.5 |
| Q9NQT4 | Exosome complex component RRP46 | 25762.2 | 4 | 13.2 | 1 | 0 |
| Q58FG1 | Putative heat shock protein HSP 90-alpha A4 | 47826.0 | 5 | 13.2 | 9 | 0 |
| P13747 | HLA class I histocompatibility antigen, alpha chain E | 40384.9 | 5 | 13.1 | 3 | 0 |
| Q92621 | Nuclear pore complex protein Nup205 | 230317.0 | 24 | 13.1 | 10 | 411522 |
| P40938 | Replication factor C subunit 3 | 38483.3 | 3 | 13.1 | 2 | 0 |
| Q9BYD2 | 39S ribosomal protein L9, mitochondrial | 30414.4 | 3 | 13.1 | 5 | 0 |
| O14744 | Protein arginine N-methyltransferase 5 | 72658.0 | 9 | 13.0 | 10 | 19506 |
| Q7L1Q6 | Basic leucine zipper and W2 domain-containing protein 1 | 47249.8 | 4 | 13.0 | 8 | 0 |
| P14923 | Junction plakoglobin | 82486.3 | 6 | 13.0 | 6 | 0 |
| Q8NE71 | ATP-binding cassette sub-family F member 1 | 94259.4 | 10 | 13.0 | 10 | 0 |
| P10319 | HLA class I histocompatibility antigen, B-58 alpha chain | 40622.3 | 3 | 13.0 | 5 | 0 |
| P18464 | HLA class I histocompatibility antigen, B-51 alpha chain | 40851.5 | 3 | 13.0 | 5 | 0 |
| P18465 | HLA class I histocompatibility antigen, B-57 alpha chain | 40566.4 | 3 | 13.0 | 5 | 0 |
| P30464 | HLA class I histocompatibility antigen, B-15 alpha chain | 40673.2 | 3 | 13.0 | 5 | 0 |
| P30475 | HLA class I histocompatibility antigen, B-39 alpha chain | 40670.2 | 3 | 13.0 | 3 | 0 |
| P30484 | HLA class I histocompatibility antigen, B-46 alpha chain | 40725.4 | 3 | 13.0 | 5 | 0 |
| P30490 | HLA class I histocompatibility antigen, B-52 alpha chain | 40806.4 | 3 | 13.0 | 5 | 0 |
| P30491 | HLA class I histocompatibility antigen, B-53 alpha chain | 40780.5 | 3 | 13.0 | 5 | 0 |
| P30495 | HLA class I histocompatibility antigen, B-56 alpha chain | 40763.4 | 3 | 13.0 | 5 | 0 |
| P30498 | HLA class I histocompatibility antigen, B-78 alpha chain | 40763.3 | 3 | 13.0 | 5 | 0 |
| P30685 | HLA class I histocompatibility antigen, B-35 alpha chain | 40740.4 | 3 | 13.0 | 5 | 0 |
| Q29718 | HLA class I histocompatibility antigen, B-82 alpha chain | 40706.3 | 3 | 13.0 | 3 | 0 |
| Q29836 | HLA class I histocompatibility antigen, B-67 alpha chain | 40627.2 | 3 | 13.0 | 3 | 0 |
| Q95365 | HLA class I histocompatibility antigen, B-38 alpha chain | 40758.4 | 3 | 13.0 | 3 | 0 |
| Q15427 | Splicing factor 3B subunit 4 | 44442.9 | 3 | 13.0 | 10 | 107868 |
| P00390 | Glutathione reductase, mitochondrial | 52274.7 | 6 | 13.0 | 10 | 0 |
| Q8WWY3 | U4/U6 small nuclear ribonucleoprotein Prp31 | 46293.5 | 7 | 12.9 | 10 | 0 |
| P18462 | HLA class I histocompatibility antigen, A-25 alpha chain | 41503.2 | 3 | 12.9 | 3 | 0 |
| P30450 | HLA class I histocompatibility antigen, A-26 alpha chain | 41347.0 | 3 | 12.9 | 3 | 0 |
| P30456 | HLA class I histocompatibility antigen, A-43 alpha chain | 41318.0 | 3 | 12.9 | 3 | 0 |
| P30457 | HLA class I histocompatibility antigen, | 41367.0 | 3 | 12.9 | 3 | 0 |

FIG. 17 (cont'd)

| | | | | | | |
|---|---|---|---|---|---|---|
| | A-66 alpha chain | | | | | |
| Q15067 | Peroxisomal acyl-coenzyme A oxidase 1 | 73589.1 | 7 | 12.9 | 6 | 0 |
| P61962 | DDB1- and CUL4-associated factor 7 | 39553.5 | 5 | 12.9 | 6 | 0 |
| Q96KS0 | Egl nine homolog 2 | 42621.9 | 6 | 12.8 | 2 | 0 |
| Q9UIJ7 | GTP:AMP phosphotransferase AK3, mitochondrial | 21590.5 | 3 | 12.8 | 6 | 0 |
| P61619 | Protein transport protein Sec61 subunit alpha isoform 1 | 48192.0 | 7 | 12.8 | 6 | 0 |
| O43765 | Small glutamine-rich tetratricopeptide repeat-containing protein alpha | 34291.3 | 4 | 12.8 | 3 | 0 |
| P30154 | Serine/threonine-protein phosphatase 2A 65 kDa regulatory subunit A beta isoform | 67558.6 | 11 | 12.8 | 10 | 0 |
| O75400 | Pre-mRNA-processing factor 40 homolog A | 107504.4 | 13 | 12.8 | 10 | 54761 |
| A5A3E0 | POTE ankyrin domain family member F | 123098.6 | 10 | 12.7 | 10 | 0 |
| O43159 | Ribosomal RNA-processing protein 8 | 51456.2 | 5 | 12.7 | 1 | 0 |
| P26440 | Isovaleryl-CoA dehydrogenase, mitochondrial | 45035.2 | 3 | 12.7 | 4 | 0 |
| P28370 | Probable global transcription activator SNF2L1 | 122557.9 | 17 | 12.7 | 10 | 0 |
| Q6IQ22 | Ras-related protein Rab-12 | 27590.6 | 3 | 12.7 | 10 | 0 |
| O95478 | Ribosome biogenesis protein NSA2 homolog | 30236.6 | 3 | 12.7 | 2 | 0 |
| P04792 | Heat shock protein beta-1 | 22839.6 | 4 | 12.7 | 1 | 0 |
| Q9BXY0 | Protein MAK16 homolog | 35710.8 | 8 | 12.7 | 2 | 0 |
| Q9NZ01 | Very-long-chain enoyl-CoA reductase | 36433.6 | 4 | 12.7 | 5 | 49911 |
| Q9NTJ3 | Structural maintenance of chromosomes protein 4 | 144414.6 | 16 | 12.7 | 10 | 0 |
| Q6ZMR3 | L-lactate dehydrogenase A-like 6A | 36849.6 | 5 | 12.7 | 10 | 0 |
| Q92526 | T-complex protein 1 subunit zeta-2 | 57604.9 | 6 | 12.6 | 10 | 94683 |
| P61020 | Ras-related protein Rab-5B | 21626.8 | 3 | 12.6 | 10 | 0 |
| Q6EEV6 | Small ubiquitin-related modifier 4 | 10742.2 | 1 | 12.6 | 10 | 0 |
| Q13427 | Peptidyl-prolyl cis-trans isomerase G | 64943.1 | 5 | 12.6 | 10 | 0 |
| Q9NTJ5 | Phosphatidylinositide phosphatase SAC1 | 67480.3 | 9 | 12.6 | 8 | 0 |
| Q9UHK6 | Alpha-methylacyl-CoA racemase | 43465.8 | 3 | 12.6 | 2 | 0 |
| P82675 | 28S ribosomal protein S5, mitochondrial | 48519.8 | 8 | 12.6 | 1 | 0 |
| Q13557 | Calcium/calmodulin-dependent protein kinase type II subunit delta | 57101.3 | 4 | 12.6 | 10 | 0 |
| O95373 | Importin-7 | 120828.4 | 13 | 12.5 | 7 | 0 |
| P11279 | Lysosome-associated membrane glycoprotein 1 | 45395.7 | 4 | 12.5 | 3 | 0 |
| Q9UEY8 | Gamma-adducin | 77755.1 | 7 | 12.5 | 6 | 21414 |
| P09471 | Guanine nucleotide-binding protein G(o) subunit alpha | 40603.4 | 5 | 12.4 | 6 | 0 |
| P30466 | HLA class I histocompatibility antigen, B-18 alpha chain | 40560.0 | 3 | 12.4 | 4 | 0 |
| P30479 | HLA class I histocompatibility antigen, B-41 alpha chain | 40881.4 | 3 | 12.4 | 5 | 0 |
| P49792 | E3 SUMO-protein ligase RanBP2 | 362590.8 | 38 | 12.4 | 10 | 17621 |

FIG. 17 (cont'd)

| | | | | | | |
|---|---|---|---|---|---|---|
| P53985 | Monocarboxylate transporter 1 | 54628.6 | 5 | 12.4 | 3 | 0 |
| Q92917 | G patch domain and KOW motifs-containing protein | 52457.0 | 5 | 12.4 | 1 | 0 |
| A6NL28 | Putative tropomyosin alpha-3 chain-like protein | 25877.3 | 4 | 12.4 | 10 | 0 |
| P08729 | Keratin, type II cytoskeletal 7 | 51442.8 | 10 | 12.4 | 10 | 0 |
| Q13428 | Treacle protein | 145011.3 | 14 | 12.3 | 10 | 47540 |
| Q8WUM4 | Programmed cell death 6-interacting protein | 97025.0 | 12 | 12.3 | 10 | 0 |
| P23786 | Carnitine O-palmitoyltransferase 2, mitochondrial | 74290.4 | 10 | 12.3 | 3 | 0 |
| P05556 | Integrin beta-1 | 92763.9 | 11 | 12.3 | 10 | 0 |
| Q9Y3T9 | Nucleolar complex protein 2 homolog | 85775.0 | 10 | 12.3 | 10 | 41582 |
| O15355 | Protein phosphatase 1G | 59956.1 | 6 | 12.3 | 2 | 0 |
| Q15599 | Na(+)/H(+) exchange regulatory cofactor NHE-RF2 | 36380.6 | 5 | 12.3 | 1 | 0 |
| Q86UY6 | N-alpha-acetyltransferase 40 | 27764.2 | 3 | 12.2 | 1 | 0 |
| P68402 | Platelet-activating factor acetylhydrolase IB subunit beta | 25740.4 | 3 | 12.2 | 1 | 0 |
| Q9NSD9 | Phenylalanine--tRNA ligase beta subunit | 66743.0 | 7 | 12.2 | 6 | 0 |
| P35611 | Alpha-adducin | 78889.8 | 5 | 12.2 | 6 | 0 |
| O75821 | Eukaryotic translation initiation factor 3 subunit G | 35896.2 | 6 | 12.2 | 9 | 0 |
| O75525 | KH domain-containing, RNA-binding, signal transduction-associated protein 3 | 33946.6 | 3 | 12.2 | 7 | 0 |
| P52298 | Nuclear cap-binding protein subunit 2 | 18172.2 | 3 | 12.2 | 3 | 0 |
| Q9H3G5 | Probable serine carboxypeptidase CPVL | 54449.0 | 4 | 12.2 | 2 | 0 |
| O14983 | Sarcoplasmic/endoplasmic reticulum calcium ATPase 1 | 111136.8 | 13 | 12.2 | 10 | 0 |
| P31153 | S-adenosylmethionine synthase isoform type-2 | 44002.9 | 5 | 12.2 | 6 | 0 |
| Q9NRR5 | Ubiquilin-4 | 63910.2 | 7 | 12.2 | 8 | 0 |
| Q9Y5X3 | Sorting nexin-5 | 47101.7 | 6 | 12.1 | 1 | 0 |
| O75083 | WD repeat-containing protein 1 | 61692.4 | 9 | 12.1 | 3 | 0 |
| P62942 | Peptidyl-prolyl cis-trans isomerase FKBP1A | 12007.8 | 2 | 12.0 | 4 | 34929 |
| O00566 | U3 small nucleolar ribonucleoprotein protein MPP10 | 78977.9 | 7 | 12.0 | 5 | 0 |
| P31947 | 14-3-3 protein sigma | 26140.7 | 6 | 12.0 | 10 | 0 |
| Q13492 | Phosphatidylinositol-binding clathrin assembly protein | 70023.0 | 4 | 12.0 | 3 | 0 |
| Q96ME7 | Zinc finger protein 512 | 65765.7 | 8 | 12.0 | 2 | 0 |
| Q96PU8 | Protein quaking | 36145.1 | 3 | 12.0 | 10 | 0 |
| Q8TED0 | U3 small nucleolar RNA-associated protein 15 homolog | 58757.5 | 10 | 12.0 | 9 | 28377 |
| P29474 | Nitric oxide synthase, endothelial | 134942.8 | 10 | 12.0 | 1 | 0 |
| P04040 | Catalase | 59984.4 | 9 | 12.0 | 2 | 0 |
| P11908 | Ribose-phosphate pyrophosphokinase 2 | 35311.0 | 2 | 12.0 | 10 | 0 |
| O60488 | Long-chain-fatty-acid--CoA ligase 4 | 77895.8 | 9 | 11.9 | 10 | 0 |
| Q6DN03 | Putative histone H2B type 2-C | 21985.3 | 4 | 11.9 | 10 | 0 |

FIG. 17 (cont'd)

| | | | | | | |
|---|---|---|---|---|---|---|
| P49588 | Alanine--tRNA ligase, cytoplasmic | 107552.0 | 11 | 11.9 | 6 | 0 |
| P50995 | Annexin A11 | 54732.0 | 6 | 11.9 | 6 | 0 |
| Q6IMN6 | Caprin-2 | 98976.8 | 2 | 11.9 | 8 | 0 |
| Q9UKA9 | Polypyrimidine tract-binding protein 2 | 53979.1 | 6 | 11.9 | 10 | 85554 |
| Q5RI15 | Cytochrome c oxidase protein 20 homolog | 14236.6 | 1 | 11.9 | 2 | 0 |
| P55081 | Microfibrillar-associated protein 1 | 51958.5 | 5 | 11.9 | 4 | 0 |
| Q05682 | Caldesmon | 68838.7 | 8 | 11.8 | 10 | 0 |
| Q96EY4 | Translation machinery-associated protein 16 | 24092.4 | 4 | 11.8 | 1 | 0 |
| Q96GC5 | 39S ribosomal protein L48, mitochondrial | 24048.9 | 2 | 11.8 | 2 | 0 |
| P62310 | U6 snRNA-associated Sm-like protein LSm3 | 11845.4 | 3 | 11.8 | 6 | 43332 |
| Q92542 | Nicastrin | 78290.4 | 6 | 11.8 | 6 | 0 |
| P61018 | Ras-related protein Rab-4B | 25831.7 | 2 | 11.7 | 10 | 0 |
| O60783 | 28S ribosomal protein S14, mitochondrial | 15252.8 | 1 | 11.7 | 1 | 0 |
| P48556 | 26S proteasome non-ATPase regulatory subunit 8 | 39897.1 | 5 | 11.7 | 1 | 0 |
| Q9NYU2 | UDP-glucose:glycoprotein glucosyltransferase 1 | 176739.4 | 16 | 11.7 | 10 | 11391 |
| Q9NVA1 | Ubiquinol-cytochrome-c reductase complex assembly factor 1 | 31416.6 | 4 | 11.7 | 3 | 0 |
| P78316 | Nucleolar protein 14 | 95447.3 | 11 | 11.7 | 10 | 0 |
| P55854 | Small ubiquitin-related modifier 3 | 11694.1 | 2 | 11.7 | 10 | 0 |
| Q9UHR5 | SAP30-binding protein | 33083.7 | 3 | 11.6 | 2 | 0 |
| P67870 | Casein kinase II subunit beta | 25284.7 | 3 | 11.6 | 2 | 0 |
| Q9Y5Q8 | General transcription factor 3C polypeptide 5 | 59858.3 | 7 | 11.6 | 6 | 0 |
| Q8N8S7 | Protein enabled homolog | 65331.5 | 4 | 11.6 | 2 | 0 |
| Q9NP81 | Serine--tRNA ligase, mitochondrial | 58612.7 | 6 | 11.6 | 4 | 0 |
| Q8WVM0 | Dimethyladenosine transferase 1, mitochondrial | 39885.2 | 3 | 11.6 | 1 | 0 |
| Q9NX20 | 39S ribosomal protein L16, mitochondrial | 28506.3 | 2 | 11.6 | 1 | 0 |
| P55196 | Afadin | 198899.8 | 17 | 11.5 | 10 | 0 |
| Q96HE7 | ERO1-like protein alpha | 55248.1 | 7 | 11.5 | 2 | 0 |
| P61086 | Ubiquitin-conjugating enzyme E2 K | 22520.7 | 3 | 11.5 | 1 | 0 |
| Q9NXF1 | Testis-expressed sequence 10 protein | 105507.5 | 7 | 11.5 | 10 | 0 |
| P15153 | Ras-related C3 botulinum toxin substrate 2 | 21828.0 | 2 | 11.5 | 2 | 0 |
| P29992 | Guanine nucleotide-binding protein subunit alpha-11 | 42408.6 | 3 | 11.4 | 2 | 0 |
| P62158 | Calmodulin | 16837.7 | 3 | 11.4 | 10 | 258525 |
| Q14344 | Guanine nucleotide-binding protein subunit alpha-13 | 44391.8 | 6 | 11.4 | 3 | 73191 |
| P10109 | Adrenodoxin, mitochondrial | 19677.9 | 1 | 11.4 | 1 | 0 |
| P34896 | Serine hydroxymethyltransferase, cytosolic | 49438.8 | 8 | 11.4 | 10 | 0 |
| Q32P28 | Prolyl 3-hydroxylase 1 | 82861.6 | 10 | 11.4 | 9 | 0 |
| Q5RKV6 | Exosome complex component MTR3 | 28520.3 | 3 | 11.4 | 1 | 0 |
| Q5SSJ5 | Heterochromatin protein 1-binding | 54569.5 | 8 | 11.4 | 10 | 44772 |

FIG. 17 (cont'd)

| | | | | | | |
|---|---|---|---|---|---|---|
| | protein 3 | | | | | |
| Q15007 | Pre-mRNA-splicing regulator WTAP | 35562.6 | 6 | 11.4 | 3 | 0 |
| Q9NQ39 | Putative 40S ribosomal protein S10-like | 20291.5 | 3 | 11.4 | 3 | 0 |
| P59998 | Actin-related protein 2/3 complex subunit 4 | 46758.0 | 6 | 11.3 | 4 | 0 |
| Q92797 | Symplekin | 125219.4 | 13 | 11.3 | 10 | 0 |
| Q96T37 | Putative RNA-binding protein 15 | 106331.2 | 9 | 11.3 | 10 | 0 |
| P38432 | Coilin | 63292.7 | 6 | 11.3 | 4 | 0 |
| O95470 | Sphingosine-1-phosphate lyase 1 | 64094.2 | 7 | 11.3 | 1 | 0 |
| Q4G0J3 | La-related protein 7 | 53009.0 | 6 | 11.2 | 3 | 0 |
| O60749 | Sorting nexin-2 | 58585.3 | 8 | 11.2 | 4 | 0 |
| Q13409 | Cytoplasmic dynein 1 intermediate chain 2 | 70430.2 | 6 | 11.1 | 10 | 0 |
| Q96TA2 | ATP-dependent zinc metalloprotease YME1L1 | 80965.9 | 8 | 11.1 | 3 | 0 |
| Q5SY16 | Polynucleotide 5'-hydroxyl-kinase NOL9 | 80577.5 | 6 | 11.1 | 6 | 18987 |
| P26358 | DNA (cytosine-5)-methyltransferase 1 | 175519.3 | 20 | 11.1 | 10 | 0 |
| Q9Y2W2 | WW domain-binding protein 11 | 69997.8 | 8 | 11.1 | 4 | 0 |
| Q8N9T8 | Protein KRI1 homolog | 83410.3 | 9 | 11.1 | 10 | 9966 |
| Q96E17 | Ras-related protein Rab-3C | 26180.4 | 4 | 11.0 | 10 | 0 |
| P26640 | Valine--tRNA ligase | 141730.8 | 11 | 11.0 | 4 | 15660 |
| Q9Y2T7 | Y-box-binding protein 2 | 38575.0 | 3 | 11.0 | 10 | 0 |
| F5H284 | Peptidyl-prolyl cis-trans isomerase A-like 4D | 18394.9 | 4 | 11.0 | 1 | 0 |
| P19388 | DNA-directed RNA polymerases I, II, and III subunit RPABC1 | 24665.3 | 3 | 11.0 | 1 | 0 |
| P30499 | HLA class I histocompatibility antigen, Cw-1 alpha chain | 41421.0 | 3 | 10.9 | 4 | 0 |
| Q52LJ0 | Protein FAM98B | 41768.3 | 5 | 10.9 | 2 | 0 |
| Q9UBF2 | Coatomer subunit gamma-2 | 98763.1 | 9 | 10.9 | 2 | 0 |
| P42685 | Tyrosine-protein kinase FRK | 58710.4 | 4 | 10.9 | 1 | 0 |
| Q92643 | GPI-anchor transamidase | 45537.0 | 3 | 10.9 | 1 | 0 |
| O15228 | Dihydroxyacetone phosphate acyltransferase | 77986.5 | 7 | 10.9 | 2 | 0 |
| P13674 | Prolyl 4-hydroxylase subunit alpha-1 | 60610.0 | 6 | 10.9 | 6 | 0 |
| Q3SY69 | Mitochondrial 10-formyltetrahydrofolate dehydrogenase | 85592.5 | 13 | 10.8 | 8 | 0 |
| Q9GZR7 | ATP-dependent RNA helicase DDX24 | 96959.2 | 6 | 10.8 | 2 | 0 |
| P30419 | Glycylpeptide N-tetradecanoyltransferase 1 | 52758.7 | 4 | 10.8 | 10 | 0 |
| Q16186 | Proteasomal ubiquitin receptor ADRM1 | 42438.5 | 6 | 10.8 | 2 | 0 |
| O75251 | NADH dehydrogenase [ubiquinone] iron-sulfur protein 7, mitochondrial | 23848.7 | 4 | 10.8 | 9 | 59140.5 |
| Q15833 | Syntaxin-binding protein 2 | 66908.9 | 6 | 10.8 | 1 | 0 |
| Q9UL33 | Trafficking protein particle complex subunit 2-like protein | 16273.2 | 2 | 10.8 | 2 | 0 |
| Q12873 | Chromodomain-helicase-DNA-binding protein 3 | 226266.3 | 21 | 10.8 | 10 | 0 |
| Q05519 | Serine/arginine-rich splicing factor 11 | 53592.2 | 4 | 10.8 | 10 | 49572 |
| P27707 | Deoxycytidine kinase | 30860.8 | 4 | 10.8 | 1 | 0 |

FIG. 17 (cont'd)

| | | | | | | |
|---|---|---|---|---|---|---|
| Q04826 | HLA class I histocompatibility antigen, B-40 alpha chain | 40847.4 | 3 | 10.8 | 2 | 0 |
| Q16762 | Thiosulfate sulfurtransferase | 33657.1 | 2 | 10.8 | 4 | 0 |
| Q8IYB3 | Serine/arginine repetitive matrix protein 1 | 102287.7 | 8 | 10.8 | 10 | 92439 |
| P27708 | CAD protein | 245322.3 | 21 | 10.7 | 7 | 7161 |
| Q31612 | HLA class I histocompatibility antigen, B-73 alpha chain | 40834.4 | 3 | 10.7 | 5 | 0 |
| Q8TEX9 | Importin-4 | 120342.1 | 10 | 10.7 | 10 | 227136 |
| P51648 | Fatty aldehyde dehydrogenase | 56714.9 | 4 | 10.7 | 10 | 0 |
| Q9NP72 | Ras-related protein Rab-18 | 23262.2 | 3 | 10.7 | 1 | 0 |
| P30501 | HLA class I histocompatibility antigen, Cw-2 alpha chain | 41494.1 | 3 | 10.7 | 2 | 0 |
| O75880 | Protein SCO1 homolog, mitochondrial | 34042.1 | 3 | 10.6 | 1 | 0 |
| Q06787 | Fragile X mental retardation protein 1 | 68860.0 | 6 | 10.6 | 10 | 0 |
| P08779 | Keratin, type I cytoskeletal 16 | 51610.1 | 5 | 10.6 | 2 | 0 |
| Q8N3U4 | Cohesin subunit SA-2 | 144566.7 | 16 | 10.6 | 10 | 0 |
| Q96KA5 | Cleft lip and palate transmembrane protein 1-like protein | 60606.2 | 4 | 10.6 | 2 | 0 |
| Q9H0U6 | 39S ribosomal protein L18, mitochondrial | 20804.7 | 2 | 10.6 | 1 | 0 |
| P30520 | Adenylosuccinate synthetase isozyme 2 | 50496.6 | 6 | 10.5 | 4 | 0 |
| Q8IVS2 | Malonyl-CoA-acyl carrier protein transacylase, mitochondrial | 43417.8 | 3 | 10.5 | 1 | 0 |
| Q9BWS9 | Chitinase domain-containing protein 1 | 44972.8 | 4 | 10.5 | 6 | 0 |
| Q9P013 | Spliceosome-associated protein CWC15 homolog | 26681.4 | 1 | 10.5 | 1 | 0 |
| Q92879 | CUGBP Elav-like family member 1 | 52702.3 | 7 | 10.5 | 10 | 0 |
| P27361 | Mitogen-activated protein kinase 3 | 40822.7 | 3 | 10.5 | 6 | 0 |
| A0FGR8 | Extended synaptotagmin-2 | 98334.8 | 7 | 10.4 | 10 | 0 |
| A8MXV4 | Nucleoside diphosphate-linked moiety X motif 19, mitochondrial | 42575.5 | 6 | 10.4 | 2 | 0 |
| P07948 | Tyrosine-protein kinase Lyn | 57760.0 | 8 | 10.4 | 2 | 0 |
| Q92900 | Regulator of nonsense transcripts 1 | 125002.3 | 12 | 10.4 | 8 | 0 |
| Q969P6 | DNA topoisomerase I, mitochondrial | 64828.8 | 6 | 10.3 | 10 | 0 |
| Q9BVL2 | Nucleoporin p58/p45 | 57048.7 | 4 | 10.3 | 10 | 0 |
| Q9Y3B9 | RRP15-like protein | 31655.3 | 4 | 10.3 | 1 | 0 |
| O43423 | Acidic leucine-rich nuclear phosphoprotein 32 family member C | 26933.0 | 3 | 10.3 | 4 | 0 |
| P19623 | Spermidine synthase | 34395.0 | 3 | 10.3 | 2 | 0 |
| P24447 | Alkaline nuclease | 57785.2 | 3 | 10.3 | 1 | 0 |
| Q9NWS8 | Required for meiotic nuclear division protein 1 homolog | 52003.2 | 6 | 10.2 | 1 | 0 |
| P12081 | Histidine--tRNA ligase, cytoplasmic | 55607.1 | 9 | 10.2 | 6 | 0 |
| P06681 | Complement C2 | 72074.6 | 3 | 10.2 | 3 | 0 |
| Q12800 | Alpha-globin transcription factor CP2 | 54681.1 | 3 | 10.2 | 4 | 0 |
| Q6UXN9 | WD repeat-containing protein 82 | 35478.3 | 2 | 10.2 | 1 | 0 |
| Q9NVJ2 | ADP-ribosylation factor-like protein 8B | 21767.2 | 2 | 10.2 | 2 | 0 |
| Q8TEQ6 | Gem-associated protein 5 | 170927.7 | 7 | 10.2 | 1 | 0 |
| Q969X6 | Cirhin | 73101.8 | 7 | 10.2 | 10 | 0 |
| Q13724 | Mannosyl-oligosaccharide glucosidase | 92088.8 | 9 | 10.2 | 7 | 0 |

FIG. 17 (cont'd)

| | | | | | | |
|---|---|---|---|---|---|---|
| P82673 | 28S ribosomal protein S35, mitochondrial | 35037.6 | 2 | 10.1 | 2 | 0 |
| P33176 | Kinesin-1 heavy chain | 110426.4 | 9 | 10.1 | 2 | 0 |
| Q3SYB3 | Forkhead box protein D4-like 6 | 46699.9 | 3 | 10.1 | 1 | 0 |
| Q6VB84 | Forkhead box protein D4-like 3 | 46732.9 | 3 | 10.1 | 1 | 0 |
| Q9H115 | Beta-soluble NSF attachment protein | 33899.2 | 6 | 10.1 | 4 | 0 |
| Q9ULX6 | A-kinase anchor protein 8-like | 68895.6 | 5 | 10.1 | 2 | 0 |
| Q29RF7 | Sister chromatid cohesion protein PDS5 homolog A | 131741.6 | 13 | 10.0 | 8 | 0 |
| Q9HD45 | Transmembrane 9 superfamily member 3 | 68629.8 | 7 | 10.0 | 9 | 0 |
| Q9NUQ7 | Ufm1-specific protease 2 | 53660.6 | 7 | 10.0 | 1 | 0 |
| Q9UMS0 | NFU1 iron-sulfur cluster scaffold homolog, mitochondrial | 27335.7 | 4 | 10.0 | 8 | 29601 |
| O14773 | Tripeptidyl-peptidase 1 | 48226.5 | 3 | 10.0 | 4 | 0 |
| O15144 | Actin-related protein 2/3 complex subunit 2 | 34447.1 | 4 | 10.0 | 1 | 0 |
| Q08378 | Golgin subfamily A member 3 | 154885.8 | 15 | 10.0 | 10 | 0 |
| Q9NSB2 | Keratin, type II cuticular Hb4 | 65983.0 | 11 | 10.0 | 10 | 0 |
| Q9UQR0 | Sex comb on midleg-like protein 2 | 78112.3 | 10 | 10.0 | 2 | 0 |
| P20020 | Plasma membrane calcium-transporting ATPase 1 | 134391.2 | 8 | 10.0 | 10 | 0 |
| Q96AY3 | Peptidyl-prolyl cis-trans isomerase FKBP10 | 64758.4 | 11 | 10.0 | 5 | 0 |
| P14136 | Glial fibrillary acidic protein | 49967.7 | 6 | 10.0 | 10 | 0 |
| Q96DU9 | Polyadenylate-binding protein 5 | 43672.9 | 5 | 10.0 | 2 | 0 |
| O15269 | Serine palmitoyltransferase 1 | 53314.3 | 5 | 9.9 | 4 | 32919 |
| O14654 | Insulin receptor substrate 4 | 134794.3 | 13 | 9.9 | 7 | 0 |
| P15313 | V-type proton ATPase subunit B, kidney isoform | 57232.4 | 4 | 9.9 | 1 | 0 |
| Q96EY1 | DnaJ homolog subfamily A member 3, mitochondrial | 51677.5 | 4 | 9.9 | 6 | 0 |
| Q13616 | Cullin-1 | 90363.0 | 8 | 9.9 | 2 | 0 |
| A6NHQ2 | rRNA/tRNA 2'-O-methyltransferase fibrillarin-like protein 1 | 34732.3 | 2 | 9.9 | 1 | 43209 |
| Q14692 | Ribosome biogenesis protein BMS1 homolog | 146662.9 | 14 | 9.9 | 10 | 35085 |
| Q02809 | Procollagen-lysine,2-oxoglutarate 5-dioxygenase 1 | 84120.6 | 7 | 9.9 | 5 | 0 |
| Q9BTC8 | Metastasis-associated protein MTA3 | 63843.2 | 8 | 9.9 | 10 | 0 |
| Q12797 | Aspartyl/asparaginyl beta-hydroxylase | 86318.9 | 7 | 9.9 | 2 | 0 |
| Q13098 | COP9 signalosome complex subunit 1 | 57168.4 | 4 | 9.9 | 9 | 0 |
| A6NHL2 | Tubulin alpha chain-like 3 | 48426.2 | 8 | 9.9 | 10 | 0 |
| P07205 | Phosphoglycerate kinase 2 | 45195.4 | 3 | 9.8 | 10 | 0 |
| O14936 | Peripheral plasma membrane protein CASK | 104338.9 | 7 | 9.8 | 5 | 0 |
| P30876 | DNA-directed RNA polymerase II subunit RPB2 | 135322.6 | 14 | 9.8 | 6 | 0 |
| P35749 | Myosin-11 | 226689.5 | 19 | 9.8 | 10 | 0 |
| Q16540 | 39S ribosomal protein L23, mitochondrial | 17781.2 | 2 | 9.8 | 2 | 0 |
| Q8TAA5 | GrpE protein homolog 2, mitochondrial | 25773.4 | 4 | 9.8 | 1 | 0 |
| Q9Y6N5 | Sulfide:quinone oxidoreductase, | 50245.9 | 6 | 9.8 | 1 | 0 |

FIG. 17 (cont'd)

| | | | | | | |
|---|---|---|---|---|---|---|
| | mitochondrial | | | | | |
| O60341 | Lysine-specific histone demethylase 1A | 94542.1 | 6 | 9.7 | 2 | 0 |
| O15127 | Secretory carrier-associated membrane protein 2 | 37105.2 | 2 | 9.7 | 3 | 0 |
| O75352 | Mannose-P-dolichol utilization defect 1 protein | 26923.0 | 3 | 9.7 | 3 | 0 |
| O96005 | Cleft lip and palate transmembrane protein 1 | 76324.9 | 5 | 9.7 | 1 | 0 |
| Q13619 | Cullin-4A | 82735.5 | 10 | 9.7 | 2 | 0 |
| Q86YP4 | Transcriptional repressor p66-alpha | 66986.4 | 5 | 9.7 | 4 | 0 |
| Q13445 | Transmembrane emp24 domain-containing protein 1 | 25376.9 | 2 | 9.7 | 1 | 0 |
| Q96S52 | GPI transamidase component PIG-S | 61445.0 | 3 | 9.7 | 6 | 0 |
| Q8NFW8 | N-acylneuraminate cytidylyltransferase | 49063.6 | 4 | 9.7 | 4 | 0 |
| Q96EK5 | KIF1-binding protein | 72498.5 | 5 | 9.7 | 2 | 0 |
| Q96ST3 | Paired amphipathic helix protein Sin3a | 145973.7 | 9 | 9.7 | 3 | 0 |
| Q9BTD8 | RNA-binding protein 42 | 48152.4 | 3 | 9.6 | 4 | 0 |
| Q8N7H5 | RNA polymerase II-associated factor 1 homolog | 57735.5 | 5 | 9.6 | 2 | 0 |
| Q9UQ88 | Cyclin-dependent kinase 11A | 76617.0 | 5 | 9.6 | 6 | 0 |
| Q7Z4V5 | Hepatoma-derived growth factor-related protein 2 | 74444.4 | 6 | 9.6 | 6 | 47655 |
| P46063 | ATP-dependent DNA helicase Q1 | 74484.0 | 7 | 9.6 | 2 | 0 |
| Q6L8Q7 | 2',5'-phosphodiesterase 12 | 63919.2 | 5 | 9.5 | 2 | 0 |
| Q9NZI7 | Upstream-binding protein 1 | 59937.7 | 5 | 9.5 | 4 | 0 |
| Q9UNE7 | E3 ubiquitin-protein ligase CHIP | 31361.0 | 3 | 9.5 | 2 | 0 |
| P14373 | Zinc finger protein RFP | 51076.6 | 8 | 9.5 | 2 | 0 |
| O60313 | Dynamin-like 120 kDa protein, mitochondrial | 114328.0 | 11 | 9.5 | 8 | 0 |
| Q01650 | Large neutral amino acids transporter small subunit 1 | 55694.7 | 3 | 9.5 | 2 | 0 |
| Q96G23 | Ceramide synthase 2 | 44990.3 | 2 | 9.5 | 1 | 0 |
| Q5VWX1 | KH domain-containing, RNA-binding, signal transduction-associated protein 2 | 38927.4 | 3 | 9.5 | 4 | 0 |
| Q3SXM5 | Inactive hydroxysteroid dehydrogenase-like protein 1 | 34330.6 | 2 | 9.5 | 2 | 0 |
| Q9NWT1 | p21-activated protein kinase-interacting protein 1 | 44534.2 | 3 | 9.4 | 2 | 0 |
| Q9Y2R0 | Cytochrome c oxidase assembly protein 3 homolog, mitochondrial | 11731.3 | 2 | 9.4 | 1 | 0 |
| P30486 | HLA class I histocompatibility antigen, B-48 alpha chain | 40704.3 | 2 | 9.4 | 3 | 0 |
| P61160 | Actin-related protein 2 | 45169.2 | 5 | 9.4 | 5 | 0 |
| Q15437 | Protein transport protein Sec23B | 87448.8 | 7 | 9.4 | 3 | 0 |
| Q31610 | HLA class I histocompatibility antigen, B-81 alpha chain | 40742.3 | 2 | 9.4 | 3 | 0 |
| Q7KZ85 | Transcription elongation factor SPT6 | 200327.6 | 17 | 9.4 | 4 | 0 |
| Q8IXI1 | Mitochondrial Rho GTPase 2 | 53997.8 | 4 | 9.4 | 3 | 0 |
| Q9NQZ2 | Something about silencing protein 10 | 54672.1 | 3 | 9.4 | 1 | 0 |
| P19022 | Cadherin-2 | 100265.7 | 7 | 9.4 | 8 | 0 |
| Q9UMR2 | ATP-dependent RNA helicase DDX19B | 50847.4 | 3 | 9.4 | 7 | 0 |

FIG. 17 (cont'd)

| | | | | | | |
|---|---|---|---|---|---|---|
| P51116 | Fragile X mental retardation syndrome-related protein 2 | 74565.6 | 7 | 9.4 | 3 | 0 |
| Q9BTE1 | Dynactin subunit 5 | 20696.8 | 4 | 9.3 | 1 | 0 |
| Q9UMY1 | Nucleolar protein 7 | 29483.5 | 3 | 9.3 | 3 | 0 |
| P0CG38 | POTE ankyrin domain family member I | 122936.4 | 12 | 9.3 | 10 | 0 |
| Q9BY44 | Eukaryotic translation initiation factor 2A | 65560.5 | 7 | 9.2 | 2 | 0 |
| P04259 | Keratin, type II cytoskeletal 6B | 60352.2 | 8 | 9.2 | 10 | 4242 |
| P10644 | cAMP-dependent protein kinase type I-alpha regulatory subunit | 43209.9 | 3 | 9.2 | 1 | 0 |
| P48449 | Lanosterol synthase | 81788.8 | 8 | 9.2 | 8 | 0 |
| Q9ULR3 | Protein phosphatase 1H | 56961.4 | 7 | 9.1 | 2 | 0 |
| Q9Y2J2 | Band 4.1-like protein 3 | 109251.6 | 9 | 9.1 | 2 | 0 |
| P03989 | HLA class I histocompatibility antigen, B-27 alpha chain | 40827.4 | 2 | 9.1 | 1 | 0 |
| P30461 | HLA class I histocompatibility antigen, B-13 alpha chain | 40816.5 | 2 | 9.1 | 1 | 0 |
| P30481 | HLA class I histocompatibility antigen, B-44 alpha chain | 40823.5 | 2 | 9.1 | 1 | 0 |
| P30483 | HLA class I histocompatibility antigen, B-45 alpha chain | 40699.3 | 2 | 9.1 | 1 | 0 |
| P30485 | HLA class I histocompatibility antigen, B-47 alpha chain | 40913.6 | 2 | 9.1 | 1 | 0 |
| P30487 | HLA class I histocompatibility antigen, B-49 alpha chain | 40866.6 | 2 | 9.1 | 1 | 0 |
| P30488 | HLA class I histocompatibility antigen, B-50 alpha chain | 40826.5 | 2 | 9.1 | 1 | 0 |
| Q15397 | Pumilio domain-containing protein KIAA0020 | 73983.8 | 6 | 9.1 | 3 | 0 |
| O75150 | E3 ubiquitin-protein ligase BRE1B | 108589.8 | 10 | 9.1 | 4 | 0 |
| Q9UBB9 | Tuftelin-interacting protein 11 | 97219.2 | 7 | 9.1 | 2 | 0 |
| O00159 | Unconventional myosin-Ic | 120556.5 | 13 | 9.1 | 6 | 0 |
| Q9HAV4 | Exportin-5 | 138421.5 | 15 | 9.1 | 4 | 0 |
| Q8IYB8 | ATP-dependent RNA helicase SUPV3L1, mitochondrial | 88846.8 | 8 | 9.0 | 6 | 0 |
| P52948 | Nuclear pore complex protein Nup98-Nup96 | 169116.8 | 17 | 9.0 | 10 | 0 |
| O00469 | Procollagen-lysine,2-oxoglutarate 5-dioxygenase 2 | 86633.5 | 6 | 9.0 | 4 | 0 |
| Q4VXU2 | Polyadenylate-binding protein 1-like | 69019.7 | 9 | 9.0 | 10 | 0 |
| Q969Z3 | MOSC domain-containing protein 2, mitochondrial | 38593.7 | 7 | 9.0 | 1 | 0 |
| Q9P287 | BRCA2 and CDKN1A-interacting protein | 36321.7 | 4 | 8.9 | 1 | 0 |
| Q5UIP0 | Telomere-associated protein RIF1 | 275216.5 | 19 | 8.9 | 10 | 19788 |
| P23634 | Plasma membrane calcium-transporting ATPase 4 | 132121.9 | 9 | 8.9 | 10 | 0 |
| P49750 | YLP motif-containing protein 1 | 228418.1 | 16 | 8.9 | 8 | 0 |
| Q15436 | Protein transport protein Sec23A | 87073.4 | 7 | 8.9 | 6 | 0 |
| Q92922 | SWI/SNF complex subunit SMARCC1 | 123380.5 | 16 | 8.9 | 9 | 0 |
| O00161 | Synaptosomal-associated protein 23 | 20885.2 | 1 | 8.9 | 4 | 0 |
| P17540 | Creatine kinase S-type, mitochondrial | 48017.8 | 5 | 8.8 | 10 | 0 |
| P48544 | G protein-activated inward rectifier potassium channel 4 | 48181.0 | 2 | 8.8 | 1 | 0 |

FIG. 17 (cont'd)

| | | | | | | |
|---|---|---|---|---|---|---|
| P80303 | Nucleobindin-2 | 50312.4 | 3 | 8.8 | 6 | 0 |
| Q8WXF0 | Serine/arginine-rich splicing factor 12 | 30683.0 | 3 | 8.8 | 10 | 0 |
| Q9NUU7 | ATP-dependent RNA helicase DDX19A | 54431.4 | 4 | 8.8 | 2 | 0 |
| O00330 | Pyruvate dehydrogenase protein X component, mitochondrial | 54350.5 | 4 | 8.8 | 2 | 0 |
| O75027 | ATP-binding cassette sub-family B member 7, mitochondrial | 82990.7 | 5 | 8.8 | 2 | 0 |
| Q7Z7L7 | Protein zer-1 homolog | 89538.3 | 5 | 8.8 | 1 | 0 |
| Q99961 | Endophilin-A2 | 39096.6 | 3 | 8.8 | 2 | 0 |
| Q96CU9 | FAD-dependent oxidoreductase domain-containing protein 1 | 45829.1 | 5 | 8.7 | 3 | 0 |
| P49590 | Probable histidine--tRNA ligase, mitochondrial | 57629.8 | 4 | 8.7 | 3 | 0 |
| Q06124 | Tyrosine-protein phosphatase non-receptor type 11 | 63604.9 | 3 | 8.7 | 3 | 0 |
| Q15382 | GTP-binding protein Rheb | 20554.6 | 1 | 8.7 | 1 | 0 |
| Q14203 | Dynactin subunit 1 | 134999.3 | 12 | 8.7 | 10 | 0 |
| P20337 | Ras-related protein Rab-3B | 24986.1 | 2 | 8.7 | 10 | 0 |
| Q96FV9 | THO complex subunit 1 | 76407.8 | 6 | 8.7 | 1 | 0 |
| P62745 | Rho-related GTP-binding protein RhoB | 22579.6 | 1 | 8.7 | 6 | 0 |
| P21127 | Cyclin-dependent kinase 11B | 76517.2 | 4 | 8.7 | 10 | 0 |
| Q5VZL5 | Zinc finger MYM-type protein 4 | 167303.5 | 12 | 8.7 | 6 | 0 |
| O14776 | Transcription elongation regulator 1 | 122995.5 | 14 | 8.6 | 10 | 50586 |
| P20336 | Ras-related protein Rab-3A | 25212.1 | 2 | 8.6 | 10 | 0 |
| Q9NYY8 | FAST kinase domain-containing protein 2 | 78911.9 | 7 | 8.6 | 4 | 0 |
| A6NKH3 | Putative 60S ribosomal protein L37a-like | 10867.8 | 1 | 8.6 | 2 | 0 |
| O43583 | Density-regulated protein | 22491.2 | 1 | 8.6 | 1 | 0 |
| P0CG39 | POTE ankyrin domain family member J | 118815.9 | 10 | 8.6 | 10 | 0 |
| Q969V3 | Nicalin | 63081.5 | 7 | 8.5 | 10 | 0 |
| P04062 | Glucosylceramidase | 59013.3 | 3 | 8.5 | 2 | 0 |
| P19525 | Interferon-induced, double-stranded RNA-activated protein kinase | 60198.8 | 5 | 8.5 | 2 | 0 |
| P35527 | Keratin, type I cytoskeletal 9 | 62292.5 | 3 | 8.5 | 1 | 0 |
| P53992 | Protein transport protein Sec24C | 119864.7 | 9 | 8.5 | 4 | 0 |
| P63151 | Serine/threonine-protein phosphatase 2A 55 kDa regulatory subunit B alpha isoform | 52859.2 | 4 | 8.5 | 2 | 0 |
| Q9Y4P3 | Transducin beta-like protein 2 | 50425.2 | 10 | 8.5 | 1 | 0 |
| Q9NY93 | Probable ATP-dependent RNA helicase DDX56 | 59831.3 | 5 | 8.5 | 8 | 20968.5 |
| Q96S66 | Chloride channel CLIC-like protein 1 | 51989.9 | 5 | 8.5 | 4 | 0 |
| Q9UBV8 | Peflin | 30666.1 | 3 | 8.5 | 3 | 0 |
| Q16134 | Electron transfer flavoprotein-ubiquinone oxidoreductase, mitochondrial | 69293.9 | 5 | 8.4 | 1 | 0 |
| P49916 | DNA ligase 3 | 111157.6 | 12 | 8.4 | 10 | 0 |
| Q15031 | Probable leucine--tRNA ligase, mitochondrial | 102888.8 | 13 | 8.4 | 4 | 0 |

FIG. 17 (cont'd)

| | | | | | | |
|---|---|---|---|---|---|---|
| Q9H0P0 | Cytosolic 5'-nucleotidase 3A | 34577.3 | 3 | 8.4 | 4 | 0 |
| Q9NPL8 | Translocase of inner mitochondrial membrane domain-containing protein 1 | 32348.9 | 4 | 8.4 | 1 | 0 |
| Q86VF2 | Immunoglobulin-like and fibronectin type III domain-containing protein 1 | 385972.8 | 42 | 8.4 | 7 | 0 |
| Q9H000 | Probable E3 ubiquitin-protein ligase makorin-2 | 48309.0 | 3 | 8.4 | 1 | 0 |
| Q8WYA6 | Beta-catenin-like protein 1 | 51084.3 | 8 | 8.4 | 7 | 28428 |
| Q92878 | DNA repair protein RAD50 | 149921.2 | 13 | 8.4 | 10 | 0 |
| Q14160 | Protein scribble homolog | 173853.4 | 12 | 8.3 | 7 | 0 |
| P12036 | Neurofilament heavy polypeptide | 109287.2 | 7 | 8.3 | 10 | 8809.5 |
| P20648 | Potassium-transporting ATPase alpha chain 1 | 115829.9 | 7 | 8.3 | 5 | 0 |
| Q6IAN0 | Dehydrogenase/reductase SDR family member 7B | 35404.2 | 3 | 8.3 | 1 | 0 |
| O95453 | Poly(A)-specific ribonuclease PARN | 69743.5 | 4 | 8.3 | 3 | 0 |
| P22420 | Regulatory protein E2 | 57592.1 | 6 | 8.3 | 1 | 0 |
| Q15904 | V-type proton ATPase subunit S1 | 52197.0 | 4 | 8.3 | 1 | 0 |
| O75691 | Small subunit processome component 20 homolog | 321009.2 | 27 | 8.3 | 9 | 16152 |
| A6NHR9 | Structural maintenance of chromosomes flexible hinge domain-containing protein 1 | 207595.3 | 14 | 8.3 | 9 | 0 |
| Q14562 | ATP-dependent RNA helicase DHX8 | 140170.2 | 13 | 8.3 | 3 | 0 |
| Q7Z6G8 | Ankyrin repeat and sterile alpha motif domain-containing protein 1B | 139321.0 | 8 | 8.3 | 1 | 0 |
| Q8IXK0 | Polyhomeotic-like protein 2 | 30452.4 | 3 | 8.2 | 1 | 0 |
| Q00526 | Cyclin-dependent kinase 3 | 35159.9 | 2 | 8.2 | 4 | 0 |
| Q99426 | Tubulin-folding cofactor B | 27610.7 | 2 | 8.2 | 1 | 0 |
| P10253 | Lysosomal alpha-glucosidase | 106179.4 | 8 | 8.2 | 2 | 0 |
| P52789 | Hexokinase-2 | 103805.8 | 13 | 8.2 | 7 | 0 |
| P82914 | 28S ribosomal protein S15, mitochondrial | 29956.2 | 3 | 8.2 | 1 | 0 |
| Q8NFH3 | Nucleoporin Nup43 | 42607.1 | 2 | 8.2 | 3 | 0 |
| Q9H9P8 | L-2-hydroxyglutarate dehydrogenase, mitochondrial | 50237.7 | 8 | 8.2 | 2 | 0 |
| Q9NQI0 | Probable ATP-dependent RNA helicase DDX4 | 73841.8 | 7 | 8.2 | 10 | 0 |
| Q9UBT2 | SUMO-activating enzyme subunit 2 | 71794.0 | 7 | 8.1 | 3 | 0 |
| Q9Y5A9 | YTH domain family protein 2 | 59776.9 | 5 | 8.1 | 4 | 0 |
| P0DJD0 | RANBP2-like and GRIP domain-containing protein 1 | 198144.8 | 14 | 8.1 | 4 | 0 |
| O60229 | Kalirin | 211910.6 | 21 | 8.1 | 5 | 0 |
| Q5ZPR3 | CD276 antigen | 56424.2 | 3 | 8.1 | 10 | 0 |
| O95347 | Structural maintenance of chromosomes protein 2 | 130776.2 | 9 | 8.1 | 8 | 0 |
| P0DJD1 | RANBP2-like and GRIP domain-containing protein 2 | 198790.6 | 14 | 8.1 | 4 | 0 |
| Q9BYP7 | Serine/threonine-protein kinase WNK3 | 194128.7 | 12 | 8.1 | 2 | 0 |
| O76031 | ATP-dependent Clp protease ATP-binding subunit clpX-like, mitochondrial | 69965.2 | 8 | 8.1 | 7 | 17778 |
| Q9NRP0 | Oligosaccharyltransferase complex | 16943.4 | 1 | 8.1 | 6 | 59808 |

FIG. 17 (cont'd)

| | | | | | | |
|---|---|---|---|---|---|---|
| | subunit OSTC | | | | | |
| Q8IWB7 | WD repeat and FYVE domain-containing protein 1 | 47350.3 | 2 | 8.1 | 1 | 0 |
| O75323 | Protein NipSnap homolog 2 | 33970.8 | 4 | 8.0 | 1 | 0 |
| O43790 | Keratin, type II cuticular Hb6 | 55154.5 | 6 | 8.0 | 9 | 0 |
| Q16352 | Alpha-internexin | 55561.8 | 6 | 8.0 | 10 | 0 |
| Q8WXA9 | Splicing regulatory glutamine/lysine-rich protein 1 | 68724.8 | 4 | 8.0 | 4 | 0 |
| Q8ND56 | Protein LSM14 homolog A | 50770.0 | 6 | 8.0 | 4 | 0 |
| O43264 | Centromere/kinetochore protein zw10 homolog | 89685.1 | 4 | 8.0 | 1 | 0 |
| P78385 | Keratin, type II cuticular Hb3 | 55963.3 | 5 | 7.9 | 10 | 0 |
| Q99996 | A-kinase anchor protein 9 | 443504.3 | 36 | 7.9 | 10 | 0 |
| Q7L576 | Cytoplasmic FMR1-interacting protein 1 | 114047.5 | 11 | 7.9 | 6 | 0 |
| Q13112 | Chromatin assembly factor 1 subunit B | 61948.8 | 8 | 7.9 | 2 | 0 |
| Q93084 | Sarcoplasmic/endoplasmic reticulum calcium ATPase 3 | 113875.3 | 8 | 7.9 | 10 | 0 |
| Q14789 | Golgin subfamily B member 1 | 378034.0 | 40 | 7.8 | 10 | 0 |
| O43747 | AP-1 complex subunit gamma-1 | 92392.8 | 7 | 7.8 | 4 | 0 |
| Q6NUQ4 | Transmembrane protein 214 | 75422.1 | 5 | 7.8 | 4 | 0 |
| P83876 | Thioredoxin-like protein 4A | 16900.5 | 1 | 7.8 | 2 | 0 |
| P0CG48 | Polyubiquitin-C | 77038.7 | 6 | 7.7 | 10 | 0 |
| P07686 | Beta-hexosaminidase subunit beta | 63567.6 | 6 | 7.7 | 4 | 0 |
| Q8NBJ5 | Procollagen galactosyltransferase 1 | 71978.4 | 6 | 7.7 | 2 | 17304 |
| O60568 | Procollagen-lysine,2-oxoglutarate 5-dioxygenase 3 | 85355.6 | 5 | 7.7 | 2 | 7053 |
| Q14533 | Keratin, type II cuticular Hb1 | 56867.3 | 6 | 7.7 | 9 | 0 |
| Q15021 | Condensin complex subunit 1 | 158608.1 | 8 | 7.7 | 3 | 0 |
| P55145 | Mesencephalic astrocyte-derived neurotrophic factor | 21156.4 | 1 | 7.7 | 2 | 0 |
| Q99805 | Transmembrane 9 superfamily member 2 | 76859.3 | 3 | 7.7 | 1 | 0 |
| P35908 | Keratin, type II cytoskeletal 2 epidermal | 65718.1 | 8 | 7.7 | 8 | 31316.71 |
| P13796 | Plastin-2 | 70858.8 | 8 | 7.7 | 10 | 0 |
| Q9BZJ0 | Crooked neck-like protein 1 | 94662.2 | 11 | 7.7 | 10 | 0 |
| P51114 | Fragile X mental retardation syndrome-related protein 1 | 63819.8 | 5 | 7.7 | 3 | 0 |
| Q53F19 | Uncharacterized protein C17orf85 | 54813.5 | 5 | 7.7 | 4 | 0 |
| Q9Y6G9 | Cytoplasmic dynein 1 light intermediate chain 1 | 56864.4 | 7 | 7.7 | 1 | 0 |
| Q9Y6E2 | Basic leucine zipper and W2 domain-containing protein 2 | 48390.6 | 6 | 7.6 | 7 | 0 |
| Q92544 | Transmembrane 9 superfamily member 4 | 75260.3 | 4 | 7.6 | 2 | 0 |
| Q7Z406 | Myosin-14 | 217862.7 | 22 | 7.6 | 10 | 0 |
| O14715 | RANBP2-like and GRIP domain-containing protein 8 | 200304.8 | 13 | 7.6 | 6 | 0 |
| Q9GZR2 | RNA exonuclease 4 | 46900.0 | 2 | 7.6 | 1 | 0 |
| Q9UNL2 | Translocon-associated protein subunit gamma | 21080.5 | 3 | 7.6 | 10 | 63744 |
| P43034 | Platelet-activating factor | 47208.3 | 6 | 7.6 | 2 | 0 |

FIG. 17 (cont'd)

| | acetylhydrolase IB subunit alpha | | | | | |
|---|---|---|---|---|---|---|
| P07864 | L-lactate dehydrogenase C chain | 36653.5 | 4 | 7.5 | 10 | 0 |
| Q8TAQ2 | SWI/SNF complex subunit SMARCC2 | 128339.9 | 11 | 7.5 | 10 | 0 |
| Q8N2C7 | Protein unc-80 homolog | 209461.0 | 6 | 7.5 | 4 | 0 |
| P54829 | Tyrosine-protein phosphatase non-receptor type 5 | 62670.6 | 3 | 7.5 | 2 | 0 |
| Q13620 | Cullin-4B | 97317.4 | 12 | 7.5 | 6 | 0 |
| P0C881 | Radial spoke head 10 homolog B | 101319.4 | 7 | 7.5 | 1 | 0 |
| Q6UWP7 | Lysocardiolipin acyltransferase 1 | 43555.7 | 3 | 7.5 | 3 | 0 |
| Q9Y2H2 | Phosphatidylinositide phosphatase SAC2 | 86796.6 | 3 | 7.5 | 2 | 0 |
| Q9BZI7 | Regulator of nonsense transcripts 3B | 57101.8 | 4 | 7.5 | 4 | 0 |
| O14787 | Transportin-2 | 102349.0 | 5 | 7.4 | 10 | 0 |
| P07602 | Prosaposin | 60142.5 | 3 | 7.4 | 3 | 0 |
| Q02539 | Histone H1.1 | 21842.1 | 3 | 7.4 | 10 | 0 |
| Q7Z794 | Keratin, type II cytoskeletal 1b | 62186.6 | 8 | 7.4 | 6 | 0 |
| P0C7P4 | Putative cytochrome b-c1 complex subunit Rieske-like protein 1 | 31100.6 | 2 | 7.4 | 4 | 0 |
| Q96MM3 | Zinc finger protein 42 homolog | 35543.2 | 2 | 7.4 | 1 | 0 |
| Q9H2F5 | Enhancer of polycomb homolog 1 | 91309.6 | 5 | 7.4 | 4 | 0 |
| Q01658 | Protein Dr1 | 19671.8 | 1 | 7.4 | 1 | 0 |
| Q9BXJ9 | N-alpha-acetyltransferase 15, NatA auxiliary subunit | 89189.7 | 9 | 7.4 | 9 | 0 |
| P04222 | HLA class I histocompatibility antigen, Cw-3 alpha chain | 41260.0 | 2 | 7.4 | 2 | 0 |
| P78386 | Keratin, type II cuticular Hb5 | 57341.9 | 7 | 7.3 | 10 | 0 |
| Q9Y2K3 | Myosin-15 | 226045.0 | 22 | 7.3 | 1 | 0 |
| P35610 | Sterol O-acyltransferase 1 | 62114.6 | 4 | 7.3 | 9 | 0 |
| Q16720 | Plasma membrane calcium-transporting ATPase 3 | 129188.9 | 7 | 7.3 | 8 | 0 |
| Q8N5C6 | S1 RNA-binding domain-containing protein 1 | 98914.7 | 10 | 7.3 | 3 | 0 |
| P51532 | Transcription activator BRG1 | 182634.7 | 15 | 7.3 | 10 | 0 |
| Q96GM8 | Target of EGR1 protein 1 | 57403.3 | 3 | 7.3 | 1 | 0 |
| P50148 | Guanine nucleotide-binding protein G(q) subunit alpha | 42427.3 | 2 | 7.2 | 1 | 0 |
| Q9BQ04 | RNA-binding protein 4B | 40491.9 | 4 | 7.2 | 3 | 0 |
| Q9NVA2 | Septin-11 | 50158.4 | 4 | 7.2 | 3 | 0 |
| Q13206 | Probable ATP-dependent RNA helicase DDX10 | 101230.3 | 7 | 7.2 | 2 | 0 |
| Q9NRZ9 | Lymphoid-specific helicase | 91212.5 | 9 | 7.2 | 10 | 0 |
| O43324 | Eukaryotic translation elongation factor 1 epsilon-1 | 17707.7 | 1 | 7.2 | 2 | 25437 |
| Q9NTI5 | Sister chromatid cohesion protein PDS5 homolog B | 162728.7 | 9 | 7.2 | 10 | 5787 |
| O95218 | Zinc finger Ran-binding domain-containing protein 2 | 37317.6 | 5 | 7.2 | 6 | 0 |
| Q96SB4 | SRSF protein kinase 1 | 84109.6 | 4 | 7.2 | 2 | 0 |
| Q6ZQT0 | Putative uncharacterized protein FLJ45035 | 16182.7 | 2 | 7.1 | 1 | 0 |
| Q9H936 | Mitochondrial glutamate carrier 1 | 34926.5 | 3 | 7.1 | 1 | 0 |
| P00451 | Coagulation factor VIII | 268492.6 | 17 | 7.1 | 2 | 0 |

FIG. 17 (cont'd)

| | | | | | | |
|---|---|---|---|---|---|---|
| Q9NVH1 | DnaJ homolog subfamily C member 11 | 60253.2 | 4 | 7.1 | 5 | 0 |
| Q02127 | Dihydroorotate dehydrogenase (quinone), mitochondrial | 42867.3 | 3 | 7.1 | 1 | 0 |
| Q8N392 | Rho GTPase-activating protein 18 | 75262.0 | 3 | 7.1 | 1 | 0 |
| Q96T76 | MMS19 nucleotide excision repair protein homolog | 113519.9 | 8 | 7.1 | 5 | 0 |
| O43251 | RNA binding protein fox-1 homolog 2 | 42158.0 | 3 | 7.1 | 10 | 36063 |
| O14646 | Chromodomain-helicase-DNA-binding protein 1 | 197779.8 | 10 | 7.1 | 6 | 0 |
| Q9HCH5 | Synaptotagmin-like protein 2 | 140359.2 | 8 | 7.1 | 3 | 0 |
| Q5TAP6 | U3 small nucleolar RNA-associated protein 14 homolog C | 87302.0 | 4 | 7.1 | 8 | 0 |
| O00506 | Serine/threonine-protein kinase 25 | 48339.8 | 3 | 7.0 | 1 | 0 |
| Q9UI15 | Transgelin-3 | 22643.8 | 2 | 7.0 | 1 | 0 |
| Q9NWB1 | RNA binding protein fox-1 homolog 1 | 42493.7 | 3 | 7.0 | 10 | 0 |
| Q9Y4W6 | AFG3-like protein 2 | 89040.0 | 12 | 7.0 | 2 | 0 |
| Q9Y606 | tRNA pseudouridine synthase A, mitochondrial | 46465.5 | 3 | 7.0 | 2 | 0 |
| Q13308 | Inactive tyrosine-protein kinase 7 | 112380.4 | 10 | 7.0 | 10 | 0 |
| Q659C4 | La-related protein 1B | 63824.4 | 7 | 7.0 | 6 | 0 |
| Q6PKG0 | La-related protein 1 | 120387.0 | 8 | 7.0 | 4 | 0 |
| Q12888 | Tumor suppressor p53-binding protein 1 | 215899.0 | 15 | 7.0 | 10 | 0 |
| Q9P1Z2 | Calcium-binding and coiled-coil domain-containing protein 1 | 75592.2 | 4 | 7.0 | 3 | 0 |
| Q8WVM7 | Cohesin subunit SA-1 | 145397.1 | 14 | 6.9 | 4 | 0 |
| P35558 | Phosphoenolpyruvate carboxykinase, cytosolic [GTP] | 69993.1 | 6 | 6.9 | 3 | 0 |
| Q9UN75 | Protocadherin alpha-12 | 102279.4 | 6 | 6.9 | 1 | 0 |
| Q7Z3J3 | RanBP2-like and GRIP domain-containing protein 4 | 198771.6 | 11 | 6.9 | 4 | 0 |
| Q9NW08 | DNA-directed RNA polymerase III subunit RPC2 | 125992.6 | 6 | 6.9 | 2 | 0 |
| Q9NXR1 | Nuclear distribution protein nudE homolog 1 | 38378.4 | 3 | 6.9 | 2 | 0 |
| Q10570 | Cleavage and polyadenylation specificity factor subunit 1 | 162138.7 | 13 | 6.9 | 6 | 0 |
| Q14008 | Cytoskeleton-associated protein 5 | 225361.1 | 16 | 6.9 | 10 | 0 |
| P30825 | High affinity cationic amino acid transporter 1 | 68493.9 | 4 | 6.8 | 3 | 0 |
| Q9UQB8 | Brain-specific angiogenesis inhibitor 1-associated protein 2 | 58361.2 | 5 | 6.8 | 6 | 0 |
| Q8IXB1 | DnaJ homolog subfamily C member 10 | 89862.6 | 7 | 6.8 | 2 | 0 |
| O60231 | Putative pre-mRNA-splicing factor ATP-dependent RNA helicase DHX16 | 119948.1 | 9 | 6.8 | 5 | 0 |
| Q9GZN1 | Actin-related protein 6 | 46266.4 | 4 | 6.8 | 1 | 0 |
| O15049 | NEDD4-binding protein 3 | 60926.1 | 3 | 6.8 | 1 | 0 |
| Q9NVI1 | Fanconi anemia group I protein | 147425.8 | 10 | 6.8 | 4 | 0 |
| P14735 | Insulin-degrading enzyme | 118767.1 | 11 | 6.8 | 2 | 0 |
| P12955 | Xaa-Pro dipeptidase | 51279.4 | 3 | 6.8 | 3 | 0 |
| Q14966 | Zinc finger protein 638 | 170501.0 | 13 | 6.8 | 10 | 0 |
| P08631 | Tyrosine-protein kinase HCK | 58876.9 | 5 | 6.8 | 4 | 0 |

FIG. 17 (cont'd)

| | | | | | | |
|---|---|---|---|---|---|---|
| Q05BV3 | Echinoderm microtubule-associated protein-like 5 | 192286.4 | 10 | 6.8 | 8 | 0 |
| Q9UL12 | Sarcosine dehydrogenase, mitochondrial | 102006.4 | 7 | 6.8 | 1 | 0 |
| Q9UBM7 | 7-dehydrocholesterol reductase | 55230.9 | 4 | 6.7 | 2 | 0 |
| Q14677 | Clathrin interactor 1 | 69112.2 | 6 | 6.7 | 5 | 0 |
| Q9Y6D6 | Brefeldin A-inhibited guanine nucleotide-exchange protein 1 | 210991.5 | 17 | 6.7 | 2 | 0 |
| Q8N1G4 | Leucine-rich repeat-containing protein 47 | 64043.3 | 6 | 6.7 | 2 | 0 |
| Q9UKN8 | General transcription factor 3C polypeptide 4 | 93294.1 | 9 | 6.7 | 1 | 0 |
| Q9ULW0 | Targeting protein for Xklp2 | 86280.5 | 10 | 6.7 | 2 | 0 |
| O60551 | Glycylpeptide N-tetradecanoyltransferase 2 | 57322.5 | 3 | 6.6 | 2 | 0 |
| Q13769 | THO complex subunit 5 homolog | 79249.3 | 6 | 6.6 | 3 | 0 |
| Q09160 | HLA class I histocompatibility antigen, A-80 alpha chain | 41076.9 | 1 | 6.6 | 1 | 0 |
| Q9HCD5 | Nuclear receptor coactivator 5 | 65764.7 | 6 | 6.6 | 4 | 0 |
| Q8N157 | Jouberin | 130124.8 | 12 | 6.6 | 2 | 0 |
| Q8NDV7 | Trinucleotide repeat-containing gene 6A protein | 201736.4 | 11 | 6.6 | 4 | 0 |
| Q9H6R4 | Nucleolar protein 6 | 115054.2 | 9 | 6.6 | 10 | 0 |
| Q3KSU7 | Protein BOLF1 | 133256.5 | 9 | 6.5 | 2 | 0 |
| Q5VT52 | Regulation of nuclear pre-mRNA domain-containing protein 2 | 154284.3 | 10 | 6.5 | 9 | 0 |
| P11216 | Glycogen phosphorylase, brain form | 97380.5 | 11 | 6.5 | 4 | 0 |
| Q14651 | Plastin-1 | 70652.8 | 8 | 6.5 | 6 | 0 |
| Q9NV06 | DDB1- and CUL4-associated factor 13 | 52029.6 | 4 | 6.5 | 2 | 0 |
| O15020 | Spectrin beta chain, non-erythrocytic 2 | 271299.9 | 23 | 6.5 | 10 | 0 |
| O60885 | Bromodomain-containing protein 4 | 116797.4 | 6 | 6.5 | 6 | 0 |
| Q86U86 | Protein polybromo-1 | 186816.0 | 14 | 6.5 | 10 | 0 |
| P50336 | Protoporphyrinogen oxidase | 51221.6 | 3 | 6.5 | 1 | 0 |
| Q96ST2 | Protein IWS1 homolog | 72447.9 | 3 | 6.5 | 3 | 0 |
| Q9Y673 | Dolichyl-phosphate beta-glucosyltransferase | 37174.3 | 7 | 6.5 | 1 | 0 |
| Q15020 | Squamous cell carcinoma antigen recognized by T-cells 3 | 110790.1 | 9 | 6.4 | 3 | 0 |
| Q9H2U1 | Probable ATP-dependent RNA helicase DHX36 | 114373.8 | 7 | 6.4 | 5 | 0 |
| Q9UG63 | ATP-binding cassette sub-family F member 2 | 71860.7 | 8 | 6.4 | 4 | 21921 |
| P0C6E5 | Putative high mobility group protein B3-like protein | 21371.4 | 2 | 6.4 | 6 | 0 |
| P51531 | Probable global transcription activator SNF2L2 | 180879.4 | 11 | 6.4 | 10 | 0 |
| Q01955 | Collagen alpha-3(IV) chain | 143482.1 | 10 | 6.4 | 1 | 0 |
| P02538 | Keratin, type II cytoskeletal 6A | 60330.2 | 8 | 6.4 | 10 | 0 |
| P48668 | Keratin, type II cytoskeletal 6C | 60310.2 | 6 | 6.4 | 9 | 0 |
| P57737 | Coronin-7 | 101688.7 | 5 | 6.4 | 1 | 0 |
| Q02952 | A-kinase anchor protein 12 | 185290.8 | 12 | 6.4 | 9 | 0 |
| P02489 | Alpha-crystallin A chain | 20023.4 | 2 | 6.4 | 1 | 0 |
| O60684 | Importin subunit alpha-7 | 60771.0 | 6 | 6.3 | 4 | 0 |

FIG. 17 (cont'd)

| | | | | | | |
|---|---|---|---|---|---|---|
| O75746 | Calcium-binding mitochondrial carrier protein Aralar1 | 75161.2 | 6 | 6.3 | 7 | 0 |
| Q68DA7 | Formin-1 | 158889.7 | 9 | 6.3 | 1 | 0 |
| Q9H254 | Spectrin beta chain, non-erythrocytic 4 | 254027.4 | 22 | 6.3 | 9 | 0 |
| P78344 | Eukaryotic translation initiation factor 4 gamma 2 | 100769.5 | 7 | 6.3 | 2 | 0 |
| Q8WWK9 | Cytoskeleton-associated protein 2 | 77557.1 | 7 | 6.3 | 1 | 0 |
| Q9NU22 | Midasin | 638409.5 | 40 | 6.3 | 10 | 7365 |
| Q9Y5L0 | Transportin-3 | 104811.6 | 4 | 6.3 | 4 | 0 |
| Q99549 | M-phase phosphoprotein 8 | 97922.8 | 5 | 6.3 | 2 | 0 |
| Q13523 | Serine/threonine-protein kinase PRP4 homolog | 117329.2 | 8 | 6.3 | 5 | 0 |
| O43663 | Protein regulator of cytokinesis 1 | 67280.3 | 4 | 6.3 | 1 | 0 |
| Q8NG31 | Protein CASC5 | 245640.9 | 19 | 6.2 | 6 | 0 |
| P46379 | Large proline-rich protein BAG6 | 114596.3 | 6 | 6.2 | 10 | 0 |
| Q15291 | Retinoblastoma-binding protein 5 | 57796.7 | 5 | 6.2 | 4 | 0 |
| P0C0L5 | Complement C4-B | 194291.5 | 10 | 6.2 | 2 | 0 |
| O60831 | PRA1 family protein 2 | 19600.1 | 1 | 6.2 | 1 | 0 |
| P16520 | Guanine nucleotide-binding protein G(I)/G(S)/G(T) subunit beta-3 | 38190.7 | 4 | 6.2 | 1 | 0 |
| Q9C0B2 | Uncharacterized protein KIAA1751 | 87583.2 | 8 | 6.2 | 1 | 0 |
| O94842 | TOX high mobility group box family member 4 | 66594.2 | 5 | 6.1 | 1 | 0 |
| Q5JRA6 | Melanoma inhibitory activity protein 3 | 211216.3 | 18 | 6.1 | 10 | 0 |
| Q9NZW5 | MAGUK p55 subfamily member 6 | 61402.2 | 5 | 6.1 | 4 | 0 |
| Q8N4C6 | Ninein | 225236.6 | 21 | 6.1 | 10 | 0 |
| Q8WWM7 | Ataxin-2-like protein | 110973.5 | 6 | 6.1 | 10 | 0 |
| Q9BZK3 | Putative nascent polypeptide-associated complex subunit alpha-like protein | 23306.1 | 1 | 6.1 | 7 | 0 |
| A6NDJ8 | Putative Rab-43-like protein ENSP00000330714 | 20438.0 | 2 | 6.1 | 10 | 0 |
| Q5VTT5 | Myomesin-3 | 100487.8 | 5 | 6.1 | 2 | 0 |
| P12883 | Myosin-7 | 223896.1 | 14 | 6.1 | 2 | 0 |
| O75874 | Isocitrate dehydrogenase [NADP] cytoplasmic | 46944.5 | 4 | 6.0 | 1 | 0 |
| O43592 | Exportin-T | 111219.0 | 6 | 6.0 | 1 | 0 |
| Q96FN4 | Copine-2 | 61874.3 | 6 | 6.0 | 7 | 0 |
| P49748 | Very long-chain specific acyl-CoA dehydrogenase, mitochondrial | 70857.9 | 4 | 6.0 | 6 | 0 |
| Q7Z3Z0 | Keratin, type I cytoskeletal 25 | 49888.3 | 6 | 6.0 | 2 | 0 |
| A7E2Y1 | Myosin-7B | 222528.6 | 14 | 6.0 | 4 | 0 |
| Q99666 | RANBP2-like and GRIP domain-containing protein 5/6 | 152298.1 | 10 | 6.0 | 10 | 0 |
| O60307 | Microtubule-associated serine/threonine-protein kinase 3 | 143935.9 | 6 | 6.0 | 1 | 0 |
| Q5TF21 | Protein SOGA3 | 103541.6 | 10 | 5.9 | 1 | 0 |
| P36268 | Gamma-glutamyltranspeptidase 2 | 61588.6 | 4 | 5.9 | 2 | 0 |
| Q9Y6Y8 | SEC23-interacting protein | 108182.6 | 8 | 5.9 | 5 | 0 |
| P25440 | Bromodomain-containing protein 2 | 90360.9 | 5 | 5.9 | 6 | 0 |
| A6NKT7 | RanBP2-like and GRIP domain-containing protein 3 | 198855.9 | 11 | 5.9 | 4 | 0 |

FIG. 17 (cont'd)

| | | | | | | |
|---|---|---|---|---|---|---|
| P11717 | Cation-independent mannose-6-phosphate receptor | 281332.4 | 19 | 5.9 | 6 | 0 |
| Q9Y6A5 | Transforming acidic coiled-coil-containing protein 3 | 91215.2 | 7 | 5.9 | 1 | 0 |
| O43670 | Zinc finger protein 207 | 50712.1 | 3 | 5.8 | 10 | 42144 |
| P35228 | Nitric oxide synthase, inducible | 130473.2 | 9 | 5.8 | 2 | 0 |
| A6NGU5 | Putative gamma-glutamyltranspeptidase 3 | 61957.9 | 3 | 5.8 | 2 | 0 |
| Q15392 | Delta(24)-sterol reductase | 60842.7 | 3 | 5.8 | 2 | 0 |
| Q9H853 | Putative tubulin-like protein alpha-4B | 27836.4 | 1 | 5.8 | 10 | 0 |
| P52179 | Myomesin-1 | 185116.2 | 20 | 5.8 | 5 | 0 |
| Q92896 | Golgi apparatus protein 1 | 139782.2 | 9 | 5.8 | 10 | 12384 |
| Q5JWF2 | Guanine nucleotide-binding protein G(s) subunit alpha isoforms XLas | 111066.8 | 10 | 5.8 | 10 | 0 |
| Q969H0 | F-box/WD repeat-containing protein 7 | 72590.4 | 4 | 5.8 | 4 | 0 |
| Q9UPN9 | E3 ubiquitin-protein ligase TRIM33 | 123704.2 | 8 | 5.8 | 2 | 0 |
| Q08209 | Serine/threonine-protein phosphatase 2B catalytic subunit alpha isoform | 57005.0 | 2 | 5.8 | 3 | 0 |
| P35251 | Replication factor C subunit 1 | 128732.5 | 14 | 5.8 | 4 | 0 |
| Q12955 | Ankyrin-3 | 371498.2 | 25 | 5.8 | 10 | 0 |
| Q96RU2 | Ubiquitin carboxyl-terminal hydrolase 28 | 121946.8 | 4 | 5.7 | 2 | 0 |
| Q9NXE4 | Sphingomyelin phosphodiesterase 4 | 90896.9 | 7 | 5.7 | 5 | 0 |
| O95602 | DNA-directed RNA polymerase I subunit RPA1 | 196807.5 | 14 | 5.7 | 2 | 0 |
| O14617 | AP-3 complex subunit delta-1 | 124619.7 | 6 | 5.7 | 5 | 0 |
| P52360 | Virion-packaging protein UL17 homolog | 52039.9 | 5 | 5.7 | 4 | 0 |
| Q8TDI0 | Chromodomain-helicase-DNA-binding protein 5 | 224646.7 | 15 | 5.7 | 10 | 0 |
| Q9Y4C0 | Neurexin-3 | 150754.6 | 11 | 5.7 | 2 | 0 |
| Q15059 | Bromodomain-containing protein 3 | 79826.8 | 7 | 5.7 | 1 | 0 |
| Q92901 | 60S ribosomal protein L3-like | 46638.2 | 3 | 5.7 | 2 | 0 |
| Q09666 | Neuroblast differentiation-associated protein AHNAK | 629616.3 | 40 | 5.6 | 10 | 18538 |
| O15553 | Pyrin | 87413.3 | 3 | 5.6 | 1 | 0 |
| O95837 | Guanine nucleotide-binding protein subunit alpha-14 | 42026.9 | 4 | 5.6 | 1 | 0 |
| Q8IX01 | SURP and G-patch domain-containing protein 2 | 118158.1 | 9 | 5.6 | 9 | 0 |
| Q9BTC0 | Death-inducer obliterator 1 | 245583.7 | 19 | 5.6 | 3 | 0 |
| P19013 | Keratin, type II cytoskeletal 4 | 57684.5 | 4 | 5.6 | 1 | 0 |
| O15067 | Phosphoribosylformylglycinamidine synthase | 146388.4 | 13 | 5.6 | 3 | 0 |
| O60518 | Ran-binding protein 6 | 126253.6 | 8 | 5.6 | 4 | 0 |
| P49454 | Centromere protein F | 371072.6 | 32 | 5.6 | 6 | 0 |
| Q8NI27 | THO complex subunit 2 | 184656.8 | 13 | 5.6 | 6 | 0 |
| Q9Y6B6 | GTP-binding protein SAR1b | 22524.0 | 1 | 5.6 | 6 | 0 |
| Q5VT06 | Centrosome-associated protein 350 | 352527.4 | 21 | 5.6 | 4 | 0 |
| P11137 | Microtubule-associated protein 2 | 199761.6 | 14 | 5.5 | 4 | 0 |
| Q8NDM7 | WD repeat-containing protein 96 | 193808.9 | 8 | 5.5 | 1 | 0 |
| P13535 | Myosin-8 | 223732.3 | 17 | 5.5 | 1 | 0 |

FIG. 17 (cont'd)

| | | | | | | |
|---|---|---|---|---|---|---|
| P35612 | Beta-adducin | 81310.6 | 10 | 5.5 | 1 | 0 |
| Q03113 | Guanine nucleotide-binding protein subunit alpha-12 | 44450.4 | 3 | 5.5 | 1 | 0 |
| P42356 | Phosphatidylinositol 4-kinase alpha | 211125.9 | 15 | 5.5 | 6 | 0 |
| Q5JQF8 | Polyadenylate-binding protein 1-like 2 | 22970.2 | 2 | 5.5 | 3 | 0 |
| Q9ULM0 | Pleckstrin homology domain-containing family H member 1 | 152829.3 | 10 | 5.5 | 1 | 0 |
| Q13867 | Bleomycin hydrolase | 53189.7 | 6 | 5.5 | 1 | 0 |
| Q68DK2 | Zinc finger FYVE domain-containing protein 26 | 288271.0 | 12 | 5.5 | 2 | 0 |
| P11277 | Spectrin beta chain, erythrocytic | 253983.7 | 17 | 5.5 | 10 | 0 |
| Q9P2B2 | Prostaglandin F2 receptor negative regulator | 99526.0 | 5 | 5.5 | 1 | 0 |
| O60306 | Intron-binding protein aquarius | 172379.1 | 13 | 5.5 | 3 | 0 |
| P02765 | Alpha-2-HS-glycoprotein | 40123.1 | 4 | 5.5 | 2 | 0 |
| Q5VT97 | Rho GTPase-activating protein SYDE2 | 115719.6 | 7 | 5.5 | 2 | 0 |
| Q15771 | Ras-related protein Rab-30 | 23400.4 | 1 | 5.4 | 10 | 0 |
| O60279 | Sushi domain-containing protein 5 | 68819.6 | 3 | 5.4 | 1 | 0 |
| O94964 | Protein SOGA1 | 154593.2 | 11 | 5.4 | 3 | 0 |
| Q8NCA5 | Protein FAM98A | 55792.9 | 4 | 5.4 | 2 | 0 |
| P22897 | Macrophage mannose receptor 1 | 168977.2 | 10 | 5.4 | 1 | 0 |
| Q6AWC2 | Protein WWC2 | 118512.4 | 8 | 5.3 | 5 | 0 |
| Q4LDE5 | Sushi, von Willebrand factor type A, EGF and pentraxin domain-containing protein 1 | 404940.5 | 20 | 5.3 | 2 | 0 |
| B2RC85 | Radial spoke head 10 homolog B2 | 101288.2 | 6 | 5.3 | 1 | 0 |
| Q92502 | StAR-related lipid transfer protein 8 | 118543.5 | 5 | 5.3 | 2 | 0 |
| O95678 | Keratin, type II cytoskeletal 75 | 59845.6 | 6 | 5.3 | 10 | 0 |
| Q969S9 | Ribosome-releasing factor 2, mitochondrial | 76380.7 | 4 | 5.3 | 5 | 0 |
| Q8WYP5 | Protein ELYS | 256155.5 | 14 | 5.3 | 10 | 0 |
| Q14315 | Filamin-C | 291772.2 | 21 | 5.2 | 10 | 0 |
| Q9HAD4 | WD repeat-containing protein 41 | 52412.4 | 5 | 5.2 | 1 | 0 |
| Q8WWQ0 | PH-interacting protein | 208457.2 | 13 | 5.2 | 1 | 0 |
| P60763 | Ras-related C3 botulinum toxin substrate 3 | 21778.1 | 1 | 5.2 | 2 | 0 |
| Q969H8 | UPF0556 protein C19orf10 | 18909.3 | 2 | 5.2 | 1 | 0 |
| Q9HBL0 | Tensin-1 | 186614.1 | 8 | 5.2 | 1 | 0 |
| O15061 | Synemin | 173110.0 | 11 | 5.2 | 2 | 0 |
| Q15058 | Kinesin-like protein KIF14 | 187860.6 | 12 | 5.2 | 1 | 0 |
| Q96DA2 | Ras-related protein Rab-39B | 24850.3 | 1 | 5.2 | 10 | 0 |
| O60287 | Nucleolar pre-ribosomal-associated protein 1 | 256670.6 | 12 | 5.2 | 5 | 0 |
| P29803 | Pyruvate dehydrogenase E1 component subunit alpha, testis-specific form, mitochondrial | 43674.7 | 2 | 5.2 | 8 | 0 |
| Q6EMB2 | Tubulin polyglutamylase TTLL5 | 144547.2 | 10 | 5.2 | 1 | 0 |
| Q6NSX1 | Coiled-coil domain-containing protein 70 | 28823.8 | 2 | 5.2 | 1 | 0 |
| Q9UJ14 | Gamma-glutamyltransferase 7 | 70866.1 | 3 | 5.1 | 1 | 0 |
| O60907 | F-box-like/WD repeat-containing | 60513.6 | 3 | 5.1 | 2 | 0 |

FIG. 17 (cont'd)

| | protein TBL1X | | | | | |
|---|---|---|---|---|---|---|
| Q96RV3 | Pecanex-like protein 1 | 258742.3 | 10 | 5.1 | 3 | 0 |
| A4UHQ7 | RNA-directed RNA polymerase L | 244374.3 | 11 | 5.1 | 5 | 0 |
| Q96F86 | Enhancer of mRNA-decapping protein 3 | 56819.0 | 2 | 5.1 | 1 | 0 |
| Q9C0F0 | Putative Polycomb group protein ASXL3 | 244485.3 | 19 | 5.1 | 3 | 0 |
| Q9UFH2 | Dynein heavy chain 17, axonemal | 474149.4 | 31 | 5.1 | 10 | 0 |
| Q9UKF6 | Cleavage and polyadenylation specificity factor subunit 3 | 78170.5 | 5 | 5.1 | 3 | 0 |
| Q8N3V7 | Synaptopodin | 90241.6 | 3 | 5.1 | 3 | 0 |
| Q96T23 | Remodeling and spacing factor 1 | 160410.1 | 12 | 5.1 | 9 | 0 |
| O14874 | [3-methyl-2-oxobutanoate dehydrogenase [lipoamide]] kinase, mitochondrial | 46645.7 | 3 | 5.1 | 1 | 0 |
| Q9UKX2 | Myosin-2 | 224071.3 | 12 | 5.1 | 5 | 0 |
| P50570 | Dynamin-2 | 98148.8 | 5 | 5.1 | 7 | 0 |
| P52888 | Thimet oligopeptidase | 79752.4 | 7 | 5.1 | 1 | 0 |
| Q15149 | Plectin | 519563.9 | 39 | 5.1 | 10 | 0 |
| Q14964 | Ras-related protein Rab-39A | 25405.9 | 1 | 5.1 | 1 | 0 |
| Q7Z6Z7 | E3 ubiquitin-protein ligase HUWE1 | 485079.1 | 20 | 5.1 | 10 | 0 |
| Q8NF37 | Lysophosphatidylcholine acyltransferase 1 | 59778.8 | 4 | 5.1 | 3 | 0 |
| Q15118 | [Pyruvate dehydrogenase (acetyl-transferring)] kinase isozyme 1, mitochondrial | 49472.4 | 4 | 5.1 | 1 | 0 |
| Q71RC2 | La-related protein 4 | 79105.4 | 3 | 5.1 | 7 | 0 |
| Q92802 | NEDD4-binding protein 2-like 2 | 87967.9 | 3 | 5.1 | 1 | 0 |
| Q92614 | Unconventional myosin-XVIIIa | 219143.8 | 16 | 5.0 | 7 | 0 |
| Q93045 | Stathmin-2 | 21429.2 | 1 | 5.0 | 10 | 0 |
| P10236 | DNA primase | 116020.4 | 10 | 5.0 | 1 | 0 |
| Q9NRK6 | ATP-binding cassette sub-family B member 10, mitochondrial | 79547.1 | 5 | 5.0 | 1 | 0 |
| O75976 | Carboxypeptidase D | 154014.8 | 8 | 5.0 | 1 | 0 |
| Q6ZRV2 | Protein FAM83H | 127635.7 | 5 | 5.0 | 1 | 0 |
| A2A3N6 | Putative PIP5K1A and PSMD4-like protein | 95789.1 | 4 | 5.0 | 4 | 0 |
| Q96RT1 | Protein LAP2 | 154064.5 | 7 | 5.0 | 10 | 0 |
| O00763 | Acetyl-CoA carboxylase 2 | 274619.4 | 18 | 5.0 | 10 | 0 |
| Q9UJV9 | Probable ATP-dependent RNA helicase DDX41 | 70522.1 | 7 | 5.0 | 2 | 0 |
| A4D0V7 | Cadherin-like and PC-esterase domain-containing protein 1 | 119373.4 | 8 | 5.0 | 1 | 0 |
| Q6PL18 | ATPase family AAA domain-containing protein 2 | 159923.0 | 10 | 5.0 | 1 | 0 |
| Q9BVC6 | Transmembrane protein 109 | 26210.0 | 3 | 4.9 | 9 | 59409 |
| Q14667 | UPF0378 protein KIAA0100 | 254520.2 | 14 | 4.9 | 2 | 0 |
| P15924 | Desmoplakin | 298313.4 | 26 | 4.9 | 4 | 0 |
| P25054 | Adenomatous polyposis coli protein | 309285.0 | 21 | 4.9 | 5 | 0 |
| Q7Z7A1 | Centriolin | 236990.1 | 21 | 4.9 | 10 | 0 |
| Q9UG01 | Intraflagellar transport protein 172 homolog | 186661.2 | 12 | 4.9 | 2 | 0 |

FIG. 17 (cont'd)

| | | | | | | |
|---|---|---|---|---|---|---|
| P49643 | DNA primase large subunit | 59262.3 | 5 | 4.9 | 1 | 0 |
| Q9Y5W8 | Sorting nexin-13 | 112406.7 | 6 | 4.9 | 3 | 0 |
| P16732 | Tripartite terminase subunit UL15 homolog | 77878.0 | 3 | 4.9 | 1 | 0 |
| Q8IXT5 | RNA-binding protein 12B | 118445.1 | 9 | 4.9 | 2 | 0 |
| Q8NCN5 | Pyruvate dehydrogenase phosphatase regulatory subunit, mitochondrial | 100220.1 | 10 | 4.9 | 2 | 0 |
| Q9Y4A5 | Transformation/transcription domain-associated protein | 440370.6 | 36 | 4.9 | 6 | 0 |
| Q9UID3 | Vacuolar protein sorting-associated protein 51 homolog | 80232.9 | 4 | 4.9 | 2 | 0 |
| P11055 | Myosin-3 | 224988.6 | 14 | 4.9 | 1 | 0 |
| Q8TCU4 | Alstrom syndrome protein 1 | 451384.6 | 23 | 4.9 | 10 | 0 |
| Q92616 | Translational activator GCN1 | 295153.9 | 23 | 4.8 | 7 | 0 |
| Q9BYT8 | Neurolysin, mitochondrial | 81393.3 | 8 | 4.8 | 1 | 0 |
| Q8NF91 | Nesprin-1 | 450114.0 | 41 | 4.8 | 10 | 0 |
| Q13111 | Chromatin assembly factor 1 subunit A | 108123.6 | 7 | 4.8 | 1 | 0 |
| Q13439 | Golgin subfamily A member 4 | 262096.3 | 22 | 4.8 | 10 | 0 |
| Q96G21 | U3 small nucleolar ribonucleoprotein protein IMP4 | 33870.7 | 3 | 4.8 | 2 | 0 |
| O75717 | WD repeat and HMG-box DNA-binding protein 1 | 127450.2 | 7 | 4.8 | 1 | 0 |
| P46939 | Utrophin | 396690.9 | 19 | 4.8 | 7 | 0 |
| Q79666 | Gag-Pol polyprotein | 163968.2 | 8 | 4.8 | 1 | 0 |
| Q12840 | Kinesin heavy chain isoform 5A | 118233.8 | 6 | 4.8 | 1 | 0 |
| Q15643 | Thyroid receptor-interacting protein 11 | 228271.0 | 17 | 4.8 | 2 | 0 |
| Q86UE8 | Serine/threonine-protein kinase tousled-like 2 | 85949.4 | 4 | 4.7 | 3 | 0 |
| Q13136 | Liprin-alpha-1 | 135416.3 | 8 | 4.7 | 2 | 0 |
| Q6UB99 | Ankyrin repeat domain-containing protein 11 | 299795.6 | 18 | 4.7 | 1 | 0 |
| Q8TCJ2 | Dolichyl-diphosphooligosaccharide--protein glycosyltransferase subunit STT3B | 94301.8 | 6 | 4.7 | 7 | 24834 |
| P24107 | Gag-Pol polyprotein | 165874.6 | 8 | 4.7 | 1 | 0 |
| Q5VYK3 | Proteasome-associated protein ECM29 homolog | 206116.2 | 12 | 4.7 | 1 | 0 |
| Q99567 | Nuclear pore complex protein Nup88 | 84682.6 | 8 | 4.7 | 1 | 0 |
| Q8NCM8 | Cytoplasmic dynein 2 heavy chain 1 | 482049.9 | 26 | 4.7 | 10 | 0 |
| Q9NQ75 | Cas scaffolding protein family member 4 | 87942.9 | 5 | 4.7 | 1 | 0 |
| Q86Z14 | Beta-klotho | 120549.5 | 3 | 4.7 | 1 | 0 |
| Q8N7X1 | RNA-binding motif protein, X-linked-like-3 | 115793.2 | 8 | 4.7 | 10 | 0 |
| Q99575 | Ribonucleases P/MRP protein subunit POP1 | 116419.7 | 7 | 4.7 | 2 | 0 |
| Q9Y485 | DmX-like protein 1 | 341660.0 | 24 | 4.7 | 4 | 0 |
| Q9QJ26 | Major capsid protein | 153589.7 | 7 | 4.7 | 1 | 0 |
| P24928 | DNA-directed RNA polymerase II subunit RPB1 | 218545.2 | 13 | 4.7 | 5 | 0 |
| P45974 | Ubiquitin carboxyl-terminal hydrolase 5 | 95431.1 | 5 | 4.7 | 2 | 0 |
| Q69YN4 | Protein virilizer homolog | 203195.1 | 11 | 4.7 | 2 | 0 |

FIG. 17 (cont'd)

| | | | | | | |
|---|---|---|---|---|---|---|
| Q8N1N4 | Keratin, type II cytoskeletal 78 | 51626.0 | 5 | 4.6 | 10 | 0 |
| Q14191 | Werner syndrome ATP-dependent helicase | 164514.2 | 5 | 4.6 | 1 | 0 |
| P30613 | Pyruvate kinase PKLR | 60561.5 | 4 | 4.6 | 10 | 0 |
| Q13596 | Sorting nexin-1 | 57094.8 | 6 | 4.6 | 5 | 0 |
| Q7LDG7 | RAS guanyl-releasing protein 2 | 73281.9 | 3 | 4.6 | 2 | 0 |
| Q9HD20 | Probable cation-transporting ATPase 13A1 | 126484.0 | 4 | 4.6 | 3 | 0 |
| Q14669 | E3 ubiquitin-protein ligase TRIP12 | 217364.6 | 16 | 4.6 | 8 | 0 |
| Q8IZC7 | Zinc finger protein 101 | 51936.2 | 3 | 4.6 | 1 | 0 |
| Q9H9S3 | Protein transport protein Sec61 subunit alpha isoform 2 | 50945.1 | 2 | 4.6 | 4 | 0 |
| Q96Q89 | Kinesin-like protein KIF20B | 210210.6 | 15 | 4.6 | 7 | 0 |
| Q9BPX3 | Condensin complex subunit 3 | 115417.8 | 5 | 4.5 | 3 | 0 |
| Q6BDS2 | UHRF1-binding protein 1 | 160683.1 | 9 | 4.5 | 10 | 365610 |
| P35573 | Glycogen debranching enzyme | 175548.4 | 8 | 4.5 | 3 | 0 |
| P89471 | DNA primase | 116251.1 | 7 | 4.5 | 3 | 0 |
| Q13332 | Receptor-type tyrosine-protein phosphatase S | 216474.0 | 10 | 4.5 | 10 | 0 |
| Q16513 | Serine/threonine-protein kinase N2 | 100368.0 | 8 | 4.5 | 5 | 0 |
| Q8TD19 | Serine/threonine-protein kinase Nek9 | 108936.5 | 8 | 4.5 | 3 | 0 |
| Q9ULH0 | Kinase D-interacting substrate of 220 kDa | 193778.1 | 10 | 4.5 | 3 | 0 |
| A8TX70 | Collagen alpha-5(VI) chain | 287981.3 | 12 | 4.5 | 5 | 0 |
| Q05193 | Dynamin-1 | 96977.5 | 5 | 4.5 | 5 | 0 |
| Q8IUD2 | ELKS/Rab6-interacting/CAST family member 1 | 122493.9 | 8 | 4.4 | 3 | 0 |
| Q9H5H4 | Zinc finger protein 768 | 61483.4 | 3 | 4.4 | 1 | 0 |
| Q01814 | Plasma membrane calcium-transporting ATPase 2 | 133303.5 | 4 | 4.4 | 8 | 0 |
| Q8IUG5 | Unconventional myosin-XVIIIb | 265201.4 | 20 | 4.4 | 7 | 0 |
| Q8TE73 | Dynein heavy chain 5, axonemal | 532842.9 | 26 | 4.4 | 7 | 0 |
| Q6ZN17 | Protein lin-28 homolog B | 27654.0 | 4 | 4.4 | 1 | 0 |
| Q4AC94 | C2 domain-containing protein 3 | 262784.2 | 12 | 4.4 | 1 | 0 |
| Q659A1 | NMDA receptor-regulated protein 2 | 111038.2 | 2 | 4.4 | 1 | 0 |
| P11511 | Aromatase | 58396.4 | 3 | 4.4 | 1 | 0 |
| Q01831 | DNA repair protein complementing XP-C cells | 106808.2 | 8 | 4.4 | 1 | 0 |
| Q9H2P0 | Activity-dependent neuroprotector homeobox protein | 124931.7 | 12 | 4.4 | 3 | 0 |
| Q03001 | Dystonin | 687877.7 | 45 | 4.4 | 10 | 0 |
| Q14168 | MAGUK p55 subfamily member 2 | 63502.7 | 2 | 4.4 | 3 | 0 |
| Q9C0G6 | Dynein heavy chain 6, axonemal | 426275.2 | 25 | 4.4 | 7 | 0 |
| P54756 | Ephrin type-A receptor 5 | 113552.8 | 5 | 4.3 | 3 | 0 |
| O15018 | PDZ domain-containing protein 2 | 299840.8 | 17 | 4.3 | 5 | 0 |
| Q2M1P5 | Kinesin-like protein KIF7 | 151499.7 | 7 | 4.3 | 1 | 0 |
| Q8WX93 | Palladin | 105376.1 | 6 | 4.3 | 8 | 0 |
| Q96A23 | Copine-4 | 64327.2 | 5 | 4.3 | 10 | 0 |
| A6H8Y1 | Transcription factor TFIIIB component B" homolog | 257461.0 | 14 | 4.3 | 10 | 0 |
| Q5T1H1 | Protein eyes shut homolog | 362315.0 | 18 | 4.3 | 4 | 0 |

FIG. 17 (cont'd)

| | | | | | | |
|---|---|---|---|---|---|---|
| Q86TB3 | Alpha-protein kinase 2 | 240035.4 | 16 | 4.3 | 1 | 0 |
| Q8IV08 | Phospholipase D3 | 55161.7 | 2 | 4.3 | 1 | 0 |
| Q9Y4G6 | Talin-2 | 273951.7 | 15 | 4.3 | 2 | 0 |
| Q9ULE3 | DENN domain-containing protein 2A | 104938.5 | 5 | 4.3 | 5 | 0 |
| A2BFH1 | Peptidyl-prolyl cis-trans isomerase A-like 4G | 18393.9 | 2 | 4.3 | 2 | 0 |
| O95104 | Splicing factor, arginine/serine-rich 15 | 125098.2 | 2 | 4.3 | 2 | 0 |
| Q06210 | Glutamine--fructose-6-phosphate aminotransferase [isomerizing] 1 | 78581.3 | 2 | 4.3 | 2 | 0 |
| Q07157 | Tight junction protein ZO-1 | 191554.8 | 10 | 4.3 | 2 | 0 |
| Q14694 | Ubiquitin carboxyl-terminal hydrolase 10 | 89753.5 | 5 | 4.3 | 9 | 0 |
| Q8NEY1 | Neuron navigator 1 | 189145.4 | 7 | 4.3 | 3 | 0 |
| B2RTY4 | Unconventional myosin-IXa | 293969.5 | 18 | 4.2 | 10 | 0 |
| Q14643 | Inositol 1,4,5-trisphosphate receptor type 1 | 314325.7 | 15 | 4.2 | 9 | 0 |
| P35658 | Nuclear pore complex protein Nup214 | 214349.6 | 11 | 4.2 | 10 | 0 |
| Q07283 | Trichohyalin | 254381.7 | 14 | 4.2 | 2 | 0 |
| Q8WXI9 | Transcriptional repressor p66-beta | 65603.0 | 6 | 4.2 | 2 | 0 |
| Q86WT1 | Tetratricopeptide repeat protein 30A | 76934.3 | 2 | 4.2 | 1 | 0 |
| Q9BZA7 | Protocadherin-11 X-linked | 135127.1 | 2 | 4.2 | 8 | 0 |
| Q96Q15 | Serine/threonine-protein kinase SMG1 | 391267.3 | 22 | 4.2 | 8 | 0 |
| P06473 | Envelope glycoprotein B | 102916.5 | 3 | 4.2 | 1 | 0 |
| P17948 | Vascular endothelial growth factor receptor 1 | 122979.9 | 8 | 4.2 | 3 | 0 |
| Q9Y4E6 | WD repeat-containing protein 7 | 164583.9 | 7 | 4.2 | 2 | 0 |
| O15083 | ERC protein 2 | 110728.9 | 8 | 4.2 | 1 | 0 |
| P52333 | Tyrosine-protein kinase JAK3 | 126923.9 | 6 | 4.2 | 1 | 0 |
| Q12979 | Active breakpoint cluster region-related protein | 95166.1 | 2 | 4.2 | 3 | 0 |
| Q9HC35 | Echinoderm microtubule-associated protein-like 4 | 109999.9 | 9 | 4.2 | 4 | 0 |
| Q9Y2U8 | Inner nuclear membrane protein Man1 | 100853.0 | 4 | 4.2 | 1 | 0 |
| P13473 | Lysosome-associated membrane glycoprotein 2 | 45599.2 | 4 | 4.2 | 10 | 0 |
| Q8IYM2 | Schlafen family member 12 | 67942.1 | 3 | 4.2 | 1 | 0 |
| Q96QD8 | Sodium-coupled neutral amino acid transporter 2 | 56368.3 | 1 | 4.2 | 2 | 0 |
| P54707 | Potassium-transporting ATPase alpha chain 2 | 116637.4 | 7 | 4.1 | 10 | 0 |
| Q96PB1 | CAS1 domain-containing protein 1 | 92991.6 | 4 | 4.1 | 1 | 0 |
| Q8WVC0 | RNA polymerase-associated protein LEO1 | 71818.2 | 4 | 4.1 | 4 | 0 |
| Q8NI0 | Dedicator of cytokinesis protein 4 | 227517.6 | 12 | 4.1 | 2 | 0 |
| Q93008 | Probable ubiquitin carboxyl-terminal hydrolase FAF-X | 294793.4 | 10 | 4.1 | 10 | 45744 |
| O15131 | Importin subunit alpha-6 | 61090.4 | 4 | 4.1 | 3 | 0 |
| Q8N3K9 | Cardiomyopathy-associated protein 5 | 451036.4 | 23 | 4.1 | 3 | 0 |
| Q9UPQ3 | Arf-GAP with GTPase, ANK repeat and PH domain-containing protein 1 | 92737.8 | 3 | 4.1 | 2 | 0 |
| Q92785 | Zinc finger protein ubi-d4 | 45296.1 | 4 | 4.1 | 1 | 0 |
| Q93050 | V-type proton ATPase 116 kDa subunit a isoform 1 | 97054.9 | 4 | 4.1 | 10 | 0 |

FIG. 17 (cont'd)

| | | | | | | |
|---|---|---|---|---|---|---|
| Q5T200 | Zinc finger CCCH domain-containing protein 13 | 197319.9 | 11 | 4.1 | 1 | 0 |
| Q9NR48 | Histone-lysine N-methyltransferase ASH1L | 336093.5 | 19 | 4.1 | 6 | 0 |
| O00186 | Syntaxin-binding protein 3 | 68676.8 | 4 | 4.1 | 1 | 0 |
| P51812 | Ribosomal protein S6 kinase alpha-3 | 84078.3 | 5 | 4.1 | 1 | 0 |
| O75899 | Gamma-aminobutyric acid type B receptor subunit 2 | 106848.2 | 6 | 4.0 | 1 | 0 |
| O95071 | E3 ubiquitin-protein ligase UBR5 | 312546.5 | 20 | 4.0 | 3 | 0 |
| Q66578 | Genome polyprotein | 248524.4 | 16 | 4.0 | 3 | 0 |
| Q8NHM5 | Lysine-specific demethylase 2B | 155067.1 | 9 | 4.0 | 1 | 0 |
| Q9H5Q4 | Dimethyladenosine transferase 2, mitochondrial | 45805.2 | 3 | 4.0 | 1 | 0 |
| P07951 | Tropomyosin beta chain | 31565.2 | 2 | 4.0 | 10 | 0 |
| Q2TB90 | Putative hexokinase HKDC1 | 103856.7 | 7 | 4.0 | 6 | 0 |
| P48634 | Protein PRRC2A | 229083.5 | 6 | 4.0 | 3 | 0 |
| Q5CZC0 | Fibrous sheath-interacting protein 2 | 649273.6 | 34 | 4.0 | 10 | 0 |
| O75127 | Pentatricopeptide repeat-containing protein 1, mitochondrial | 79483.2 | 4 | 4.0 | 1 | 0 |
| Q86WZ0 | HEAT repeat-containing protein 4 | 118031.0 | 3 | 4.0 | 1 | 0 |
| O43896 | Kinesin-like protein KIF1C | 123802.2 | 4 | 4.0 | 1 | 0 |
| Q8NFC6 | Biorientation of chromosomes in cell division protein 1-like 1 | 332633.9 | 19 | 4.0 | 2 | 0 |
| Q86WI1 | Fibrocystin-L | 470582.4 | 19 | 4.0 | 1 | 0 |
| Q02224 | Centromere-associated protein E | 312506.7 | 24 | 4.0 | 10 | 0 |
| P20929 | Nebulin | 775894.2 | 53 | 3.9 | 10 | 0 |
| Q6N022 | Teneurin-4 | 312576.3 | 10 | 3.9 | 2 | 0 |
| Q96JI7 | Spatacsin | 264317.1 | 20 | 3.9 | 6 | 0 |
| Q9Y6E0 | Serine/threonine-protein kinase 24 | 48895.9 | 2 | 3.9 | 2 | 0 |
| P0C6X7 | Replicase polyprotein 1ab | 803537.1 | 46 | 3.9 | 10 | 0 |
| O94979 | Protein transport protein Sec31A | 126451.1 | 4 | 3.9 | 8 | 0 |
| P13533 | Myosin-6 | 224533.5 | 14 | 3.9 | 6 | 0 |
| P55283 | Cadherin-4 | 96676.5 | 5 | 3.9 | 4 | 0 |
| P0C7X5 | Zinc finger protein 806 | 69462.0 | 2 | 3.9 | 1 | 0 |
| Q08188 | Protein-glutamine gamma-glutamyltransferase E | 76974.1 | 4 | 3.9 | 1 | 0 |
| Q8NEZ3 | WD repeat-containing protein 19 | 153520.2 | 9 | 3.9 | 1 | 0 |
| Q9ULM3 | YEATS domain-containing protein 2 | 151694.3 | 4 | 3.9 | 1 | 0 |
| O15254 | Peroxisomal acyl-coenzyme A oxidase 3 | 74371.9 | 3 | 3.9 | 2 | 0 |
| P17693 | HLA class I histocompatibility antigen, alpha chain G | 38566.4 | 1 | 3.9 | 1 | 0 |
| P28749 | Retinoblastoma-like protein 1 | 119107.9 | 6 | 3.9 | 2 | 0 |
| Q8NB25 | Protein FAM184A | 131875.9 | 10 | 3.9 | 2 | 0 |
| Q9QJ37 | Deneddylase | 241483.3 | 14 | 3.9 | 1 | 0 |
| Q5TZA2 | Rootletin | 212823.5 | 14 | 3.8 | 5 | 0 |
| Q9HBZ2 | Aryl hydrocarbon receptor nuclear translocator 2 | 78779.1 | 2 | 3.8 | 2 | 0 |
| Q9UPN3 | Microtubule-actin cross-linking factor 1, isoforms 1/2/3/5 | 680390.7 | 45 | 3.8 | 10 | 0 |
| O95714 | E3 ubiquitin-protein ligase HERC2 | 533843.8 | 23 | 3.8 | 8 | 0 |

FIG. 17 (cont'd)

| | | | | | | |
|---|---|---|---|---|---|---|
| P04114 | Apolipoprotein B-100 | 516974.1 | 25 | 3.8 | 7 | 0 |
| Q5BJE1 | Coiled-coil domain-containing protein 178 | 102638.6 | 4 | 3.8 | 1 | 0 |
| Q9BYB0 | SH3 and multiple ankyrin repeat domains protein 3 | 186451.3 | 6 | 3.8 | 2 | 0 |
| O75417 | DNA polymerase theta | 269194.9 | 17 | 3.8 | 4 | 0 |
| O95425 | Supervillin | 225979.4 | 13 | 3.8 | 6 | 0 |
| O95477 | ATP-binding cassette sub-family A member 1 | 256526.7 | 13 | 3.8 | 1 | 0 |
| P39880 | Homeobox protein cut-like 1 | 158756.5 | 8 | 3.8 | 6 | 0 |
| Q9P217 | Zinc finger SWIM domain-containing protein 5 | 132401.6 | 6 | 3.8 | 1 | 0 |
| Q92576 | PHD finger protein 3 | 226783.3 | 8 | 3.8 | 4 | 0 |
| P0C6U8 | Replicase polyprotein 1a | 494585.5 | 27 | 3.8 | 5 | 0 |
| O43819 | Protein SCO2 homolog, mitochondrial | 29981.1 | 3 | 3.8 | 1 | 0 |
| Q8JPR2 | RNA-directed RNA polymerase L | 265351.5 | 23 | 3.8 | 1 | 0 |
| P09960 | Leukotriene A-4 hydrolase | 63805.7 | 6 | 3.8 | 4 | 0 |
| Q00722 | 1-phosphatidylinositol 4,5-bisphosphate phosphodiesterase beta-2 | 134821.9 | 12 | 3.7 | 4 | 0 |
| Q9BV73 | Centrosome-associated protein CEP250 | 277961.2 | 14 | 3.7 | 5 | 0 |
| Q99707 | Methionine synthase | 141839.1 | 9 | 3.7 | 3 | 0 |
| Q9UNS2 | COP9 signalosome complex subunit 3 | 47370.3 | 4 | 3.7 | 2 | 0 |
| K7ZRV2 | Tetratricopeptide repeat protein 28 | 272823.9 | 15 | 3.7 | 4 | 0 |
| Q08379 | Golgin subfamily A member 2 | 92264.3 | 11 | 3.7 | 4 | 0 |
| Q96AY4 | Tetratricopeptide repeat protein 28 | 272823.9 | 15 | 3.7 | 4 | 0 |
| Q15120 | [Pyruvate dehydrogenase (acetyl-transferring)] kinase isozyme 3, mitochondrial | 47662.2 | 2 | 3.7 | 2 | 0 |
| O95302 | Peptidyl-prolyl cis-trans isomerase FKBP9 | 63539.9 | 2 | 3.7 | 1 | 0 |
| Q9NY33 | Dipeptidyl peptidase 3 | 81290.5 | 5 | 3.7 | 2 | 0 |
| Q0VDD8 | Dynein heavy chain 14, axonemal | 469461.9 | 27 | 3.7 | 10 | 0 |
| Q9BQW3 | Transcription factor COE4 | 67037.1 | 2 | 3.7 | 2 | 0 |
| Q58EX2 | Protein sidekick-2 | 233970.6 | 8 | 3.6 | 4 | 0 |
| Q14EB0 | Spike glycoprotein | 153993.9 | 5 | 3.6 | 1 | 0 |
| Q96QC0 | Serine/threonine-protein phosphatase 1 regulatory subunit 10 | 99400.1 | 6 | 3.6 | 1 | 0 |
| O60610 | Protein diaphanous homolog 1 | 140846.9 | 4 | 3.6 | 3 | 0 |
| Q86YS3 | Rab11 family-interacting protein 4 | 72612.6 | 6 | 3.6 | 1 | 0 |
| O75037 | Kinesin-like protein KIF21B | 183221.2 | 7 | 3.6 | 5 | 0 |
| Q86VZ4 | Low-density lipoprotein receptor-related protein 11 | 54337.9 | 4 | 3.6 | 1 | 0 |
| Q96JH7 | Deubiquitinating protein VCIP135 | 135689.4 | 11 | 3.6 | 1 | 0 |
| Q77377 | Envelope glycoprotein gp160 | 98418.1 | 3 | 3.6 | 1 | 0 |
| Q96A65 | Exocyst complex component 4 | 111239.6 | 3 | 3.6 | 1 | 0 |
| Q8WYP3 | Ras and Rab interactor 2 | 103943.5 | 3 | 3.6 | 2 | 0 |
| Q5VU43 | Myomegalin | 236281.8 | 13 | 3.6 | 10 | 0 |
| Q7Z3K3 | Pogo transposable element with ZNF domain | 152605.7 | 5 | 3.6 | 8 | 0 |
| Q9UMN6 | Histone-lysine N-methyltransferase 2B | 297849.3 | 10 | 3.6 | 1 | 0 |

FIG. 17 (cont'd)

| | | | | | | |
|---|---|---|---|---|---|---|
| Q9Y623 | Myosin-4 | 224041.3 | 18 | 3.6 | 2 | 0 |
| O60282 | Kinesin heavy chain isoform 5C | 110065.3 | 3 | 3.6 | 1 | 0 |
| Q5XKE5 | Keratin, type II cytoskeletal 79 | 58120.8 | 3 | 3.6 | 8 | 0 |
| Q86YQ8 | Copine-8 | 63678.0 | 4 | 3.6 | 6 | 0 |
| Q9P2P6 | StAR-related lipid transfer protein 9 | 522160.8 | 24 | 3.6 | 7 | 0 |
| P31327 | Carbamoyl-phosphate synthase [ammonia], mitochondrial | 141601.1 | 9 | 3.5 | 2 | 0 |
| Q13535 | Serine/threonine-protein kinase ATR | 301651.1 | 15 | 3.5 | 8 | 0 |
| Q68CZ2 | Tensin-3 | 156463.4 | 4 | 3.5 | 1 | 0 |
| Q7Z407 | CUB and sushi domain-containing protein 3 | 392779.9 | 13 | 3.5 | 8 | 0 |
| Q99698 | Lysosomal-trafficking regulator | 434443.2 | 19 | 3.5 | 2 | 0 |
| O15360 | Fanconi anemia group A protein | 164942.5 | 5 | 3.5 | 1 | 0 |
| O60271 | C-Jun-amino-terminal kinase-interacting protein 4 | 145933.9 | 10 | 3.5 | 1 | 0 |
| Q5THJ4 | Vacuolar protein sorting-associated protein 13D | 494217.1 | 31 | 3.5 | 10 | 0 |
| Q96F07 | Cytoplasmic FMR1-interacting protein 2 | 148975.2 | 5 | 3.5 | 4 | 0 |
| Q8IYA2 | Putative coiled-coil domain-containing protein 144C | 144195.3 | 12 | 3.5 | 2 | 0 |
| Q8JTG9 | Large structural protein | 244558.2 | 11 | 3.5 | 3 | 0 |
| Q8TER5 | Rho guanine nucleotide exchange factor 40 | 153439.5 | 10 | 3.5 | 7 | 0 |
| Q15413 | Ryanodine receptor 3 | 521998.0 | 32 | 3.5 | 10 | 0 |
| A4UGR9 | Xin actin-binding repeat-containing protein 2 | 381452.2 | 18 | 3.5 | 10 | 0 |
| P53804 | E3 ubiquitin-protein ligase TTC3 | 217012.6 | 15 | 3.5 | 4 | 0 |
| Q7Z589 | Protein EMSY | 133033.5 | 3 | 3.5 | 2 | 0 |
| P33056 | Early transcription factor 70 kDa subunit | 73945.1 | 4 | 3.5 | 1 | 0 |
| P35711 | Transcription factor SOX-5 | 73009.5 | 3 | 3.5 | 4 | 0 |
| Q14997 | Proteasome activator complex subunit 4 | 177701.7 | 5 | 3.5 | 2 | 0 |
| Q8IYJ1 | Copine-9 | 62320.4 | 6 | 3.4 | 7 | 0 |
| Q9NR16 | Scavenger receptor cysteine-rich type 1 protein M160 | 136478.0 | 4 | 3.4 | 3 | 0 |
| Q14999 | Cullin-7 | 197280.5 | 9 | 3.4 | 2 | 0 |
| Q9NY15 | Stabilin-1 | 287116.1 | 14 | 3.4 | 1 | 0 |
| Q9NZJ4 | Sacsin | 500709.2 | 23 | 3.4 | 10 | 0 |
| Q12830 | Nucleosome-remodeling factor subunit BPTF | 332210.9 | 15 | 3.4 | 10 | 0 |
| P09278 | Deneddylase | 308225.0 | 12 | 3.4 | 4 | 0 |
| Q4JQX9 | Deneddylase | 308218.0 | 12 | 3.4 | 4 | 0 |
| Q63HN8 | E3 ubiquitin-protein ligase RNF213 | 601218.4 | 33 | 3.4 | 10 | 0 |
| Q92736 | Ryanodine receptor 2 | 570070.3 | 29 | 3.4 | 10 | 0 |
| Q9UFC0 | Leucine-rich repeat and WD repeat-containing protein 1 | 72115.9 | 2 | 3.4 | 1 | 0 |
| P49641 | Alpha-mannosidase 2x | 117560.1 | 9 | 3.4 | 3 | 0 |
| Q9UMD9 | Collagen alpha-1(XVII) chain | 146780.9 | 5 | 3.4 | 2 | 0 |
| O14497 | AT-rich interactive domain-containing protein 1A | 222994.1 | 11 | 3.4 | 3 | 0 |
| O14802 | DNA-directed RNA polymerase III | 157637.8 | 14 | 3.4 | 1 | 0 |

FIG. 17 (cont'd)

| | subunit RPC1 | | | | | |
|---|---|---|---|---|---|---|
| Q12860 | Contactin-1 | 113449.2 | 5 | 3.4 | 2 | 0 |
| Q5T848 | Probable G-protein coupled receptor 158 | 136971.9 | 4 | 3.4 | 1 | 0 |
| Q9HC77 | Centromere protein J | 154198.1 | 11 | 3.4 | 2 | 0 |
| O75113 | NEDD4-binding protein 1 | 101291.4 | 4 | 3.4 | 1 | 0 |
| P23229 | Integrin alpha-6 | 121410.8 | 4 | 3.4 | 8 | 0 |
| Q15910 | Histone-lysine N-methyltransferase EZH2 | 87302.2 | 6 | 3.4 | 1 | 0 |
| Q5TAX3 | Terminal uridylyltransferase 4 | 188131.4 | 7 | 3.4 | 1 | 0 |
| Q92932 | Receptor-type tyrosine-protein phosphatase N2 | 112070.0 | 6 | 3.4 | 1 | 0 |
| P51587 | Breast cancer type 2 susceptibility protein | 388559.8 | 25 | 3.3 | 4 | 0 |
| P58107 | Epiplakin | 558016.8 | 17 | 3.3 | 5 | 0 |
| P11362 | Fibroblast growth factor receptor 1 | 87093.1 | 3 | 3.3 | 10 | 0 |
| P23468 | Receptor-type tyrosine-protein phosphatase delta | 182947.7 | 6 | 3.3 | 6 | 0 |
| O91080 | Gag-Pol polyprotein | 164492.1 | 3 | 3.3 | 1 | 0 |
| P16234 | Platelet-derived growth factor receptor alpha | 123639.2 | 5 | 3.3 | 1 | 0 |
| Q9NYQ8 | Protocadherin Fat 2 | 482397.4 | 19 | 3.3 | 5 | 0 |
| Q9UBC3 | DNA (cytosine-5)-methyltransferase 3B | 96114.5 | 2 | 3.3 | 1 | 0 |
| O60333 | Kinesin-like protein KIF1B | 206123.5 | 14 | 3.3 | 3 | 0 |
| Q6XZF7 | Dynamin-binding protein | 178830.1 | 7 | 3.3 | 1 | 0 |
| Q9UKX3 | Myosin-13 | 224745.6 | 16 | 3.3 | 4 | 0 |
| P33793 | DNA polymerase | 118012.8 | 8 | 3.3 | 1 | 0 |
| Q16666 | Gamma-interferon-inducible protein 16 | 82675.1 | 6 | 3.3 | 4 | 0 |
| Q8IVF4 | Dynein heavy chain 10, axonemal | 518035.2 | 31 | 3.3 | 7 | 0 |
| Q9NRY4 | Rho GTPase-activating protein 35 | 172054.1 | 10 | 3.3 | 1 | 0 |
| P90493 | Major viral transcription factor ICP4 homolog | 135902.0 | 6 | 3.3 | 1 | 0 |
| Q13085 | Acetyl-CoA carboxylase 1 | 264830.9 | 10 | 3.3 | 4 | 0 |
| P42858 | Huntingtin | 351595.8 | 16 | 3.3 | 1 | 0 |
| Q8IVF2 | Protein AHNAK2 | 612223.8 | 39 | 3.3 | 10 | 0 |
| Q9IFX2 | Non-structural polyprotein 1AB | 162756.4 | 8 | 3.3 | 2 | 0 |
| Q04544 | Genome polyprotein | 200236.5 | 8 | 3.2 | 1 | 0 |
| Q13469 | Nuclear factor of activated T-cells, cytoplasmic 2 | 101058.4 | 5 | 3.2 | 1 | 0 |
| Q6PD62 | RNA polymerase-associated protein CTR9 homolog | 134414.9 | 7 | 3.2 | 2 | 0 |
| Q9IDV9 | Gag-Pol polyprotein | 162809.3 | 5 | 3.2 | 1 | 0 |
| Q9P2D1 | Chromodomain-helicase-DNA-binding protein 7 | 337752.7 | 18 | 3.2 | 4 | 0 |
| O95741 | Copine-6 | 62903.7 | 4 | 3.2 | 6 | 0 |
| Q14C86 | GTPase-activating protein and VPS9 domain-containing protein 1 | 167651.4 | 9 | 3.2 | 1 | 0 |
| Q15147 | 1-phosphatidylinositol 4,5-bisphosphate phosphodiesterase beta-4 | 136170.9 | 8 | 3.2 | 3 | 0 |
| Q8TD57 | Dynein heavy chain 3, axonemal | 434624.2 | 32 | 3.2 | 10 | 0 |

FIG. 17 (cont'd)

| | | | | | | |
|---|---|---|---|---|---|---|
| P13647 | Keratin, type II cytoskeletal 5 | 62606.6 | 5 | 3.2 | 7 | 0 |
| Q6N069 | N-alpha-acetyltransferase 16, NatA auxiliary subunit | 66701.4 | 2 | 3.2 | 10 | 0 |
| A5YKK6 | CCR4-NOT transcription complex subunit 1 | 245116.9 | 16 | 3.2 | 10 | 0 |
| Q5VVP1 | Spermatogenesis-associated protein 31A6 | 149528.9 | 6 | 3.2 | 1 | 0 |
| Q7Z2Z1 | Treslin | 212817.6 | 8 | 3.2 | 2 | 0 |
| Q96JC1 | Vam6/Vps39-like protein | 102429.7 | 7 | 3.2 | 2 | 0 |
| Q9UGU0 | Transcription factor 20 | 212166.9 | 10 | 3.2 | 4 | 0 |
| Q9UIF9 | Bromodomain adjacent to zinc finger domain protein 2A | 213136.9 | 9 | 3.2 | 1 | 0 |
| P10721 | Mast/stem cell growth factor receptor Kit | 111026.7 | 8 | 3.2 | 4 | 0 |
| Q5TGJ6 | Hepatoma-derived growth factor-like protein 1 | 27404.8 | 1 | 3.2 | 1 | 0 |
| Q7L523 | Ras-related GTP-binding protein A | 36965.4 | 3 | 3.2 | 1 | 0 |
| Q13905 | Rap guanine nucleotide exchange factor 1 | 120549.4 | 6 | 3.2 | 3 | 0 |
| Q16549 | Proprotein convertase subtilisin/kexin type 7 | 87216.6 | 3 | 3.2 | 1 | 0 |
| Q8NI08 | Nuclear receptor coactivator 7 | 106789.0 | 5 | 3.2 | 1 | 0 |
| Q92523 | Carnitine O-palmitoyltransferase 1, muscle isoform | 84348.9 | 5 | 3.2 | 3 | 0 |
| Q9Y2F5 | Uncharacterized protein KIAA0947 | 250913.5 | 10 | 3.2 | 1 | 0 |
| Q8NDA2 | Hemicentin-2 | 503544.6 | 22 | 3.2 | 10 | 0 |
| Q4UJ75 | Ankyrin repeat domain-containing protein 20A4 | 95061.3 | 3 | 3.2 | 1 | 0 |
| Q9H9B1 | Histone-lysine N-methyltransferase EHMT1 | 144089.8 | 4 | 3.2 | 1 | 0 |
| Q9NRD9 | Dual oxidase 1 | 159016.5 | 7 | 3.2 | 2 | 0 |
| P08F94 | Fibrocystin | 437224.5 | 18 | 3.2 | 5 | 0 |
| Q14146 | Unhealthy ribosome biogenesis protein 2 homolog | 172483.3 | 10 | 3.2 | 1 | 0 |
| Q8WXH0 | Nesprin-2 | 753672.4 | 49 | 3.2 | 10 | 0 |
| P11488 | Guanine nucleotide-binding protein G(t) subunit alpha-1 | 40497.1 | 1 | 3.1 | 2 | 0 |
| Q5T3I0 | G patch domain-containing protein 4 | 50882.6 | 3 | 3.1 | 2 | 0 |
| Q8NB90 | Spermatogenesis-associated protein 5 | 98531.9 | 3 | 3.1 | 1 | 0 |
| Q9UPX8 | SH3 and multiple ankyrin repeat domains protein 2 | 202344.6 | 8 | 3.1 | 1 | 0 |
| O75164 | Lysine-specific demethylase 4A | 56123.0 | 2 | 3.1 | 1 | 0 |
| A8MTJ3 | Guanine nucleotide-binding protein G(t) subunit alpha-3 | 40870.3 | 1 | 3.1 | 3 | 0 |
| O15050 | TPR and ankyrin repeat-containing protein 1 | 340555.6 | 14 | 3.1 | 2 | 0 |
| P0C6U2 | Replicase polyprotein 1a | 462313.8 | 19 | 3.1 | 4 | 0 |
| P19087 | Guanine nucleotide-binding protein G(t) subunit alpha-2 | 40746.2 | 1 | 3.1 | 2 | 0 |
| P48552 | Nuclear receptor-interacting protein 1 | 127740.5 | 5 | 3.1 | 1 | 0 |
| Q86V20 | Protein FAM35A | 99051.4 | 3 | 3.1 | 2 | 0 |
| Q8IWZ3 | Ankyrin repeat and KH domain-containing protein 1 | 274011.3 | 9 | 3.1 | 3 | 0 |
| Q9NR99 | Matrix-remodeling-associated protein 5 | 314260.8 | 14 | 3.1 | 1 | 0 |

FIG. 17 (cont'd)

| | | | | | | |
|---|---|---|---|---|---|---|
| Q9NRC6 | Spectrin beta chain, non-erythrocytic 5 | 419515.9 | 25 | 3.1 | 9 | 0 |
| Q9NYU1 | UDP-glucose:glycoprotein glucosyltransferase 2 | 175362.9 | 5 | 3.1 | 1 | 0 |
| P21817 | Ryanodine receptor 1 | 570535.4 | 28 | 3.1 | 10 | 0 |
| P35916 | Vascular endothelial growth factor receptor 3 | 151231.2 | 7 | 3.1 | 4 | 0 |
| Q12789 | General transcription factor 3C polypeptide 1 | 240059.2 | 10 | 3.1 | 9 | 0 |
| Q9NQT8 | Kinesin-like protein KIF13B | 204035.5 | 13 | 3.1 | 2 | 0 |
| O75592 | Probable E3 ubiquitin-protein ligase MYCBP2 | 517994.5 | 27 | 3.1 | 10 | 39702 |
| P33069 | Primase D5 | 91554.3 | 5 | 3.1 | 1 | 0 |
| O60566 | Mitotic checkpoint serine/threonine-protein kinase BUB1 beta | 120857.0 | 4 | 3.1 | 1 | 0 |
| Q5TEA6 | Protein sel-1 homolog 2 | 78192.2 | 4 | 3.1 | 1 | 0 |
| P0C6X3 | Replicase polyprotein 1ab | 822836.6 | 34 | 3.0 | 9 | 0 |
| Q9UL10 | ATPase family AAA domain-containing protein 2B | 166161.1 | 8 | 3.0 | 4 | 0 |
| O14647 | Chromodomain-helicase-DNA-binding protein 2 | 206979.4 | 7 | 3.0 | 4 | 0 |
| Q9NQX4 | Unconventional myosin-Vc | 204122.4 | 12 | 3.0 | 2 | 0 |
| Q01546 | Keratin, type II cytoskeletal 2 oral | 66411.1 | 5 | 3.0 | 6 | 0 |
| Q96HP0 | Dedicator of cytokinesis protein 6 | 231440.3 | 12 | 3.0 | 1 | 0 |
| Q01484 | Ankyrin-2 | 436224.4 | 27 | 3.0 | 4 | 0 |
| Q9NRL2 | Bromodomain adjacent to zinc finger domain protein 1A | 178697.6 | 5 | 3.0 | 2 | 0 |
| Q16787 | Laminin subunit alpha-3 | 375888.1 | 19 | 2.9 | 1 | 0 |
| Q96SB3 | Neurabin-2 | 89363.3 | 3 | 2.9 | 1 | 0 |
| Q9NR96 | Toll-like receptor 9 | 120171.0 | 4 | 2.9 | 1 | 0 |
| Q09MP3 | RAD51-associated protein 2 | 135845.9 | 8 | 2.9 | 1 | 0 |
| P12109 | Collagen alpha-1(VI) chain | 109670.1 | 5 | 2.9 | 1 | 0 |
| P46821 | Microtubule-associated protein 1B | 271832.3 | 15 | 2.9 | 1 | 0 |
| Q8WXW3 | Progesterone-induced-blocking factor 1 | 90089.9 | 8 | 2.9 | 2 | 0 |
| Q96N67 | Dedicator of cytokinesis protein 7 | 242195.1 | 14 | 2.9 | 10 | 0 |
| Q9Y5Q9 | General transcription factor 3C polypeptide 3 | 74835.6 | 4 | 2.9 | 2 | 0 |
| P08546 | DNA polymerase catalytic subunit | 138926.9 | 4 | 2.9 | 1 | 0 |
| Q6SW77 | DNA polymerase catalytic subunit | 138983.0 | 3 | 2.9 | 1 | 0 |
| Q7Z7G8 | Vacuolar protein sorting-associated protein 13B | 453703.3 | 19 | 2.9 | 10 | 0 |
| P38405 | Guanine nucleotide-binding protein G(olf) subunit alpha | 48952.0 | 1 | 2.9 | 2 | 0 |
| Q5VZM2 | Ras-related GTP-binding protein B | 42167.6 | 2 | 2.9 | 2 | 0 |
| P04275 | von Willebrand factor | 322609.4 | 17 | 2.9 | 1 | 0 |
| Q9NYC9 | Dynein heavy chain 9, axonemal | 492768.6 | 29 | 2.9 | 10 | 0 |
| Q9UM54 | Unconventional myosin-VI | 150380.6 | 4 | 2.9 | 3 | 0 |
| Q5VV42 | Threonylcarbamoyladenosine tRNA methylthiotransferase | 60545.2 | 5 | 2.9 | 2 | 0 |
| Q9NS87 | Kinesin-like protein KIF15 | 121143.7 | 8 | 2.9 | 3 | 0 |
| O15078 | Centrosomal protein of 290 kDa | 243644.4 | 17 | 2.9 | 7 | 0 |
| P61764 | Syntaxin-binding protein 1 | 68551.7 | 3 | 2.9 | 2 | 0 |

FIG. 17 (cont'd)

| | | | | | | |
|---|---|---|---|---|---|---|
| Q6ZNJ1 | Neurobeachin-like protein 2 | 297891.3 | 10 | 2.8 | 6 | 0 |
| Q9UHB6 | LIM domain and actin-binding protein 1 | 72638.8 | 4 | 2.8 | 4 | 0 |
| Q9UK61 | Protein FAM208A | 182192.3 | 8 | 2.8 | 3 | 0 |
| Q13219 | Pappalysin-1 | 185763.1 | 3 | 2.8 | 1 | 0 |
| Q15075 | Early endosome antigen 1 | 163435.4 | 4 | 2.8 | 1 | 0 |
| O14578 | Citron Rho-interacting kinase | 227866.6 | 12 | 2.8 | 7 | 0 |
| O75116 | Rho-associated protein kinase 2 | 162040.7 | 10 | 2.8 | 1 | 0 |
| O75165 | DnaJ homolog subfamily C member 13 | 256696.5 | 17 | 2.8 | 1 | 0 |
| Q5VT25 | Serine/threonine-protein kinase MRCK alpha | 197933.5 | 8 | 2.8 | 6 | 0 |
| P16726 | Virion-packaging protein UL25 homolog | 71643.1 | 4 | 2.8 | 1 | 0 |
| P35968 | Vascular endothelial growth factor receptor 2 | 153408.9 | 8 | 2.8 | 2 | 0 |
| Q5THR3 | EF-hand calcium-binding domain-containing protein 6 | 145815.9 | 11 | 2.8 | 1 | 0 |
| Q9H6T0 | Epithelial splicing regulatory protein 2 | 78709.5 | 6 | 2.8 | 6 | 0 |
| P0C6X1 | Replicase polyprotein 1ab | 767794.0 | 33 | 2.8 | 8 | 0 |
| Q14571 | Inositol 1,4,5-trisphosphate receptor type 2 | 311257.8 | 12 | 2.8 | 2 | 0 |
| Q96RW7 | Hemicentin-1 | 617405.7 | 24 | 2.8 | 10 | 0 |
| Q9BY66 | Lysine-specific demethylase 5D | 175786.4 | 8 | 2.8 | 3 | 0 |
| Q9HD67 | Unconventional myosin-X | 239343.2 | 16 | 2.8 | 3 | 0 |
| A8MQ14 | Zinc finger protein 850 | 129651.2 | 3 | 2.8 | 1 | 0 |
| P29375 | Lysine-specific demethylase 5A | 191901.2 | 8 | 2.8 | 2 | 0 |
| P0C025 | Nucleoside diphosphate-linked moiety X motif 17 | 36151.6 | 1 | 2.7 | 1 | 0 |
| P52735 | Guanine nucleotide exchange factor VAV2 | 100695.0 | 7 | 2.7 | 3 | 0 |
| Q8NCM2 | Potassium voltage-gated channel subfamily H member 5 | 113017.4 | 4 | 2.7 | 1 | 0 |
| P50416 | Carnitine O-palmitoyltransferase 1, liver isoform | 89052.2 | 7 | 2.7 | 1 | 0 |
| Q8N3C0 | Activating signal cointegrator 1 complex subunit 3 | 253057.5 | 9 | 2.7 | 1 | 0 |
| Q9NR09 | Baculoviral IAP repeat-containing protein 6 | 536528.8 | 13 | 2.7 | 2 | 0 |
| Q9UL16 | Coiled-coil domain-containing protein 19, mitochondrial | 65843.9 | 4 | 2.7 | 1 | 0 |
| Q1MSJ5 | Centrosome and spindle pole-associated protein 1 | 145807.4 | 4 | 2.7 | 1 | 0 |
| A4FU28 | cTAGE family member 9 | 88295.2 | 2 | 2.7 | 1 | 0 |
| P0CG41 | cTAGE family member 8 | 88419.3 | 3 | 2.7 | 1 | 0 |
| Q5JPF3 | Ankyrin repeat domain-containing protein 36C | 201516.2 | 10 | 2.7 | 1 | 0 |
| Q6GYQ0 | Ral GTPase-activating protein subunit alpha-1 | 223209.2 | 13 | 2.7 | 1 | 0 |
| Q86UF2 | cTAGE family member 6 | 88299.1 | 3 | 2.7 | 1 | 0 |
| Q8IX94 | cTAGE family member 4 | 88331.2 | 4 | 2.7 | 1 | 0 |
| Q96BY6 | Dedicator of cytokinesis protein 10 | 251983.5 | 10 | 2.7 | 1 | 0 |
| Q9UPU7 | TBC1 domain family member 2B | 110564.9 | 4 | 2.7 | 1 | 0 |
| Q02241 | Kinesin-like protein KIF23 | 104994.8 | 8 | 2.7 | 2 | 0 |

FIG. 17 (cont'd)

| | | | | | | |
|---|---|---|---|---|---|---|
| Q9NZM1 | Myoferlin | 235395.5 | 13 | 2.7 | 3 | 0 |
| A6QL64 | Ankyrin repeat domain-containing protein 36A | 219289.7 | 11 | 2.7 | 2 | 0 |
| Q14517 | Protocadherin Fat 1 | 509694.9 | 16 | 2.7 | 3 | 0 |
| Q9BX26 | Synaptonemal complex protein 2 | 177349.9 | 8 | 2.7 | 2 | 0 |
| Q03164 | Histone-lysine N-methyltransferase 2A | 434225.8 | 16 | 2.7 | 6 | 0 |
| Q6ZN16 | Mitogen-activated protein kinase kinase kinase 15 | 90107.7 | 7 | 2.7 | 1 | 0 |
| P78559 | Microtubule-associated protein 1A | 306968.2 | 15 | 2.6 | 1 | 0 |
| Q8N7X0 | Androglobin | 190796.9 | 8 | 2.6 | 1 | 0 |
| Q9P260 | LisH domain and HEAT repeat-containing protein KIAA1468 | 137628.2 | 6 | 2.6 | 2 | 0 |
| Q9NYV4 | Cyclin-dependent kinase 12 | 164839.1 | 7 | 2.6 | 1 | 0 |
| O95613 | Pericentrin | 369583.2 | 20 | 2.6 | 6 | 0 |
| Q8NDH2 | Coiled-coil domain-containing protein 168 | 279776.4 | 15 | 2.6 | 2 | 0 |
| Q5BJF6 | Outer dense fiber protein 2 | 82546.6 | 3 | 2.6 | 10 | 0 |
| Q68E01 | Integrator complex subunit 3 | 119609.8 | 7 | 2.6 | 1 | 0 |
| Q8IVG5 | Sterile alpha motif domain-containing protein 9-like | 186243.7 | 8 | 2.6 | 1 | 0 |
| Q8IZT6 | Abnormal spindle-like microcephaly-associated protein | 385841.8 | 20 | 2.6 | 7 | 0 |
| Q9P2M7 | Cingulin | 136614.2 | 5 | 2.6 | 1 | 0 |
| P27448 | MAP/microtubule affinity-regulating kinase 3 | 82355.6 | 3 | 2.6 | 7 | 0 |
| Q5TCQ9 | Membrane-associated guanylate kinase, WW and PDZ domain-containing protein 3 | 145329.3 | 3 | 2.6 | 4 | 0 |
| Q8IYT4 | Katanin p60 ATPase-containing subunit A-like 2 | 57302.2 | 2 | 2.6 | 2 | 0 |
| Q8IYW2 | Tetratricopeptide repeat protein 40 | 306979.5 | 11 | 2.6 | 1 | 0 |
| Q86YW9 | Mediator of RNA polymerase II transcription subunit 12-like protein | 242813.8 | 9 | 2.6 | 2 | 0 |
| P0C6U7 | Replicase polyprotein 1a | 500201.7 | 23 | 2.6 | 8 | 0 |
| Q5T4S7 | E3 ubiquitin-protein ligase UBR4 | 580958.0 | 22 | 2.6 | 10 | 0 |
| Q14004 | Cyclin-dependent kinase 13 | 162420.5 | 4 | 2.6 | 2 | 0 |
| Q96JG9 | Zinc finger protein 469 | 414422.2 | 15 | 2.6 | 2 | 0 |
| P0C6X6 | Replicase polyprotein 1ab | 812570.9 | 34 | 2.5 | 10 | 0 |
| P98161 | Polycystin-1 | 467516.5 | 15 | 2.5 | 3 | 0 |
| Q8WXE9 | Stonin-2 | 102798.4 | 3 | 2.5 | 2 | 0 |
| P11532 | Dystrophin | 393673.9 | 22 | 2.5 | 9 | 0 |
| Q86UQ4 | ATP-binding cassette sub-family A member 13 | 551367.3 | 21 | 2.5 | 9 | 0 |
| Q9Y6C5 | Protein patched homolog 2 | 126334.8 | 3 | 2.5 | 1 | 0 |
| Q8TDW7 | Protocadherin Fat 3 | 507483.2 | 23 | 2.5 | 7 | 0 |
| Q9NRD8 | Dual oxidase 2 | 176790.3 | 4 | 2.5 | 1 | 0 |
| Q02388 | Collagen alpha-1(VII) chain | 294713.2 | 15 | 2.5 | 2 | 0 |
| Q96DT5 | Dynein heavy chain 11, axonemal | 525207.0 | 31 | 2.5 | 7 | 0 |
| Q15751 | Probable E3 ubiquitin-protein ligase HERC1 | 539129.2 | 21 | 2.5 | 5 | 0 |
| O75110 | Probable phospholipid-transporting ATPase IIA | 113283.8 | 4 | 2.5 | 2 | 0 |

FIG. 17 (cont'd)

| | | | | | | |
|---|---|---|---|---|---|---|
| Q70CQ2 | Ubiquitin carboxyl-terminal hydrolase 34 | 397112.9 | 15 | 2.5 | 7 | 0 |
| Q96JM3 | Chromosome alignment-maintaining phosphoprotein 1 | 90068.7 | 3 | 2.5 | 1 | 0 |
| O36635 | RNA-directed RNA polymerase L | 251991.4 | 9 | 2.5 | 1 | 0 |
| P31629 | Transcription factor HIVEP2 | 271277.7 | 6 | 2.5 | 1 | 0 |
| P09619 | Platelet-derived growth factor receptor beta | 125051.8 | 6 | 2.4 | 1 | 0 |
| Q86UV5 | Ubiquitin carboxyl-terminal hydrolase 48 | 118105.9 | 5 | 2.4 | 2 | 0 |
| Q8WZ42 | Titin | 635331.7 | 34 | 2.4 | 10 | 0 |
| Q96J65 | Multidrug resistance-associated protein 9 | 153723.4 | 3 | 2.4 | 1 | 0 |
| Q4G0P3 | Hydrocephalus-inducing protein homolog | 581310.5 | 24 | 2.4 | 9 | 0 |
| Q8WUB8 | PHD finger protein 10 | 56963.3 | 2 | 2.4 | 2 | 0 |
| O95622 | Adenylate cyclase type 5 | 122582.0 | 3 | 2.4 | 2 | 0 |
| P23467 | Receptor-type tyrosine-protein phosphatase beta | 230757.9 | 13 | 2.4 | 3 | 0 |
| Q96QP1 | Alpha-protein kinase 1 | 140286.8 | 4 | 2.4 | 1 | 0 |
| Q9UPZ6 | Thrombospondin type-1 domain-containing protein 7A | 192948.4 | 7 | 2.4 | 1 | 0 |
| P0C6X4 | Replicase polyprotein 1ab | 821124.2 | 31 | 2.4 | 9 | 0 |
| Q8IWU2 | Serine/threonine-protein kinase LMTK2 | 166098.2 | 4 | 2.4 | 1 | 0 |
| Q92608 | Dedicator of cytokinesis protein 2 | 213260.4 | 9 | 2.4 | 2 | 0 |
| Q9BXT6 | Putative helicase Mov10l1 | 133663.6 | 3 | 2.4 | 3 | 0 |
| Q9NRF8 | CTP synthase 2 | 66362.0 | 2 | 2.4 | 1 | 0 |
| P0C6X2 | Replicase polyprotein 1ab | 826282.9 | 33 | 2.4 | 9 | 0 |
| P52790 | Hexokinase-3 | 100679.3 | 4 | 2.4 | 5 | 0 |
| Q9NPG3 | Ubinuclein-1 | 122090.9 | 8 | 2.4 | 1 | 0 |
| O60281 | Zinc finger protein 292 | 301255.9 | 11 | 2.4 | 4 | 0 |
| Q04912 | Macrophage-stimulating protein receptor | 152255.0 | 6 | 2.4 | 2 | 0 |
| Q9H2D6 | TRIO and F-actin-binding protein | 260733.5 | 11 | 2.4 | 3 | 0 |
| Q5VST9 | Obscurin | 846371.9 | 36 | 2.4 | 10 | 0 |
| Q8IY18 | Structural maintenance of chromosomes protein 5 | 130061.3 | 5 | 2.4 | 1 | 0 |
| Q8IY85 | EF-hand calcium-binding domain-containing protein 13 | 111212.8 | 6 | 2.4 | 1 | 0 |
| Q8NDW8 | Tetratricopeptide repeat protein 21A | 150710.2 | 8 | 2.4 | 4 | 0 |
| Q9Y4D8 | Probable E3 ubiquitin-protein ligase HECTD4 | 408591.6 | 22 | 2.4 | 5 | 0 |
| P0C6U5 | Replicase polyprotein 1a | 506638.9 | 18 | 2.4 | 3 | 0 |
| Q8IWB6 | Inactive serine/threonine-protein kinase TEX14 | 169212.6 | 10 | 2.3 | 1 | 0 |
| Q9H4L7 | SWI/SNF-related matrix-associated actin-dependent regulator of chromatin subfamily A containing DEAD/H box 1 | 118301.1 | 2 | 2.3 | 2 | 0 |
| O75445 | Usherin | 588001.9 | 15 | 2.3 | 8 | 0 |
| P0C6U3 | Replicase polyprotein 1a | 511828.6 | 18 | 2.3 | 3 | 0 |
| Q9P273 | Teneurin-3 | 305285.0 | 10 | 2.3 | 1 | 0 |
| P56715 | Oxygen-regulated protein 1 | 243513.0 | 12 | 2.3 | 1 | 0 |

FIG. 17 (cont'd)

| | | | | | | |
|---|---|---|---|---|---|---|
| Q8N3P4 | Vacuolar protein sorting-associated protein 8 homolog | 160194.6 | 5 | 2.3 | 3 | 0 |
| Q9BYC2 | Succinyl-CoA:3-ketoacid coenzyme A transferase 2, mitochondrial | 56767.3 | 1 | 2.3 | 1 | 0 |
| Q96L96 | Alpha-protein kinase 3 | 203553.4 | 8 | 2.3 | 2 | 0 |
| Q96M86 | Dynein heavy chain domain-containing protein 1 | 539803.8 | 16 | 2.3 | 3 | 0 |
| O15085 | Rho guanine nucleotide exchange factor 11 | 168560.1 | 3 | 2.3 | 1 | 0 |
| Q86XX4 | Extracellular matrix protein FRAS1 | 454646.5 | 12 | 2.3 | 3 | 0 |
| O14522 | Receptor-type tyrosine-protein phosphatase T | 164922.4 | 7 | 2.3 | 2 | 0 |
| O15417 | Trinucleotide repeat-containing gene 18 protein | 316173.3 | 15 | 2.3 | 3 | 0 |
| Q8TD26 | Chromodomain-helicase-DNA-binding protein 6 | 308264.0 | 13 | 2.3 | 3 | 0 |
| Q8TD84 | Down syndrome cell adhesion molecule-like protein 1 | 214433.4 | 7 | 2.3 | 2 | 0 |
| Q9IFX3 | Non-structural polyprotein 1A | 104120.9 | 2 | 2.3 | 1 | 0 |
| Q9UMZ3 | Phosphatidylinositol phosphatase PTPRQ | 262292.8 | 9 | 2.3 | 2 | 0 |
| P03362 | Gag-Pro-Pol polyprotein | 163995.0 | 8 | 2.3 | 1 | 0 |
| P14078 | Gag-Pro-Pol polyprotein | 164169.1 | 8 | 2.3 | 1 | 0 |
| P23497 | Nuclear autoantigen Sp-100 | 102421.7 | 5 | 2.3 | 2 | 0 |
| Q5TBA9 | Protein furry homolog | 342296.9 | 12 | 2.3 | 3 | 0 |
| Q8I862 | Non-structural polyprotein pORF1 | 187620.7 | 6 | 2.2 | 1 | 0 |
| P36888 | Receptor-type tyrosine-protein kinase FLT3 | 114785.6 | 4 | 2.2 | 1 | 0 |
| Q9HCU4 | Cadherin EGF LAG seven-pass G-type receptor 2 | 322414.2 | 7 | 2.2 | 1 | 0 |
| O43432 | Eukaryotic translation initiation factor 4 gamma 3 | 178106.9 | 8 | 2.2 | 4 | 0 |
| Q5H8C1 | FRAS1-related extracellular matrix protein 1 | 245979.5 | 6 | 2.2 | 1 | 0 |
| Q8N4S9 | MARVEL domain-containing protein 2 | 63938.6 | 3 | 2.2 | 2 | 0 |
| P12111 | Collagen alpha-3(VI) chain | 328793.5 | 16 | 2.2 | 8 | 0 |
| Q32M45 | Anoctamin-4 | 110677.7 | 2 | 2.2 | 2 | 0 |
| Q8WXG9 | G-protein coupled receptor 98 | 615656.6 | 25 | 2.2 | 6 | 0 |
| O75970 | Multiple PDZ domain protein | 220815.0 | 9 | 2.2 | 5 | 0 |
| Q9Y5S2 | Serine/threonine-protein kinase MRCK beta | 196311.6 | 7 | 2.2 | 1 | 0 |
| Q2M1Z3 | Rho GTPase-activating protein 31 | 158353.8 | 3 | 2.2 | 1 | 0 |
| Q9Y6V0 | Protein piccolo | 547391.7 | 18 | 2.2 | 10 | 0 |
| Q5SRE5 | Nucleoporin NUP188 homolog | 191506.6 | 8 | 2.1 | 4 | 0 |
| Q9NYQ7 | Cadherin EGF LAG seven-pass G-type receptor 3 | 363317.4 | 21 | 2.1 | 2 | 0 |
| Q9Y4B5 | Protein SOGA2 | 179028.5 | 5 | 2.1 | 1 | 0 |
| Q15811 | Intersectin-1 | 192460.7 | 3 | 2.1 | 2 | 0 |
| Q8NB66 | Protein unc-13 homolog C | 252850.8 | 12 | 2.1 | 2 | 0 |
| Q9BXT5 | Testis-expressed sequence 15 protein | 319442.6 | 7 | 2.1 | 1 | 0 |
| O75179 | Ankyrin repeat domain-containing protein 17 | 276104.7 | 9 | 2.1 | 2 | 0 |
| P22059 | Oxysterol-binding protein 1 | 90276.1 | 4 | 2.1 | 1 | 0 |

FIG. 17 (cont'd)

| | | | | | |
|---|---|---|---|---|---|
| Q9NZR2 | Low-density lipoprotein receptor-related protein 1B | 535173.0 | 13 | 2.1 | 1 | 0 |
| Q5VYJ5 | MAM and LDL-receptor class A domain-containing protein C10orf112 | 168156.9 | 2 | 2.1 | 1 | 0 |
| Q96T58 | Msx2-interacting protein | 403275.1 | 15 | 2.1 | 3 | 0 |
| P10071 | Transcriptional activator GLI3 | 171517.2 | 4 | 2.1 | 1 | 0 |
| Q9P2N5 | RNA-binding protein 27 | 119174.3 | 6 | 2.1 | 2 | 0 |
| Q8NFP9 | Neurobeachin | 330274.3 | 16 | 2.1 | 3 | 0 |
| Q92794 | Histone acetyltransferase KAT6A | 227708.5 | 13 | 2.1 | 1 | 0 |
| Q96PZ7 | CUB and sushi domain-containing protein 1 | 396967.7 | 16 | 2.1 | 2 | 0 |
| Q9HC10 | Otoferlin | 228269.6 | 6 | 2.1 | 2 | 0 |
| P52294 | Importin subunit alpha-5 | 60963.2 | 1 | 2.0 | 1 | 0 |
| Q99715 | Collagen alpha-1(XII) chain | 329942.2 | 16 | 2.0 | 6 | 0 |
| O43861 | Probable phospholipid-transporting ATPase IIB | 130290.9 | 3 | 2.0 | 2 | 0 |
| P33817 | Major core protein 4a precursor | 103060.9 | 2 | 2.0 | 1 | 0 |
| Q7Z2Y8 | Interferon-induced very large GTPase 1 | 282128.0 | 9 | 2.0 | 1 | 0 |
| Q8IWJ2 | GRIP and coiled-coil domain-containing protein 2 | 196993.4 | 13 | 2.0 | 3 | 0 |
| P09252 | DNA polymerase catalytic subunit | 135645.0 | 3 | 2.0 | 1 | 0 |
| P0C6X5 | Replicase polyprotein 1ab | 766503.7 | 38 | 2.0 | 8 | 0 |
| Q3V6T2 | Girdin | 214163.7 | 10 | 2.0 | 6 | 0 |
| Q9NYV6 | RNA polymerase I-specific transcription initiation factor RRN3 | 74905.8 | 1 | 2.0 | 1 | 0 |
| Q008S8 | Epithelial cell-transforming sequence 2 oncogene-like | 105849.3 | 5 | 2.0 | 2 | 0 |
| Q96RL7 | Vacuolar protein sorting-associated protein 13A | 355446.8 | 9 | 2.0 | 10 | 0 |
| Q9BYW2 | Histone-lysine N-methyltransferase SETD2 | 290619.5 | 11 | 2.0 | 1 | 0 |
| Q9P2D7 | Dynein heavy chain 1, axonemal | 484359.2 | 20 | 2.0 | 10 | 0 |
| Q9UI36 | Dachshund homolog 1 | 76252.5 | 2 | 2.0 | 2 | 0 |
| O43306 | Adenylate cyclase type 6 | 129365.6 | 2 | 2.0 | 2 | 0 |
| P09848 | Lactase-phlorizin hydrolase | 219670.5 | 8 | 2.0 | 1 | 0 |
| P0C6U4 | Replicase polyprotein 1a | 508662.7 | 21 | 2.0 | 4 | 0 |
| Q7Z3Y8 | Keratin, type I cytoskeletal 27 | 50449.7 | 2 | 2.0 | 1 | 0 |
| Q9H6S0 | Probable ATP-dependent RNA helicase YTHDC2 | 161674.4 | 4 | 2.0 | 1 | 0 |
| Q7Z3Y7 | Keratin, type I cytoskeletal 28 | 51194.8 | 2 | 1.9 | 1 | 0 |
| Q9BZ29 | Dedicator of cytokinesis protein 9 | 238670.1 | 15 | 1.9 | 1 | 0 |
| Q9H251 | Cadherin-23 | 349046.7 | 13 | 1.9 | 10 | 0 |
| Q9NT68 | Teneurin-2 | 304357.9 | 18 | 1.9 | 2 | 0 |
| Q709C8 | Vacuolar protein sorting-associated protein 13C | 414905.0 | 17 | 1.9 | 10 | 0 |
| Q7Z3Y9 | Keratin, type I cytoskeletal 26 | 52652.1 | 1 | 1.9 | 1 | 0 |
| P02533 | Keratin, type I cytoskeletal 14 | 51903.7 | 2 | 1.9 | 1 | 0 |
| Q3L8U1 | Chromodomain-helicase-DNA-binding protein 9 | 326902.2 | 17 | 1.9 | 6 | 0 |
| Q6TFL3 | Coiled-coil domain-containing protein 171 | 154629.9 | 6 | 1.9 | 2 | 0 |
| Q8WXX0 | Dynein heavy chain 7, axonemal | 464695.5 | 18 | 1.9 | 4 | 0 |

FIG. 17 (cont'd)

| | | | | | | |
|---|---|---|---|---|---|---|
| P42345 | Serine/threonine-protein kinase mTOR | 290945.3 | 15 | 1.9 | 3 | 0 |
| P02549 | Spectrin alpha chain, erythrocytic 1 | 281098.9 | 11 | 1.9 | 3 | 0 |
| Q96JB1 | Dynein heavy chain 8, axonemal | 516149.5 | 28 | 1.9 | 6 | 0 |
| Q96PN6 | Adenylate cyclase type 10 | 189715.8 | 8 | 1.9 | 1 | 0 |
| Q5VZ46 | Uncharacterized protein KIAA1614 | 127687.4 | 3 | 1.9 | 1 | 36894 |
| O75147 | Obscurin-like protein 1 | 210026.4 | 3 | 1.9 | 1 | 0 |
| Q8NF50 | Dedicator of cytokinesis protein 8 | 235455.4 | 9 | 1.9 | 4 | 0 |
| P13569 | Cystic fibrosis transmembrane conductance regulator | 165895.7 | 5 | 1.8 | 2 | 0 |
| P03369 | Gag-Pol polyprotein | 163155.8 | 4 | 1.8 | 1 | 0 |
| P04585 | Gag-Pol polyprotein | 163182.7 | 4 | 1.8 | 1 | 0 |
| P04588 | Gag-Pol polyprotein | 163263.1 | 2 | 1.8 | 1 | 0 |
| P05959 | Gag-Pol polyprotein | 163259.2 | 6 | 1.8 | 2 | 0 |
| P03366 | Gag-Pol polyprotein | 164429.2 | 4 | 1.8 | 1 | 0 |
| P03367 | Gag-Pol polyprotein | 164420.0 | 3 | 1.8 | 1 | 0 |
| P08581 | Hepatocyte growth factor receptor | 157879.7 | 4 | 1.8 | 1 | 0 |
| Q6ZS30 | Neurobeachin-like protein 1 | 305320.1 | 8 | 1.8 | 2 | 0 |
| Q9H0L4 | Cleavage stimulation factor subunit 2 tau variant | 64664.8 | 2 | 1.8 | 1 | 0 |
| Q9P219 | Protein Daple | 229371.1 | 12 | 1.8 | 1 | 0 |
| O95996 | Adenomatous polyposis coli protein 2 | 215624.5 | 5 | 1.8 | 1 | 0 |
| Q86V48 | Leucine zipper protein 1 | 120845.3 | 5 | 1.8 | 1 | 0 |
| P12882 | Myosin-1 | 224115.3 | 6 | 1.8 | 1 | 0 |
| Q68D86 | Coiled-coil domain-containing protein 102B | 60847.4 | 2 | 1.8 | 1 | 0 |
| Q75N90 | Fibrillin-3 | 320657.8 | 8 | 1.7 | 1 | 0 |
| Q672I1 | Genome polyprotein | 252775.1 | 13 | 1.7 | 1 | 0 |
| Q66479 | Genome polyprotein | 244938.7 | 7 | 1.7 | 3 | 0 |
| Q6P4R8 | Nuclear factor related to kappa-B-binding protein | 140387.0 | 5 | 1.7 | 3 | 0 |
| Q9HCK8 | Chromodomain-helicase-DNA-binding protein 8 | 282954.0 | 11 | 1.7 | 3 | 0 |
| Q9UKN1 | Mucin-12 | 559076.4 | 7 | 1.7 | 1 | 0 |
| Q9H799 | Uncharacterized protein C5orf42 | 350239.8 | 12 | 1.7 | 4 | 0 |
| Q12923 | Tyrosine-protein phosphatase non-receptor type 13 | 278624.5 | 12 | 1.7 | 7 | 0 |
| Q96KV7 | WD repeat-containing protein 90 | 190801.8 | 5 | 1.7 | 2 | 0 |
| A2RUR9 | Coiled-coil domain-containing protein 144A | 150754.7 | 6 | 1.7 | 2 | 0 |
| Q12768 | WASH complex subunit strumpellin | 135199.2 | 4 | 1.6 | 1 | 0 |
| Q8NEZ4 | Histone-lysine N-methyltransferase 2C | 517253.9 | 18 | 1.6 | 6 | 0 |
| Q9Y4I1 | Unconventional myosin-Va | 217133.8 | 9 | 1.6 | 4 | 0 |
| P22105 | Tenascin-X | 468287.7 | 13 | 1.6 | 10 | 0 |
| Q7Z6E9 | E3 ubiquitin-protein ligase RBBP6 | 202477.0 | 5 | 1.6 | 1 | 0 |
| Q9P2L0 | WD repeat-containing protein 35 | 134695.5 | 3 | 1.6 | 2 | 0 |
| Q9P212 | 1-phosphatidylinositol 4,5-bisphosphate phosphodiesterase epsilon-1 | 261908.5 | 6 | 1.6 | 1 | 0 |
| Q9UBL6 | Copine-7 | 67111.6 | 1 | 1.6 | 10 | 0 |
| P00352 | Retinal dehydrogenase 1 | 55489.2 | 3 | 1.6 | 1 | 0 |

FIG. 17 (cont'd)

| | | | | | | |
|---|---|---|---|---|---|---|
| Q7Z5N4 | Protein sidekick-1 | 242064.4 | 6 | 1.6 | 2 | 0 |
| P03186 | Deneddylase | 338929.3 | 9 | 1.6 | 2 | 0 |
| P11217 | Glycogen phosphorylase, muscle form | 92603.9 | 2 | 1.6 | 2 | 0 |
| Q1HVH9 | Deneddylase | 339418.7 | 10 | 1.6 | 2 | 0 |
| P78363 | Retinal-specific ATP-binding cassette transporter | 258396.5 | 7 | 1.6 | 1 | 0 |
| Q9UPA5 | Protein bassoon | 418579.9 | 10 | 1.6 | 1 | 0 |
| Q3KSU8 | Deneddylase | 341575.1 | 9 | 1.6 | 2 | 0 |
| Q96SN8 | CDK5 regulatory subunit-associated protein 2 | 213836.3 | 9 | 1.6 | 3 | 0 |
| Q9NZK5 | Adenosine deaminase CECR1 | 59218.9 | 3 | 1.6 | 1 | 0 |
| P23458 | Tyrosine-protein kinase JAK1 | 135102.2 | 9 | 1.6 | 1 | 0 |
| Q9HC84 | Mucin-5B | 611966.3 | 11 | 1.6 | 1 | 0 |
| Q9P225 | Dynein heavy chain 2, axonemal | 500727.0 | 19 | 1.6 | 5 | 0 |
| P10220 | Deneddylase | 337231.0 | 11 | 1.6 | 1 | 0 |
| Q6UVK1 | Chondroitin sulfate proteoglycan 4 | 251221.4 | 11 | 1.6 | 1 | 0 |
| Q00537 | Cyclin-dependent kinase 17 | 59870.5 | 2 | 1.5 | 2 | 0 |
| Q07864 | DNA polymerase epsilon catalytic subunit A | 264198.6 | 3 | 1.5 | 1 | 0 |
| O00139 | Kinesin-like protein KIF2A | 79694.8 | 3 | 1.5 | 4 | 0 |
| Q96JQ0 | Protocadherin-16 | 346922.6 | 6 | 1.5 | 1 | 0 |
| Q9HCH3 | Copine-5 | 66361.0 | 1 | 1.5 | 8 | 0 |
| Q86UP3 | Zinc finger homeobox protein 4 | 399723.0 | 9 | 1.5 | 3 | 0 |
| P50851 | Lipopolysaccharide-responsive and beige-like anchor protein | 321496.2 | 8 | 1.5 | 5 | 0 |
| Q13796 | Protein Shroom2 | 177607.9 | 8 | 1.5 | 1 | 0 |
| Q9ULD4 | Bromodomain and PHD finger-containing protein 3 | 137399.0 | 4 | 1.5 | 1 | 0 |
| O75376 | Nuclear receptor corepressor 1 | 271122.6 | 6 | 1.5 | 1 | 0 |
| Q6UXZ4 | Netrin receptor UNC5D | 107795.6 | 2 | 1.5 | 2 | 0 |
| P26676 | RNA-directed RNA polymerase L | 258493.5 | 6 | 1.5 | 1 | 0 |
| Q92824 | Proprotein convertase subtilisin/kexin type 5 | 218119.6 | 12 | 1.5 | 1 | 0 |
| A0JNW5 | UHRF1-binding protein 1-like | 165624.5 | 6 | 1.4 | 1 | 0 |
| Q8WWI1 | LIM domain only protein 7 | 190717.7 | 6 | 1.4 | 3 | 0 |
| Q9NYQ6 | Cadherin EGF LAG seven-pass G-type receptor 1 | 334562.1 | 17 | 1.4 | 2 | 0 |
| Q14573 | Inositol 1,4,5-trisphosphate receptor type 3 | 307015.5 | 8 | 1.4 | 1 | 0 |
| Q8IWB9 | Testis-expressed sequence 2 protein | 126278.1 | 2 | 1.4 | 2 | 0 |
| Q9C0D2 | Centrosomal protein KIAA1731 | 296751.9 | 5 | 1.4 | 2 | 0 |
| Q9UKN7 | Unconventional myosin-XV | 397859.4 | 15 | 1.4 | 2 | 0 |
| O43795 | Unconventional myosin-Ib | 133011.7 | 6 | 1.4 | 1 | 0 |
| O60494 | Cubilin | 407518.9 | 7 | 1.4 | 1 | 0 |
| Q9NVV4 | Poly(A) RNA polymerase, mitochondrial | 79688.7 | 1 | 1.4 | 1 | 0 |
| P98160 | Basement membrane-specific heparan sulfate proteoglycan core protein | 479551.6 | 13 | 1.4 | 1 | 0 |
| Q6ZS17 | Protein FAM65A | 134148.9 | 7 | 1.4 | 4 | 0 |
| Q9H0J4 | Glutamine-rich protein 2 | 181340.2 | 5 | 1.4 | 1 | 0 |
| Q9UIF8 | Bromodomain adjacent to zinc finger | 234604.9 | 6 | 1.4 | 5 | 0 |

FIG. 17 (cont'd)

| | domain protein 2B | | | | | |
|---|---|---|---|---|---|---|
| Q15788 | Nuclear receptor coactivator 1 | 156549.5 | 4 | 1.4 | 3 | 0 |
| Q2LD37 | Uncharacterized protein KIAA1109 | 492719.9 | 17 | 1.4 | 10 | 0 |
| Q86VF7 | Nebulin-related-anchoring protein | 196429.0 | 6 | 1.4 | 4 | 0 |
| Q92887 | Canalicular multispecific organic anion transporter 1 | 175348.2 | 4 | 1.4 | 1 | 0 |
| Q9UPS8 | Ankyrin repeat domain-containing protein 26 | 197521.5 | 7 | 1.4 | 1 | 0 |
| Q9H5I5 | Piezo-type mechanosensitive ion channel component 2 | 319452.1 | 10 | 1.3 | 6 | 0 |
| Q6ZQQ2 | Spermatogenesis-associated protein 31D1 | 177272.3 | 6 | 1.3 | 1 | 0 |
| Q16363 | Laminin subunit alpha-4 | 204745.3 | 11 | 1.3 | 2 | 0 |
| Q8IWI9 | MAX gene-associated protein | 333989.9 | 10 | 1.3 | 2 | 0 |
| Q96QB1 | Rho GTPase-activating protein 7 | 172302.5 | 3 | 1.3 | 1 | 0 |
| O94915 | Protein furry homolog-like | 342392.9 | 5 | 1.3 | 1 | 0 |
| P20872 | Envelope glycoprotein gp160 | 100667.1 | 2 | 1.3 | 1 | 0 |
| Q8NDA8 | Maestro heat-like repeat-containing protein family member 1 | 183816.0 | 6 | 1.3 | 1 | 0 |
| Q5THK1 | Protein PRR14L | 241291.9 | 4 | 1.3 | 1 | 0 |
| Q5RHP9 | Uncharacterized protein C1orf173 | 169150.5 | 5 | 1.2 | 1 | 0 |
| Q13635 | Protein patched homolog 1 | 156402.6 | 3 | 1.2 | 4 | 0 |
| Q9UI47 | Catenin alpha-3 | 100835.4 | 1 | 1.2 | 1 | 0 |
| Q6V0I7 | Protocadherin Fat 4 | 546608.0 | 14 | 1.2 | 5 | 0 |
| O60658 | High affinity cAMP-specific and IBMX-insensitive 3',5'-cyclic phosphodiesterase 8A | 94444.7 | 3 | 1.2 | 1 | 0 |
| Q9BYK8 | Helicase with zinc finger domain 2 | 298472.1 | 12 | 1.2 | 2 | 0 |
| Q9NZB2 | Constitutive coactivator of PPAR-gamma-like protein 1 | 122700.5 | 6 | 1.2 | 3 | 0 |
| Q6ZS81 | WD repeat- and FYVE domain-containing protein 4 | 348114.0 | 8 | 1.2 | 3 | 0 |
| Q92766 | Ras-responsive element-binding protein 1 | 187451.3 | 7 | 1.2 | 2 | 0 |
| Q7Z408 | CUB and sushi domain-containing protein 2 | 387738.3 | 4 | 1.2 | 1 | 0 |
| O12158 | Gag-Pol polyprotein | 162868.7 | 7 | 1.1 | 1 | 0 |
| P05961 | Gag-Pol polyprotein | 163357.9 | 6 | 1.1 | 1 | 0 |
| P12035 | Keratin, type II cytoskeletal 3 | 64588.2 | 2 | 1.1 | 6 | 0 |
| Q9P2P1 | Protein NYNRIN | 209849.3 | 7 | 1.1 | 1 | 0 |
| P21359 | Neurofibromin | 321767.3 | 9 | 1.1 | 2 | 0 |
| Q96Q04 | Serine/threonine-protein kinase LMTK3 | 154687.4 | 4 | 1.1 | 1 | 0 |
| P61129 | Zinc finger CCCH domain-containing protein 6 | 132354.3 | 1 | 1.1 | 1 | 0 |
| Q69YH5 | Cell division cycle-associated protein 2 | 114216.2 | 2 | 1.1 | 1 | 0 |
| P24043 | Laminin subunit alpha-2 | 353201.3 | 15 | 1.1 | 1 | 0 |
| Q9C093 | Sperm flagellar protein 2 | 210190.4 | 2 | 1.1 | 2 | 0 |
| Q9Y2Q0 | Probable phospholipid-transporting ATPase IA | 131513.7 | 5 | 1.0 | 3 | 0 |
| Q7Z5J4 | Retinoic acid-induced protein 1 | 203666.5 | 3 | 1.0 | 2 | 0 |
| O75145 | Liprin-alpha-3 | 133501.3 | 6 | 1.0 | 2 | 0 |

FIG. 17 (cont'd)

| | | | | | | |
|---|---|---|---|---|---|---|
| Q8N283 | Ankyrin repeat domain-containing protein 35 | 110878.3 | 4 | 1.0 | 1 | 0 |
| P22607 | Fibroblast growth factor receptor 3 | 89126.8 | 5 | 1.0 | 1 | 0 |
| Q9P2G4 | Microtubule-associated protein 10 | 101428.3 | 1 | 1.0 | 1 | 0 |
| P35963 | Gag-Pol polyprotein | 163120.6 | 2 | 1.0 | 1 | 0 |
| Q8IVV2 | Lipoxygenase homology domain-containing protein 1 | 223886.0 | 9 | 1.0 | 1 | 0 |
| Q86VH2 | Kinesin-like protein KIF27 | 157439.3 | 7 | 1.0 | 4 | 0 |
| Q7Z478 | ATP-dependent RNA helicase DHX29 | 156319.4 | 5 | 1.0 | 1 | 0 |
| O75581 | Low-density lipoprotein receptor-related protein 6 | 183452.1 | 8 | 0.9 | 1 | 0 |
| O15040 | Tectonin beta-propeller repeat-containing protein 2 | 155844.4 | 5 | 0.9 | 1 | 0 |
| Q66GS9 | Centrosomal protein of 135 kDa | 133946.6 | 7 | 0.9 | 1 | 0 |
| Q7Z410 | Transmembrane protease serine 9 | 116188.1 | 3 | 0.9 | 1 | 0 |
| O93215 | Gag-Pol polyprotein | 163261.1 | 7 | 0.8 | 1 | 0 |
| P04936 | Genome polyprotein | 244715.4 | 8 | 0.8 | 1 | 0 |
| Q07889 | Son of sevenless homolog 1 | 153433.8 | 6 | 0.8 | 1 | 0 |
| O14795 | Protein unc-13 homolog B | 182789.0 | 2 | 0.8 | 1 | 0 |
| Q12802 | A-kinase anchor protein 13 | 309934.1 | 4 | 0.8 | 3 | 0 |
| Q96Q06 | Perilipin-4 | 138437.5 | 4 | 0.8 | 2 | 0 |
| Q9P267 | Methyl-CpG-binding domain protein 5 | 161264.0 | 5 | 0.8 | 1 | 0 |
| Q8TDJ6 | DmX-like protein 2 | 319814.1 | 5 | 0.8 | 3 | 0 |
| Q8IVL1 | Neuron navigator 2 | 253434.2 | 6 | 0.7 | 10 | 0 |
| Q9BXT8 | RING finger protein 17 | 187324.0 | 5 | 0.7 | 1 | 0 |
| P42695 | Condensin-2 complex subunit D3 | 171058.1 | 5 | 0.7 | 1 | 0 |
| Q8IWT3 | Cullin-9 | 285620.7 | 11 | 0.7 | 1 | 0 |
| Q76L83 | Putative Polycomb group protein ASXL2 | 155131.7 | 5 | 0.7 | 1 | 0 |
| Q8TDX9 | Polycystic kidney disease protein 1-like 1 | 319655.4 | 6 | 0.7 | 1 | 0 |
| Q0VF96 | Cingulin-like protein 1 | 149649.7 | 3 | 0.7 | 1 | 0 |
| Q5T9S5 | Coiled-coil domain-containing protein 18 | 161189.7 | 3 | 0.7 | 2 | 0 |
| Q8IZQ1 | WD repeat and FYVE domain-containing protein 3 | 398818.7 | 9 | 0.7 | 2 | 0 |
| Q86VI3 | Ras GTPase-activating-like protein IQGAP3 | 185383.4 | 5 | 0.7 | 1 | 0 |
| Q96RT7 | Gamma-tubulin complex component 6 | 200726.4 | 4 | 0.7 | 3 | 0 |
| A2VEC9 | SCO-spondin | 579611.0 | 3 | 0.7 | 1 | 0 |
| Q4KWH8 | 1-phosphatidylinositol 4,5-bisphosphate phosphodiesterase eta-1 | 191333.3 | 6 | 0.7 | 1 | 0 |
| O94953 | Lysine-specific demethylase 4B | 123778.7 | 2 | 0.6 | 1 | 0 |
| Q9BZF9 | Uveal autoantigen with coiled-coil domains and ankyrin repeats | 163646.2 | 7 | 0.6 | 1 | 0 |
| B2C4J3 | RNA-directed RNA polymerase L | 255733.6 | 8 | 0.5 | 1 | 0 |
| A0AVI2 | Fer-1-like protein 5 | 244130.4 | 5 | 0.5 | 1 | 0 |
| A3KMH1 | von Willebrand factor A domain-containing protein 8 | 213901.0 | 6 | 0.5 | 2 | 0 |
| Q13315 | Serine-protein kinase ATM | 355790.6 | 7 | 0.5 | 1 | 0 |
| Q38SD2 | Leucine-rich repeat serine/threonine- | 228529.7 | 7 | 0.5 | 2 | 0 |

| | protein kinase 1 | | | | | |
|---|---|---|---|---|---|---|
| Q7Z5P9 | Mucin-19 | 604455.9 | 14 | 0.5 | 1 | 0 |
| P32537 | Genome polyprotein | 246881.6 | 11 | 0.5 | 1 | 0 |
| Q96L73 | Histone-lysine N-methyltransferase, H3 lysine-36 and H4 lysine-20 specific | 288188.8 | 3 | 0.5 | 3 | 0 |
| Q9DWR1 | Genome polyprotein | 254115.1 | 4 | 0.5 | 2 | 0 |
| Q9Y6R7 | IgGFc-binding protein | 596824.1 | 4 | 0.4 | 1 | 0 |
| P06441 | Genome polyprotein | 254352.5 | 6 | 0.4 | 1 | 0 |
| P13901 | Genome polyprotein | 253880.1 | 6 | 0.4 | 1 | 0 |
| Q6ZR08 | Dynein heavy chain 12, axonemal | 360022.1 | 10 | 0.4 | 1 | 0 |

FIG. 19

| Uniprot ID | Top3 Ratio (SO2H : Unenriched) | Protein Name |
|---|---|---|
| Q6S8J3 | 53.10 | POTE ankyrin domain family member E |
| Q99497 | 24.95 | Protein DJ-1 |
| O43242 | 23.29 | 26S proteasome non-ATPase regulatory subunit 3 |
| Q9Y490 | 15.64 | Talin-1 |
| P39748 | 14.33 | Flap endonuclease 1 |
| P54577 | 9.82 | Tyrosine--tRNA ligase, cytoplasmic |
| Q7L2H7 | 8.54 | Eukaryotic translation initiation factor 3 subunit M |
| Q9P2J5 | 8.11 | Leucine--tRNA ligase, cytoplasmic |
| Q9P258 | 7.99 | Protein RCC2 |
| P00918 | 7.72 | Carbonic anhydrase 2 |
| Q92499 | 7.63 | ATP-dependent RNA helicase DDX1 |
| P37802 | 7.40 | Transgelin-2 |
| Q14257 | 7.29 | Reticulocalbin-2 |
| P41252 | 7.11 | Isoleucine--tRNA ligase, cytoplasmic |
| P00558 | 6.77 | Phosphoglycerate kinase 1 |
| P22314 | 6.62 | Ubiquitin-like modifier-activating enzyme 1 |
| P31939 | 6.46 | Bifunctional purine biosynthesis protein PURH |
| Q02790 | 6.39 | Peptidyl-prolyl cis-trans isomerase FKBP4 |
| Q13547 | 6.31 | Histone deacetylase 1 |
| P07814 | 6.27 | Bifunctional glutamate/proline--tRNA ligase |
| O43776 | 6.26 | Asparagine--tRNA ligase, cytoplasmic |
| P49792 | 6.21 | E3 SUMO-protein ligase RanBP2 |
| P24534 | 6.12 | Elongation factor 1-beta |
| P11586 | 6.08 | C-1-tetrahydrofolate synthase, cytoplasmic |
| P13010 | 6.01 | X-ray repair cross-complementing protein 5 |
| Q13509 | 5.69 | Tubulin beta-3 chain |
| P27348 | 5.68 | 14-3-3 protein theta |
| P62942 | 5.63 | Peptidyl-prolyl cis-trans isomerase FKBP1A |
| P29966 | 5.62 | Myristoylated alanine-rich C-kinase substrate |
| Q9UQE7 | 5.45 | Structural maintenance of chromosomes protein 3 |
| P26196 | 5.22 | Probable ATP-dependent RNA helicase DDX6 |
| P40227 | 5.06 | T-complex protein 1 subunit zeta |
| P04075 | 5.05 | Fructose-bisphosphate aldolase A |
| Q14739 | 5.05 | Lamin-B receptor |
| P22102 | 4.99 | Trifunctional purine biosynthetic protein adenosine-3 |
| P56192 | 4.97 | Methionine--tRNA ligase, cytoplasmic |
| Q15046 | 4.91 | Lysine--tRNA ligase |
| Q9Y4L1 | 4.83 | Hypoxia up-regulated protein 1 |

FIG. 19 (cont'd)

| O00425 | 4.75 | Insulin-like growth factor 2 mRNA-binding protein 3 |
|---|---|---|
| Q9Y3F4 | 4.73 | Serine-threonine kinase receptor-associated protein |
| P27816 | 4.69 | Microtubule-associated protein 4 |
| P35998 | 4.68 | 26S protease regulatory subunit 7 |
| P55786 | 4.63 | Puromycin-sensitive aminopeptidase |
| Q9Y3I0 | 4.62 | tRNA-splicing ligase RtcB homolog |
| P31948 | 4.54 | Stress-induced-phosphoprotein 1 |
| Q99798 | 4.45 | Aconitate hydratase, mitochondrial |
| Q15181 | 4.45 | Inorganic pyrophosphatase |
| Q09666 | 4.33 | Neuroblast differentiation-associated protein AHNAK |
| Q04760 | 4.32 | Lactoylglutathione lyase |
| P39687 | 4.31 | Acidic leucine-rich nuclear phosphoprotein 32 family member A |
| P30041 | 4.29 | Peroxiredoxin-6 |
| P41250 | 4.26 | Glycine--tRNA ligase |
| P12268 | 4.23 | Inosine-5'-monophosphate dehydrogenase 2 |
| Q9UQ80 | 4.20 | Proliferation-associated protein 2G4 |
| P05455 | 4.17 | Lupus La protein |
| O76094 | 4.15 | Signal recognition particle subunit SRP72 |
| P49321 | 4.12 | Nuclear autoantigenic sperm protein |
| O94826 | 4.08 | Mitochondrial import receptor subunit TOM70 |
| Q7L014 | 4.07 | Probable ATP-dependent RNA helicase DDX46 |
| Q99460 | 4.07 | 26S proteasome non-ATPase regulatory subunit 1 |
| P15311 | 4.07 | Ezrin |
| P99999 | 4.04 | Cytochrome c |
| P13797 | 4.02 | Plastin-3 |
| P23528 | 3.97 | Cofilin-1 |
| Q14683 | 3.88 | Structural maintenance of chromosomes protein 1A |
| P42166 | 3.87 | Lamina-associated polypeptide 2, isoform alpha |
| Q9Y617 | 3.85 | Phosphoserine aminotransferase |
| P10599 | 3.83 | Thioredoxin |
| Q13283 | 3.80 | Ras GTPase-activating protein-binding protein 1 |
| Q9Y224 | 3.76 | UPF0568 protein C14orf166 |
| Q01518 | 3.67 | Adenylyl cyclase-associated protein 1 |
| O43175 | 3.66 | D-3-phosphoglycerate dehydrogenase |
| Q9NSE4 | 3.63 | Isoleucine--tRNA ligase, mitochondrial |
| P12277 | 3.54 | Creatine kinase B-type |
| Q9Y2L1 | 3.47 | Exosome complex exonuclease RRP44 |
| P83916 | 3.45 | Chromobox protein homolog 1 |
| Q13423 | 3.42 | NAD(P) transhydrogenase, mitochondrial |
| P12956 | 3.40 | X-ray repair cross-complementing protein 6 |
| P48643 | 3.39 | T-complex protein 1 subunit epsilon |
| P30101 | 3.39 | Protein disulfide-isomerase A3 |
| P04406 | 3.35 | Glyceraldehyde-3-phosphate dehydrogenase |
| P17987 | 3.33 | T-complex protein 1 subunit alpha |
| P46940 | 3.32 | Ras GTPase-activating-like protein IQGAP1 |

FIG. 19 (cont'd)

| | | |
|---|---|---|
| Q04917 | 3.29 | 14-3-3 protein eta |
| P62081 | 3.25 | 40S ribosomal protein S7 |
| P15531 | 3.25 | Nucleoside diphosphate kinase A |
| P37837 | 3.23 | Transaldolase |
| P23526 | 3.21 | Adenosylhomocysteinase |
| P40925 | 3.20 | Malate dehydrogenase, cytoplasmic |
| P50990 | 3.14 | T-complex protein 1 subunit theta |
| P27695 | 3.09 | DNA-(apurinic or apyrimidinic site) lyase |
| P06744 | 3.08 | Glucose-6-phosphate isomerase |
| P22234 | 3.08 | Multifunctional protein ADE2 |
| P55036 | 3.05 | 26S proteasome non-ATPase regulatory subunit 4 |
| P13995 | 3.02 | Bifunctional methylenetetrahydrofolate dehydrogenase/cyclohydrolase, mitochondrial |
| O75131 | 3.01 | Copine-3 |
| P26641 | 2.99 | Elongation factor 1-gamma |
| P00492 | 2.98 | Hypoxanthine-guanine phosphoribosyltransferase |
| P43487 | 2.98 | Ran-specific GTPase-activating protein |
| P17980 | 2.97 | 26S protease regulatory subunit 6A |
| P46778 | 2.97 | 60S ribosomal protein L21 |
| P63104 | 2.96 | 14-3-3 protein zeta/delta |
| P25205 | 2.93 | DNA replication licensing factor MCM3 |
| P25398 | 2.92 | 40S ribosomal protein S12 |
| P23284 | 2.91 | Peptidyl-prolyl cis-trans isomerase B |
| Q06830 | 2.91 | Peroxiredoxin-1 |
| Q96SI9 | 2.81 | Spermatid perinuclear RNA-binding protein |
| P31040 | 2.80 | Succinate dehydrogenase [ubiquinone] flavoprotein subunit, mitochondrial |
| P13693 | 2.79 | Translationally-controlled tumor protein |
| P13639 | 2.74 | Elongation factor 2 |
| Q13310 | 2.74 | Polyadenylate-binding protein 4 |
| P40939 | 2.68 | Trifunctional enzyme subunit alpha, mitochondrial |
| Q13162 | 2.67 | Peroxiredoxin-4 |
| P27797 | 2.65 | Calreticulin |
| P48047 | 2.64 | ATP synthase subunit O, mitochondrial |
| Q96A35 | 2.64 | 39S ribosomal protein L24, mitochondrial |
| P31946 | 2.61 | 14-3-3 protein beta/alpha |
| Q71U36 | 2.61 | Tubulin alpha-1A chain |
| P39023 | 2.58 | 60S ribosomal protein L3 |
| P34931 | 2.54 | Heat shock 70 kDa protein 1-like |
| Q00341 | 2.54 | Vigilin |
| P07437 | 2.52 | Tubulin beta chain |
| P35579 | 2.52 | Myosin-9 |
| P46060 | 2.50 | Ran GTPase-activating protein 1 |
| O14980 | 2.45 | Exportin-1 |
| Q86VP6 | 2.44 | Cullin-associated NEDD8-dissociated protein 1 |
| P42704 | 2.43 | Leucine-rich PPR motif-containing protein, mitochondrial |

FIG. 19 (cont'd)

| | | |
|---|---|---|
| O43707 | 2.38 | Alpha-actinin-4 |
| Q02543 | 2.35 | 60S ribosomal protein L18a |
| P05091 | 2.34 | Aldehyde dehydrogenase, mitochondrial |
| Q13011 | 2.33 | Delta(3,5)-Delta(2,4)-dienoyl-CoA isomerase, mitochondrial |
| P13667 | 2.29 | Protein disulfide-isomerase A4 |
| Q96I99 | 2.27 | Succinyl-CoA ligase [GDP-forming] subunit beta, mitochondrial |
| P10515 | 2.26 | Dihydrolipoyllysine-residue acetyltransferase component of pyruvate dehydrogenase complex, mitochondrial |
| P09874 | 2.25 | Poly [ADP-ribose] polymerase 1 |
| Q9NX63 | 2.25 | Coiled-coil-helix-coiled-coil-helix domain-containing protein 3, mitochondrial |
| Q15050 | 2.23 | Ribosome biogenesis regulatory protein homolog |
| P68104 | 2.23 | Elongation factor 1-alpha 1 |
| Q9UMS4 | 2.22 | Pre-mRNA-processing factor 19 |
| Q15365 | 2.21 | Poly(rC)-binding protein 1 |
| P61981 | 2.21 | 14-3-3 protein gamma |
| P50395 | 2.20 | Rab GDP dissociation inhibitor beta |
| P50454 | 2.20 | Serpin H1 |
| P12270 | 2.18 | Nucleoprotein TPR |
| P62826 | 2.17 | GTP-binding nuclear protein Ran |
| P33316 | 2.17 | Deoxyuridine 5'-triphosphate nucleotidohydrolase, mitochondrial |
| Q9BVK6 | 2.16 | Transmembrane emp24 domain-containing protein 9 |
| P62937 | 2.13 | Peptidyl-prolyl cis-trans isomerase A |
| Q13151 | 2.12 | Heterogeneous nuclear ribonucleoprotein A0 |
| Q99459 | 2.10 | Cell division cycle 5-like protein |
| P50991 | 2.09 | T-complex protein 1 subunit delta |
| P24752 | 2.08 | Acetyl-CoA acetyltransferase, mitochondrial |
| P30084 | 2.08 | Enoyl-CoA hydratase, mitochondrial |
| Q9H7B2 | 2.08 | Ribosome production factor 2 homolog |
| P07195 | 2.07 | L-lactate dehydrogenase B chain |
| P46776 | 2.07 | 60S ribosomal protein L27a |
| P68371 | 2.07 | Tubulin beta-4B chain |
| P39019 | 2.04 | 40S ribosomal protein S19 |
| P16949 | 2.03 | Stathmin |
| P22087 | 2.03 | rRNA 2'-O-methyltransferase fibrillarin |
| Q14974 | 2.03 | Importin subunit beta-1 |
| P18754 | 2.02 | Regulator of chromosome condensation |
| Q03252 | 2.00 | Lamin-B2 |
| Q15459 | 2.00 | Splicing factor 3A subunit 1 |
| Q9Y265 | 1.99 | RuvB-like 1 |
| Q1KMD3 | 1.97 | Heterogeneous nuclear ribonucleoprotein U-like protein 2 |
| Q6NVV1 | 1.96 | Putative 60S ribosomal protein L13a-like MGC87657 |
| P62195 | 1.94 | 26S protease regulatory subunit 8 |
| P55060 | 1.93 | Exportin-2 |
| P62753 | 1.93 | 40S ribosomal protein S6 |
| P46782 | 1.91 | 40S ribosomal protein S5 |

FIG. 19 (cont'd)

| Q01780 | 1.89 | Exosome component 10 |
|---|---|---|
| Q3ZCM7 | 1.89 | Tubulin beta-8 chain |
| P36776 | 1.88 | Lon protease homolog, mitochondrial |
| P06493 | 1.88 | Cyclin-dependent kinase 1 |
| P62917 | 1.87 | 60S ribosomal protein L8 |
| P15880 | 1.86 | 40S ribosomal protein S2 |
| P62244 | 1.85 | 40S ribosomal protein S15a |
| P55072 | 1.84 | Transitional endoplasmic reticulum ATPase |
| P22061 | 1.82 | Protein-L-isoaspartate(D-aspartate) O-methyltransferase |
| P30050 | 1.82 | 60S ribosomal protein L12 |
| P16989 | 1.81 | Y-box-binding protein 3 |
| Q99832 | 1.80 | T-complex protein 1 subunit eta |
| P19338 | 1.80 | Nucleolin |
| Q9NZI8 | 1.78 | Insulin-like growth factor 2 mRNA-binding protein 1 |
| P40926 | 1.78 | Malate dehydrogenase, mitochondrial |
| P50502 | 1.77 | Hsc70-interacting protein |
| Q9Y5B9 | 1.77 | FACT complex subunit SPT16 |
| Q14566 | 1.75 | DNA replication licensing factor MCM6 |
| Q15185 | 1.74 | Prostaglandin E synthase 3 |
| P11021 | 1.74 | 78 kDa glucose-regulated protein |
| P78371 | 1.72 | T-complex protein 1 subunit beta |
| P84098 | 1.72 | 60S ribosomal protein L19 |
| Q86UP2 | 1.71 | Kinectin |
| P20700 | 1.71 | Lamin-B1 |
| P03243 | 1.71 | E1B protein, large T-antigen |
| Q14980 | 1.71 | Nuclear mitotic apparatus protein 1 |
| P46777 | 1.69 | 60S ribosomal protein L5 |
| P38646 | 1.68 | Stress-70 protein, mitochondrial |
| Q92945 | 1.68 | Far upstream element-binding protein 2 |
| O00567 | 1.67 | Nucleolar protein 56 |
| O75390 | 1.67 | Citrate synthase, mitochondrial |
| O95292 | 1.67 | Vesicle-associated membrane protein-associated protein B/C |
| P09622 | 1.66 | Dihydrolipoyl dehydrogenase, mitochondrial |
| Q9HAV7 | 1.66 | GrpE protein homolog 1, mitochondrial |
| P27694 | 1.65 | Replication protein A 70 kDa DNA-binding subunit |
| Q9Y262 | 1.64 | Eukaryotic translation initiation factor 3 subunit L |
| Q13185 | 1.63 | Chromobox protein homolog 3 |
| Q12905 | 1.62 | Interleukin enhancer-binding factor 2 |
| P26583 | 1.62 | High mobility group protein B2 |
| P08238 | 1.60 | Heat shock protein HSP 90-beta |
| Q08211 | 1.60 | ATP-dependent RNA helicase A |
| Q99873 | 1.58 | Protein arginine N-methyltransferase 1 |
| P49411 | 1.57 | Elongation factor Tu, mitochondrial |
| P10809 | 1.56 | 60 kDa heat shock protein, mitochondrial |
| Q9BUF5 | 1.56 | Tubulin beta-6 chain |

FIG. 19 (cont'd)

| Q07021 | 1.55 | Complement component 1 Q subcomponent-binding protein, mitochondrial |
|---|---|---|
| P04080 | 1.54 | Cystatin-B |
| P06576 | 1.54 | ATP synthase subunit beta, mitochondrial |
| P06733 | 1.54 | Alpha-enolase |
| Q13885 | 1.53 | Tubulin beta-2A chain |
| P60174 | 1.53 | Triosephosphate isomerase |
| P61313 | 1.53 | 60S ribosomal protein L15 |
| P00505 | 1.51 | Aspartate aminotransferase, mitochondrial |
| Q15019 | 1.51 | Septin-2 |
| Q14157 | 1.50 | Ubiquitin-associated protein 2-like |
| P12814 | 1.50 | Alpha-actinin-1 |
| P09211 | 1.50 | Glutathione S-transferase P |
| P14618 | 1.48 | Pyruvate kinase PKM |
| P07737 | 1.48 | Profilin-1 |
| Q9P035 | 1.48 | Very-long-chain (3R)-3-hydroxyacyl-[acyl-carrier protein] dehydratase 3 |
| Q07065 | 1.47 | Cytoskeleton-associated protein 4 |
| P12236 | 1.47 | ADP/ATP translocase 3 |
| P13804 | 1.46 | Electron transfer flavoprotein subunit alpha, mitochondrial |
| Q9H0A0 | 1.46 | N-acetyltransferase 10 |
| P63244 | 1.45 | Guanine nucleotide-binding protein subunit beta-2-like 1 |
| P36578 | 1.45 | 60S ribosomal protein L4 |
| P62888 | 1.44 | 60S ribosomal protein L30 |
| Q01105 | 1.43 | Protein SET |
| P55769 | 1.43 | NHP2-like protein 1 |
| Q9Y6M1 | 1.43 | Insulin-like growth factor 2 mRNA-binding protein 2 |
| P62979 | 1.42 | Ubiquitin-40S ribosomal protein S27a |
| P49368 | 1.42 | T-complex protein 1 subunit gamma |
| P07237 | 1.42 | Protein disulfide-isomerase |
| P0CW22 | 1.41 | 40S ribosomal protein S17-like |
| Q9UNL2 | 1.41 | Translocon-associated protein subunit gamma |
| O43390 | 1.41 | Heterogeneous nuclear ribonucleoprotein R |
| Q96AE4 | 1.40 | Far upstream element-binding protein 1 |
| Q53H12 | 1.40 | Acylglycerol kinase, mitochondrial |
| Q12874 | 1.40 | Splicing factor 3A subunit 3 |
| Q9Y2X3 | 1.39 | Nucleolar protein 58 |
| Q08945 | 1.38 | FACT complex subunit SSRP1 |
| P21333 | 1.37 | Filamin-A |
| P39656 | 1.37 | Dolichyl-diphosphooligosaccharide--protein glycosyltransferase 48 kDa subunit |
| O15371 | 1.37 | Eukaryotic translation initiation factor 3 subunit D |
| Q96QK1 | 1.36 | Vacuolar protein sorting-associated protein 35 |
| P07954 | 1.36 | Fumarate hydratase, mitochondrial |
| Q9GZL7 | 1.34 | Ribosome biogenesis protein WDR12 |
| O43852 | 1.28 | Calumenin |
| P83881 | 1.28 | 60S ribosomal protein L36a |
| Q13263 | 1.27 | Transcription intermediary factor 1-beta |

FIG. 19 (cont'd)

| P31943 | 1.24 | Heterogeneous nuclear ribonucleoprotein H |
| --- | --- | --- |
| P47985 | 1.24 | Cytochrome b-c1 complex subunit Rieske, mitochondrial |
| O75533 | 1.23 | Splicing factor 3B subunit 1 |
| Q8TAA3 | 1.23 | Proteasome subunit alpha type-7-like |
| O14818 | 1.23 | Proteasome subunit alpha type-7 |
| Q9NYU2 | 1.22 | UDP-glucose:glycoprotein glucosyltransferase 1 |
| Q9H2U2 | 1.21 | Inorganic pyrophosphatase 2, mitochondrial |
| O75643 | 1.20 | U5 small nuclear ribonucleoprotein 200 kDa helicase |
| Q9BQE3 | 1.20 | Tubulin alpha-1C chain |
| Q02878 | 1.19 | 60S ribosomal protein L6 |
| P30837 | 1.18 | Aldehyde dehydrogenase X, mitochondrial |
| P07900 | 1.15 | Heat shock protein HSP 90-alpha |
| P14866 | 1.15 | Heterogeneous nuclear ribonucleoprotein L |
| Q00610 | 1.14 | Clathrin heavy chain 1 |
| Q13813 | 1.14 | Spectrin alpha chain, non-erythrocytic 1 |
| P14314 | 1.14 | Glucosidase 2 subunit beta |
| P62906 | 1.14 | 60S ribosomal protein L10a |
| P60891 | 1.13 | Ribose-phosphate pyrophosphokinase 1 |
| Q15287 | 1.12 | RNA-binding protein with serine-rich domain 1 |
| P63167 | 1.12 | Dynein light chain 1, cytoplasmic |
| P08133 | 1.11 | Annexin A6 |
| P14625 | 1.11 | Endoplasmin |
| Q16891 | 1.11 | Mitochondrial inner membrane protein |
| Q92598 | 1.10 | Heat shock protein 105 kDa |
| P35637 | 1.10 | RNA-binding protein FUS |
| P23246 | 1.10 | Splicing factor, proline- and glutamine-rich |
| Q07666 | 1.10 | KH domain-containing, RNA-binding, signal transduction-associated protein 1 |
| P13929 | 1.10 | Beta-enolase |
| O76021 | 1.08 | Ribosomal L1 domain-containing protein 1 |
| P30048 | 1.07 | Thioredoxin-dependent peroxide reductase, mitochondrial |
| Q15029 | 1.06 | 116 kDa U5 small nuclear ribonucleoprotein component |
| P62241 | 1.06 | 40S ribosomal protein S8 |
| P42167 | 1.06 | Lamina-associated polypeptide 2, isoforms beta/gamma |
| P62857 | 1.05 | 40S ribosomal protein S28 |
| P26368 | 1.04 | Splicing factor U2AF 65 kDa subunit |
| P05023 | 1.03 | Sodium/potassium-transporting ATPase subunit alpha-1 |
| Q92804 | 1.03 | TATA-binding protein-associated factor 2N |
| Q14697 | 1.03 | Neutral alpha-glucosidase AB |
| Q96I24 | 1.02 | Far upstream element-binding protein 3 |
| Q9HB71 | 1.02 | Calcyclin-binding protein |
| P11310 | 1.02 | Medium-chain specific acyl-CoA dehydrogenase, mitochondrial |
| P53618 | 1.01 | Coatomer subunit beta |
| P28074 | 1.00 | Proteasome subunit beta type-5 |
| Q9UJZ1 | 0.99 | Stomatin-like protein 2, mitochondrial |
| P62995 | 0.98 | Transformer-2 protein homolog beta |

FIG. 19 (cont'd)

| | | |
|---|---|---|
| P33991 | 0.98 | DNA replication licensing factor MCM4 |
| Q9UKV3 | 0.97 | Apoptotic chromatin condensation inducer in the nucleus |
| P62424 | 0.96 | 60S ribosomal protein L7a |
| P61353 | 0.95 | 60S ribosomal protein L27 |
| P35221 | 0.95 | Catenin alpha-1 |
| P35580 | 0.94 | Myosin-10 |
| P27824 | 0.94 | Calnexin |
| O43172 | 0.93 | U4/U6 small nuclear ribonucleoprotein Prp4 |
| Q6P2Q9 | 0.92 | Pre-mRNA-processing-splicing factor 8 |
| O75694 | 0.91 | Nuclear pore complex protein Nup155 |
| Q96DB5 | 0.89 | Regulator of microtubule dynamics protein 1 |
| P08670 | 0.89 | Vimentin |
| P61247 | 0.88 | 40S ribosomal protein S3a |
| P04350 | 0.88 | Tubulin beta-4A chain |
| O75369 | 0.88 | Filamin-B |
| O95202 | 0.86 | LETM1 and EF-hand domain-containing protein 1, mitochondrial |
| P60709 | 0.86 | Actin, cytoplasmic 1 |
| B2RPK0 | 0.86 | Putative high mobility group protein B1-like 1 |
| P18077 | 0.86 | 60S ribosomal protein L35a |
| Q9NYF8 | 0.85 | Bcl-2-associated transcription factor 1 |
| Q13765 | 0.84 | Nascent polypeptide-associated complex subunit alpha |
| Q8NC51 | 0.83 | Plasminogen activator inhibitor 1 RNA-binding protein |
| P32969 | 0.82 | 60S ribosomal protein L9 |
| Q9H9B4 | 0.82 | Sideroflexin-1 |
| O00148 | 0.82 | ATP-dependent RNA helicase DDX39A |
| P02545 | 0.81 | Prelamin-A/C |
| Q9BXP5 | 0.81 | Serrate RNA effector molecule homolog |
| P52907 | 0.80 | F-actin-capping protein subunit alpha-1 |
| P52272 | 0.80 | Heterogeneous nuclear ribonucleoprotein M |
| P84077 | 0.79 | ADP-ribosylation factor 1 |
| Q7Z7K6 | 0.79 | Centromere protein V |
| P05141 | 0.79 | ADP/ATP translocase 2 |
| P78527 | 0.79 | DNA-dependent protein kinase catalytic subunit |
| Q96PK6 | 0.79 | RNA-binding protein 14 |
| O43143 | 0.78 | Putative pre-mRNA-splicing factor ATP-dependent RNA helicase DHX15 |
| P62701 | 0.78 | 40S ribosomal protein S4, X isoform |
| P62314 | 0.77 | Small nuclear ribonucleoprotein Sm D1 |
| Q9Y3B4 | 0.77 | Pre-mRNA branch site protein p14 |
| O00264 | 0.76 | Membrane-associated progesterone receptor component 1 |
| P53999 | 0.76 | Activated RNA polymerase II transcriptional coactivator p15 |
| Q9BZZ5 | 0.75 | Apoptosis inhibitor 5 |
| P11177 | 0.75 | Pyruvate dehydrogenase E1 component subunit beta, mitochondrial |
| P63208 | 0.74 | S-phase kinase-associated protein 1 |
| Q13838 | 0.74 | Spliceosome RNA helicase DDX39B |
| Q14498 | 0.73 | RNA-binding protein 39 |

FIG. 19 (cont'd)

| P61604 | 0.73 | 10 kDa heat shock protein, mitochondrial |
|---|---|---|
| P00338 | 0.73 | L-lactate dehydrogenase A chain |
| P61326 | 0.73 | Protein mago nashi homolog |
| P52597 | 0.72 | Heterogeneous nuclear ribonucleoprotein F |
| O14979 | 0.72 | Heterogeneous nuclear ribonucleoprotein D-like |
| P18621 | 0.71 | 60S ribosomal protein L17 |
| Q02880 | 0.71 | DNA topoisomerase 2-beta |
| P21796 | 0.70 | Voltage-dependent anion-selective channel protein 1 |
| P43246 | 0.70 | DNA mismatch repair protein Msh2 |
| P35268 | 0.70 | 60S ribosomal protein L22 |
| P78347 | 0.70 | General transcription factor II-I |
| Q8IYB3 | 0.70 | Serine/arginine repetitive matrix protein 1 |
| Q14684 | 0.70 | Ribosomal RNA processing protein 1 homolog B |
| Q12931 | 0.69 | Heat shock protein 75 kDa, mitochondrial |
| Q07020 | 0.67 | 60S ribosomal protein L18 |
| P04843 | 0.67 | Dolichyl-diphosphooligosaccharide--protein glycosyltransferase subunit 1 |
| P08107 | 0.67 | Heat shock 70 kDa protein 1A/1B |
| P42766 | 0.65 | 60S ribosomal protein L35 |
| Q9BVJ6 | 0.65 | U3 small nucleolar RNA-associated protein 14 homolog A |
| O43684 | 0.64 | Mitotic checkpoint protein BUB3 |
| Q96EP5 | 0.64 | DAZ-associated protein 1 |
| P12532 | 0.64 | Creatine kinase U-type, mitochondrial |
| Q7Z4V5 | 0.64 | Hepatoma-derived growth factor-related protein 2 |
| P51991 | 0.63 | Heterogeneous nuclear ribonucleoprotein A3 |
| Q00839 | 0.63 | Heterogeneous nuclear ribonucleoprotein U |
| P60866 | 0.63 | 40S ribosomal protein S20 |
| Q5JRX3 | 0.62 | Presequence protease, mitochondrial |
| P56537 | 0.61 | Eukaryotic translation initiation factor 6 |
| P28838 | 0.60 | Cytosol aminopeptidase |
| Q01130 | 0.60 | Serine/arginine-rich splicing factor 2 |
| P43243 | 0.59 | Matrin-3 |
| Q15393 | 0.59 | Splicing factor 3B subunit 3 |
| P09234 | 0.59 | U1 small nuclear ribonucleoprotein C |
| Q99623 | 0.59 | Prohibitin-2 |
| P25705 | 0.58 | ATP synthase subunit alpha, mitochondrial |
| P29692 | 0.57 | Elongation factor 1-delta |
| P46779 | 0.57 | 60S ribosomal protein L28 |
| P26599 | 0.56 | Polypyrimidine tract-binding protein 1 |
| Q15233 | 0.56 | Non-POU domain-containing octamer-binding protein |
| Q09028 | 0.56 | Histone-binding protein RBBP4 |
| Q9Y3C6 | 0.55 | Peptidyl-prolyl cis-trans isomerase-like 1 |
| P62318 | 0.54 | Small nuclear ribonucleoprotein Sm D3 |
| P62263 | 0.54 | 40S ribosomal protein S14 |
| P55884 | 0.53 | Eukaryotic translation initiation factor 3 subunit B |
| O60812 | 0.53 | Heterogeneous nuclear ribonucleoprotein C-like 1 |

FIG. 19 (cont'd)

| P55795 | 0.53 | Heterogeneous nuclear ribonucleoprotein H2 |
|---|---|---|
| P30044 | 0.51 | Peroxiredoxin-5, mitochondrial |
| P50213 | 0.51 | Isocitrate dehydrogenase [NAD] subunit alpha, mitochondrial |
| O60506 | 0.50 | Heterogeneous nuclear ribonucleoprotein Q |
| P00387 | 0.50 | NADH-cytochrome b5 reductase 3 |
| Q92841 | 0.50 | Probable ATP-dependent RNA helicase DDX17 |
| Q00325 | 0.50 | Phosphate carrier protein, mitochondrial |
| Q13428 | 0.49 | Treacle protein |
| P09651 | 0.49 | Heterogeneous nuclear ribonucleoprotein A1 |
| P28066 | 0.49 | Proteasome subunit alpha type-5 |
| O94906 | 0.49 | Pre-mRNA-processing factor 6 |
| P38919 | 0.48 | Eukaryotic initiation factor 4A-III |
| P61289 | 0.48 | Proteasome activator complex subunit 3 |
| P26373 | 0.47 | 60S ribosomal protein L13 |
| P49755 | 0.47 | Transmembrane emp24 domain-containing protein 10 |
| Q9Y277 | 0.47 | Voltage-dependent anion-selective channel protein 3 |
| P62136 | 0.46 | Serine/threonine-protein phosphatase PP1-alpha catalytic subunit |
| P61956 | 0.46 | Small ubiquitin-related modifier 2 |
| P23396 | 0.46 | 40S ribosomal protein S3 |
| P22626 | 0.46 | Heterogeneous nuclear ribonucleoproteins A2/B1 |
| P67809 | 0.46 | Nuclease-sensitive element-binding protein 1 |
| Q05639 | 0.45 | Elongation factor 1-alpha 2 |
| Q08170 | 0.45 | Serine/arginine-rich splicing factor 4 |
| P48444 | 0.45 | Coatomer subunit delta |
| P62847 | 0.45 | 40S ribosomal protein S24 |
| O75367 | 0.45 | Core histone macro-H2A.1 |
| P06730 | 0.44 | Eukaryotic translation initiation factor 4E |
| Q9UJS0 | 0.44 | Calcium-binding mitochondrial carrier protein Aralar2 |
| P18124 | 0.44 | 60S ribosomal protein L7 |
| P35613 | 0.43 | Basigin |
| P53396 | 0.42 | ATP-citrate synthase |
| P60842 | 0.42 | Eukaryotic initiation factor 4A-I |
| Q14103 | 0.41 | Heterogeneous nuclear ribonucleoprotein D0 |
| P38117 | 0.41 | Electron transfer flavoprotein subunit beta |
| P62277 | 0.40 | 40S ribosomal protein S13 |
| P54819 | 0.39 | Adenylate kinase 2, mitochondrial |
| Q9Y5S9 | 0.38 | RNA-binding protein 8A |
| Q5BKZ1 | 0.38 | DBIRD complex subunit ZNF326 |
| P62304 | 0.38 | Small nuclear ribonucleoprotein E |
| P04637 | 0.37 | Cellular tumor antigen p53 |
| Q99729 | 0.37 | Heterogeneous nuclear ribonucleoprotein A/B |
| Q15637 | 0.37 | Splicing factor 1 |
| P08559 | 0.37 | Pyruvate dehydrogenase E1 component subunit alpha, somatic form, mitochondrial |
| Q14444 | 0.36 | Caprin-1 |

FIG. 19 (cont'd)

| P08621 | 0.36 | U1 small nuclear ribonucleoprotein 70 kDa |
| --- | --- | --- |
| Q15717 | 0.36 | ELAV-like protein 1 |
| P05388 | 0.35 | 60S acidic ribosomal protein P0 |
| O95831 | 0.35 | Apoptosis-inducing factor 1, mitochondrial |
| P17844 | 0.35 | Probable ATP-dependent RNA helicase DDX5 |
| P41091 | 0.35 | Eukaryotic translation initiation factor 2 subunit 3 |
| P55209 | 0.34 | Nucleosome assembly protein 1-like 1 |
| P45880 | 0.33 | Voltage-dependent anion-selective channel protein 2 |
| Q13148 | 0.33 | TAR DNA-binding protein 43 |
| Q01081 | 0.32 | Splicing factor U2AF 35 kDa subunit |
| P62269 | 0.31 | 40S ribosomal protein S18 |
| P61978 | 0.30 | Heterogeneous nuclear ribonucleoprotein K |
| P07197 | 0.30 | Neurofilament medium polypeptide |
| P06748 | 0.30 | Nucleophosmin |
| O00571 | 0.30 | ATP-dependent RNA helicase DDX3X |
| P12235 | 0.29 | ADP/ATP translocase 1 |
| Q8NBS9 | 0.28 | Thioredoxin domain-containing protein 5 |
| P11388 | 0.27 | DNA topoisomerase 2-alpha |
| P04844 | 0.26 | Dolichyl-diphosphooligosaccharide--protein glycosyltransferase subunit 2 |
| Q12906 | 0.26 | Interleukin enhancer-binding factor 3 |
| Q5T8P6 | 0.26 | RNA-binding protein 26 |
| P34897 | 0.26 | Serine hydroxymethyltransferase, mitochondrial |
| P11940 | 0.26 | Polyadenylate-binding protein 1 |
| Q5SSJ5 | 0.26 | Heterochromatin protein 1-binding protein 3 |
| P49821 | 0.26 | NADH dehydrogenase [ubiquinone] flavoprotein 1, mitochondrial |
| P07355 | 0.26 | Annexin A2 |
| Q9BXW7 | 0.25 | Cat eye syndrome critical region protein 5 |
| Q15366 | 0.25 | Poly(rC)-binding protein 2 |
| P52815 | 0.25 | 39S ribosomal protein L12, mitochondrial |
| Q9BWF3 | 0.25 | RNA-binding protein 4 |
| P46781 | 0.24 | 40S ribosomal protein S9 |
| Q9NR30 | 0.23 | Nucleolar RNA helicase 2 |
| P38159 | 0.23 | RNA-binding motif protein, X chromosome |
| P35659 | 0.22 | Protein DEK |
| O75947 | 0.20 | ATP synthase subunit d, mitochondrial |
| Q92769 | 0.20 | Histone deacetylase 2 |
| Q13247 | 0.19 | Serine/arginine-rich splicing factor 6 |
| P16615 | 0.17 | Sarcoplasmic/endoplasmic reticulum calcium ATPase 2 |
| Q9P2R7 | 0.17 | Succinyl-CoA ligase [ADP-forming] subunit beta, mitochondrial |
| Q8IX12 | 0.17 | Cell division cycle and apoptosis regulator protein 1 |
| Q04637 | 0.16 | Eukaryotic translation initiation factor 4 gamma 1 |
| P28331 | 0.16 | NADH-ubiquinone oxidoreductase 75 kDa subunit, mitochondrial |
| Q16576 | 0.14 | Histone-binding protein RBBP7 |
| P51572 | 0.14 | B-cell receptor-associated protein 31 |
| Q16836 | 0.13 | Hydroxyacyl-coenzyme A dehydrogenase, mitochondrial |

FIG. 19 (cont'd)

| | | |
|---|---|---|
| O14744 | 0.12 | Protein arginine N-methyltransferase 5 |
| Q9Y3Y2 | 0.11 | Chromatin target of PRMT1 protein |
| P42126 | 0.11 | Enoyl-CoA delta isomerase 1, mitochondrial |
| O00410 | 0.11 | Importin-5 |
| P08243 | 0.10 | Asparagine synthetase [glutamine-hydrolyzing] |
| P40429 | 0.09 | 60S ribosomal protein L13a |
| Q9Y2Q3 | 0.09 | Glutathione S-transferase kappa 1 |
| Q13243 | 0.08 | Serine/arginine-rich splicing factor 5 |
| Q96HS1 | 0.08 | Serine/threonine-protein phosphatase PGAM5, mitochondrial |
| P04181 | 0.07 | Ornithine aminotransferase, mitochondrial |
| Q9H0U4 | 0.07 | Ras-related protein Rab-1B |
| Q9ULV4 | 0.07 | Coronin-1C |
| Q10567 | 0.07 | AP-1 complex subunit beta-1 |
| Q92526 | 0.07 | T-complex protein 1 subunit zeta-2 |
| O00231 | 0.05 | 26S proteasome non-ATPase regulatory subunit 11 |
| P22392 | 0.05 | Nucleoside diphosphate kinase B |
| P68363 | 0.02 | Tubulin alpha-1B chain |

FIG. 20A       FIG. 20C
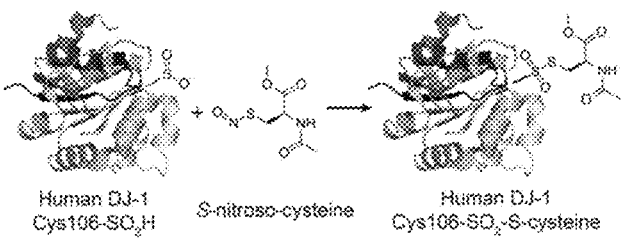
FIG. 20B
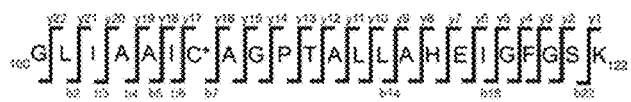
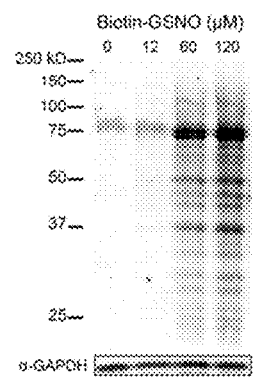
FIG. 21
Protein: Human PARK7 (DJ-1), recombinant
Peptide: GLIAAIC*AGPTALLAHEIGFGSK
Modification: C* = -SO$_2$-S-$N$-Ac-Cys-OMe
Retention Time: 73.49 minutes
Peptide Charge: +3
Peptide [M+H]$^+$: 2417.2234
Product Ions Observed: b2 b3 b4 b5 b6 b7 b14°b18 b18°b22 b23 y1 y2 y2° y3 y3° y4 y5 y5° y6 y7 y8 y9 y9° y10 y11 y12 y13 y13° y14 y15 y15° y16 y17 y18 y19 y20 y21 y22 y23
Mass Error: 1.2899 ppm
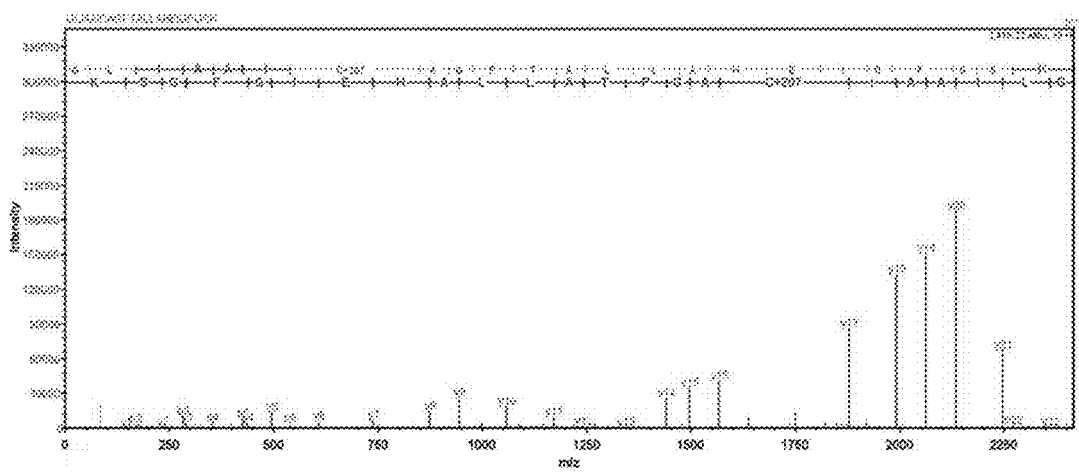

FIG. 27A
FIG. 27B
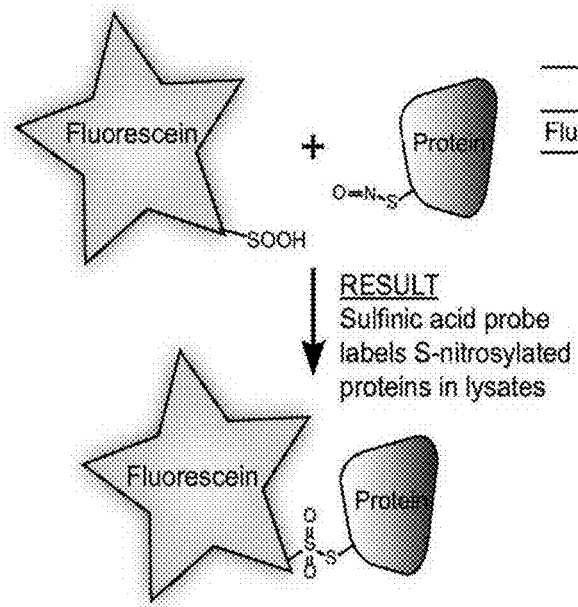
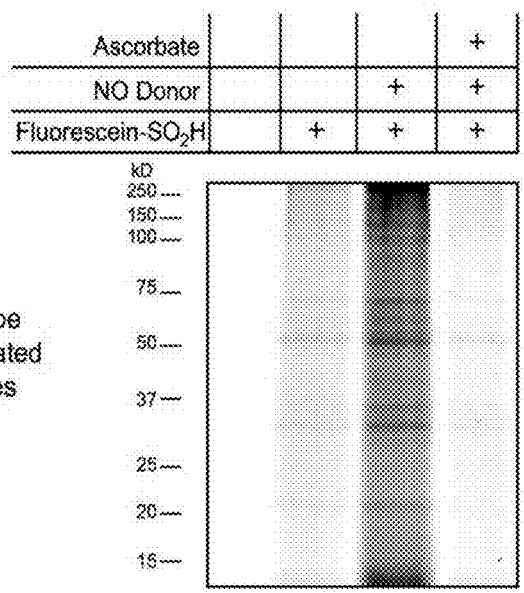
FIG. 28
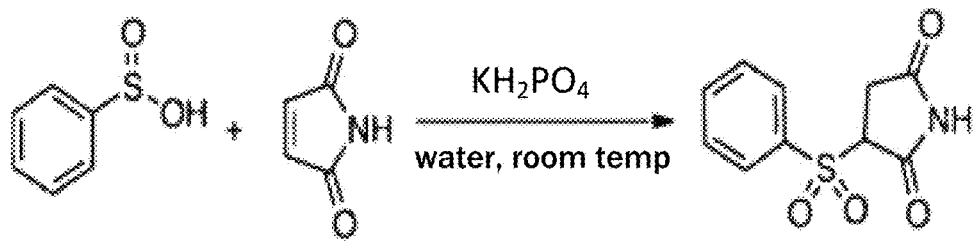

COMPOSITIONS AND METHODS FOR DETECTING S-NITROSYLATION AND S-SULFINYLATION

CROSS-REFERENCE TO RELATED APPLICATION

This application is a continuation of U.S. patent application Ser. No. 14/888,904, filed Nov. 3, 2015, which is a 371 U.S. National Phase Entry of International Application No. PCT/US2014/037111, filed May 7, 2014, which claims priority to U.S. Provisional Patent Application No. 61/820,401, filed May 7, 2013, the contents of which are incorporated by reference in their entireties.

FIELD OF THE INVENTION

The present invention relates to methods for detecting protein S-nitrosylation and S-sulfinylation within thiol groups in proteins, metabolites, or materials.

BACKGROUND OF THE INVENTION

Reversible redox post-translational modifications on protein thiols have been implicated in several signaling pathways of biological importance. Protein S-nitrosylation and proteins S-sulfinylation are two of these modifications that play critical roles in maintaining the redox balance of proteins. Redox imbalance has recently been shown to play a crucial role in heart disease, neurodegeneration and cancer. Protein S-nitrosylation describes the reversible, post-translational modification of select thiols with nitric oxide (NO) and/or its oxidized products to form S-nitrosothiols (SNO). Protein S-sulfinylation describes the oxidation of cysteine thiols to a SOOH (sulfinic acid) motif via a peroxide-mediated pathway.

Current methods to study S-nitrosylation and S-sulfinylation lack sufficient selectivity, and may over-represent the functional role of S-nitrosylation and S-sulfinylation.

For example, several methods have been reported to label and enrich sites of protein S-nitrosylation, including several versions of the biotin switch technique (BST), gold nanoparticle based enrichment, organomercury based methods and phosphine-based probes. By far, the most popular method is BST, which relies on ascorbate reduction to selectively reduce sites of S-nitrosylation. Sodium ascorbate has been shown to reduce activated disulfides and its reactivity with cysteine sulfenic acids and thiocysteines has not been thoroughly investigated. This suggests that the BST may be contaminated with weak disulfides, thiosulfhydrylation (R-SSH), or other activated thiol modifications. Such findings demonstrate that knowledge about SNO modifications derived from such methods are indirect.

New selective methods for detecting S-nitrosylation and S-sulfinylation are needed.

SUMMARY OF THE INVENTION

The sulfhydryl group of the amino acid cysteine is a key target of oxidative stress, and is readily modified to induce temporary and sometimes permanent protein damage (see, e.g., Paulsen, C. E. & Carroll, K. S. Chem Rev 113, 4633-79 (2013)). Depending on the abundance and type of radical species, cysteine is covalently modified to one of a series of distinct chemical moieties. For example, reactive nitrogen species can induce the formation of S-nitrosocysteine (R-SNO) (see, e.g., Majmudar, J. D. & Martin, B. R. Biopolymers (2013)), while reactive oxygen species can induce formation of S-sulfenylcysteine (R-SOH) (see, e.g., Paulsen, C. E. & Carroll, K. S. Chem Rev 113, 4633-79 (2013)). These modifications are unstable and transient, and often act to temporarily inactivate functional cysteines (see, e.g., Nakamura, T. et al. Neuron 78, 596-614 (2013)). In some cases, reversible cysteine modifications have evolved as redox regulatory switches that transmit or enhance cellular cues (see, e.g., Paulsen, C. E. & Carroll, K. S. Chem Rev 113, 4633-79 (2013)). When these mechanisms are left unchecked, irreversible oxidation can occur (such as $R-SO_2H$, $R-SO_3H$), decorating the proteome with oxidative damage.

Nitric oxide is a critical second messenger involved in vasorelaxation, immunity, and neurotransmission. Under oxidative conditions, elevated nitric oxide promotes covalent S-nitrosylation of cysteine thiols in proteins. Aberrant S-nitrosylation is implicated in the pathology of many diseases, including inflammation, stroke, and neurodegeneration. Both the ascorbate-dependent biotin-switch (see, e.g., Jaffrey, S. R. & Snyder, S. H. Sci STKE 2001, pl1 (2001)) and organomercury enrichment (see, e.g., Doulias, P. T. et al. Sci Signal 6, rs1 (2013)) have been used to annotate protein S-nitrosylation by mass spectrometry. Using these methods, hundreds of endogenous S-nitrosylated proteins have been identified, highlighting particular enrichment of abundant metabolic enzymes with nucleophilic or redox-active thiols (see, e.g., Doulias, P. T. et al. Sci Signal 6, rs1 (2013)). While both methods have led to important biological revelations of the significance of S-nitrosylation, more robust methods are necessary (see, e.g., Forrester, M. T., Foster, M. W. & Stamler, J. S. J Biol Chem 282, 13977-83 (2007); Giustarini, D. et al. Nitric Oxide-Biology and Chemistry 19, 252-258 (2008)). The ascorbate-dependent biotin-switch can lead to reduction of weak disulfides (see, e.g., Giustarini, D. et al. Nitric Oxide-Biology and Chemistry 19, 252-258 (2008)) and other reversible cysteine modifications (see, e.g., Reisz, J. A. et al. FEBS J 280, 6150-61 (2013)), which can scramble with existing disulfides. Similarly, the selectivity of organomercury enrichment has not been thoroughly explored, and may introduce false-positives after performic acid oxidation of disulfide-capped thiols, and oxidize other amino acid side chains. While emerging triarylphosphine-catalyzed methods for detecting nitrosothiol are promising (see, e.g., Seneviratne, U. et al. J Am Chem Soc 135, 7693-704 (2013)), these methods have not been thoroughly validated in complex proteomes.

Experiments conducted during the course of developing embodiments for the present invention showed sulfinic acids and nitrosothiols to react to form a thiosulfonate bond. This reactivity was leveraged to enrich and annotate ~1000 endogenous S-nitrosylated proteins (see, FIG. 16). In parallel, S-nitrosothiol probes were used to label endogenous S-sulfinylated proteins, demonstrating a direct, bi-directional method to profile distinct cysteine modifications based on the inherent reactivity of sulfinic acids. As such, the present invention provides new chemoselective ligation methods for the detection of protein S-nitrosylation and S-sulfinylation that simplifies and improves the detection of these redox modifications.

Accordingly, in certain embodiments, the present invention provides methods for detecting protein S-nitrosylation within thiol groups in proteins, metabolites, or materials. In particular, the present invention provides methods for detecting protein S-nitrosylation within cysteine residues of a protein, comprising providing a biological sample comprising proteins having cysteine residues and a composition comprising a labeled sulfinic acid moiety (e.g., a sulfinic acid probe), exposing the composition to the biological sample such that the labeled sulfinic acid moiety is able to interact with the nitrosothiols on cysteine side chains of the protein so as to generate labeled sulfonothioate moieties, and characterizing the cysteine residues of a protein having labeled sulfonothioate moieties as having undergone S-nitrosylation. In some embodiments, the methods further comprise identifying the protein having been characterized as having undergone S-nitrosylation and/or identifying the exact amino acid sites on the protein having been characterized as having undergone S-nitrosylation.

In some embodiments, the labeled sulfinic acid moiety comprises a labeling agent (e.g., a fluorescent dye detectable by in-gel fluorescence) and/or an enrichment agent (such as biotin and/or desthiobiotin for affinity enrichment). In some embodiments, flash chromatography is used to characterize the cysteine residues of a protein having sulfonothioate moieties as having undergone S-nitrosylation. In certain embodiments, flash chromatography (normal or reverse phase) is used to purify the sulfonothioate adduct following reaction between a nitrosothiol and a sulfinic acid to validate probe reactivity. In some embodiments, high performance liquid chromatography is used to characterize the cysteine residues of a protein having sulfonothioate moieties as having undergone S-nitrosylation by reaction with a labeled sulfinic acid moiety. In some embodiments, mass spectrometry is used to characterize the cysteine residues of a protein having sulfonothioate moieties as having undergone S-nitrosylation by reaction with a labeled sulfinic acid moiety.

In some embodiments, the biological sample is an in vivo sample, an ex vivo sample, or an in vitro sample. In some embodiments, the biological sample is a mammalian biological sample. In some embodiments, the biological sample is a human biological sample.

In certain embodiments, the present invention provides methods for identifying pharmaceutical agents capable of inhibiting S-nitrosylation, comprising providing a pharmaceutical agent and a biological sample comprising proteins having cysteine residues known to undergo S-nitrosylation, exposing the pharmaceutical agent to the biological sample, characterizing the cysteine residues of a protein having S-nitrosothiol moieties as having or not having undergone S-nitrosylation with the methods for detecting protein S-nitrosylation within cysteine residues of a protein (described herein), and identifying the pharmaceutical agent as a S-nitrosylation inhibitor if the characterization indicates an absence of S-nitrosylation.

In certain embodiments, the present invention provides methods for detecting protein S-sulfinylation within cysteine residues of a protein, comprising providing a biological sample comprising one or more proteins having cysteine residues and a composition comprising a labeled nitrosothiol moiety, exposing the composition to the biological sample such that the labeled nitrosothiol moiety is able to interact with sulfinic acid side chains of the cysteine residues so as to generate labeled sulfonothioate moieties, characterizing the cysteine residues of the one or more proteins having labeled sulfonothioate moieties as having undergone S-sulfinylation.

In some embodiments, the methods further comprise identifying the protein having been characterized as having undergone S-sulfinylation and/or identifying the exact amino acid sites on the protein having been characterized as having undergone S-sulfinylation.

In some embodiments, the labeled nitrosothiol moiety is a labeled nitrosoglutathione moiety. In some embodiments, the labeled nitrosothiol moiety is a labeled S-Nitroso-N-acetylpenicillamine moiety.

In some embodiments, labeled nitrosothiol moiety comprises an imaging agent and/or an enrichment tag. In some embodiments, the imaging agent is a fluorescent dye. In some embodiments, the in-gel fluorescence is used to characterize the cysteine residues of a protein having labeled sulfonothioate moieties as having undergone S-sulfinylation. In some embodiments, the enrichment agent is biotin or desthiobiotin.

In some embodiments, flash chromatography followed by NMR and/or mass spectrometry is used to structurally identify the product of the reaction between a sulfinic acid side chain of a cysteine residue and a labeled nitrosothiol moiety.

In some embodiments, high performance liquid chromatography is used to characterize the cysteine residues of a protein having labeled sulfonothioate moieties as having undergone S-sulfinylation.

In some embodiments, mass spectrometry is used to characterize the cysteine residues of a protein having labeled sulfonothioate moieties moieties as having undergone S-nitrosylation.

In some embodiments, the biological sample is an in vivo sample, an ex vivo sample, or an in vitro sample.

In some embodiments, the biological sample is a mammalian biological sample. In some embodiments, the biological sample is a human biological sample.

In certain embodiments, the present invention provides methods for identifying pharmaceutical agents capable of inhibiting S-sulfinylation, comprising providing a pharmaceutical agent and a biological sample comprising one or more proteins having cysteine residues known to undergo S-sulfinylation, exposing the pharmaceutical agent to the biological sample, characterizing the cysteine residues of a protein having labeled sulfonothioate moieties as having or not having undergone S-sulfinylation with the methods for detecting protein S-sulfinylation within cysteine residues of a protein, and identifying the pharmaceutical agent as a S-sulfinylation inhibitor if the characterization indicates an absence of S-sulfinylation.

In certain embodiments, the present invention provides methods for annotating and profiling the exact amino acid sites on proteins that have undergone S-nitrosylation or S-sulfinylation. For example, in some embodiments such methods utilize "in-built" cleavable linkers (such as, for example, dialkyl or diaryl dialkoxysilanes, orthoesters, vinyl ethers and such) to enable cleavage of a sulfonothiaote adduct (post reaction with a nitrosothiols) thereby leaving behind a chemical reporter tag that can be utilized as a mass-spectrometric signature for the particular amino acid. In some embodiments, the sulfonothioate adduct may itself be used as a cleavable linker (e.g., cleaved with tris-carboxyethyl phosphine or similar reducing agents) in presence of an orthogonal thiol capture reagent to provide a mass spectrometry reporter ion.

DESCRIPTION OF THE DRAWINGS

FIG. 15. Biotin-SO₂H reacts with human GAPDH and forms a thiosulfonate. Recombinant human GADPH was labeled with biotin-SO₂H for site-specific analysis of S-nitrosylation by high-resolution mass spectrometry.

FIG. 16. Quantitative analysis of biotin-SO2H enrichment in 293T cell lysates. Samples were prepared in two sets, one with biotin-SO2H in the "Light" matched with biotin-SO3H in the "Heavy" (N=2), and the other in reverse (N=2). Each was ran as two technical replicated and SILAC ratios (biotin-SO2H/biotin-SO3H) were combined across experiments. "Directions Detected" describes the set of SILAC samples where the protein was quantified. FORWARD refers to biotin-SO2H (light)/biotin-SO3H (heavy), and REVERSE is the opposite direction, biotin-SO2H (heavy)/biotin-SO3H (light). A ratio of 1000 was assigned to proteins with an infinite ratio, meaning there was not detectable signal in the SILAC pair labeled with biotin-SO3H. Label-free quantification was performed using the Top3 method from the biotin-SO2H labeled pair.

FIG. 19. Ratio of S-nitrosylation enrichment to total abundance. Label-free abundance was derived from Top3 quantification.

FIG. 20A-C. S-nitrosothiol probes detect endogenous S-sulfinylation. (a) Direct conjugation of human DJ-1 (Cys106-SO₂H) with N-acetyl-S-nitrosocysteine methyl ester. (b) MS/MS assignment of product ions from the S-sulfinylated peptide of human DJ-1, confirming direct thiosulfonate formation. (c) Gel-based analysis of S-sulfinylation in mammalian lysates with biotin-GSNO. Lysates are denatured and pre-alkylated with iodoacetamide.

FIG. 21. S-nitroso-N-Acetyl-Cysteine methyl ester reacts with oxidized DJ-1 to form a thiosulfonate. Data was collected in MS$^E$ mode.

FIG. 27A-B shows sulfinic acid probe labels nitrosylated proteins in cell lysates. Labeling was eliminated by ascorbate pretreatment. Gel analyzed using a GE Typhoon laser fluorescence scanner (ex. 488 nm, em. 535/25). No reducing agent added to loading buffer.

FIG. 28 shows the reaction between maleimide and a sulfinic acid.

DETAILED DESCRIPTION OF THE INVENTION

Figure 1A:
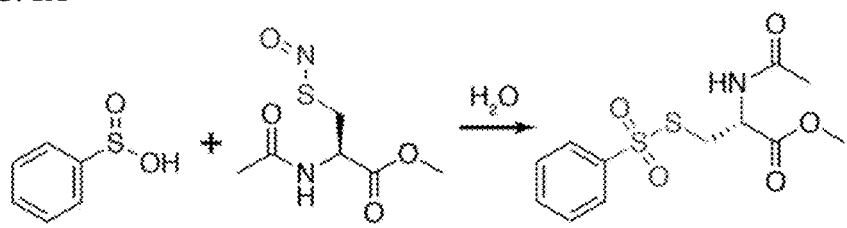
FIG. 1A-E. Sulfinic acid probes detect endogenous S-nitrosylation. (a) Phenylsulfinic acid reacts with N-acety-S-nitroso-cysteine methyl ester to form a thiosulfonate bond. (b) Biotin-hypotaurine (biotin-$SO_2H$) reacts with S-nitrosylated proteins to form a thiosulfonate linkage. Lysates are denatured and reduced thiols are alkylated with iodoacetamide to prevent disulfide exchange. (c) Biotin-SO$_2$H labels distinct mammalian proteins, but biotin-taurine (biotin-SO$_3$H) is unreactive. (d) Biotin-SO$_2$H labeling is enhanced by the nitric oxide donor MAHMA-NONOate. (e) Biotin-SO$_2$H labeling is unaffected by the sulfenic acid probe dimedone.

S-nitrosylation involves the covalent incorporation of a nitric oxide moiety into thiol groups, to form S-nitrosothiol (SNO). Where the thiol group belongs to a subset of specific cysteine residues in proteins, the resulting SNO is an S-nitrosoprotein. S-Nitrosylation is a form of post-translational protein modification with similarities to phosphorylation (see, e.g., Anand P, Stamler J S., J. Mol. Med. 90(3): 233-244 (2012)). Generally, S-Nitrosylation operates as a signaling mechanism in that it is stimulus evoked (see, e.g., Hoffmann, J, Dimmeler, S, Haendeler, J. FEBS Lett. 551: 153-158 (2003)), precisely targeted (see, e.g., Sun J H, Xin C L, Eu J P, Stamler J S, Meissner G. Proc. Natl. Acad. Sci. USA 98:11158-11162 (2003), reversible (see, e.g., Padgett C M, Whorton A R. Am. J. Physiol. 269:739-749 (1995)), spatiotemporally restricted (see, e.g., Fang M, Jaffrey S R, Sawa A, Ye K, Luo X, Snyder S H. Neuron 28:183-193 (2000); Iwakiri Y, Satoh A, Chatterjee S, Toomre D K, Chalouni C M, Fulton D, Groszmann R J, Shah V H, Sessa W C. Proc. Natl. Acad. Sci. USA 103:19777-19782 (2006)), and necessary for specific cell responses (see, e.g., Hess D T, Matsumoto A, Kim S O, Marshall H E, Stamler J S. Nat. Rev. Mol. Cell. Biol. 6:150-166 (2005)).

Aberrant or dysregulated denitrosylation or S-nitrosylation has been associated with stroke (cerebral ischemia) (see, e.g., Gu Z, Kaul M, Yan B, Kridel S J, Cui J, Strongin A, Smith J W, Liddington R C, Lipton S A. Science 297(5584): 1186-90 (2002)) and a number of chronic degenerative diseases, including Parkinson's and Alzheimer's disease (see, e.g., Yao D, Gu Z, Nakamura T, Shi Z-Q, Ma Y, Gaston B, Palmer L A, Rockenstein E M, Zhang Z, Masliah E, Uehara T, Lipton S A. Proc. Natl. Acad. Sci. USA 101(29): 10810-4 (2004); Uehara T, Nakamura T, Yao D, Shi Z-Q, Gu Z, Masliah E, Nomura Y, Lipton S A. Nature 2441(7092):513-7 (2006); Benhar M, Forrester M T, Stamler J S. ACS Chem. Biol. 1(6):355-8 (2006); Cho D-H, Nakamura T, Fang J, Cieplak P, Godzik A, Gu Z, Lipton S A. Science 324(5923):102-5 (2009)) and Amyotrophic Lateral Sclerosis (ALS) (see, e.g., Schonhoff C M, et al. Proc. Natl. Acad. Sci. USA 103(7):2404-9 (2006)). In addition, there is an emerging role of S-nitrosylation in cancer biology (see, e.g., Aranda E, López-Pedrera C, De La Haba-Rodriguez J R, Rodriguez-Ariza A. Curr. Mol. Med. 12(1):50-67 (2012); Aranda E, López-Pedrera C, De La Haba-Rodriguez J R, Rodriguez-Ariza A. Curr. Mol. Med. 12(1):50-67 (2012)).

S-nitrosylation has not yet been used within diagnostic and/or therapeutic methods. Yet, research publications on the topic increased from 69 in 2000 to 163 in 2012 according to Pubmed (CAGR 7%).

Current methods for detecting S-nitrosylation include several versions of the biotin switch technique, gold nanoparticle based enrichment, organomercury based methods, and phosphine-based probes. Limitation of biotin switch-based method is high false identification rate, due to mainly three reasons. First, the efficiency/sensitivity of this assay relies on complete blocking of reduced cysteine residues. Second, the efficiency of ascorbate reduction has been questioned. Third, there is the possibility of disulfide exchange after ascorbate reduction. Other methods for detecting S-nitrosylation include gold nanoparticle based enrichment, organomercury based methods, and phosphine-based probes. Limitations for gold nanoparticle based enrichment include, for example, that AuNPs react with both S-nitrosylated and S-glutathionylated cysteines, providing a challenge for absolute assignment of specific post-translational modifications to these residues. Phosphine based probes have yet to be evaluated in biological systems and organomercury approaches may be toxic.

The present invention overcomes such limitations, and provides new chemoselective ligation methods for the detection of protein S-nitrosylation. Indeed, experiments conducted during the course of developing embodiments for the present invention provide novel S-nitrosocysteine specific mild ligation approaches to directly label sites of proteins S-nitrosylation. In some embodiments, such approaches enable a one-step, direct covalent enrichment of SNO modified proteins with no cross-reactivity towards other cysteine post-translational modifications (PTMs).

Figure 26A:
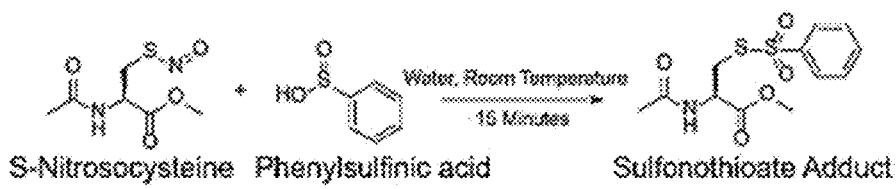
FIG. 26A-B shows (A) reaction of sulfinic acids with S-Nitrosocysteine. (B) HPLC traces of starting materials and product in a standard gradient. Traces shown for purified and isolated product.
Figure 26B:
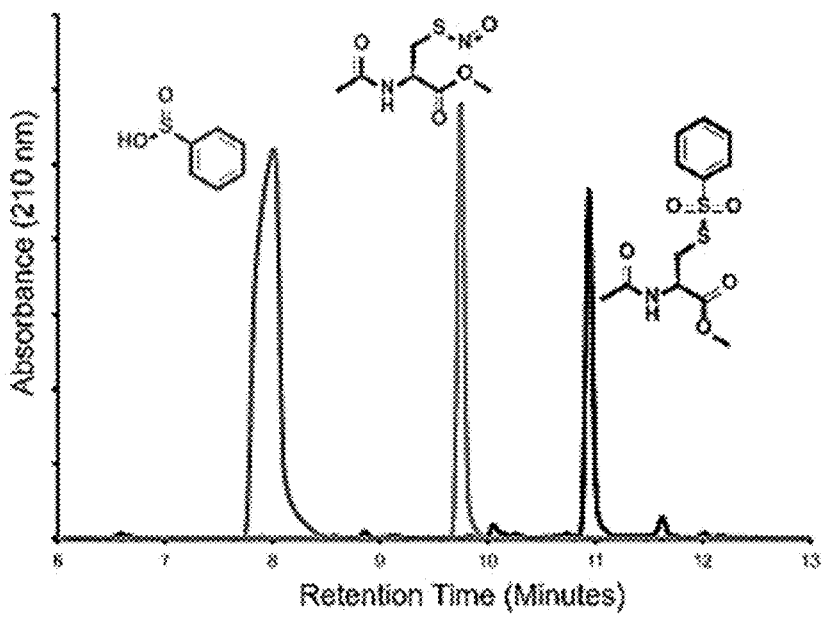
Figure 29:
FIG. 29 shows sulfinic acid cross-reactivity table. Cross-reactivity was determined by allowing components to react for 4 hours. HPLC analysis (every 30 minutes) was used to monitor reactions. Reduction in peak intensity of initial components and the appearance of new peak was termed as a positive reaction. Partial reaction indicates incomplete reaction.

In particular, such experiments determined that S-nitrosocysteine reacts with sulfinic acids in water at ambient temperature to form stable sulfonothioates and that this adduct is stable for flash chromatography, HPLC, and mass spectrometry analysis (see, FIG. 26). The cross-reactivity of the sulfinic acid with various thiol modifying reagents and other thiol modifications using an HPLC assay was next determined (FIG. 29). It was found that sulfinic acids react quickly and selectively with S-nitrosocysteines, but do not react with free thiols or disulfides. The sulfonothioate adduct was susceptible to thiol exchange with free cysteine, but this is prevented by pre-alkylation with iodoacetamide, but not maleimide.

Based on such findings, a strategy was devised to link the sulfinic acid group to a fluorescent dye or a biotin label. The fluorescent probe (e.g., sulfinic acid probe) was synthesized in good yield (~73% isolated) from fluorescein NHS-ester and hypotaurine and purified on a preparative HPLC. Whether the probe could label S-nitrosylated proteins in cultured cancer cell lysates in the presence of NO donor (MAHMA-NONOate) was next tested (see, FIG. 27). After incubation, the protein was analyzed by SDS-PAGE and analyzed by in-gel fluorescence. Addition of the NO donor radically increased labeling, and pre-incubation with sodium ascorbate eliminated nearly all labeling. This indicated NO-dependent protein labeling.

Accordingly, in some embodiments, the present invention provides a selective, one-step SNO detection technique. The present invention is not limited to particular methods for SNO detection. In some embodiments, compositions comprising sulfinic acid are provided. In some embodiments, such compositions are exposed to cell samples having proteins with cysteine residues such that the sulfinic acid binds with such cysteine residues having undergone S-nitrosolyation. In some embodiments, the sulfinic acid binds with such S-nitrosothiol moieties resulting in a sulfonothioate adduct. In some embodiments, generation of a protein with a sulfonothioate adduct moiety following exposure to sulfinic acid indicates that such cysteine residue associated with a particular protein had undergone S-nitrosylation. In some embodiments, the protein can subsequently be separated from the sample and identified.

These probes efficiently labeled endogenous S-nitrosylated proteins, providing a direct method to covalently label, enrich, and annotate S-nitrosylated cysteines in cell and tissue lysates. Enrichment and mass spectrometry studies using biotin-hypotaurine (biotin-$SO_2H$) led to the identification of nearly 1000 endogenous S-nitrosylated proteins under basal conditions in cultured mammalian cells, providing the most sensitive and in-depth analysis of S-nitrosylation to date (see, FIG. 16). When compared with native protein abundance, a subset of S-nitrosylated proteins were found with enhanced stoichiometry, indicating functional enrichment. In addition, it was shown that this reaction is bi-directional, and S-nitrosothiol probes directly label S-sulfinylated proteins, such as the S-sulfinylated protein DJ-1.

As such, in certain embodiments, the present invention provides methods for detecting protein S-nitrosylation within thiol groups in proteins, metabolites, or materials. In particular, the present invention provides methods for detecting protein S-nitrosylation within cysteine residues of a protein, comprising providing a biological sample comprising proteins having cysteine residues and a composition comprising a labeled sulfinic acid moiety (e.g., a sulfinic acid probe), exposing the composition to the biological sample such that the labeled sulfinic acid moiety is able to interact with the nitrosothiols on cysteine side chains of the protein so as to generate labeled sulfonothioate moieties, and characterizing the cysteine residues of a protein having labeled sulfonothioate moieties as having undergone S-nitrosylation. In some embodiments, the methods further comprise identifying the protein having been characterized as having undergone S-nitrosylation and/or identifying the exact amino acid sites on the protein having been characterized as having undergone S-nitrosylation.

In certain embodiments, the present invention further provides methods for detecting proteins having cysteine residues having undergone S-sulfinylation. Protein S-sulfinylation describes the oxidation of cysteine thiols to a SOOH motif via a peroxide-mediated pathway. The present invention is not limited to particular methods for detecting proteins having cysteine residues having undergone S-sulfinylation. In some embodiments, such methods involve detecting proteins having cysteine residues having undergone S-sulfinylation through, for example, exposing such cysteine residues to a composition comprising maleimide in aqueous buffers at ambient temperature to provide a stable and detectable sulfone adduct (see, FIG. 28). In some embodiments, such methods involve detecting proteins having cysteine residues having undergone S-sulfinylation through, for example, exposing such cysteine residues to a composition comprising a labeled nitrosothiol moiety (e.g., biotin-GSNO). In some embodiments, generation of a protein with a sulfone adduct moiety following exposure to a composition comprising maleimide indicates that such cysteine residues associated with a particular protein had undergone S-sulfinylation. In some embodiments, the protein can subsequently be separated from the sample and identified. In some embodiments, the maleimide is labeled with an imaging agent (e.g., a fluorescent dye) to facilitate detection of the sulfone adduct. In some embodiments, such methods for S-sulfinylation detection may be used within in vivo samples, ex vivo samples, and/or in vitro samples.

The methods for S-sulfinylation detection are not limited to utilizing a particular type or kind of detection technique for detecting generation of a sulfone adduct moiety associated with a cysteine residue for a particular protein following exposure to a composition comprising maleimide in aqueous buffer (thereby indicating that such protein had undergone S-sulfinylation). In some embodiments wherein the maleimide is labeled with a fluorescent dye, in-gel fluorescence techniques are used. In some embodiments, flash chromatography is used to detect generation of a sulfone adduct moiety associated with a cysteine residue for a particular protein following exposure to a composition comprising maleimide in aqueous buffers. In some embodiments, high performance liquid chromatography (HPLC) is used to detect generation of a sulfone adduct moiety associated with a cysteine residue for a particular protein following exposure to a composition comprising maleimide in aqueous buffers. In some embodiments, mass spectrometry is used to detect generation of a sulfone adduct moiety associated with a cysteine residue for a particular protein following exposure to a composition comprising maleimide and aqueous buffer. In some embodiments, such methods are used to identify pharmaceutical agents (e.g., compounds, medicaments) capable of inhibiting or facilitating S-sulfinylation. In some embodiments, such identified pharmaceutical agents are used in the treatment of a disorder characterized by aberrant S-sulfinylation.

In certain embodiments, the present invention provides methods for detecting protein S-sulfinylation within cysteine residues of a protein, comprising providing a biological sample comprising one or more proteins having cysteine residues and a composition comprising a labeled nitrosothiol moiety, exposing the composition to the biological sample such that the labeled nitrosothiol moiety is able to interact with sulfinic acid side chains of the cysteine residues so as to generate labeled sulfonothioate moieties, characterizing the cysteine residues of the one or more proteins having labeled sulfonothioate moieties as having undergone S-sulfinylation. In some embodiments, the methods further comprise identifying the protein having been characterized as having undergone S-sulfinylation and/or identifying the exact amino acid sites on the protein having been characterized as having undergone S-sulfinylation.

In some embodiments, the labeled nitrosothiol moiety is a labeled nitrosoglutathione moiety. In some embodiments, the labeled nitrosothiol moiety is a labeled S-Nitroso-N-acetylpenicillamine moiety.

In some embodiments, the labeled sulfinic acid moiety comprises a labeling agent and/or an enrichment agent. In some embodiments, the labeled nitrosothiol moiety comprises a labeling agent and/or an enrichment agent. The methods for nitrosylation detection and sulfinylation detection are not limited to utilizing a particular type or kind of labeling agent. In some embodiments, the labeling agent is a fluorescent dye. Examples of such imaging agents include, but are not limited to, molecular dyes, fluorescein isothiocyanate (FITC), 6-TAMARA, acridine orange, and cis-parinaric acid. In some embodiments, the imaging agents are molecular dyes from the alexa fluor (Molecular Probes) family of molecular dyes. For example, examples of imaging agents include, but are not limited to, Alexa Fluor 350 (blue), Alexa Fluor 405 (violet), Alexa Fluor 430 (green), Alexa Fluor 488 (cyan-green), Alexa Fluor 500 (green), Alexa Fluor 514 (green), Alexa Fluor 532 (green), Alexa Fluor 546 (yellow), Alexa Fluor 555 (yellow-green), Alexa Fluor 568 (orange), Alexa Fluor 594 (orange-red), Alexa Fluor 610 (red), Alexa Fluor 633 (red), Alexa Fluor 647 (red), Alexa Fluor 660 (red), Alexa Fluor 680 (red), Alexa Fluor 700 (red), Alexa Fluor 750 (red), fluorescein isothiocyanate (FITC), 6-TAMARA, acridine orange, cis-parinaric acid, Hoechst 33342, Brilliant Violet™ 421, BD Horizon™ V450, Pacific Blue™, AmCyan, phycoerythrin (PE), Brilliant Violet™ 605, BD Horizon™ PE-CF594, PI, 7-AAD, allophycocyanin (APC), PE-Cy™5, PerCP, PerCP-Cy™5.5, PE-Cy™7, APC-Cy7, BD APC-H7, Texas Red, Lissamine Rhodamine B, X-Rhodamine, TRITC, Cy2, Cy3, Cy3B, Cy3.5, Cy5.5, Cy7, BODIPY-FL, FluorX™, TruRed, Red 613, NMD, Lucifer yellow, Pacific Orange, Pacific Blue, Cascade Blue, Methoxycoumarin, coumarin, hydroxycoumarin, aminocoumarin, 3-azidocoumarin, DyLight 350, DyLight 405, DyLight 488, DyLight® 550, DyLight 594, DyLight 633, DyLight® 650, DyLight 680, DyLight 755, DyLight 800, Tracy 645, Tracy 652, Atto 488, Atto 520, Atto 532, Atto Rho6G, Atto 550, Atto 565, Atto 590, Atto 594, Atto 633, Atto Rho11, Atto Rho14, Atto 647, Atto 647N, Atto 655, Atto 680, Atto 700, CF™350, CF™405S, CF™405M, CF™488A, CF™543, CF™555, CF™568, CF™594, CF™620R, CF™633, CF™640R, CF™647, CF™660, CF™660R, CF™680, CF™680R, CF™750, CF™770, and CF™790. In some embodiments, the imaging agent is a mass-spec label selected from the group consisting of 139La, 141Pr, 142Nd, 143Nd, 144Nd, 145Nd, 146Nd, 147Sm, 148Nd, 149Sm, 150Nd, 151Eu, 152Sm, 153Eu, 154Sm, 156Gd, 158Gd, 159Tb, 160Gd, 162Dy, 164Dy, 165Ho, 166Er, 167Er, 168Er, 169Tm, 170Er, 171Yb, 172Yb, 174Yb, 175Lu, and 176Yb.

The methods for nitrosylation detection and sulfinylation detection are not limited to utilizing a particular type or kind of enrichment agent. In some embodiments, the enrichment agent is biotin and/or desthiobiotin for affinity enrichment.

The methods for nitrosylation detection and sulfinylation detection are not limited to utilizing a particular type or kind of detection technique for detecting generation of a labeled sulfonothioate moiety (thereby indicating that such protein had undergone S-nitrosylation or S-sulfinylation).

In some embodiments wherein the labeling agent is a fluorescent dye, in-gel fluorescence techniques are used to detect a labeled sulfonothioate moiety associated with a cysteine residue for a particular protein following exposure to either a labeled sulfinic acid moiety or a labeled nitrosothiol moiety.

In some embodiments, flash chromatography followed by nuclear magnetic resonance (NMR) analysis and/or mass spectrometry is used to detect generation of a labeled sulfonothioate moiety associated with a cysteine residue for a particular protein following exposure to either a labeled sulfinic acid moiety or a labeled nitrosothiol moiety.

In some embodiments, high performance liquid chromatography (HPLC) coupled with by mass spectrometry is used to detect generation of a labeled sulfonothioate moiety associated with a cysteine residue for a particular protein following exposure to either a labeled sulfinic acid moiety or a labeled nitrosothiol moiety.

In some embodiments, mass spectrometry used to detect a labeled sulfonothioate moiety associated with a cysteine residue for a particular protein following exposure to either a labeled sulfinic acid moiety or a labeled nitrosothiol moiety. In some embodiments, the sulfonothioate moiety associated with a cysteine residue for a particular protein following exposure to either a labeled sulfinic acid moiety or a labeled nitrosothiols moiety is cleaved by TCEP to generate either a free thiol or a sulfinic acid on the cysteine residue. Mass spectroscopy is used to identify the newly generated sulfinic acid and is also used to identify the newly generated free thiol, which is capped by N-ethyl maleimide. This additional manipulation permits annotation of the site of nitrosylation or sulfinylation in the protein.

As used herein, the term "flash chromatography" means the separation of mixtures by passing a fluid mixture dissolved in a "mobile phase" under pressure through a column comprising a stationary phase, which separates the analyte (i.e., the target substance) from other molecules in the mixture and allows it to be isolated (see, e.g., J. Org. Chem. 1978, 43, 2923).

"Mass spectrometry," as used herein, refers to a method comprising employing an ionization source to generate gas phase ions from a biological entity of a sample presented on a biologically active surface, and detecting the gas phase ions with an ion detector. Comparison of the time the gas phase ions take to reach the ion detector from the moment of ionization with a calibration equation derived from at least one molecule of known mass allows the calculation of the estimated mass to charge ratio of the ion being detected. The term "mass spectrometer" refers to a gas phase ion spectrometer that includes an inlet system, an ionization source, an ion optic assembly, a mass analyzer, and a detector.

As used herein, the term "nuclear magnetic resonance (NMR) signal" is intended to mean an output representing the frequency of energy absorbed by a population of magnetically equivalent atoms in a magnetic field, the magnitude of energy absorbed at the frequency by the population and distribution of frequencies around a central frequency. The frequency of energy absorbed by with an atom in a magnetic field can be determined from the location of a peak in an NMR spectrum. The magnitude of energy absorbed at a frequency by a population of atoms can be determined from relative peak intensity. The distribution of frequencies around a central frequency can be determined from the shape of a peak in an NMR spectrum. Accordingly, a collection of nuclear magnetic resonance signals for a molecule or sample containing multiple atoms can be represented in an NMR spectrum, as an atom having a signal of characteristic frequency, intensity and line-shape.

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

In certain embodiments, the present invention provides methods for identifying proteins having undergone S-nitrosylation and/or to annotate/profile particular locations of such S-nitrosylation. In certain embodiments, the present invention provides methods for identifying proteins having undergone S-sulfinylation and/or to annotate/profile particular locations of such S-sulfinylation. For example, in some embodiments, complex cell lysates or tissue samples are treated with a labeled sulfinic acid moiety or a labeled nitrosothiol moiety, such treated samples treated are prepared for mass spectrometric analysis, and peptidic fragments are separated by liquid chromatography (LC) followed by mass spectrometry. In some embodiments, the methods further involve proteomic analysis using bioinformatics and the raw data is searched against, for example, a defined database to identify particular proteins and to detect peptides bearing the sulfonothioate adduct (or the corresponding mass reporter ion) to annotate and profile sites of labeling. Indeed, experiments conducted during the course of developing embodiments for the present invention, through enrichment and mass spectrometry studies using biotin-hypotaurine (biotin-$SO_2H$) led to the identification of nearly 1000 endogenous S-nitrosylated proteins under basal conditions in cultured mammalian cells, providing the most sensitive and in-depth analysis of S-nitrosylation to date (see, FIG. 16). In addition, when compared with native protein abundance, a subset of S-nitrosylated proteins were found with enhanced stoichiometry, indicating functional enrichment.

The methods for nitrosylation detection and sulfinylation detection are not limited to particular uses. In some embodiments, such methods for nitrosylation detection and sulfinylation detection are used within biological settings. For example, in some embodiments, the methods for nitrosylation detection are used to screen biological samples for the presence of nitrosothiols. In some embodiments, the methods for nitrosylation detection are used to detect the presence of nitrosothiols within a particular biological sample (e.g., a biological sample from a patient (e.g., a clinical biopsy)).

In some embodiments, such methods for nitrosylation detection and sulfinylation detection may be used within in vivo samples, ex vivo samples, and/or in vitro samples.

In some embodiments, such methods for nitrosylation detection and sulfinylation detection are used to assist in characterizing disorders (e.g., strokes, chronic degenerative diseases, including Parkinson's and Alzheimer's disease; Amyotrophic Lateral Sclerosis (ALS); cancer) involving the occurrence of protein S-nitrosylation (e.g., through SNO detection) (e.g., through quantification of SNO presence).

In some embodiments, such methods for nitrosylation detection are used to identify pharmaceutical agents (e.g., compounds, medicaments) capable of preventing S-nitrosylation. The present invention is not limited to particular methods for identifying pharmaceutical agents capable of preventing S-nitrosylation. In some embodiments, identification of pharmaceutical agents capable of preventing S-nitrosylation involves, for example, exposing a sample having proteins having cysteine residues known to undergo S-nitrosylation to a pharmaceutical agent, detecting the presence or absence of S-nitrosylation with the methods of the present invention, and identifying such pharmaceutical agent as being capable of preventing S-nitrosylation if such methods are unable to detect S-nitrosylation. In some embodiments, pharmaceutical agents identified as S-nitrosylation inhibitors are further characterized with regard to its inhibitory effect on specific proteins. In some embodiments, such pharmaceutical agents identified as S-nitrosylation inhibitors are used in methods for treating subjects (e.g., human patients) suffering from disorders involving the aberrant occurrence of protein S-nitrosylation (e.g., chronic degenerative diseases, including Parkinson's and Alzheimer's disease; Amyotrophic Lateral Sclerosis (ALS); cancer).

In some embodiments, such methods for nitrosylation detection are used to identify pharmaceutical agents (e.g., compounds, medicaments) capable of facilitating S-nitrosylation. The present invention is not limited to particular methods for identifying pharmaceutical agents capable of facilitating S-nitrosylation. In some embodiments, identification of pharmaceutical agents capable of facilitating S-nitrosylation involves, for example, exposing a sample having proteins having cysteine residues known to not undergo S-nitrosylation to a pharmaceutical agent, detecting the presence or absence of S-nitrosylation with the methods of the present invention, and identifying such pharmaceutical agent as being capable of facilitating S-nitrosylation if such methods are able to detect S-nitrosylation. In some embodiments, pharmaceutical agents identified as S-nitrosylation facilitators are further characterized with regard to its facilitating effect on specific proteins. In some embodiments, such pharmaceutical agents identified as S-nitrosylation facilitators are used in methods for treating subjects (e.g., human patients) suffering from disorders involving the aberrant occurrence of protein S-nitrosylation.

In some embodiments, such methods for sulfinylation detection are used to identify pharmaceutical agents (e.g., compounds, medicaments) capable of preventing S-sulfinylation. The present invention is not limited to particular methods for identifying pharmaceutical agents capable of preventing S-sulfinylation. In some embodiments, identification of pharmaceutical agents capable of preventing S-sulfinylation involves, for example, exposing a sample having proteins having cysteine residues known to undergo S-sulfinylation to a pharmaceutical agent, detecting the presence or absence of S-sulfinylation with the methods of the present invention, and identifying such pharmaceutical agent as being capable of preventing S-sulfinylation if such methods are unable to detect S-sulfinylation. In some embodiments, pharmaceutical agents identified as S-sulfinylation inhibitors are further characterized with regard to its inhibitory effect on specific proteins. In some embodiments, such pharmaceutical agents identified as S-sulfinylation inhibitors are used in methods for treating subjects (e.g., human patients) suffering from disorders involving the aberrant occurrence of protein S-sulfinylation.

In some embodiments, such methods for sulfinylation detection are used to identify pharmaceutical agents (e.g., compounds, medicaments) capable of facilitating S-sulfinylation. The present invention is not limited to particular methods for identifying pharmaceutical agents capable of facilitating S-sulfinylation. In some embodiments, identification of pharmaceutical agents capable of facilitating S-sulfinylation involves, for example, exposing a sample having proteins having cysteine residues known to not undergo S-sulfinylation to a pharmaceutical agent, detecting the presence or absence of S-sulfinylation with the methods of the present invention, and identifying such pharmaceutical agent as being capable of facilitating S-sulfinylation if such methods are able to detect S-sulfinylation. In some embodiments, pharmaceutical agents identified as S-sulfinylation facilitators are further characterized with regard to its facilitating effect on specific proteins. In some embodiments, such pharmaceutical agents identified as S-sulfinylation facilitators are used in methods for treating subjects (e.g., human patients) suffering from disorders involving the aberrant occurrence of protein S-sulfinylation.

EXPERIMENTAL

Example I

Figure 2:
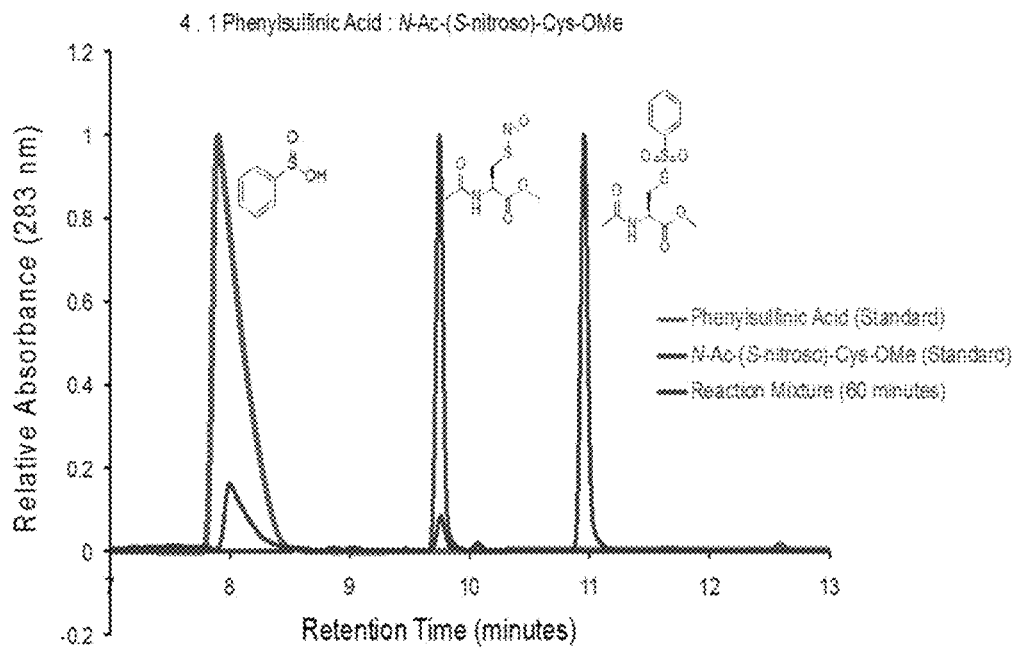
FIG. 2. Sulfinic acids react with S-nitrosothiols to form thiosulfonates. A 5 mM solution of N-Acetyl-(S-nitroso)-cysteine methyl ester in phosphate buffered saline (PBS, pH 7.4) was treated (in the dark) with a 20 mM aqueous solution of phenylsulfinic acid in PBS. After 60 minutes, the reaction mixture was separated using gradient elution (5% ACN to 95% ACN over 15 minutes) using an Atlantis C$_{18}$ reverse phase column, and the absorbance was measured at 281 nm. The two reactants were also individually analyzed under identical conditions (HPLC traces in green and blue). The HPLC trace unambiguously shows the reactivity of sulfinic acids and nitrosothiols to form thiosulfonates (retention time 11.1 min). The thiosulfonate product was separately purified and characterized (HPLC, NMR, MS analysis). Similar results were obtained with hypotaurine (an aliphatic sulfinic acid). However, hypotaurine does not absorb in the UV-vis spectrum, so phenylsulfinic acid was throughout our studies as a model sulfinic acid for HPLC assays.
Figure 3:
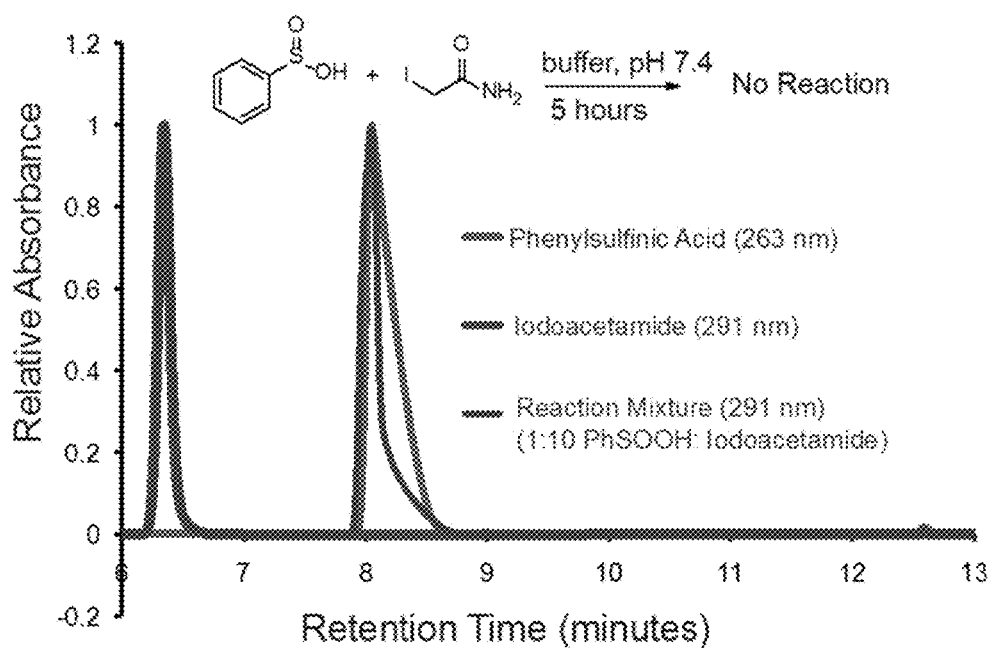
FIG. 3. Sulfinic acids do not react with iodoacetamide. A 10 mM solution of phenylsulfinic acid was allowed to react with a 20 mM solution of iodoacetamide in potassium phosphate buffer pH 7.4 for 5 hours. After 5 hours, the reaction mixture was injected on an HPLC and separated using gradient elution (5% ACN to 95% ACN over 15 minutes). Absence of additional peaks (over 202-798 nm, monitored on a PDA detector) was interpreted as no reaction between the sulfinic acid and iodoacetamide.
Figure 4A:
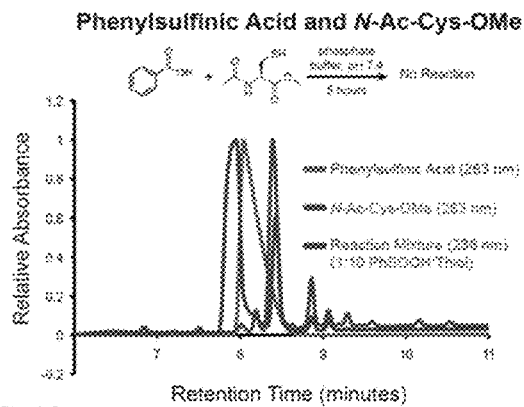
FIG. 4A-D. Sulfinic acids do not react with thiols, disulfides, or aldehydes. A 2 mM solution of phenylsulfinic acid was allowed to stand with 20 mM solutions of N-acetyl-cysteine-methyl ester, benzaldehyde, cystine dimethyl ester, and 5,5'-dithiobis-(2-nitrobenzoic acid) in phosphate buffer pH 7.4 for 5 hours. The reaction mixtures were injected on an HPLC and analyzed using gradient elution (5% ACN to 95% ACN over 15 minutes). Peaks beyond minute 8.6 in (a) are contaminants present in the commercial cysteine sample (Sigma-Aldrich). The absence of any reaction with benzaldehyde suggests no reaction occurs with carbonylated amino acids.
Figure 4B:
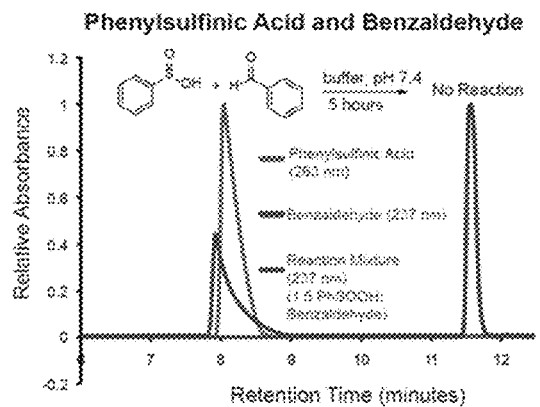
Figure 4C:
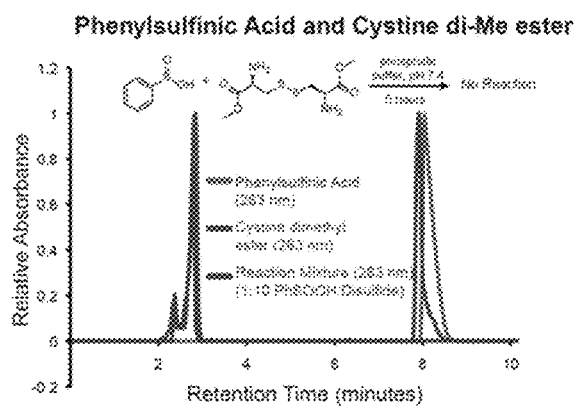
Figure 4D:
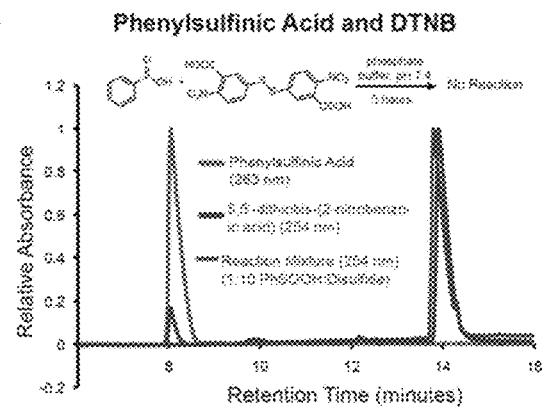
Figure 5A:
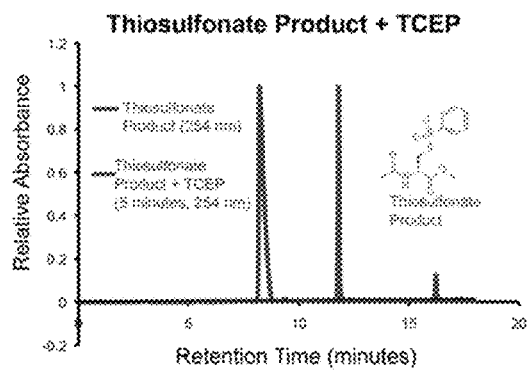
FIG. 5A-B. The thiosulfonate product is reduced by TCEP, but not ascorbate. A 0.5 mM solution of the thiosulfonate product was incubated with 2.5 mM TCEP or 2.5 mM sodium ascorbate in in phosphate buffer (pH 7.4) in the dark at room temperature. After 5 minutes and 60 minutes, an aliquot injected for HPLC analysis and separated using gradient elution (5% ACN to 95% ACN over 15 minutes). TCEP immediately cleaves the thiosulfonate bond, while ascorbate does not after 60 minutes of co-incubation.
Figure 5B:
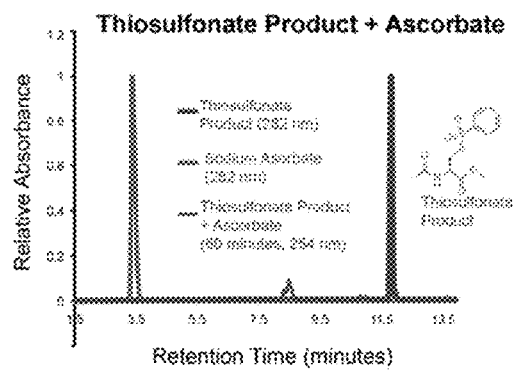

While exploring the interplay of cysteine post-translational modifications, a reported reaction between phenylsulfinic acid and S-nitrosocysteine was identified, leading to thiosulfonate formation in aqueous buffers at room temperature (see, e.g., Hart. T. W. Tetrahedron Letters 26, 2013-2016 (1985)) (FIG. 1a, FIG. 2). Thiosulfonates are readily exchangeable with thiols, serving as the basis for the cysteine capping agent methyl methanethiosulfonate (MMTS). To prevent such exchange, it was found that sulfinic acids do not react with iodoacetamide, enabling orthogonal alkylation of thiols without perturbing nitrosothiols or sulfinic acids (FIG. 3). Furthermore, it was found that sulfinic acids do not react with thiols (cysteine), disulfides (cystine or 5,5'-dithiobis-(2-nitrobenzoic acid) (DTNB)), or aldehydes (benzaldehyde) (FIG. 4). Additionally, the thiosulfonate product is unaffected by ascorbate, but reduced by tris(2-carboxyethyl)phosphine (TCEP) (FIG. 5). Most S-sulfinylation studies alkylate thiols with MMTS (see, e.g., Doulias, P. T. et al. Sci Signal 6, rs1 (2013); Forrester, M. T., Foster, M. W. & Stamler, J. S. J Biol Chem 282, 13977-83 (2007); Jaffrey, S. R. et al. Nat Cell Biol 3, 193-7 (2001)), which reacts with cysteine to release methylsulfinic acid. Based on our findings, methylsulfinic acid will react with S-nitrosothiols to form a thiosulfonate, which can then catalyze disulfide formation with free thiols and hamper S-sulfinylation detection.

Figure 6A:
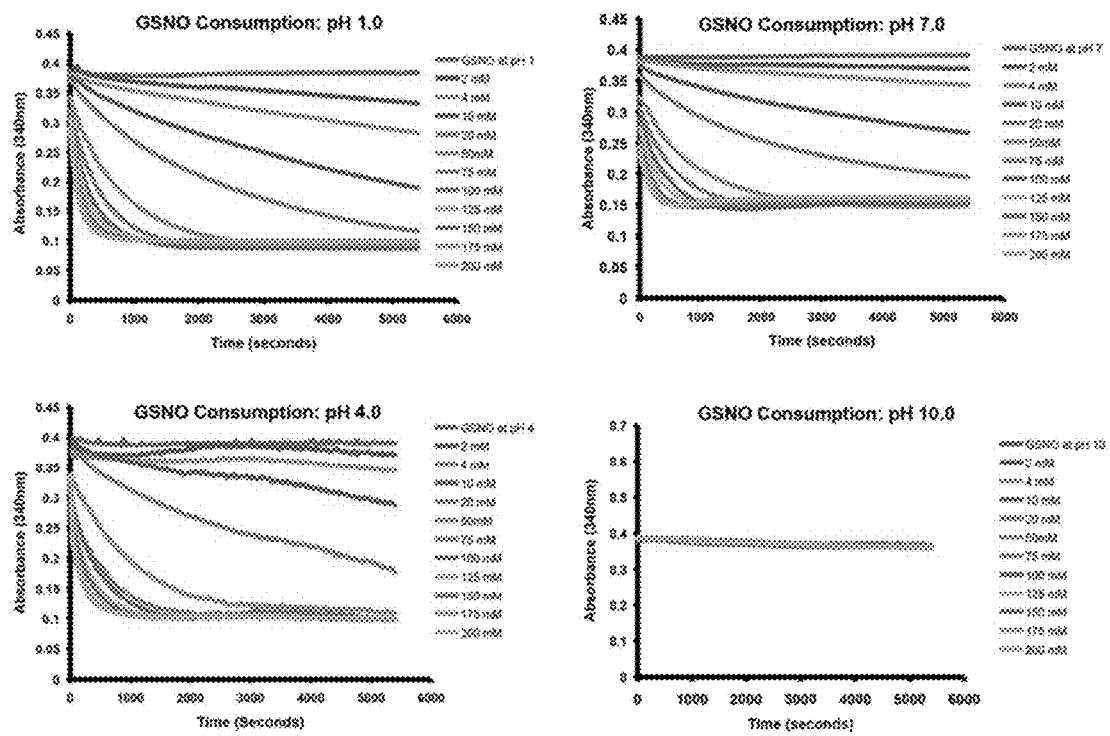
FIG. 6A-B. GSNO is consumed by increasing concentrations of sodium phenylsulfinate. (a) A 2 mM solution of S-nitrosoglutathione (GSNO, Cayman) was treated with increasing concentrations of phenylsulfinic acid, and the absorbance of GSNO was monitored over a period of 90 minutes at 340 nm using a plate reader in varying pH buffers. (b) Calculation of rate constants at differing pH values. At pH 7, the rate becomes more hyperbolic.
Figure 6B:
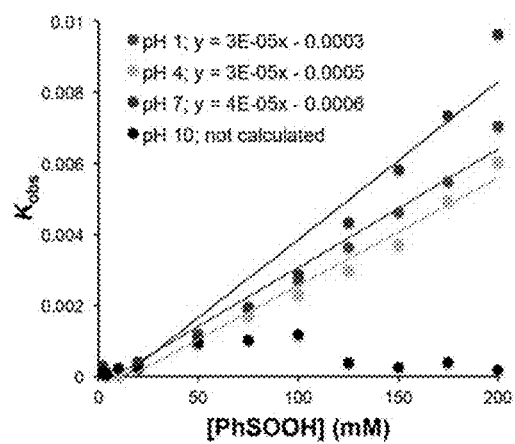
Figure 7A:
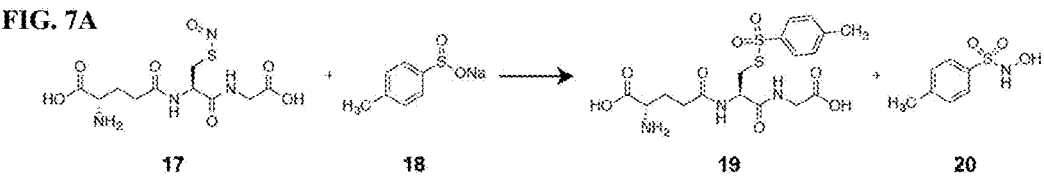
FIGS. 7A, B and C: Determination of reaction efficiency and quantification of products and by-products. (a) Reaction between GSNO and 4-Me-phenylsulfinic acid. The products 19 and 20 were quantified by LC-MS. The product of GSNO and phenylsulfinic acid was not resolved from products during HPLC purification, and was excluded from further analysis. (b) LC-MS standard curves were generated from the HPLC purified thiosulfonate product (19) and commercial 4-Me-piloty's acid (20). (c) Quantification of thiosulfonate product and the 4-Me-piloty's acid side product by LC-MS, presented as 3 replicates with standard deviations.
Figure 7B:
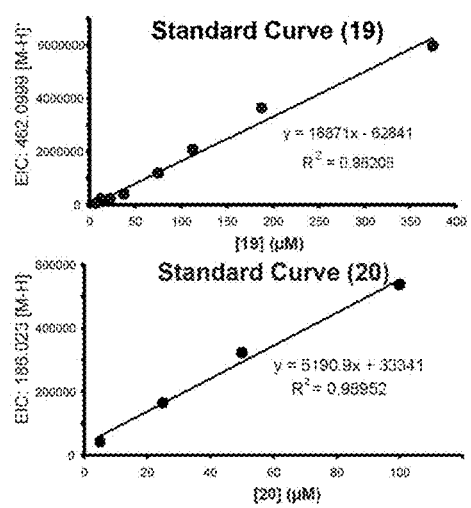
Figure 7C:
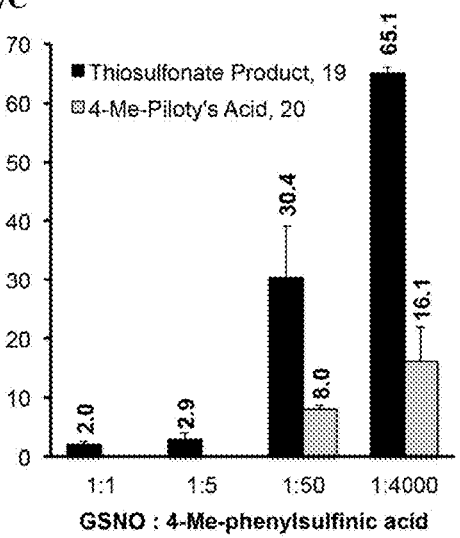

Thiosulfonate formation was further characterized by measuring the loss of S-nitroso-glutathione (GSNO) absorbance after phenylsulfinic acid addition (FIG. 6). At pH 1 and 4, the reaction rate is first order and proceeds at $3 \times 10^{-5}$ $M \cdot sec^{-1}$. At neutral pH, a mild sigmoidal concentration dependence is observed, and no reaction occurs under basic conditions. Further LC-MS analysis revealed fractional formation of piloty's acid (N-hydroxybenzenesulfonamide) (FIG. 7). This is consistent with protonation of the nitrosothiol species, followed by addition by the phenylsulfinate anion to form a transient intermediate susceptible to attack by a second phenylsufinate anion to form thiosulfonate and piloty's acid (see, e.g., Reeves, B. D. et al. Tetrahedron Lett 54 (2013)).

Figure 1B:
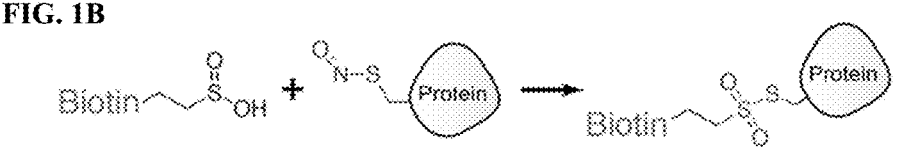
Figure 1C:
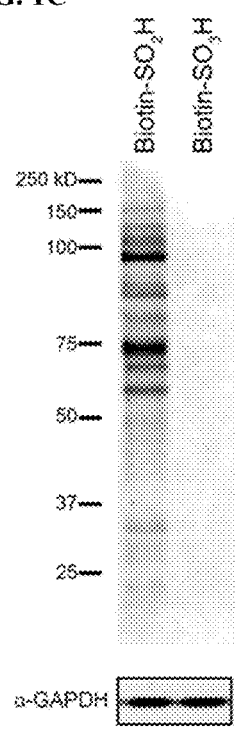
Figure 1D:
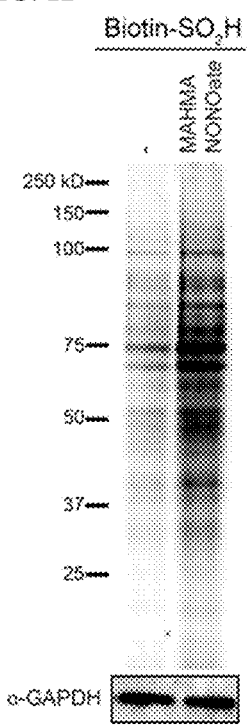
Figure 1E:
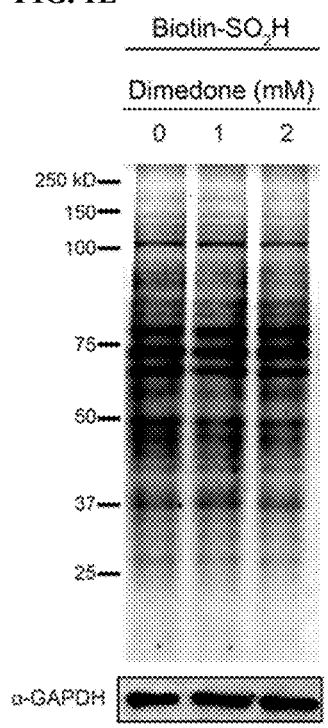
Figure 8:
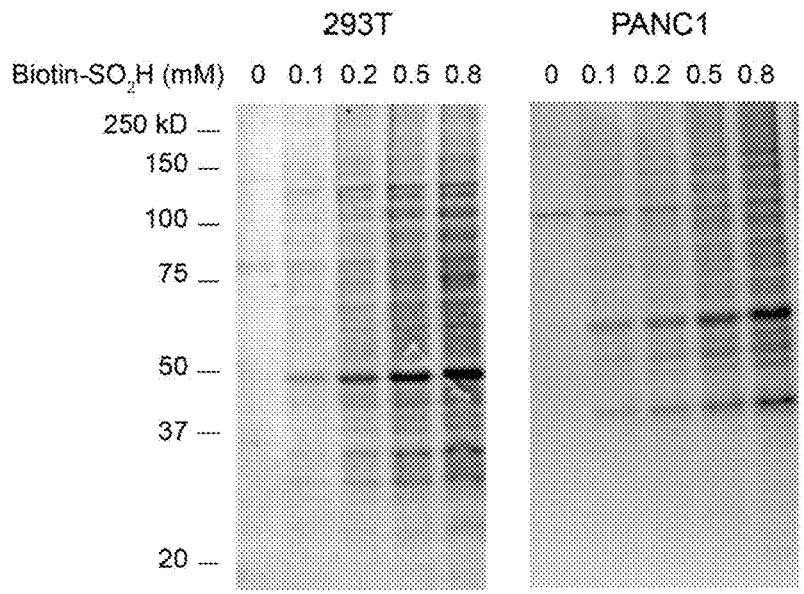
FIG. 8. Dose-dependent labeling of S-nitrosylated proteins by biotin-SO$_2$H. 293T and PANC1 cells were lysed in 6 M urea/PBS and alkylated with 50 mM iodoacetamide for 30 minutes, followed by incubation with increasing concentrations of biotin-SO$_2$H for 45 minutes.
Figure 9:
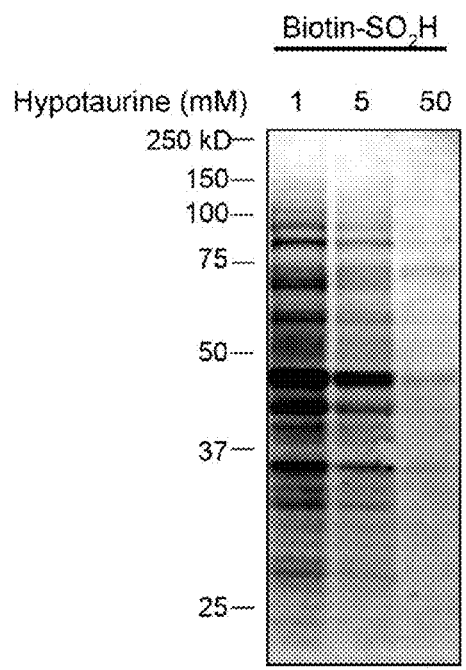
FIG. 9. Hypotaurine competes with biotin-SO$_2$H. 293T cell lysates were pre-incubated with 5 mM or 50 mM hypotaurine for 30 minutes, followed by treatment with 50 mM iodoacetamide for 30 minutes. The lysate was then labeled with biotin-SO$_2$H for 30 minutes, separated by SDS-PAGE, and transferred to nitrocellulose for streptavidin detection of endogenous S-nitrosylation.
Figure 10:
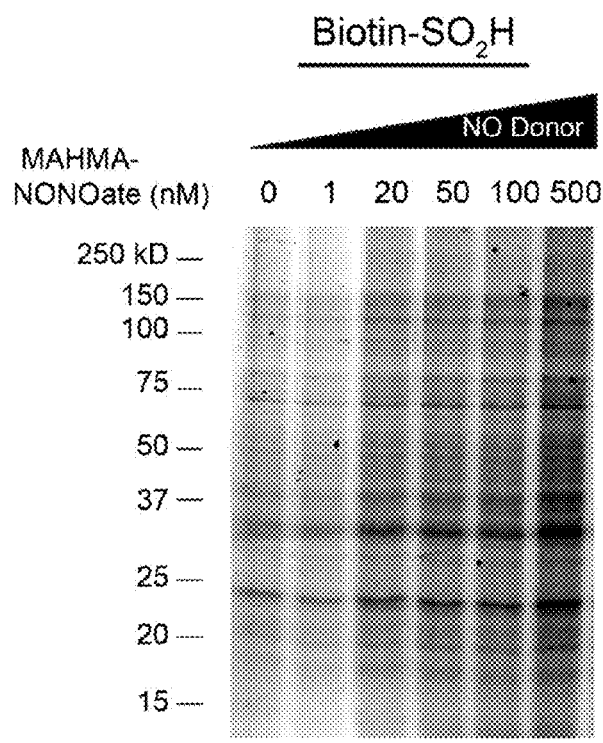
FIG. 10. Dose-dependent enhancement of S-nitrosylation by the nitric oxide donor (MAHMA NONOate). 293T cell lysates were treated with increasing concentrations of nitric oxide donor, MAHMA NONOate for 5 minutes, followed by treatment with 50 mM iodoacetamide for 20 minutes to alkylate free thiols. S-nitrosylated proteins were detected by incubation with fluorescein-SO$_2$H for 45 minutes, and separated by SDS-PAGE for in-gel fluorescence detection.
Figure 11:
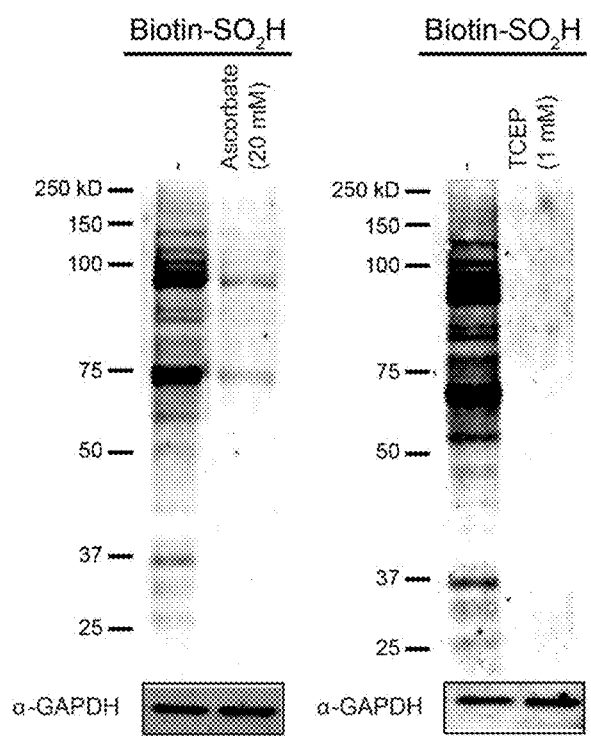
FIG. 11. S-nitrosylation is reduced by ascorbate, and thiosulfonates are reduced by TCEP. 293T cell lysates were treated with 50 mM iodoacetamide for 30 minutes to alkylate any reduced thiols. Next, sodium ascorbate was added for 30 minutes to reduce S-nitrosothiols. Lysates were then treated with 400 µM biotin-SO$_2$H for 30 minutes, and analyzed by non-reducing SDS-PAGE and streptavidin blotting. Ascorbate efficiently blocks biotin-SO$_2$H detection of endogenous S-nitrosylation. Next, lysates labeled with biotin-SO$_2$H were treated with 1 mM TCEP for 15 minutes, demonstrating complete loss of labeling by reduction of the thiosulfonate linkage and confirms there are no TCEP-resistant covalent adducts formed.
Figure 12:
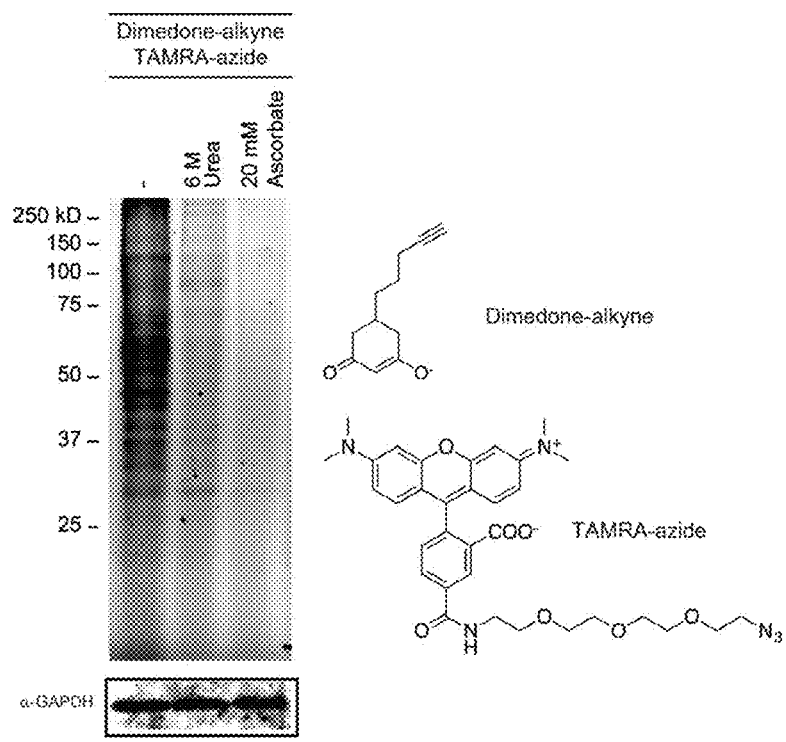
FIG. 12. Sulfenic acids are eliminated by ascorbate reduction or denaturing buffers. Lysates were labeled for 1 hour with 1 mM dimedone-alkyne, and precipitated with chloroform:methanol. The protein fraction was sonicated in PBS and diluted to 1 mg/mL, and incubated with 20 µM TAMRA-azide, 1 mM CuSO$_4$, and 100 µM Tris[(1-benzyl-1H-1,2,3-triazol-4-yl)methyl]amine (TBTA) for 1 hour, boiled in reducing loading buffer, and separated by SDS-PAGE. After transfer and Cy5-streptavidin binding, the gel was visualized using a GE Typhoon fluorescence scanner. Dimedone alkyne (compound 14) detection of sulfenic acids in 293T cell lysates is most efficient in PBS. When the lysate is denatured in 6 M urea/PBS, dimedone labeling is nearly completely eliminated. Pre-treatment with sodium ascorbate (20 mM) for 30 minutes efficiently reduces sulfenic acids. These data demonstrates sulfenic acids are eliminated under the denaturing conditions used for biotin-SO$_2$H labeling of endogenous S-nitrosylated proteins. Furthermore, ascorbate reduces sulfenic acids, and confirms non-selective enrichment of an additional cysteine oxidative modification by the biotin-switch method.
Figure 13:
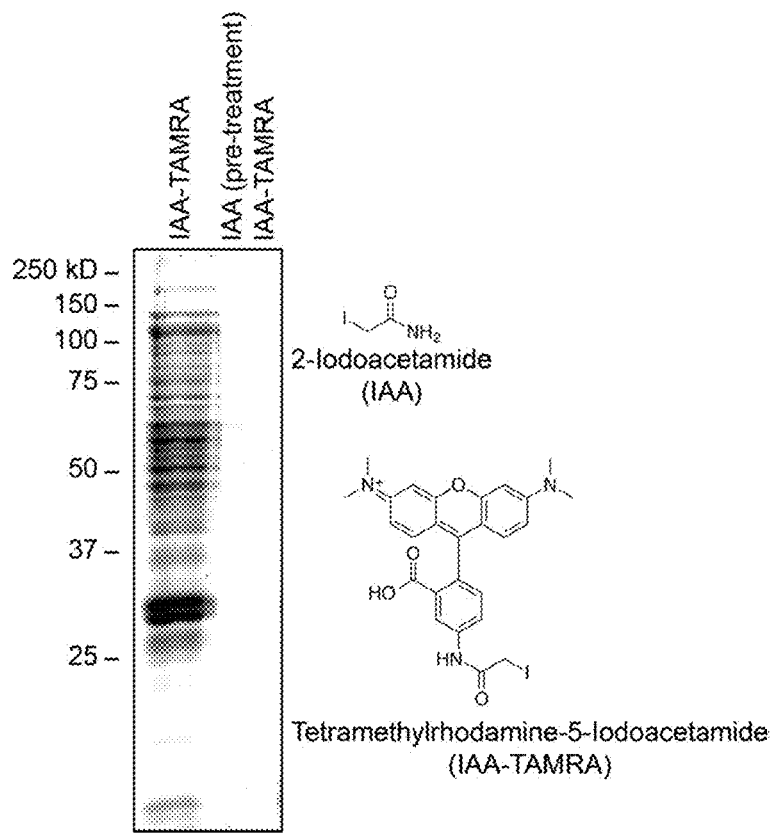
FIG. 13. Iodoacetamide alkylates all free thiols. 293T cell lysates were treated with commercially available iodoacetamide-TAMRA (100 µM, lane 1), or with 50 mM iodoacetamide (30 minutes pre-incubation, room temperature) followed by iodoacetamide-TAMRA (100 µM, lane 2). 50 mM iodoacetamide blocks all labeling by iodoacetamide- TAMRA, providing evidence that biotin-GSNO labels sulfinic acids, and not does not lead to disulfide formation with un-blocked thiols.

Next, the reactivity of sulfinic acids with native S-nitrosylated proteins was examined. Biotin and fluorescein N-hydroxysuccinimide (NHS) esters were directly coupled to the biological sulfinic acid metabolite hypotaurine (biotin-$SO_2H$) or the sulfonic acid metabolite taurine (biotin-$SO_3H$). Each probe was incubated with mammalian cell lysates pre-alkylated with excess iodoacetamide (FIG. 1b) in 6 M urea/phosphate buffered saline (PBS), and separated by non-reducing SDS-PAGE for transfer to nitrocellulose and streptavidin detection. In contrast to biotin-$SO_3H$, biotin-$SO_2H$ labeled a rich profile of proteins (FIG. 1c and FIG. 8) competed by excess hypotaurine (FIG. 9). Lysates treated with the NO donor methylamine hexamethylene methylamine NONOate (MAHMA-NONOate) showed increased labeling (FIG. 1d and FIG. 10), which was blocked by pre-treatment with ascorbate, and eliminated by post-incubation with TCEP (FIG. 11). Addition of the sulfenic acid blocking agent dimedone (see, e.g., Paulsen, C. E. & Carroll, K. S. Chem Rev 113, 4633-79 (2013): Benitez, L. V. & Allison, W. S. J Biol Chem 249, 6234-43 (1974)) had no effect on biotin-$SO_2H$ conjugation (FIG. 1e), suggesting little or no cross-reactivity. Importantly, dimedone labeling is largely eliminated in such denaturing conditions, as well as by ascorbate treatment (see, e.g., Reisz. J. A. et al. FEBS J 280, 6150-61 (2013)) (common to biotin-switch methods) (FIG. 12). Such reactivity is not unprecedented, and is used by the mitochondrial enzyme sulfide quinone oxidoreductase (SQR) in the conversion of hydrogen sulfide to a persulfide intermediate (SQR-SSH), which is then attacked by sulfinate to release thiosulfate (see, e.g., Jackson, M. R, Melideo, S. L. & Jorns, M. S. Biochemistry 51, 6804-6815 (2012)). Since all thiols are completely alkylated by continuous incubation with iodoacetamide (FIG. 13), persulfidation (R-SSH) is constitutively blocked (see, e.g., Pan, J. & Carroll, K. S. ACS Chem Biol 8, 1110-6 (2013)), providing an orthogonal workflow for selective conjugation and detection of endogenous S-nitrosothiols.

Figure 14:
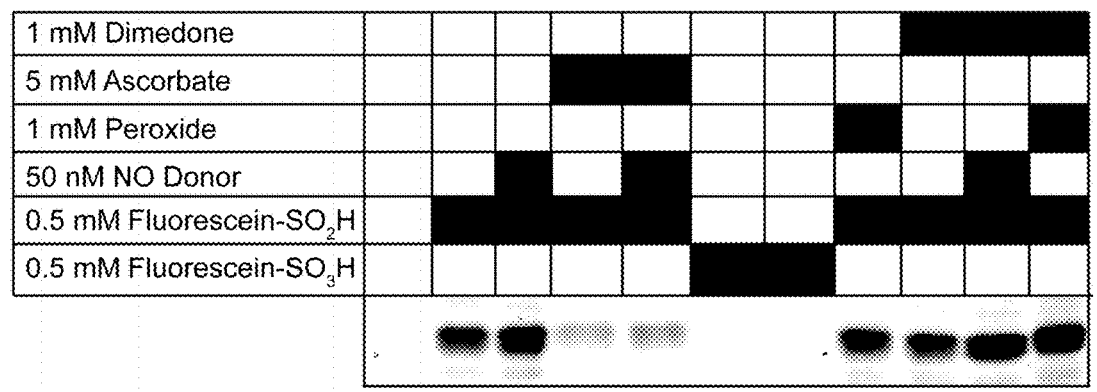
FIG. 14. Profiling fluorescein-SO₂H reactivity and selectivity on S-nitrosylated GAPDH. Recombinant human GAPDH was resuspended in 6 M urea/PBS, treated with 50 mM iodoacetamide for 30 minutes, and mixed with dimedone, ascorbate, peroxide or NO donor (5 minutes). Fluorescein-SO₂H (500 µM) was then added to the GAPDH sample for 45 minutes. S-nitrosylated human GAPDH labeling increases upon incubation with the NO donor MAHMA-NONOate, and decreases following treatment with ascorbate. The control probe, fluorescein-SO₃H, does not label GAPDH. Fluorescein-SO₂H labeling is unaffected by pre-incubation with peroxide or dimedone.

Given the efficient and selective conjugation of sulfinic acids and nitrosothiols, recombinant human GAPDH were next purified for targeted analysis of S-sulfinylation with biotin-SO$_2$H. Detection of GAPDH S-sulfinylation was enhanced by nitric oxide donors, unaffected by dimedone, and slightly diminished by addition of hydrogen peroxide (FIG. 14), likely caused by further oxidation and inactivation of the probe. Biotin-SO$_2$H-labeled GAPDH protein was digested with trypsin and analyzed by high-resolution mass spectrometry, identifying a biotin-thiosulfonate modified peptide encompassing the GAPDH catalytic cysteine (FIG. 15). Interestingly, MS/MS analysis identified S-sulfinylation of Cys156, and not the catalytic nucleophile Cys152 that is reported to mediate trans-sulfinylation to other targets (see, e.g., Kornberg, M. D. et al. Nat Cell Biol 12, 1094-100 (2010)). These studies confirm direct detection of native of S-sulfinylation by sulfinic acid probes for mass spectrometry analysis.

Next, biotin-SO$_2$H labeling was combined with stable-isotope labeling with amino acids in cell culture (SILAC) for quantitative mass spectrometry annotation of endogenous S-sulfinylation in mammalian cells. Heavy or light cell 293T cell lysates were separately alkylated with excess iodoacetamide in denaturing buffers, followed by incubation with biotin-SO$_2$H or biotin-SO$_3$H, respectively. After chloroform/methanol precipitation, the two lysates were combined for streptavidin enrichment, trypsin digestion, and mass spectrometry analysis using an in-line fractioning column for multidimensional analytical separation, electrospray nanoLC, and high-resolution analysis by a quadrupole ion mobility time-of-flight mass spectrometer. Peptides were analyzed using data-independent acquisition methods in combination with ion mobility separation (HDMS$^E$) and mobility-dependent collision energy assignment for enhanced fragmentation (see, e.g., Distler, U. et al. Nat Methods (2013)). Through a combination of 4 biological replicates, each with 2 technical replicates, a total of 992 proteins were identified with SILAC ratios >5 (biotin-SO$_2$H/biotin-SO$_3$H), quantified in ≥3 replicates, and represented by ≥3 quantified peptides (FIG. 16). This list includes nearly all previously annotated S-nitrosylated proteins, including ion channels, chaperones, peroxiredoxins, p53, HDACs, hundreds of metabolic enzymes, as well as a rich set of novel proteins. Site-specific profiling of endogenous S-sulfinylation will require additional adaptations, since dithionite used to reduce azobenzene cleavable linkers (see, e.g., Yang. Y. Y. et al. Chem Biol 17, 1212-22 (2010)) also reduces thiosulfonates, and release by thiosulfonate reduction will also reduce latent disulfides.

Figures 17, 18:
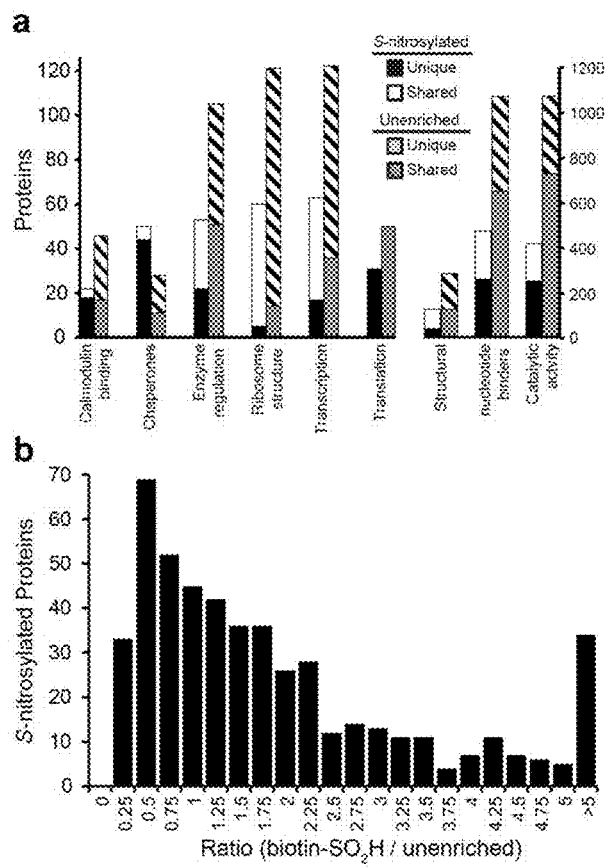
FIG. 17. Annotation and label-free quantification of proteins from 293T whole cell lysates.
FIG. 18. S-nitrosylated protein classification and stoichiometry. (a) Gene ontology (GO) term classification of biotin-SO₂H enriched, S-nitrosylated proteins and unenriched proteins identified by LC-MS analysis. GO term results common across separate categories are denoted as "shared", and those solely classified in one category are denoted as "unique". Structural, nucleotide binders, and catalytic activity are displayed on an expanded scale (right). (b) Histogram of S-nitrosylated proteins compared to their corresponding enrichment efficiency. Higher ratios signify more efficient enrichment (and higher stoichiometry) compared to total protein abundance.

Matched unenriched cell lysates were digested with trypsin for mass spectrometry analysis, and the relative abundance of ~3000 proteins were determined by label-free quantitative methods (FIG. 17). Approximately 500 S-nitrosylated proteins were quantified in the unenriched analysis. Comparison of gene ontology identifiers in both datasets showed little functional enrichment across protein classes (see, e.g., Huang da, W., Sherman, B. T. & Lempicki, R. A. Nat Protoc 4, 44-57 (2009)), except an increased representation of S-nitrosylated chaperone proteins (FIG. 18).

Next, S-sulfinylation enrichment was qualified in comparison with native abundance to identify S-nitrosylated proteins with particularly high stoichiometry. Label-free absolute quantification was performed for each dataset using the top three ionized tryptic peptides, which is directly proportional to protein abundance over a wide dynamic range (see, e.g., Silva. J. C. et al. Molecular & Cellular Proteomics 5, 144-156 (2006); Ahme. E., Molzahn, L., Glatter, T. & Schmidt, A. Proteomics 13, 2567-78 (2013)). Individual protein values from the biotin-SO$_2$H enrichment were divided by their corresponding abundance observed in the unenriched analysis, providing a distribution of ratios reflecting proportionally higher S-sulfinylation occupancy (FIG. 18 and FIG. 19). The majority of proteins were observed with low ratios, signifying poor relative enrichment and low S-sulfinylation stoichiometry, including several heat shock proteins, tubulin, and ribosomal proteins. In contrast, S-nitrosylated proteins with large ratios signify high stoichiometry, including several metabolic enzymes and proteins with metal coordination sites, such as HDAC1 and carbonic anhydrase. While only half of the putative S-nitrosylated proteins assigned in our enrichment were assessed in this comparison, we can infer that basal nitrosative damage fractionally modifies many abundant proteins, while a subset of proteins demonstrate higher native S-sulfinylation occupancy. Understandably, S-sulfinylation is presumably amplified in cells cultured in atmospheric oxygen, warranting further analysis under physiological oxygen conditions.

It was next asked what would happen if the detection scheme was reversed, using S-nitrosothiol-linked probes to detect endogenous S-sulfinylation. Similar reactivity was recently reported using aryl-nitroso ligation to several sulfinic acid standards, including glutathione, to form a stable N-sulfonylbenzisoxazolone (see, e.g., Lo Conte, M. & Carroll, K. S. Angew Chem Int Ed Engl 51, 6502-5 (2012)). Despite such progress, there are no reported methods to selectively profile endogenous S-sulfinylation in complex proteomes. In order to test this approach, recombinant human DJ-1 was purified, a redox chaperone that spontaneously forms a stable sulfinic acid at Cys106 (see, e.g., Canet-Aviles, R. M. et al. Proc Natl Acad Sci USA 101, 9103-8 (2004)). After iodoacetamide alkylation of free thiols, N-acetyl-S-nitrosocysteine methyl ester was added to DJ-1, and processed for high-resolution LC-MS analysis (FIG. 20A and FIG. 21)). MS/MS analysis unambiguously confirmed thiosulfonate formation at Cys106-SO$_2$H (FIG. 20B). Furthermore, there were no detectable N-hydroxysulfonamide cysteine modifications, implying one sulfinic can be sufficient for thiosulfonate formation. Next, biotin-GSNO was synthesized in one step from biotin-NHS and GSNO, and added to mammalian lysates denatured in 6 M urea/PBS and pre-alkylated with iodoacetamide. Gel-based analysis revealed a distinct profile of putative S-sulfinylated proteins (FIG. 3C), validating the intrinsic cross-reactivity nitrosothiols and sulfinic acids. Because these probes are particularly light sensitive, probe synthesis and purification immediately preceded proteome labeling. Future efforts will apply these methods for selective profiling of proteome-wide dynamics of S-sulfinylation, and develop new orthogonal strategies based on the sulfinic acid nucleophilicity.

In summary, by harnessing the inherent cross-reactivity between sulfinic acids and nitrosothiols we demonstrate bi-directional profiling of native cysteine modifications. While the rate of this reaction is relatively slow in solution, certain S-sulfinylated enzymes may accelerate thiosulfonate formation, and could promote exchange with cellular thiols to regenerate the sulfinic acid. Overall, these findings establish that sulfinic acids are nucleophilic, and possess intrinsic reactivity that may contribute to cellular redox regulation.

Example II

This example describes synthetic methods pertaining to Example I.

All compounds were purchased from Sigma-Aldrich, unless otherwise noted. NMR analysis was performed using a Varian 400 MHz NMR instrument. Small molecule high-resolution mass spectrometry was performed using an electrospray Agilent Q-TOF mass spectrometer (accuracy 1-5 ppm). Low-resolution mass spectrometry was performed using an electrospray Micromass LCT time-of-flight mass coupled to a HPLC pump with a rheodyne loop injector. Compounds were purified by normal phase silica column chromatography or by semi-prep High-Performance Column Chromatography (HPLC). HPLC purifications were performed using a Waters semi-preparative 1525 binary pump system coupled to a photodiode array detector, an autosampler, and an automatic fraction collector. Separations were carried out on an Atlantis prep T3 $C_{18}$ column (10×250 mm), in 95/5 water/acetonitrile 0.1% formic acid for 2 minutes, followed by a 40 minute gradient increasing the mobile phase to 5/95 water/acetonitrile with 0.1% formic acid. Data were analyzed using Waters Empower software. Resulting HPLC fractions were lyophilized using a Labconco FreeZone2.5-Plus freeze-drying system.

Synthetic Scheme 1. Synthesis of compound 3, the thiosulfonate product of reaction between a N-acetyl-S-nitroso-cysteine methyl ester and phenyl sulfinic acid.

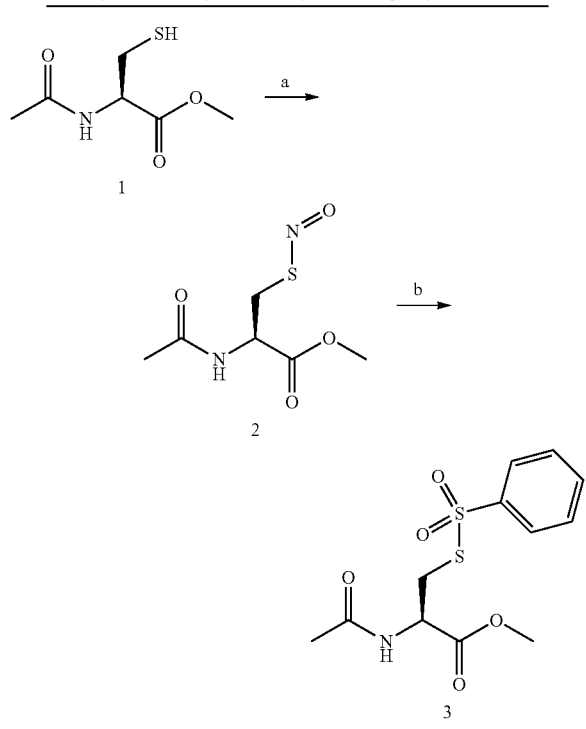

(a) 1N HCl, Methanol, sodium nitrite (b) sodium phenylsulfinate, water (R)-methyl 2-acetamido-3-(nitrosothio)propanoate (2)

Figure 22:
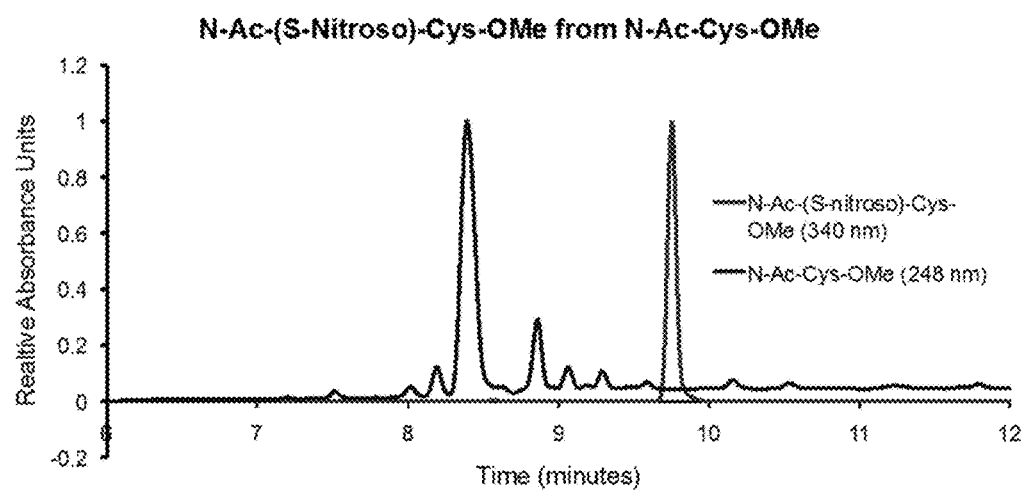
FIG. 22. HPLC trace of N-acetyl-cysteine-OMe starting material and the S-nitroso product formed upon reaction with sodium nitrite in 1 N HCl and methanol.

The nitrosothiol was synthesized based on the method reported earlier[1]. Briefly, an amber round bottom flask was charged with N-acetyl-L-cysteine methyl ester (1, 1 eq., 100 mg, 0.56 mmol). The contents were dissolved in methanol (3 mL) and 1 N hydrochloric acid (2 mL), and cooled to 0° C. for 15 minutes. An ice-cold solution of sodium nitrite (1.1 eq., 42.8 mg, 0.62 mmol) in water (1 mL) was then slowly added to the solution of N-acetyl-L-cysteine methyl ester in hydrochloric acid and methanol. The reaction mixture was constantly kept in the dark at 0° C., and allowed to proceed for 30 minutes. HPLC analysis of the crude reaction mixture was performed to monitor completion of the reaction. The crude product was then transferred to an amber separatory funnel and extracted with ethyl acetate (3×2 mL). The combined organic extracts were pooled, dried with sodium sulfate (200 mg), filtered and evaporated under vacuum (in the absence of light). This afforded a reddish-pink residue, which was used directly for subsequent reactions within 30 minutes. An HPLC trace of both the starting materials and the S-nitroso product is shown in FIG. 22 (HPLC trace of N-acetyl-cysteine-OMe starting material and the S-nitroso product formed upon reaction with sodium nitrite in 1 N HCl and methanol).

(R)-methyl 2-acetamido-3-((phenylsulfonyl)thio) propanoate (3)

Figure 23A:
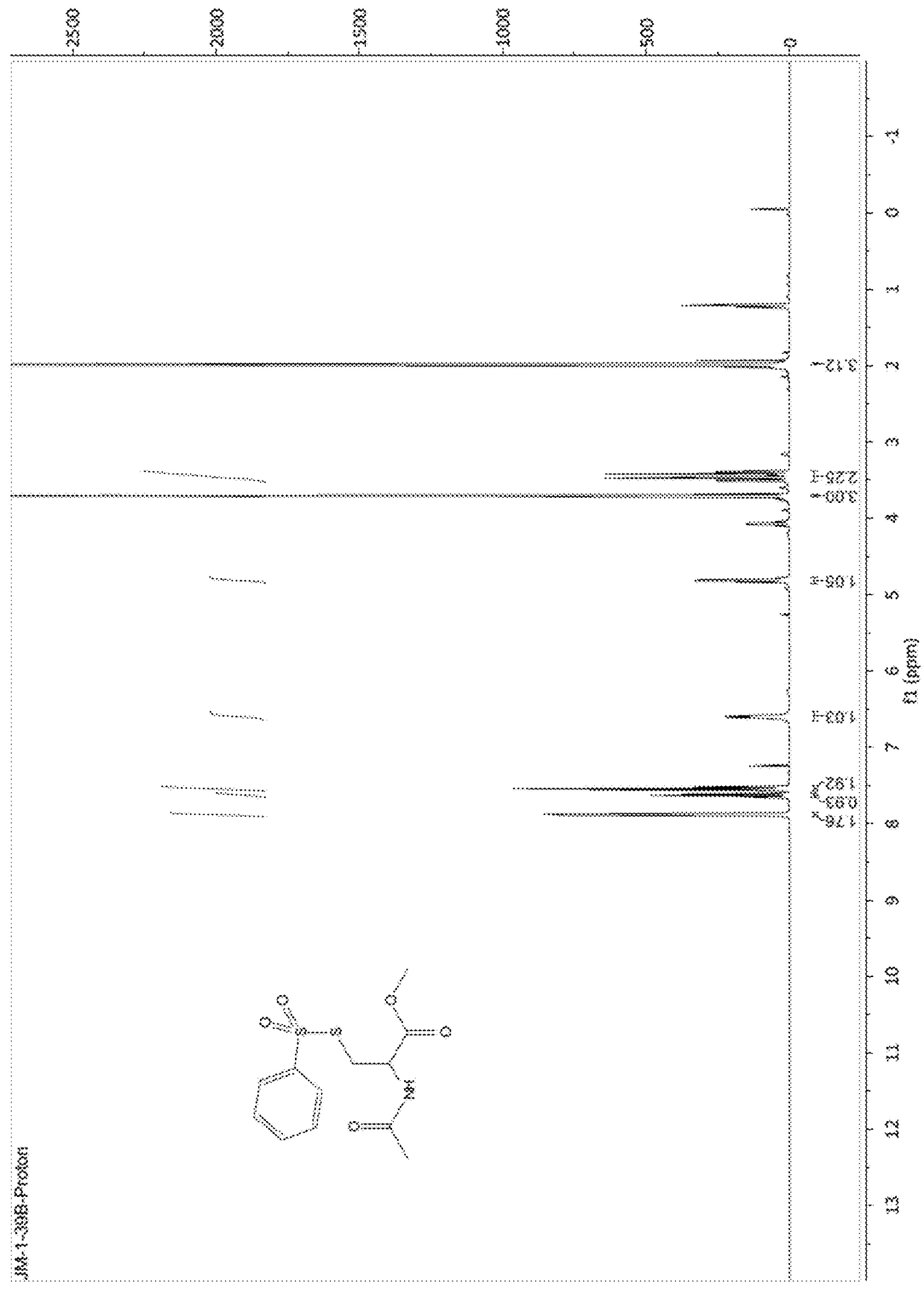
FIG. 23A-B. Spectra of (a) ¹H NMR of compound 3. (b) ¹³C NMR of compound 3.
Figure 23B:
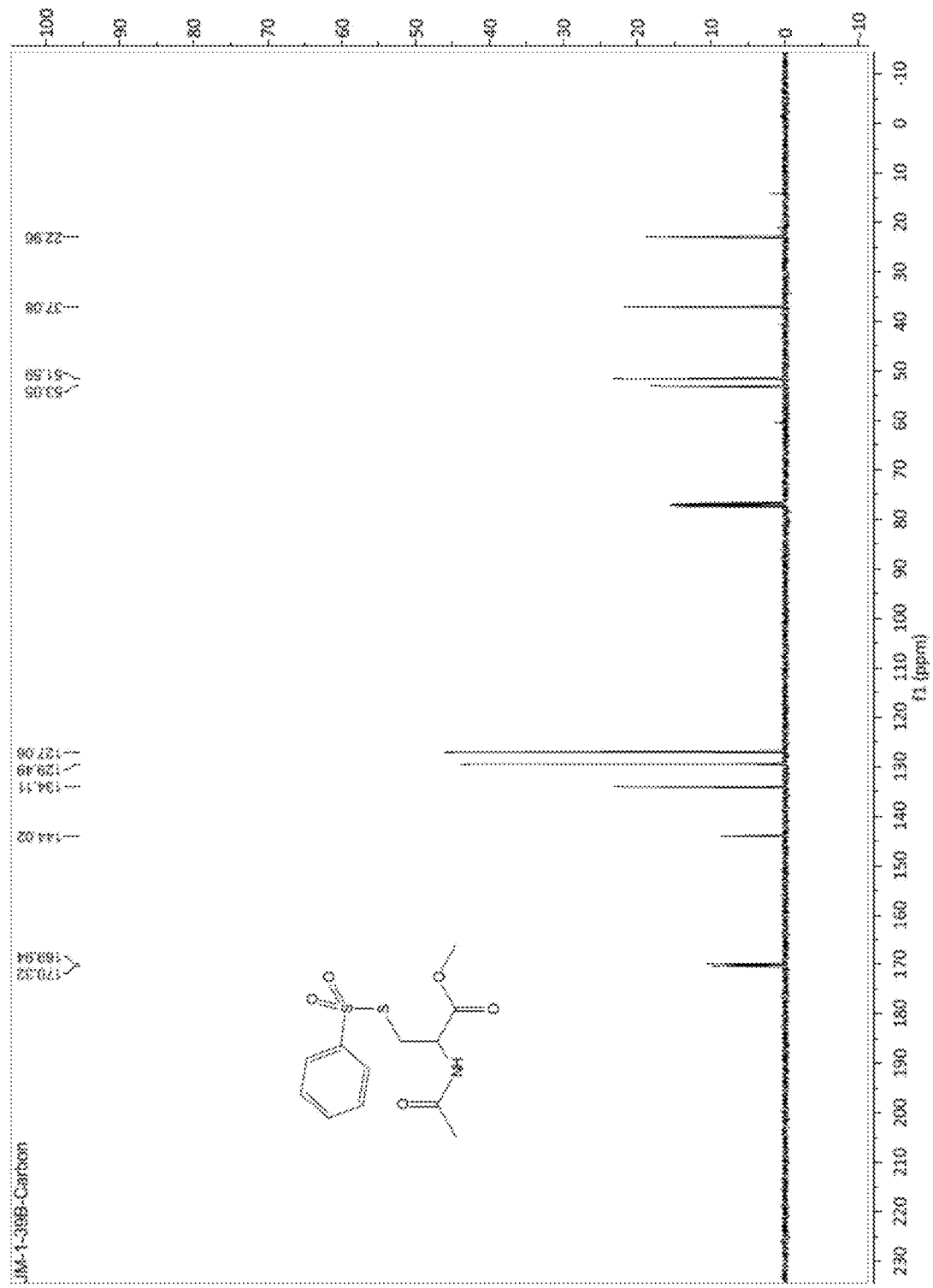

Thiosulfonate compound 3 was synthesized based on a method reported earlier[1,2]. Briefly, the N-acetyl-S-nitroso-cysteine methyl ester, 2, obtained in reaction above was dissolved in water followed by addition of sodium benzenesulfinate (3 eq., 1.68 mmol, 275.8 mg). The contents were allowed to react for 3 hours at ambient temperature in darkness. The contents were then transferred to a separatory funnel and extracted with ethyl acetate (3×10 mL). The organic fractions were pooled, washed with brine (10 mL), dried over sodium sulfate (500 mg), and concentrated under vacuum to afford an oily residue, which was further purified by flash column chromatography (isocratic elution 5% methanol in methylene chloride). This yielded 178 mg of thiosulfonate product 3. $^1$H NMR (400 MHz, CDCl$_3$) δ 7.91-7.85 (m, 2H), 7.66-7.59 (m, 1H), 7.57-7.51 (m, 2H), 6.60 (d, J=7.5 Hz, 1H), 4.81 (dt, J=7.5, 5.1 Hz, 1H), 3.71 (s, 3H), 3.54-3.36 (m, 2H), 1.99 (s, 3H). $^{13}$C NMR (100 MHz, CDCl$_3$) δ 170.32, 169.94, 144.02, 134.11, 129.49, 127.06, 53.05, 51.59, 37.08, 22.96. LR-ESI (Pos): m/z=318.04 [M+H]$^+$. FIG. 23 shows spectra of (a) $^1$H NMR of compound 3. (b)$^{13}$C NMR of compound 3.

Synthetic Scheme 2. Synthesis of fluorescein sulfinic acid probe (compound 5) and the negative control fluorescein sulfonic acid probe (compound 6).

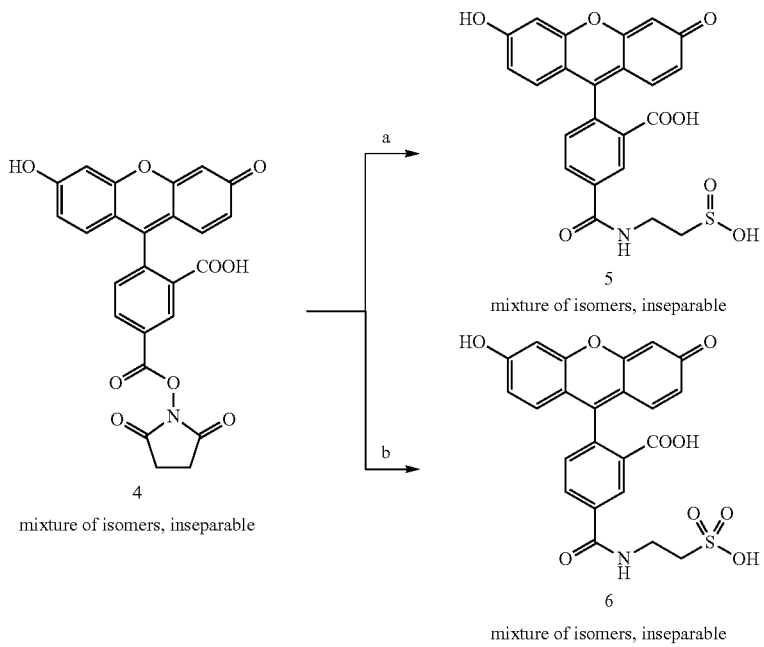

(a) water, THF, 100 μL 0.01N NaOH, Hypotaurine, 4 hours, 0° C., 32%
(b) water, THF, 100 μL 0.01N NaOH, Taurine, 10 hours, 0° C.-rt, 54%

2-(6-hydroxy-3-oxo-3H-xanthen-9-yl)-5-((2-sulfinoethyl)carbamoyl)benzoic Acid (5)

A scintillation vial was charged with a solution of NHS-fluorescein, 4 (Pierce, 1 eq., 7 mg, 0.015 mmol) in degassed THF (1 mL), and the contents were allowed to cool to 0° C. The atmosphere in the flask was replaced with nitrogen. A solution of hypotaurine (3.0 eq., 4.8 mg, 0.045 mmol) in degassed (sonication, 3 freeze-thaw cycles) 0.01N sodium hydroxide (100 μL) was then added to the NHS-flourescein. The contents were allowed to react for 4 hours under an atmosphere of nitrogen and progress was monitored by HPLC and mass spectrometry (LR-ESI-Pos). The product, 5, was purified to homogeneity by semi-preparative HPLC and lyophilized to yield compound 5 as a bright yellow solid in 29% yield. HRMS (ESI Negative), [M−H]⁻ Calculated: m/z=466.0602, Found: m/z=466.0570.

2-(6-hydroxy-3-oxo-3H-xanthen-9-yl)-5-((2-sulfoethyl)carbamoyl)benzoic Acid (6)

A scintillation vial was charged with a solution of NHS-fluorescein, 4, (Pierce, 1 eq., 15 mg, 0.032 mmol) in THF and the contents were allowed to cool to 0° C. A solution of taurine (3 eq., 11.9 mg, 0.095 mmol) in 0.01N sodium hydroxide (100 μL) was then added to the NHS-flourescein. The contents were allowed to react for 10 hours and progress was monitored by HPLC and mass spectrometry (LR-ESI-Pos). The product was purified to homogeneity by semi-preparative HPLC and then lyophilized to afford compound 6 as a bright yellow solid in 55% yield. HRMS (ESI Positive), [M+H]⁺ Calculated: m/z=484.0697, Found: m/z=484.0693.

Synthetic Scheme 3. Synthesis of biotinylated sulfinic acid probe (8) and the negative control biotinylated sulfonic acid probe (9).

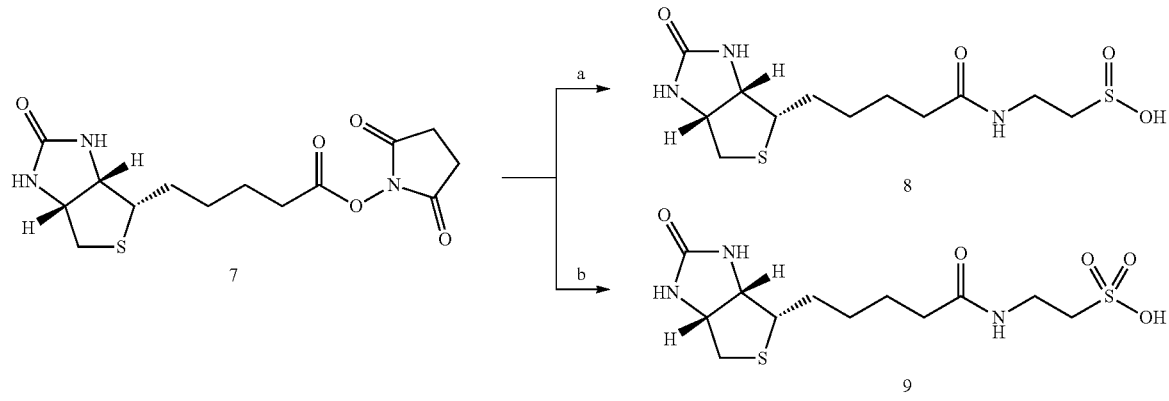

(a) water, THF, 100 μL 0.01N NaOH, Hypotaurine, 4 hours, 0° C., 24%
(b) water, THF, 100 μL 0.01N NaOH, Taurine, 10 hours, 0° C.-rt, 43%

2-(5-((3aS,4S,6aR)-2-oxohexahydro-1H-thieno[3,4-d]imidazol-4-yl)pentanamido)ethanesulfinic Acid (8)

Figure 24A:
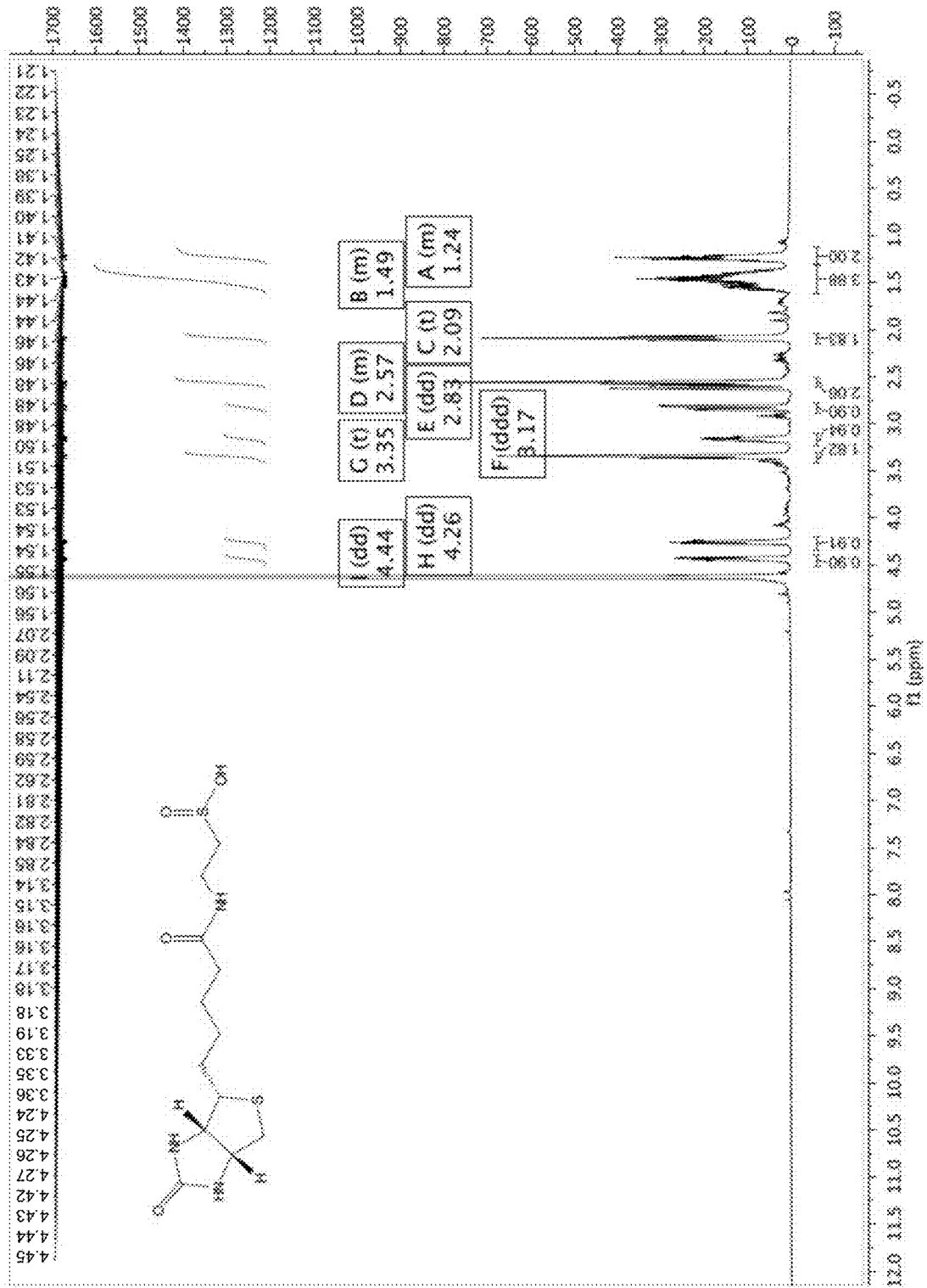
FIG. 24A-B. Spectra of (a) Proton NMR of compound 8 (b) Carbon NMR of compound 8.
Figure 24B:
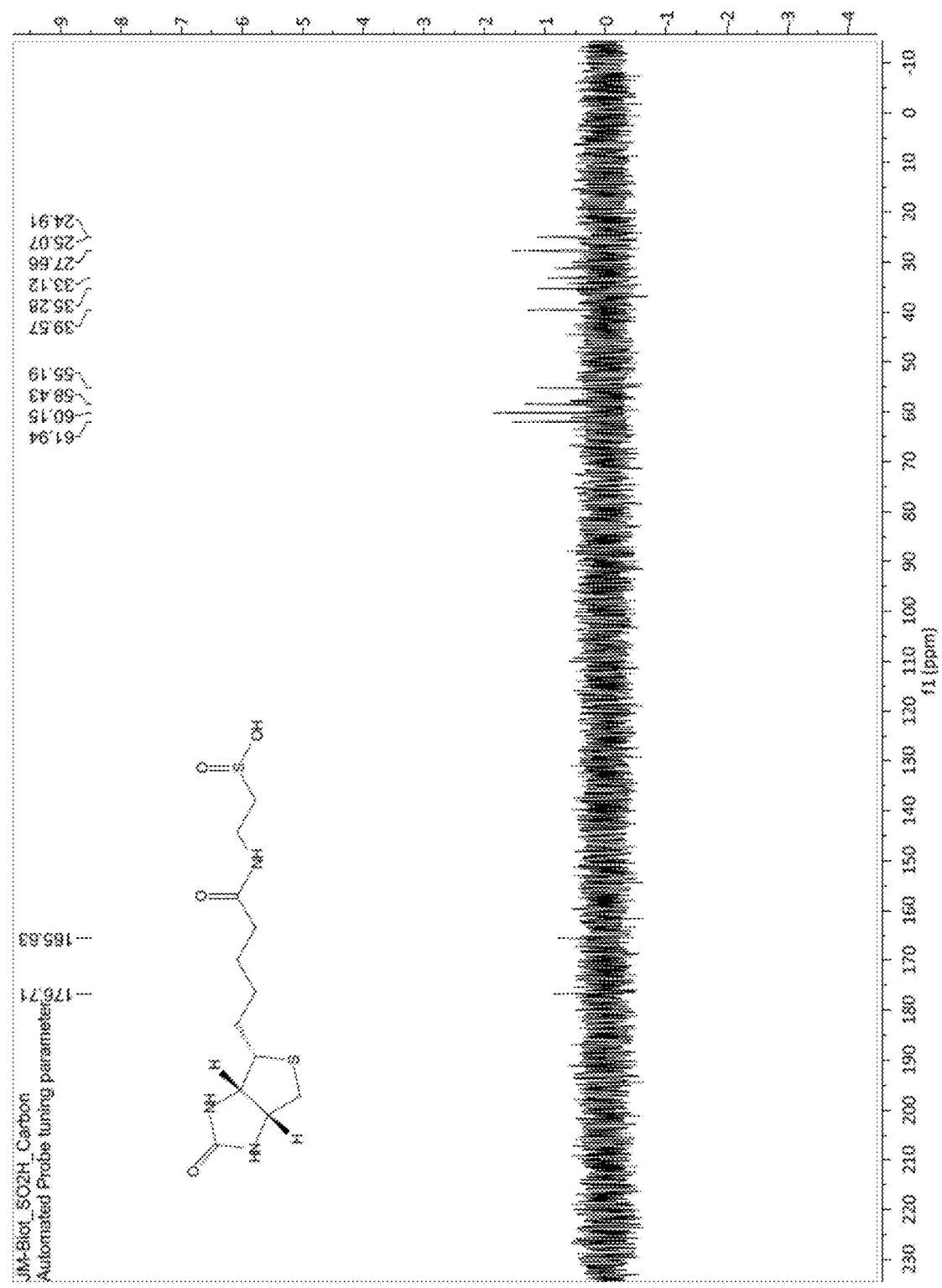
Figure 25:
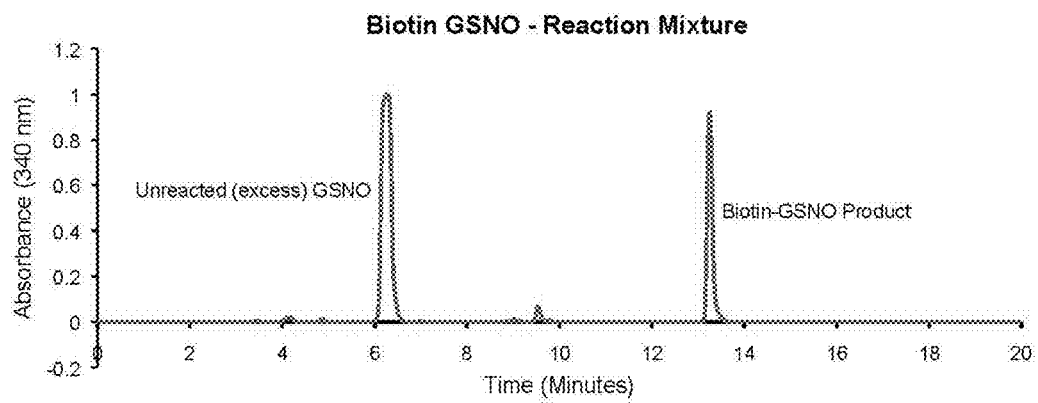
FIG. 25. HPLC trace of reaction mixture of biotin-GSNO, compound 16; Peak at minute 13.4 represents product as confirmed by MS analysis.

A scintillation vial was charged with a solution of NHS-biotin, 7, (Pierce, 1.0 eq., 35 mg, 0.1 mmol) in a 1:1 mixture of degassed THF and water and the contents were allowed to cool to 0° C. A solution of hypotaurine (3 eq., 34 mg, 0.3 mmol) in degassed (sonication under vacuum followed by three freeze-thaw cycles under vacuum) 0.01 N sodium hydroxide (100 μL) was then added to the NHS-biotin. The contents were allowed to react for 2 hours and the reaction progress was monitored by HPLC and mass spectrometry (LR-ESI-Neg). The product was purified to homogeneity by semi-preparative HPLC and then lyophilized to afford compound 8 as a white solid in 34% yield. $^1$H NMR (400 MHz, Deuterium Oxide) δ 4.44 (dd, J=7.9, 4.8 Hz, 1H), 4.26 (dd, J=7.9, 4.4 Hz, 1H), 3.35 (t, J=6.5 Hz, 2H), 3.17 (ddd, J=8.8, 5.8, 4.4 Hz, 1H), 2.83 (dd, J=13.0, 4.9 Hz, 1H), 2.68-2.45 (m, 2H), 2.09 (t, J=7.2 Hz, 2H), 1.63-1.31 (m, 4H), 1.32-1.11 (m, 2H). $^{13}$C NMR (100 MHz, D$_2$O) δ 176.71, 165.63, 61.94, 60.15, 58.43, 55.19, 39.57, 35.28, 33.12, 27.66, 25.07, 24.91. HRMS (ESI Negative), [M−H]$^-$ Calculated: m/z=334.0901, Found: m/z=334.0896. FIG. 24 shows spectra of (a) Proton NMR of compound 8 (b) Carbon NMR of compound 8.

2-(5-((3aS,4S,6aR)-2-oxohexahydro-1H-thieno[3,4-d]imidazol-4-yl)pentanamido)ethanesulfonic Acid (9)

A scintillation vial was charged with a solution of NHS-biotin, 7, (Pierce, 10 mg, 0.03 mmol) in a 1:1 mixture of THF and water and the contents were allowed to cool to 0° C. A solution of taurine (3 eq., 11 mg, 0.09 mmol) in 0.01 N sodium hydroxide (100 μL) was then added to the NHS-biotin. The contents were allowed to react for 2 hours and progress was monitored by HPLC and mass spectrometry (LR-ESI-Pos). The product was purified to homogeneity by semi-preparative HPLC and lyophilized to afford compound 9 as white solid in 43% yield. $^1$H NMR (400 MHz, Deuterium Oxide) δ 4.44 (dd, J=7.9, 4.8 Hz, 1H), 4.26 (dd, J=8.0, 4.5 Hz, 1H), 3.40 (t, J=6.8 Hz, 2H), 3.24-3.07 (m, 1H), 2.91 (t, J=6.7 Hz, 2H), 2.83 (dd, J=13.0, 4.9 Hz, 1H), 2.61 (d, J=13.2 Hz, 1H), 2.10 (t, J=7.4 Hz, 2H), 1.48 (dtt, J=26.3, 14.6, 7.1 Hz, 4H), 1.25 (q, J=7.6 Hz, 2H). HRMS (ESI Positive) [M+H]$^+$ Calculated: m/z=352.0995, Found: m/z=352.0995.

Synthetic Scheme 4: Synthesis of dimedone alkyne:

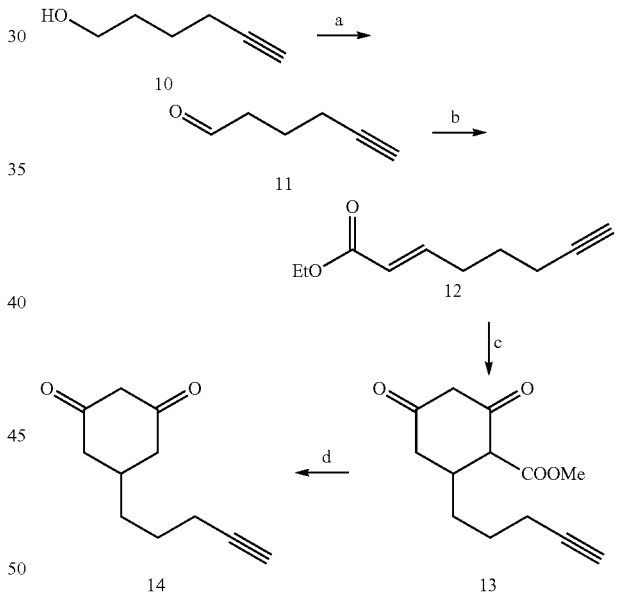

(a) TEMPO, (diacetoxy iodo) benzene, anhydrous DCM, 4 hours, room temp, 64% (b) triethyl phosphonoacetate, DBU, 12 hours, room temp, 93% (c) anhydrous methanol, sodium methoxide, 32% (d) 20% NaOH, 2 hours, reflux; then H$_2$SO$_4$, 99%.

5-hexyn-1-al (11)

Compound 11 was synthesized as described previously[3]. Briefly, to a stirring solution of (2,2,6,6-tetramethylpiperidin-1-yl)oxyl (TEMPO, 0.1 eq., 0.48 g, 3 mmol,) and (diacetoxyiodo)benzene (1.1 eq., 10.83 g, 33 mmol,) in anhydrous methylene chloride, 5-hexyn-1-ol (1 eq., 3.37 mL, 30 mmol,) was added drop-wise over the course of 30 minutes at ambient temperature and allowed to react for 3 hours. The reaction mixture was then transferred to a separatory funnel and extracted with saturated sodium bicarbonate (2×20 mL) and brine (2×10 mL). The organic layer was then dried over anhydrous magnesium sulfate (1.5 g) and filtered. The solvent was removed under vacuum using a rotary evaporator the residue was impregnated onto a silica gel column and purified using flash column chromatography (gradient elution using 100% hexanes, 50% hexanes: 50% DCM and 100% DCM) to afford 1.907 g (64%) of compound 11 as a yellowish oil. $^1$H NMR (400 MHz, Chloroform-d) δ 9.60 (s, 1H), 2.41 (td, J=7.2, 1.3 Hz, 2H), 2.07 (td, J=6.9, 2.6 Hz, 2H), 1.85 (t, J=2.7 Hz, 1H), 1.65 (p, J=7.0 Hz, 2H). $^{13}$C NMR (100 MHz, CDCl$_3$) δ 201.46, 83.08, 69.29, 42.30, 20.66, 17.53.

Ethyl (E)-oct-2-en-7-ynoate (12)

Compound 12 was synthesized by adapting a protocol described earlier[4]. Briefly, to stirring neat 5-hexyn-al (11, 1 eq., 0.50 g, 5 mmol,) triethyl phosphonoacetate (1.1 eq., 1.13 mL, 6 mmol,) and 1,8-diazabicyclo[5.4.0]undec-7-ene (DBU, 1.5 eq., 1.17 mL, 8 mmol,) were added left for 12 hours at ambient temperature. The resulting reaction mixture was diluted with ethyl acetate, transferred to a separatory funnel, and extracted with 1 M hydrochloric acid (2×20 mL) and brine (2×20 mL). The organic layer was collected and dried over anhydrous magnesium sulfate (500 mg), filtered, and dried under vacuum. The residue was impregnated onto a silica gel column and purified using flash column chromatography (isocratic elution using 1:1 hexanes:methylene chloride) to afford 806 mg (93%) of compound 12 as a yellowish oil. $^1$H NMR (400 MHz, Chloroform-d) δ 6.86 (dtd, J=15.4, 7.0, 1.0 Hz, 1H), 5.78 (dt, J=15.6, 1.4 Hz, 1H), 4.11 (q, J=7.2, 1.0 Hz, 2H), 2.29-2.24 (m, 2H), 2.21 (dd, J=17.9, 1.2 Hz, 2H), 1.91 (td, J=2.7, 1.0 Hz, 1H), 1.68-1.54 (m, 2H), 1.24-1.18 (m, 3H).

Synthesis of Ethyl 2,4-dioxo-6-(pent-4-yn-1-yl) cyclohexane-1-carboxylate (13)

Compound 13 was synthesized through minor modifications of a protocol described earlier (see, e.g., Focella, A., et al., J Organic Chemistry 42, 3456-3457 (1977)). Briefly, the atmosphere in a flame-dried round-bottom flask was replaced with dry nitrogen and the flask was allowed to attain ambient temperature. The cooled flask was charged with anhydrous methanol, followed by addition of ethyl (E)-oct-2-en-7-ynoate (1 eq., 5 mmol, 880 mg), and ethyl acetoacetate (3 eq., 16 mmol, 2.03 mL) and sodium methoxide (5 eq., 26 mmol, 1.43 g) were added. The mixture was refluxed under nitrogen for 6 hours, dried under vacuum, and extracted with methylene chloride (2×20 mL). The aqueous layer was acidified to pH 4 and extracted again with methylene chloride (2×20 mL). The organic layer was dried over anhydrous magnesium sulfate (500 mg), filtered, and the solvent removed under reduced pressure. The mixture was then purified by HPLC and lyophilized to yield 55 mg (32%) of compound 13 as a while solid (mixture of diastereomers). $^1$H NMR (400 MHz, Chloroform-d) δ 3.79 (s, 3H), 3.78-3.66 (m, 2H), 3.12 (d, J=9.8 Hz, 1H), 3.08-2.98 (m, 1H), 2.53 (d, J=4.2 Hz, 1H), 2.14 (dtd, J=13.5, 6.3, 3.5 Hz, 2H), 1.91 (dt, J=10.4, 2.7 Hz, 2H), 1.46 (d, J=7.3 Hz, 2H), 1.31-1.14 (m, 2H). HRMS (ESI positive) [M+H]+: Calculated m/z: 237.1126, Found m/z=237.1118.

5-(pent-4-yn-1-yl)cyclohexane-1,3-dione (14)

A round bottom flask was charged with ethyl 2,4-dioxo-6-(pent-4-yn-1-yl)cyclohexane-1-carboxylate, 13, and 20 mL of 20% aqueous sodium hydroxide. The contents were allowed to react under reflux for 2 hours, and then cooled to ambient temperature, acidified with concentrated sulfuric acid, and refluxed for two additional hours. Next, the pH was adjusted to pH 4.0 and the reaction extracted with ethyl acetate. The organic layer was dried with magnesium sulfate (500 mg), filtered and the solvent removed under reduced pressure. The reaction mixture was purified by HPLC and lyophilized to yield 99% of compound 14 as a white solid. $^1$H NMR (400 MHz, Chloroform-d) δ 2.59-2.27 (m, 4H), 2.24-2.05 (m, 4H), 1.98-1.88 (m, 1H), 1.50 (dtt, J=21.4, 12.7, 5.0 Hz, 4H). $^{13}$C NMR (100 MHz, CDCl$_3$) δ 178.03, 83.94, 68.60, 57.89, 47.49, 46.21, 37.98, 33.17, 30.27, 25.68, 18.40. HRMS (ESI positive) [M+H]+: Calculated m/z: 179.1072, Found m/z=179.1059.

Synthetic Scheme 5: Synthesis of Biotin-(S-Nitroso)-Glutathione (Biotin GSNO, 16)

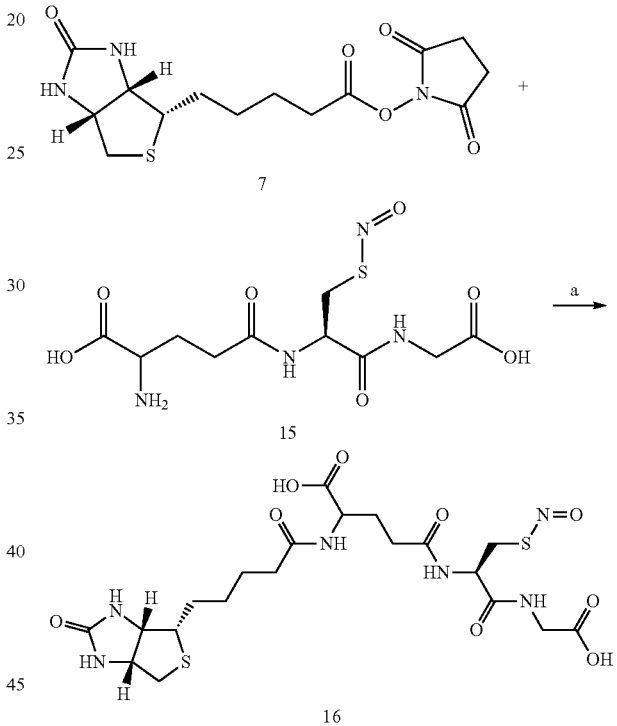

(a) THF, water, (1:1), 2 mL, triethyl amine, 0° C., 2 hours, dark

Biotin-GSNO. 5-(((R)-1-((carboxymethyl)amino)-3-(nitrosothio)-1-oxopropan-2-yl)amino)-5-oxo-2-(5-((3aS,4S,6aR)-2-oxohexahydro-1H-thieno[3,4-d] imidazol-4-yl)pentanamido)pentanoic Acid (16)

A 25 mL scintillation vial was charged with 11 mg of Biotin-NHS ester (30 μmol, 1.1 eq), 10 mg S-nitrosoglutathione (Cayman, 30 μmol, 1 eq.), and 17 μL triethylamine (119 μmol, 4 eq) in water/THF (2 mL) and stirred in the dark for 2 hours. The mixture was then purified by HPLC in the dark. The purified product (retention time 13 minutes) was lyophilized in the dark to obtain compound 16 in 43% yield. HRMS (ESI positive): Calculated m/z: [M+Na]+ =585.1408, Found m/z [M+Na]+=585.1407. FIG. shows HPLC trace of reaction mixture of biotin-GSNO, compound 16; Peak at minute 13.4 represents product as confirmed by MS analysis.

Synthetic Scheme 6: Synthesis of thiosulfonate product 19 from GSNO and 4-methyl-phenyl sulfinic acid.

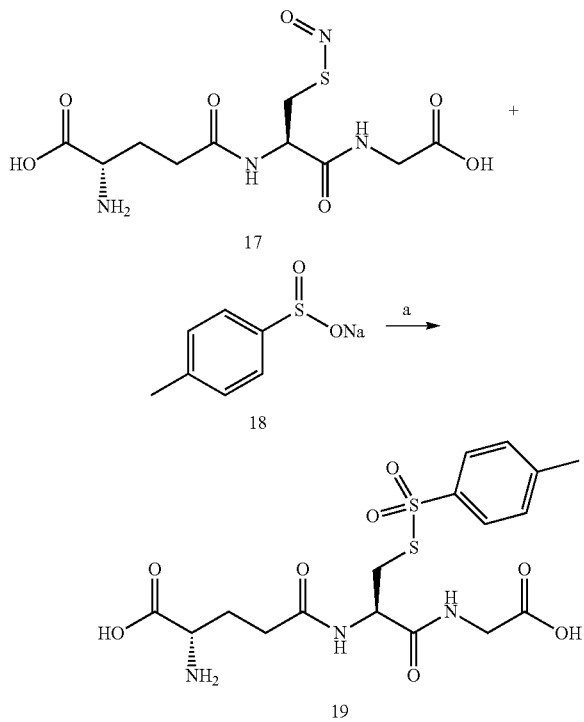

(a) Water, 0° C.-room temp, 2 hours, dark

(S)-2-amino-5-(((R)-1-((carboxymethyl)amino)-1-oxo-3-(tosylthio)propan-2-yl)amino)-5-oxopentanoic Acid (19)

Compound 19 was synthesized based on a protocol described above[2]. Briefly, to a cooled solution of S-nitrosoglutathione, 17, (GSNO, Cayman, 1.0 eq., 20 mg, 0.06 mmol) in degassed water, sodium 4-methyl-phenylsulfinate, 18 (3.0 eq., 32 mg, 0.18 mmol) was added allowed to react for 2 hours at ambient temperature in the dark. Compound 19 was purified from the crude reaction by semi-preparative HPLC. $^1$H NMR (400 MHz, Methanol-d4) δ 7.87-7.76 (m, 1H), 7.69 (d, J=8.2 Hz, 1H), 7.43 (d, J=8.2 Hz, 1H), 7.21 (d, J=8.1 Hz, 1H), 4.68 (dd, J=8.1, 5.0 Hz, 1H), 3.90-3.84 (m, 2H), 3.79 (t, J=6.3 Hz, 1H), 3.41 (dd, J=14.1, 5.0 Hz, 1H), 3.26-3.21 (m, 1H), 2.50 (t, J=7.0 Hz, 2H), 2.44 (s, 3H), 2.35 (s, 2H), 2.17-2.07 (m, 2H). HRMS (ESI positive), [M+H]$^+$ Calculated m/z: 461.0927, Found m/z=461.0924.

Example III

This example describes materials and methods pertaining to Examples I and II.

Rate Constant Determination.

S-nitrosoglutathione (GSNO, Cayman) and sodium phenylsulfinate (Sigma-Aldrich) were used for rate-determination studies at four pH values: pH 1.0 (0.2 N HCl/KCl buffer), pH 4.0 (0.1 M Sodium acetate/Acetic Acid buffer), pH 7.0 (0.1 M potassium phosphate buffer) and pH 10.0 (0.1 M Sodium bicarbonate/Sodium hydroxide buffer). The purity of S-nitrosoglutathione was calculated as 94±1.3% by absorbance at 334 nm using the molar extinction coefficient of 900 M$^{-1}$ cm$^{-1}$. Assays were performed using a plate reader (Tecan Infinite F500) monitoring absorbance of 2 mM GSNO at 340 nm over a course of 90 minutes in the presence of varying concentrations of sodium phenylsulfinate. Additional experiments confirmed thiosulfonate stability for >5 hours at pH 1, 4, and 7, but hydrolysis at pH 10. GSNO was stable in 6 M urea/PBS for >1 hour. Absorbance data was imported into KaleidaGraph (version 4.02, Synergy Software), and logarithmically fit to the first order exponential decay. The $K_{obs}$ was calculated for each phenylsulfinic acid concentration, and plotted to calculate the rate constant for the overall reaction.

Quantification of Products and by-Products.

LC-MS analysis was performed using an Agilent Q-TOF mass spectrometer (1-5 ppm accuracy) coupled with the ultra-high pressure HPLC system connected to a photodiode array detector. Compounds and reaction mixtures were injected in 5 μL volumes on an Agilent Zorbax Eclipse plus C18 rapid resolution column (2.1×50 mm, 1.8μ), and separated using the 10-minute gradient starting at 5% and increasing to 100% acetonitrile in 8 minutes. A solution of 500 μM GSNO was made in water (correcting for the 90% purity of GSNO) and allowed to react with various concentrations of 4-methyl-phenylsulfinic acid for 3 hours at ambient temperature before measurement. To generate standard curves, commercial N-hydroxy-4-methylbenzenesulfonamide (Combi-Blocks) was diluted in LC-MS grade water (pH 6.9) for LC-MS analysis. The thiosulfonate product, of GSNO and 4-methyl-phenylsulfinic acid was purified by semi-preparative HPLC. Extracted ion chromatograms were integrated for quantification of specific ions.

Mammalian Cell Culture.

Human 293T cells were grown in Dulbecco's Modified Eagle Medium (DMEM, Life Technologies) supplemented with 10% (v/v) fetal bovine serum (FBS, JR Scientific) and 1% (v/v) penicillin-streptomycin-glutamine solution (PSQ, Life Technologies). Cells were harvested at 80% confluence in phosphate buffered saline (PBS) (Life Technologies), and lysed by sonication at 4° C. For stable isotope labeling with amino acids in cell culture (SILAC), 293T cells were grown in SILAC DMEM (Thermo), 100 μg/mL [$^{13}C_6$,$^1N_4$] L-Arginine-HCl and [$^{13}C_6$,$^{15}N_2$] L-Lysine-HCl (Sigma) or L-Arginine-HCl and L-Lysine-HCl (Sigma) for greater than 6 passages.

Gel-Based Analysis of S-Sulfinylation.

Cells and lysates were protected from light and kept on ice throughout the labeling protocol, except when noted. 293T cell pellets were lysed by sonication (4° C., dark, 10% duty cycle, 10 seconds) in 6 M urea/PBS buffer. Lysate protein concentrations were quantified using the Bio-Rad DC assay, and diluted 3 mg/mL in 6 M urea/PBS. Next, lysates were treated with 50 mM iodoacetamide at room temperature for 30 minutes to alkylate all free thiols, and subsequently treated with the specific perturbant (such as ascorbate, hypotaurine etc—as mentioned in the specific experiment). Afterwards, lysates were incubated with 500 μM biotin-hypotaurine or fluorescein-hypotaurine for 30 minutes at room temperature. For in-gel fluorescence analysis, samples were loaded without boiling using non-reducing SDS-PAGE loading buffer for SDS-PAGE separation. Gels were transferred to 0.45 μm polyvinylidine difluoride membrane (Immobilon-P, Millipore) and blocked with 5% bovine serum albumin (BSA, Fisher) in Tris buffered saline-Tween 20 buffer (TBS-T, pH 7.4) for 2 hours at room temperature. After washing, the membrane was incubated and probed with a streptavidin conjugated to DyLight 633 (Thermo, 50 μg/L, 2.5% BSA, 0.02% NaN$_3$, TBS-T, pH 7.4) for 1 hour at room temperature and washed with TBS-T. For GAPDH detection, blots were probed with the anti-GAPDH mouse monoclonal antibody (mAb 6C5, Calbiochem, 1 µg/mL, 2.5% BSA, 0.02% $NaN_3$, TBS-T, pH 7.0), washed and probed with a secondary Alexa Fluor 532 nm goal-anti-mouse antibody conjugate (IgG H+L, Life Technologies, 2 µg/mL antibody, 0.06% $NaN_3$, TBS-T) for 1 hour at room temperature. In-gel fluorescence and streptavidin blots were analyzed using a GE typhoon scanner at appropriate wavelengths (488/526 for fluorescein and 633/670 for Cy5-Streptavidin).

Purification Recombinant GAPDH AND DJ-1.

Human GAPDH and DJ-1 cDNAs were amplified from 293T cDNA, cloned into the bacterial 6His expression vector pET45b, and transformed into BL21 E. coli. Bacteria were grown in LB media at 37° C. to an OD600 of 0.6, and induced with 0.4 mM IPTG for 4 additional hours at 37° C. After lysozyme treatment and sonication, the cleared lysate was incubated with Talon resin (Clontech), and loaded on a column. After sufficient washing, the purified recombinant protein was eluted with imidazole and dialyzed into PBS, typically yielding 10-15 mg/L of culture.

LC-MS Analysis of Purified Proteins.

Purified human GAPDH was diluted to 0.2 mg/mL in phosphate buffered saline (pH 7.3), and treated with 20 mM iodoacetamide for 30 minutes. Next, the sample was treated with 100 µM biotin-$SO_2H$. Purified human DJ-1 was diluted to 0.2 mg/mL in PBS, and incubated with 20 mM iodoacetamide to alkylated free thiols. Next, the sample was treated with 2 mM hydrogen peroxide for 20 minutes to promote Cys106 sulfinic acid formation. The resulting DJ-1 protein was mixed with excess N-acetyl-(S-Nitroso)-Cys-OMe for 30 minutes in the dark at room temperature. After labeling, the separate protein-probe mixtures were dried using a Savant SPD1010 concentrator (Thermo) and reconstituted in 200 µL of 2 M urea in 25 mM ammonium bicarbonate buffer with 2 µL of 100 mM $CaCl_2$. The reconstituted sampled incubated with mass spectrometry grade Trypsin (Promega, 2 µL of 0.5 mg/mL) for 6 hours at 37° C. with agitation. After trypsin digestion, additional salts were removed using a Waters Oasis HLB µElution plates (30 µm) following the manufacturer's protocol. The eluted peptide sample was dried and reconstituted in LC-MS buffer (0.1% formic acid in 3% acetonitrile/water with 5 fmol/µL Saccharomyces cerevisiae alcohol dehydrogenase (P00330)). Tryptic peptides were then separated on the Waters NanoAcquity chromatography system fitted with a 5 µM Symmetry C18 (180 µm×20 mm) trap column and a 1.8 µm High Strength Silica (HSS-T3) analytical column (75 µm×150 mm) over a 80 minute gradient from 5% to 35% acetonitrile, followed by a 85% acetonitrile wash for approximately 10 minutes and re-equilibration to 5% acetonitrile at a flow rate of 0.5 µL/min. Eluted peptides were analyzed using a Waters Synapt G2-S HDMS time-of-flight mass spectrometer in positive mode. Glu-1-Fibrinopeptide B (Glu-Fib) was used as an internal lock-mass. MS data was searched using Waters Protein Lynx Global Server v3.0 using the exact mass calculated for the cysteine thiosulfonate modification.

Labeling and Enrichment of Cell Lysates for LC-MS Analysis.

Cells and lysates were protected from light and kept on ice throughout the labeling protocol, except when noted. SILAC paired lysates were prepared separately in 6 M urea/PBS at 3 mg/mL. Approximately 1.2 mg of each lysate was used for each biological replicate. All samples were treated with 50 mM iodoacetamide for 30 minutes to alkylate reduced thiols. Next, "light" and "heavy" lysates were treated with 400 µM of the biotin-$SO_2H$ probe, and the other "light" and "heavy" lysates were treated with 400 µM of the biotin-$SO_3H$ probe. The lysates were allowed to incubate with the probes for 45 minutes in the dark. After 45 minutes, the lysates were quenched by chloroform-methanol addition, and centrifuged to isolate the protein interface while removing excess probe and iodoacetamide. The isolated protein pellet was washed 3 times with cold methanol, each time sonicating the protein pellet and removing the supernatant after centrifugation. The precipitated lysates were re-solubilized in 500 µL of 6 M urea/25 mM ammonium bicarbonate, which required vigorous vortexing and heating (37° C., 10 min). Protein concentrations were measured again using the BioRad DC assay, and normalized to the lowest concentration obtained across the 8 samples. The "light" and "heavy" samples were mixed in a 1:1 ratio (vol/vol), matching a "light" lysate labeled with the biotin-$SO_2H$ probe with a "heavy" lysate labeled with the biotin-$SO_3H$ probe and vice-versa, yielding a total of four independent biological replicates. Each combined sample was transferred to a 15 mL conical tube containing 280 µL of 10% SDS. After brief heating (50° C., 2 min), samples were diluted with 5.5 mL PBS. 100 µL of a 50% streptavidin slurry (Millipore) was washed three times with PBS, and transferred to the solubilized, labeled lysate. Each sample was incubated on a rotary mixer for 2 hours at room temperature, and washed 3 times with 3 mL of 1% SDS in PBS, and 7 times with 3 mL of PBS. The resin was then transferred to a 1.5 mL screw-top conical tube in 200 µL of 2 M urea/25 mM ammonium bicarbonate supplemented with 1 mM aqueous calcium chloride, and 2 µg of trypsin was added to each tube. Samples were incubated 37° C. with agitation for 6-8 hours, and the supernatant was collected and pooled with 2×150 µL washes, and cleaned up using the Oasis HLB µElution plates (30 µm). The eluted peptide sample was dried and reconstituted in final 2D-LC-MS buffer, which consists of 20 mM ammonium formate, pH 10.0 buffer with 5 fmol/µL Saccharomyces cerevisiae alcohol dehydrogenase (Waters) as internal standard. Tryptic peptides were stored at −80° C. until subjected to LC-MS analysis.

2-D LC-MS of Enriched Samples.

In-line liquid chromatography of tryptic peptides was performed on the Waters 2D-NanoAcquity chromatography system fitted with a X-BRIDGE BEH130 C18 5 µM (300 µM×50 mm) peptide separation technology fractioning column (column chemistry: 1,2-bis(siloxyethane) [—$O_3SiCH_2CH_2SiO_3$—]), a 5 µM Symmetry C18 (180 µm×20 mm) trap column and a 1.8 µm High Strength Silica (HSS-T3) analytical column (75 µm×150 mm) using gradients described in Tables 2 and 3. In a 2D chromatography system, tryptic peptides are first loaded onto the fractioning column, followed by fractionation by sequential gradients that gradually increase in the organic component. In the 2D NanoAcquity workflow, peptides are first delivered in a pH 10.0 buffer, and loaded on to the fractioning column ($1^{st}$ dimension) using 20 mM ammonium formate solution as the aqueous phase. The organic phase on the $1^{st}$ dimension is 100% acetonitrile. In each step, a fraction of the peptides are eluted to the trapping column, and delivered to the analytical column ($2^{nd}$ dimension) for separation. The $2^{nd}$ dimension uses 0.1% formic acid in water and 0.1% formic acid in acetonitrile as the solvents. During trapping stage, the basic buffers are diluted 1:10 with the acidic solvents to capture the peptide fraction on the trapping column, transferred to the analytical column, and separated over a reverse phase gradient for direct electrospray ionization to the instrument source. Peptides were analyzed using a Waters Synapt G2S HDMS time-of-flight mass spectrometer using ion mobility separation and data independent fragmentation algorithms[17].

TABLE 2

Fractioning Column gradient. Fraction 1 shown. Fractions 2, 3, 4, and 5 reached 14%, 16.7%, 20.4%, and 50% acetonitrile, respectively.

| Step | Time (min) | Flow Rate (μL/min) | % Water | % Acetonitrile |
|---|---|---|---|---|
| 1 | Initial | 2.0 | 97 | 3 |
| 2 | 0.5 | 2.0 | 97 | 3 |
| 3 | 1.0 | 2.0 | 89.2 | 10.8 |
| 4 | 5.0 | 2.0 | 89.2 | 10.8 |
| 5 | 5.5 | 2.0 | 97 | 3 |
| 6 | 20.5 | 2.0 | 97 | 3 |

TABLE 3

Analytical Column gradient. Common gradient for all 5 fractions in 2D mode.

| Step | Time (min) | Flow Rate (μL/min) | % Water | % Acetonitrile |
|---|---|---|---|---|
| 1 | Initial | 0.5 | 93 | 7 |
| 2 | 37.11 | 0.5 | 15 | 85 |
| 3 | 42.11 | 0.5 | 15 | 85 |
| 4 | 43.11 | 0.5 | 93 | 3 |
| 5 | 45.00 | 0.5 | 93 | 7 |

SILAC Data Analysis.

Raw data files searched against the reviewed human database (Uniprot) using Waters Protein Lynx Global Server (PLGS) version 3.0 at a protein false discovery rate of 4%. Using in-house scripts, all data from technical and biological replicates were merged, removing in-source fragments, unlabeled peptides not containing an arginine or lysine, and any precursors greater than +5 ppm in mass difference from the calculated theoretical mass. Data was sorted to match SILAC peptides with their corresponding "Heavy" or "Light" partners. Peptides without a pair were labeled as potential "uniques". Additional data custom scripts were used to calculate the average SILAC ratio, the estimated top3 abundance, the number of SILAC peptides pairs identified for each protein, the SILAC ratio standard deviation, and the number of times the protein was identified across all replicates. The potential "unique" list was further processed to assess their true "uniqueness". Each unpaired "Light" peptide was assigned a value of "0"; and every unpaired "Heavy" peptide was assigned a value of "1". If a protein had 10 peptides that were all "light", then its average "value" from the pivot table analysis is "0", and assigned as a "unique" protein. Conversely, if all peptides for a protein were "Heavy", then its average value is "1". All proteins with a value greater than 0 or less than 1 were deleted from further analysis. If a protein had 50 peptides associated with it, and of those peptides had pairs and 10 did not, then the protein was removed from the "unique" category.

Analysis of Unenriched Lysates.

293T cells were lysed in 20 mM ammonium bicarbonate containing 2 M urea and the protein concentration was determined. Lysates from two different biological replicates were used diluted to 3 mg/mL, and reduced with 20 mM dithiothreitol (DTT), followed by alkylation with 50 mM iodoacetamide and digested with trypsin. Tryptic digests were injected to a 1D Waters NanoAcquity UPLC system equipped with a 5 μM Symmetry C18 (180 μm×20 mm) trap column and a 1.8 μm High Strength Silica (HSS-T3) analytical column (75 μm×150 mm) using a gradient described in Table 4. Eluted peptides were analyzed using a Waters Synapt G2S HDMS time-of-flight mass spectrometer using ion mobility separation and data-independent fragmentation algorithms[17] (2 biological replicates×5 technical replicates for each biological replicate). Top3 analysis of the identified proteins was performed to compare relative abundance of the identified proteins across different biological and technical replicates.

TABLE 4

Analytical gradient for unenriched proteomics. Common gradient for 2 biological replicates each with 5 technical replicates.

| Step | Time (min) | Flow Rate (μL/min) | % Water | % Acetonitrile |
|---|---|---|---|---|
| 1 | Initial | 0.5 | 93 | 7 |
| 2 | 85.00 | 0.5 | 65 | 35 |
| 3 | 90.00 | 0.5 | 50 | 50 |
| 4 | 92.00 | 0.5 | 20 | 80 |
| 5 | 100.00 | 0.5 | 20 | 80 |
| 6 | 102.00 | 0.5 | 93 | 7 |
| 7 | 120 | 0.5 | 93 | 7 |

Gene Ontology (GO) Analysis for Functional Annotation.

Gene ontology analysis was performed on both the enriched and the unenriched 293T cell proteomic datasets. Identified proteins were analyzed using the AmiGO term enrichment algorithm, which classified proteins into various GO terms[24]. The entire Uniprot human database was used as the background dataset and electronically inferred data were excluded from the GO term analysis. The p-value was set at 0.0001 (maximum). Additional validation was performed using the DAVID functional annotation tool (see, e.g., Huang, D. W., Sherman, B. T. & Lempicki, R. A. Nature Protocols 4, 44-57 (2009)).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical sciences are intended to be within the scope of the following claims.

We claim:

1. A method for detecting native S-nitrosylation within cysteine residues of a protein, comprising:
    providing a biological sample comprising one or more proteins having cysteine residues and a composition comprising a sulfinic acid moiety, wherein the cysteine residues may or may not have a S-nitrosothiol side chain,
    exposing the composition to the biological sample such that an interaction between the sulfinic acid moiety and a S-nitrosothiol side chain of a cysteine residue results in generation of a labeled sulfonothioate moiety, and
    characterizing the cysteine residues of the one or more proteins having sulfonothioate moieties as having undergone S-nitrosylation.

2. The method of claim 1, further comprising identifying the protein having been characterized as having undergone S-nitrosylation and/or identifying the exact amino acid sites on the protein having been characterized as having undergone S-nitrosylation.

3. The method of claim 1, wherein the sulfinic acid moiety is a labeled sulfinic acid moiety.

4. The method of claim 3, wherein the labeled sulfinic acid moiety comprises an imaging agent and/or an enrichment tag.

5. The method of claim 4, wherein said imaging agent is a fluorescent dye.

6. The method of claim 5, wherein in-gel fluorescence is used to characterize the cysteine residues of a protein having a labeled sulfonothioate moiety as having undergone S-nitrosylation.

7. The method of claim 4, wherein said enrichment tag is biotin or desthiobiotin.

8. The method of claim 3, wherein flash chromatography followed by NMR and/or mass spectrometry is used to structurally identify the product of the reaction between a labeled sulfinic acid moiety and a S-nitrosothiol side chain of a cysteine residue.

9. The method of claim 3, wherein high performance liquid chromatography is used to characterize the cysteine residues of a protein having labeled sulfonothioate moieties as having undergone S-nitrosylation.

10. The method of claim 3, wherein mass spectrometry is used to characterize the cysteine residues of a protein having labeled sulfonothioate moieties as having undergone S-nitrosylation.

11. The method of claim 3, wherein the sulfonothionate moiety is a labeled sulfonothionate moiety.

12. The method of claim 1, wherein the one or more proteins having cysteine residues is selected from one or more of the proteins recited in FIG. 16.

13. A method for detecting native S-nitrosylation within cysteine residues of a protein, comprising:
providing a biological sample comprising one or more proteins having cysteine residues and a composition comprising a nitrosothiol moiety, wherein the cysteine residues may or may not have a S-nitrosothiol side chain,
exposing the composition to the biological sample such that an interaction between the nitrosothiol moiety and a sulfinic acid side chain of a cysteine residue results in generation of a sulfonothioate moiety, and
characterizing the cysteine residues of the one or more proteins having sulfonothioate moieties as having undergone S-nitrosylation.

14. The method of claim 13, wherein the nitrosothiol moiety is a labeled nitrosothiol moiety.

15. The method of claim 14, wherein the sulfonothioate moiety is a labeled sulfonothioate moiety.

16. The method of claim 13, further comprising identifying the protein having been characterized as having undergone S-nitrosylation and/or identifying the exact amino acid sites on the protein having been characterized as having undergone S-nitrosylation.

17. The method of claim 14, wherein the labeled nitrosothiol moiety comprises an imaging agent and/or an enrichment tag.

18. The method of claim 17, wherein said imaging agent is a fluorescent dye.

19. The method of claim 18, wherein in-gel fluorescence is used to characterize the cysteine residues of a protein having a labeled sulfonothioate moiety as having undergone S-nitrosylation.

20. The method of claim 17, wherein said enrichment tag is biotin or desthiobiotin.

21. The method of claim 14, wherein flash chromatography followed by NMR and/or mass spectrometry is used to structurally identify the product of the reaction between a labeled nitrosothiol moiety and a sulfinic acid side chain of a cysteine residue.

22. The method of claim 14, wherein high performance liquid chromatography is used to characterize the cysteine residues of a protein having labeled sulfonothioate moieties as having undergone S-nitrosylation.

23. The method of claim 14, wherein mass spectrometry is used to characterize the cysteine residues of a protein having labeled sulfonothioate moieties as having undergone S-nitrosylation.

* * * * *